US010842863B2

(12) United States Patent
Thirion et al.

(10) Patent No.: US 10,842,863 B2
(45) **Date of Patent: *Nov. 24, 2020**

(54) VACCINE AGAINST BETA-HERPESVIRUS INFECTION AND USE THEREOF

(71) Applicants: Christian Thirion, Munich (DE); Ulrich Koszinowski, Feldafing (DE); Christian A. Mohr, Munich (DE); Zsolt Ruzsics, Diessen am Ammersee (DE)

(72) Inventors: Christian Thirion, Munich (DE); Ulrich Koszinowski, Feldafing (DE); Christian A. Mohr, Munich (DE); Zsolt Ruzsics, Diessen am Ammersee (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/194,558

(22) Filed: Nov. 19, 2018

(65) Prior Publication Data

US 2019/0117766 A1 Apr. 25, 2019

Related U.S. Application Data

(60) Continuation of application No. 14/734,415, filed on Jun. 9, 2015, now abandoned, which is a division of application No. 13/695,668, filed as application No. PCT/EP2011/002252 on May 5, 2011, now Pat. No. 9,078,867.

(30) Foreign Application Priority Data

May 5, 2010 (EP) .................................... 10004751
May 12, 2010 (EP) .................................... 10005045

(51) Int. Cl.

| | |
|---|---|
| ***A61K 39/245*** | (2006.01) |
| ***C12N 7/00*** | (2006.01) |
| ***A61K 39/12*** | (2006.01) |
| ***A61K 39/00*** | (2006.01) |

(52) U.S. Cl.

CPC ............ *A61K 39/245* (2013.01); *A61K 39/12* (2013.01); *C12N 7/00* (2013.01); *A61K 2039/525* (2013.01); *A61K 2039/5254* (2013.01); *A61K 2039/575* (2013.01); *C12N 2710/16111* (2013.01); *C12N 2710/16121* (2013.01); *C12N 2710/16134* (2013.01); *C12N 2710/16152* (2013.01); *C12N 2710/16162* (2013.01); *C12N 2710/16171* (2013.01); *C12N 2710/16511* (2013.01); *C12N 2830/003* (2013.01)

(58) Field of Classification Search

CPC ................ A61K 35/763; A61K 39/245; A61K 2039/5254; A61K 2039/525; A61K 39/12; A61K 39/25; A61K 2039/575; C12N 15/86; C12N 15/8258; C12N 2710/16062; C12N 2710/16032; C12N 15/869; C12N 2710/16121; C12N 2710/16152; C12N 2710/16161; C12N 7/00; C12N 2710/16171; C12N 2710/16511; C12N 2710/16111; C12N 2710/16134; C12N 2710/16162; C12N 2830/003; A61P 35/00; A61P 33/00; A61P 31/22; A61P 31/12; A61P 31/04

See application file for complete search history.

(56) References Cited

U.S. PATENT DOCUMENTS

2005/0064394 A1 3/2005 Liu

FOREIGN PATENT DOCUMENTS

| | | |
|---|---|---|
| WO | 2000034497 | 6/2000 |
| WO | 2005/012545 | 2/2005 |

OTHER PUBLICATIONS

Mohr et al: “A Cytomegalovirus deficient in viral spread has full immunogenic competence”, poster presented at 12th International CMV/BetaHerpesvirus Workshop, Boston, Massachusettes, May 10-14, 2009.

Mohr et al: “A Cytomegalovirus defiicent in viral spread has full immunogenic competence”, abstract of poster contained in the abstract book presented at 12th International CMV/ZBetaHerpesvirus Workshop, Boston, Massachusettes, May 10-14, 2009.

Heineman TC. Human cytomegalovirus vaccines. In: Arvin A., Campadelli-Fiume G, Mocarski E, et al., editors. Human Herpesviruses: Biology, Therapy, and Immunoprophylaxis, Cambridge: Cambridge University Press; 2007. Chapter 71. Available from http://www.ncbi.nlm.nih.gov/books/NZBK47380/.

Isaacson MK, Compton T. Human cytomegalovirus glycoprotein B is required for virus entry and cell-to-cell spread but not for virion attachment, assembly, or egress J. Virol. Apr. 2009; 83(8):3891-903. Epub Feb. 4, 2009.

Dudek T et al.: “Replication-defective viruses as vaccines and vaccine vectors”, Virology, Academic Press, Orlando, US, vol. 344, No. 1, Jan. 5, 2006 (Jan. 5, 2006), pp. 230-239, XP02489631, ISSN: 0042-6822, DOI: 10.1016/J. virol.2005.09.020 [retrieved on Jan. 5, 2006] cited in teh application p. 232, right-hand column, line 3—p. 233, left-hand column, line 5, figure 1.

A. Bubeck et al.: “Comprehensive Mutational Analysis of a Herpesvirus Gene in the Vital Genome Context Reveals a Region Essential for Virus Replicatioin”, Journal of Virology, vol. 78, No. 15, Aug. 1, 2004 (Aug. 1, 2004), pp. 8026-8035, XP55004753, ISSN: 0022-538X, DOI: 10.1128/JVI.78.15 8026-004; p. 8026, paragraph 2—p. 8029, right-hand column, paragraph 1; table 2.

B. Rupp et al.: “Conditional Cytomegalovirus Replication In Vitro and In Vivo”, Journal of Virology. vol. 79, No. 1, Jan. 1, 2005 (2995-01-01), pp. 486-494, XP55004778, ISSN: 0022-538X, DOI: 1128/JVI.79.1-486-494.2005 *concerns Invention 1*: p. 488, right-hand column, paragraph 2; figures 1C, 3.

(Continued)

*Primary Examiner* — Rachel B Gill

(74) *Attorney, Agent, or Firm* — Barnes & Thornburg LLP; Jeffrey R. Stone

(57) ABSTRACT

The present invention is related to a beta-herpesvirus, wherein the beta-herpesvirus is spread-deficient.

20 Claims, 9 Drawing Sheets

Specification includes a Sequence Listing.

(56) References Cited

OTHER PUBLICATIONS

Christopher M. Snyder et al. "Cross-Presentation of a Spread-Defective MCMV is Suthicient to Prime the Majority of Virus-Specific CD8+ T Cells", Plos one, vol. 5, No. 3, Jan. 1, 2010 (Jan. 1, 2010), pp. E9681-E9681, XP55004357, ISSN: 1932-6203, DOI: 10.1371/journal.pone.0009681 p. 2, left-hand column, paragraph 2—p. 3, right-hand column, paragraph 1; figures 1, 2, p. 6, left-hand column, paragraph 2.

W. Dunn: "Functional profiling of a human cytomegalovirus genome", Proceedings of the National Academy of Sciences, vol. 100, No. 24, Jan. 1, 2003 (Jan. 1, 2003), pp. 14223-14228, XP55004412, ISSN: 0027-8424, DOI: 10.1073/pnas.2334032100 * concerns Invention 3*; figure 1; table.

D. Yu et al: "Functional map of human cytomegalovirus AD169 defined by global mutational analysis", Proceedings of the National Academy of Sciences, vol . 100, No. 21, Oct. 1, 2003 (Oct. 1, 2003), pp. 12396-12401, XP55037376, ISSN: 0027-8424, DOI: 1073/pnas.1635160100 *concerns Invention 3* p. 12400, right-hand column, lines 13-15, figure 2; table 1.

C,A, Mohr et al: "A Spread-Deficient Cytomegalovirus for Assessment of First-Target Cells in Vaccination" Journal of Virology, vol. 84, No. 15, Aug. 1, 2010 (Aug. 1, 2010), pp. 7730-7742, XP5500990, ISSN: 0022-538X, DOI: 10.1128/JVI.02696-09: the whole document.

C. Sinzger et al: "Cloning and sequencing of a highly productive, endotheliotropic virus strain derived from human cytomegalovirus TB40/E", Journal of General Virology, vol. 89, No. 2, Feb. 1, 2008 (Feb. 1, 2008), pp. 359-368, XP55001586, ISSN: 0022-1317, DOI: 10.1099/vir.0.83286-0 the whole document.

Cui X et al: Cytomegalovirus vaccines fail to induce epithelial entry neutralizing antibodies comparable to natural Infection:, Vaccine Elsevier Ltd, GB, vol. 26 No. 45, Oct. 23, 2008 (Octg. 23, 2008), pp. 5760-5766, XP026046073, ISSN: 0264-410X, DOI: 0.1016/J.Vaccine.2008.07.092 [retrieved on Sep. 19, 2008] the whole document.

Mohr CA, Mein Saki L, Wagner M. Sacher T. Schnee M, Ruzsics Z, Koszinowski UH. Engineering of cytomegalovirus genomes for recombinant live herpesvirus vaccines. Int J Med Microbiol. Jan. 2008; 298(1-2):115-25. Epub Aug. 16, 2007.

Rawlinson WD, Farrell HE, Farrell BG. Analysis of the complete DNA sequence of murine cytomegalovirus. J Virol. Dec. 1996; 70(12):8833-49.

Pass RF. Development and evidence for efficacy of CMV glycoprotein B vaccine with MF59 Adjuvant. J Clin Virol. Dec. 2009; 46 Supp 4: S73-6. Epub Jul. 31, 2009.

Liu Y. Cui Z, Zhang Z, Wei H, Zhou Y, Wang, M, Zhang XE. The tegument protein UL94 of human cytomegalovirus as a binding partner for tegument protein pp28 identified by intracellular imaging. Virology. May 25, 2009; 388(1); 68-77.

Scalzo, Anthony A., et al, "The Interplay between host and viral factors in shaping the outcome of cytomegalovirus infection", Immunology and Cell Biology (2007) 85, pp. 46-54.

Jiang XJ, Adler B. Sampaio KL, Digel M. Jahn G. Ettischer N. Stierhof YD, Scrivano L, Koszinowski U, Mach M. Singer C. UL74 of human cytomegalovirus contributes to virus release by promoting secondary envelopement of virions. J. Virol. Mar. 2008; 82(6): 2802-12. doi: 10.1128/JVI.01550-07. Epub Jan. 9, 2008.

Gao H, Tao R, Zheng Q, Xu J. Shang S, Recombinant HCMV UL128 expression and functional identification of PBMC-attracting activity in vitro. Arch Virol. Jan. 2003; 158(1):173-7, Epub Aug. 1, 2012.

Brune W. Human herpesvirus 5 strain TB40/E clone TB40-BAC4, complete sequence. GenBank: EF999921.1. Dep. Oct. 30, 2007.

Vales-Gomez M, Winterhalter A, Roda-Navarro P. Zimmerman A. Boyle L. Hengel H, Brooks A, Reyburn HT. The human cytomegalovirus glycoprotein UL16 traffics through the plasma membrane and the nuclear envelope. Cell Microbiol. Apr. 2006;8(4)58-90.

Klupp BG, Bottcher S, Granzow H. Kopp M, Mettenleiter TC. Complex formation between the UL16 and UL21 tegument proteins of pseudorables virus. J. Virol. Feb. 2005;79(3):1510-22.

Lorz K. Hoffman H. Berndt A. Tavalai N, Mueller R, Schlotzer-Schrehardt U, Stamminger T. Deletion of open reading frame UL26 from the human cytomegalovirus genome results in reduced viral growth, which involves impaired stability of viral particles. J. Virol. Jun. 2006;80(11):5423-34.

Sattentau Q. Avoiding the void: cell-to-cell spread of human viruses. Nat Rev Microbiol. Nov. 2008:6(11):815-26. doi:10.1038/nrmicro 1972. Review. PubMed PMID: 18923409.

Figure 3A
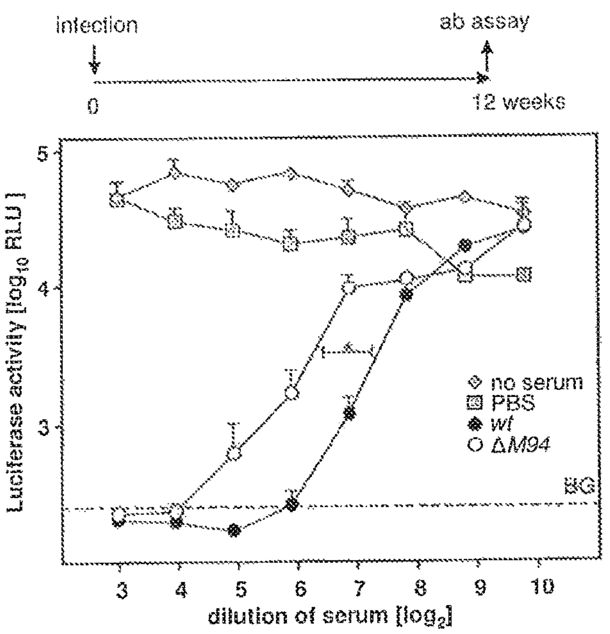
Figure 3B
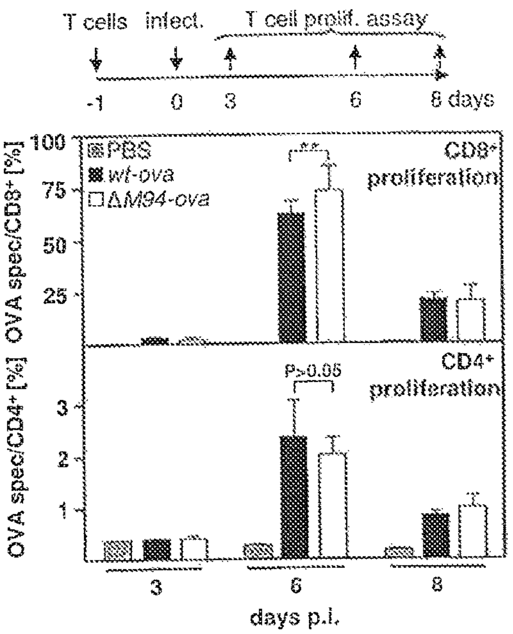
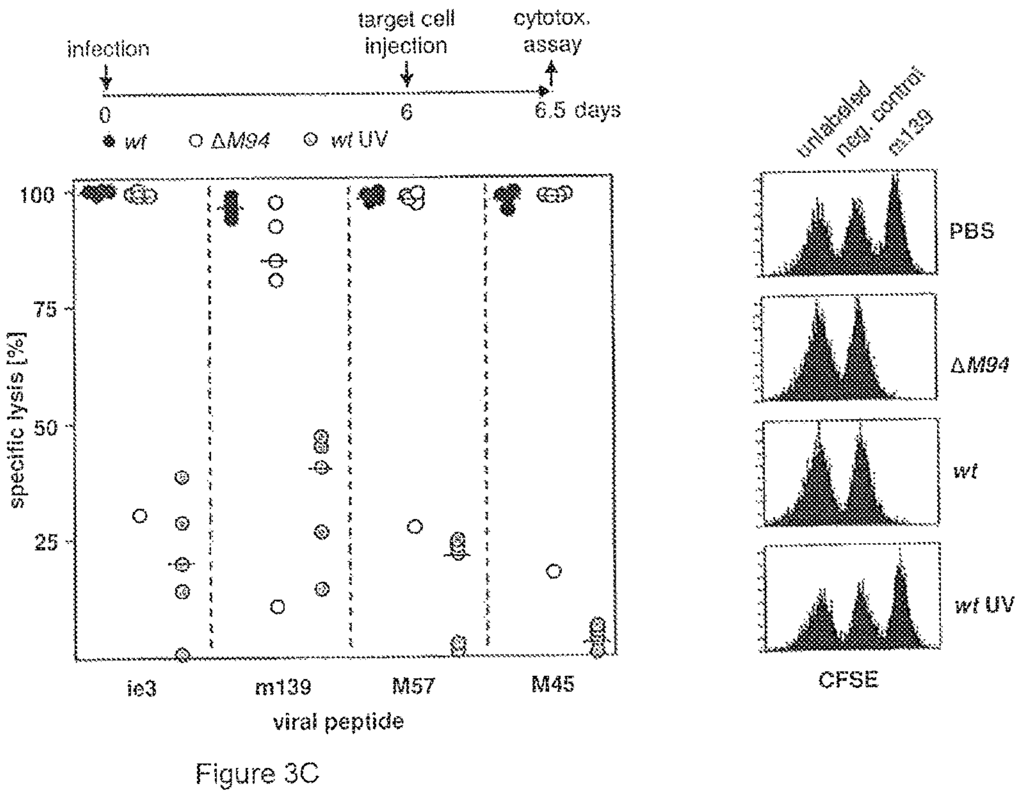
Figure 3C

Figure 9A
Figure 9B
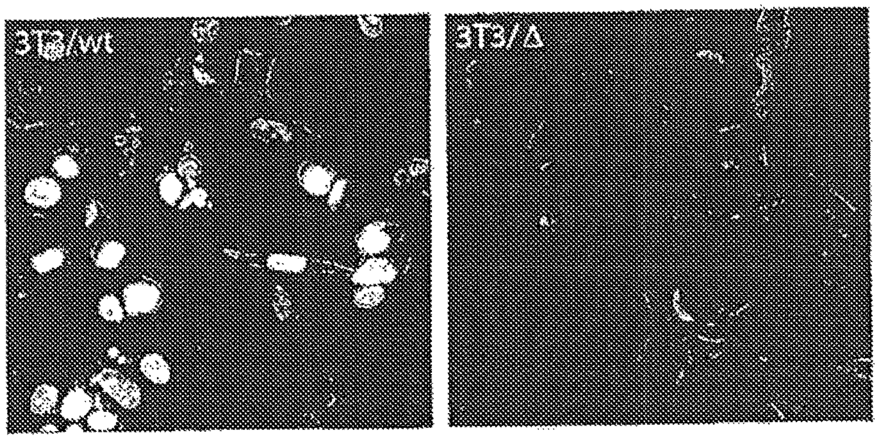
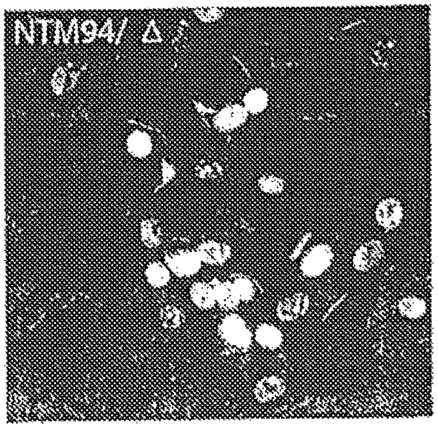
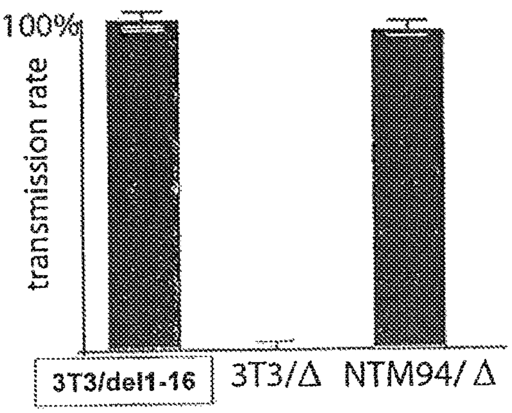
Figure 9C

VACCINE AGAINST BETA-HERPESVIRUS INFECTION AND USE THEREOF

CROSS-REFERENCE TO RELATED APPLICATIONS

This application is a divisional of U.S. patent application Ser. No. 13/695,668 filed Dec. 14, 2012, which is a national stage application of PCT/EP2011/002252 filed May 5, 2011, the entirety of which prior filed applications are hereby incorporated by reference.

The present invention is related to a beta-herpesvirus, preferably a recombinant beta-herpesvirus, the use of the beta-herpesvirus for the manufacture of a medicament, the use of the beta-herpesvirus for the manufacture of a vaccine, a nucleic acid coding for the beta-herpesvirus, a vector comprising the nucleic acid coding for the beta-herpesvirus, and a host cell comprising the nucleic acid coding for the beta-herpesvirus or the vector. In a preferred embodiment, the beta-herpesvirus is a human cytomegalovirus.

Human cytomegalovirus (CMV), a member of the beta-herpesvirus subfamily is the medically most significant herpesvirus infecting humans (Arvin et al. 2004 Clin. Infect. Dis. 39:233-239; Stratton et al. 1999 Vaccines for the 21st Century: A Tool for Decisionmaking National Academy Press). Most of the human CMV infection is acquired without symptomatic disease via breast feeding or saliva/urine contact in early childhood. This results in nearly 100% prevalence of HCMV in developing countries. In industrialized countries about 30% of the population gets infected in the childhood and the prevalence of human CMV infection increases up to 50% by early adulthood.

Human CMV can also be transmitted from the mother to the fetus during pregnancy leading to mental retardation and developmental disabilities in the infected child. Human CMV is the most important causative agent of congenital infections in industrialized countries with one out of 1000 newborn affected. To date 30,000-40,000 infants are annually born with congenital cytomegalovirus infection in the United States, making cytomegalovirus by far the most common and important of all congenital infections. The likelihood of congenital infection and the extent of disease in the newborn depend on the maternal immune status. If primary maternal infection occurs during pregnancy, the average rate of transmission to the fetus is 40%; about 65% of these newborns will have congenital inclusion disease (CID). With recurrent maternal infection going along with reactivation from latency, the risk of transmission to the fetus becomes lower ranging only from 0.5 to 1.5% and the majority of these infants will also be symptomless. Although natural infections before pregnancy cause a risk of reactivation associated feto-maternal transmission the induced immunity is a major protective factor against CID.

The infection at birth bears the risk of serious complications; the primary infection with HCMV is generally symptomless in immunologically competent individuals. The major risk groups comprise organ transplant recipients and acquired immunodeficiency syndrome (AIDS) patients in which human CMV induces life-threatening inflammatory diseases with high probability. Moreover, after primary infection at any age, CMV establishes lifelong latency, leaving the infected individuals at danger of later reactivation upon immune suppression.

Although enormous progress has recently been made in molecular biology and immunology of cytomegaloviruses (Murphy et al. 2008 Curr. Top. Microbiol. Immunol. 325:1-19), to date there is no commercially available vaccine and the single hit chemotherapy is the only way of controlling acute HCMV infection (Mocarski et al. 2007, p. 2701-2772 in D. M. Knipe and P. M. Howley (eds.), Fields Virology, Lippincott Williams and Wilkins, a Wolters Kluwer Business, Philadelphia, Pa.). This chemotherapy causes severe side effects and application is often restricted to the most severe cases.

The development of vaccines against CMV infection is reviewed in Schleiss et al. (Schleiss et al. 2005 Herpes. 12:66-75; Schleiss et al. 2008 Curr. Top. Microbiol. Immunol. 325:361-382.).

One strategy for the development of a human CMV vaccine is the use of live attenuated HCMV. Live attenuated CMV are generated by multiple cell culture passages. In accordance therewith, in live attenuated vaccines the administered viruses are infectious. However due to the adaptation to the cell culture a loss of functional genes occurs whereby the lost genes are not required for virus propagation in vitro, but are important for virus infection in vivo. Such live attenuated CMV are therefore less pathogenic to the host.

The first human CMV vaccine candidate which was tested in clinical trials was a live attenuated vaccine. This was the AD169 strain of HCMV which was attenuated by extensive tissue culture passages in human primary fibroblasts. This attenuation is a result of a selective adaptation of the virus to the conditions of the cell and cell culture. It is likely that the loss of virulence is the result of affecting genes not relevant for the in vitro situation but important for the virus in its natural host. Therefore, it is not surprising that AD169, extensively passaged on fibroblasts, lost its ability to infect endothelial cells and monocytes. The majority of seronegative adults inoculated with AD169 vaccine developed HCMV specific immune response. This vaccine was found to be safe and generally well tolerated. However, injection site reactions were common, and several patients developed mild systemic symptoms consisting of fever, headache, fatigue and myalgia.

Since the AD169 strain was too aggressive, a more attenuated preparation of laboratory adapted HCMV, the Towne strain, was developed in a manner similar to AD169 as a potential live attenuated vaccine. This strain was more extensively passaged in cell culture and in vitro appeared to be also phenotypically similar to AD169.

The initial human trial showed that, as expected, the Towne strain was much better tolerated than the AD169. After this positive initial test the efficacy of the Towne vaccine was extensively studied. These studies showed that the Towne vaccine is safe and well tolerated in humans and induces both humoral and cellular immunity specific to human CMV. Although the Towne vaccine appears to provide some protection against human CMV disease in certain settings, unfortunately, vaccination is less protective than natural immunity. Therefore, the Towne strain is most likely over-attenuated rendering it of suboptimal efficacy as a vaccine.

Consequently, new human CMV strains with intermediate attenuation have been produced. Chimeric viruses have been constructed by genetic recombination between Towne strain and Toledo strain, which is a wild type like clinical isolate of human CMV not attenuated by tissue culture passages.

Interestingly, an essential feature of the Towne strain and the vaccine based thereon is its incapability of efficiently infecting endothelial cells. Furthermore, vaccination with the Towne strain does not induce antibodies that are capable of neutralizing endotheliotropic CMV infection, more specifically Towne does not induce antibodies against endotheliotropic human CMV strains (Cui et al. 2008 Vaccine 26:5760-5766).

To differentiate between neutralization of endotheliotropic and non-endotheliotropic viruses, Gerna et al. (Gerna et al. 2008 J Gen Virol 89:853-865.) proposed the testing of human sera and quantification of the neutralizing potency against human CMV clinical isolates via propagation and testing in endothelial (or epithelial) cells and against the same virus infecting human fibroblasts (Gerna et al. supra).

It is important to note that in addition to the inability of the Towne strain to infect endothelial cells and the inability of the Towne strain to induce antibodies that are capable of neutralizing endotheliotropic human CMV infection, the Towne strain is lacking genes compared with clinical wild type human CMV isolates. More specifically, the Towne strain is lacking the genes UL133, UL134, UL135, UL136, UL137, UL139, UL140, UL141, UL142, UL143, UL144, and UL145 as also described by Cha et al. (Cha et al. 1996 J. Virol Vol. 70, No. 1 p. 78-83).

A further strategy for developing a HCMV vaccine is based on the deletion of an essential gene from a viral genome and was described for many viruses such as adenoviruses, alpha-herpesviruses, and retroviruses. Immunization trials using replication defective or single-cycle viruses as vaccines against herpesviruses were, to date, only described for alpha-herpesviruses (Dudek et al. 2006 Virology 344:230-239). The propagation of these viruses is facilitated by complementing cells that express the lacking genomes and support the growth of the defective viruses. Propagation of such viruses with the deletion of a gene on complementing cells results in vaccine-virus particles that possess a wild type virion surface and a tropism like wild type virus for the first target cells. These viruses are infectious upon vaccination for the first line target cells. In said first line target cells, the deleted or inactivated gene leads to either the abrogation of virus replication or the formation of virus particles with diminished infectivity or tropism.

The design of an alpha-herpesvirus vaccine by deletion of one gene essential for DNA replication or the abrogation of production of infectious particles by deletion of the targeting complex, namely glycoprotein gB is reviewed in Dudek et al. (Dudek et al. supra). Two types of these viruses were described: the so called “replication-defective” and the so called “single-cycle” viruses.

Replication-defective alpha-herpesviruses were generated by the deletion of genes essential for the DNA replication cycle. The deletion of genes essential for the viral DNA replication e.g. the major DNA binding protein ICP8, was used to generate respective deletion viruses. Said viruses can be propagated in vitro by using stably transformed cells that complement the product of the lacking gene (Forrester et al. 1992 J Virol 66:341-348.). Several publications from Knipe and colleagues prove that such viruses can induce protective immune responses (see Morrison et al. 1998 Virology 243: 178-187; Morrison et al. 1994 J Virol 68:689-696; Morrison et al. 1996 Virology 220:402-413; Morrison et al. 1997 Virology 239:315-326.).

Single-cycle viruses lack glycoproteins of targeting complexes e.g. glycoprotein gB or fusion complexes e.g. (Dudek et al. supra). Such virus mutants are described in U.S. Pat. No. 7,374,768 by Inglis et al. Said complexes are described to be important for the attachment to the cell and/or fusion of virus and cell, as initiation steps for infection of this cell. The deletion of said glycoproteins will generate single-cycle vaccine virus particles that infect first line target cells. It is important to note that said cells in the host form virus particles which do not possess a wild type-like virion surface since they lack the glycoprotein mentioned above. These particles lacking the glycoprotein, are not infectious or at least possess limited tropism or infectivity for the next cells to be infected. Further, the deletion of said glycoprotein leads to a lacking expression of said glycoprotein preferably being effective as an antigen in the infected cell.

Due to society costs caused by human CMV infection in both morbidity groups and the emerging epidemiological situation the development of an effective HCMV vaccine has been emphasize as a highest level priority by the National Vaccine Committee of the Institute of Medicine (US) (Stratton et al. supra).

Thus the problem underlying the present invention was to provide an effective HCMV vaccine and a beta-herpesvirus contained in such vaccine, respectively.

This problem is solved by the attached independent claims. Preferred embodiments may be taken from the attached dependent claims.

The claims are recited in the following as embodiments. It will be acknowledged that further embodiments may result from the disclosure of the instant specification which is insofar not limited to the embodiments being a recitation of the claims.

Embodiment 1

A beta-herpesvirus, preferably a recombinant beta-herpesvirus, wherein the beta-herpesvirus is spread-deficient.

Embodiment 2

The beta-herpesvirus according to embodiment 1, wherein the beta-herpesvirus is endotheliotropic and for has a wild type-like virion surface.

Embodiment 3

The beta-herpesvirus according to any one of embodiments 1 to 2, wherein the beta-herpesvirus is endotheliotropic and has a wild type-like virion surface.

Embodiment 4

The beta-herpesvirus according to any one of embodiments 1 to 3, wherein the beta-herpesvirus is suitable to or capable of inducing an immune response, wherein preferably the immune response comprises neutralizing antibodies against beta-herpesvirus and $CD4^+$ and $CD8^+$ T-cells directed against epitopes of beta-herpesvirus.

Embodiment 5

The beta-herpesvirus according to embodiment 4, wherein the immune response comprises neutralizing antibodies, wherein beta-herpesvirus is prevented from infecting endothelial cells and/or epithelial cells by the neutralizing antibodies.

Embodiment 6

The beta-herpesvirus according to embodiment 5, wherein beta-herpesvirus which is prevented from infecting endothelial cells author epithelial cells by the neutralizing antibodies, is a pathogen, preferably a human pathogen.

Embodiment 7

The beta-herpesvirus according to any one of embodiments 1 to 6, wherein the beta-herpesvirus is a human beta-herpesvirus.

Embodiment 8

The beta-herpesvirus according to any one of embodiments 1 to 7 wherein the beta-herpesvirus is a cytomegalovirus.

Embodiment 9

The beta-herpesvirus according to any one of embodiments 7 and 8, wherein the beta-herpesvirus is a human cytomegalovirus.

Embodiment 10

The beta-herpesvirus according to any one of embodiment 1 to 9, preferable embodiment 9, wherein the beta-herpesvirus is deficient in at least one gene product involved in primary and/or secondary envelopment.

Embodiment 11

The beta-herpesvirus according to embodiment 10, wherein the at least one gene product is involved in primary envelopment Embodiment 12

The beta-herpesvirus according to embodiment 11, wherein the at least one gene product is encoded by a gene selected from the group comprising UL50 and UL 53 and homologs of each thereof.

Embodiment 13

The beta-herpesvirus according to embodiment 10, wherein the at least one gene product is involved in secondary envelopment.

Embodiment 14

The beta-herpesvirus according to embodiment 13, wherein the at least one gene product is encoded by a gene selected from the group comprising UL94 and UL99 and homologs each thereof.

Embodiment 15

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 122630 of the nucleotide sequence according to SEQ.ID.NO:20 is covalently linked to nucleotide 123668 of the nucleotide sequence according to SEQ.ID.NO:20 and wherein nucleotide 181652 of the nucleotide sequence according to SEQ.ID.NO:20 is covalently linked to nucleotide 189192 of the nucleotide sequence according to SEQ-.ID.NO:20.

Embodiment 16

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.NO:34.

Embodiment 17

The beta-herpesvirus according to embodiment 16, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ-.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 18

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 181652 of the nucleotide sequence according to SEQ.ID.NO:20 and a fourth nucleotide sequence represented by nucleotides 189192 to 233681 of the nucleotide sequence according to SEQ-.ID.NO:20 and wherein nucleotide 122630 of the nucleotide sequence according to SEQ.ID.NO:20 is covalently linked to nucleotide 123668 of the nucleotide sequence according to SEQ.ID.NO:20, wherein the nucleotide 130670 of the nucleotide sequence according to SEQ.ID.NO:20 is covalently linked to the nucleotide 131243 of the nucleotide sequence according to SEQ.ID.NO:20 and wherein the nucleotide 181652 of the nucleotide sequence according to SEQ.ID.NO:20 is covalently linked to the nucleotide 189192 of the nucleotide sequence according to SEQ-.ID.NO:20.

Embodiment 19

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 181652 of the nucleotide sequence according to SEQ.ID.NO:20, a fourth nucleotide sequence represented by nucleotides 189192 to 233681 of the nucleotide sequence according to SEQ.ID.NO:20, a fifth nucleotide sequence comprising a nucleotide sequence according to SEQ.ID.No: 34 and a sixth nucleotide sequence comprising a nucleotide sequence according to SEQ.ID.No: 35.

Embodiment 20

The beta-herpesvirus according to embodiment 19, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ-.ID.NO:20, wherein nucleotide 130670 of the nucleotide sequence according to SEQ.ID.NO:20 is covalently linked to nucleotide 1 of the nucleotide sequence according to SEQ.ID.No: 35, wherein nucleotide 67 of the nucleotide sequence according to SEQ.ID.NO:35 is covalently linked to nucleotide 131243 of the nucleotide sequence according to SEQ.ID.No: 20, and wherein nucleotide 181652 of the nucleotide sequence according to SEQ.ID.NO:20 is covalently linked to nucleotide 189192 of the nucleotide sequence according to SEQ.ID.NO:20.

Embodiment 21

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ.ID.NO:20 and wherein nucleotide 181652 of the nucleotide sequence according to SEQ.ID.NO:20 is covalently linked to the nucleotide 189192 of the nucleotide sequence according to SEQ.ID.NO:20.

Embodiment 22

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.No: 32.

Embodiment 23

The beta-herpesvirus according to embodiment 22, wherein nucleotide 58442 of the nucleotide sequence according to SEQ.ID.NO:20 is covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ-.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 24

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 62129 of the nucleotide sequence according to SEQ.ID.NO:20 is covalently linked to nucleotide 63261 of the nucleotide sequence according to SEQ.ID.NO:20 and wherein the nucleotide 181652 of the nucleotide sequence according to SEQ.ID.NO:20 is covalently linked to the nucleotide 189192 of the nucleotide sequence according to SEQ.ID.NO:20.

Embodiment 25

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.No: 33.

Embodiment 26

The beta-herpesvirus according to embodiment 25, wherein nucleotide 62129 of the nucleotide sequence according to SEQ.ID.NO:20 is covalently linked to nucleotide 1 of the nucleotide sequence according to SEQ.ID.No: 33, wherein nucleotide 38 of the nucleotide sequence according to SEQ.ID.No: 33 is covalently linked to nucleotide 632611 of the nucleotide sequence according to SEQ-.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 27

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, third nucleotide sequence represented by nucleotides 632161 to 181652 of the nucleotide sequence according to SEQ.ID.NO:20 and a fourth nucleotide sequence represented by nucleotides 189192 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ-.ID.NO:20, wherein the nucleotide 62129 of the nucleotide sequence according to SEQ.ID.NO:20 is covalently linked to the nucleotide 63261 of the nucleotide sequence according to SEQ.ID.NO:20 and wherein the nucleotide 181652 of the nucleotide sequence according to SEQ.ID.NO:20 is covalently linked to the nucleotide 189192 of the nucleotide sequence according to SEQ.ID.NO:20.

Embodiment 28

The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 63261 to 181652 of the nucleotide sequence according to SEQ.ID.NO:20, a fourth nucleotide sequence represented by nucleotides 189192 to 233681 of the nucleotide sequence according to SEQ.ID.NO:20, a fifth nucleotide sequence comprising a nucleotide sequence according to SEQ.ID.No: 32 and a sixth nucleotide sequence comprising a nucleotide sequence according to SEQ.ID.No: 33.

Embodiment 29

The beta-herpesvirus according to embodiment 28, wherein nucleotide 58442 of the nucleotide sequence according to SEQ.ID.NO:20 is covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ-.ID.NO:20, wherein nucleotide 62129 of the nucleotide sequence according to SEQ.ID.NO:20 is covalently linked to nucleotide 1 of the nucleotide sequence according to SEQ.ID.No: 33, wherein nucleotide 38 of the nucleotide sequence according to SEQ.ID.NO:33 is covalently linked to nucleotide 63261 of the nucleotide sequence according to SEQ.ID.No: 20, and wherein nucleotide 181552 of the nucleotide sequence according to SEQ.ID.NO:20 is covalently linked to nucleotide 189192 of the nucleotide sequence according to SEQ.ID.NO:20.

Embodiment 30

The beta-herpesvirus according to any one of embodiment 1 to 29, wherein the beta-herpesvirus comprises one or more genes selected from the group comprising UL133, UL134, UL135, UL136, UL137, UL138, UL139, UL140, UL141, UL142, UL143, UL144 and UL145

Embodiment 31

The beta-herpesvirus according to any one of embodiment 1 to 30, wherein the beta herpesvirus comprises the nucleotide sequence according to SEQ.ID.NO:23.

Embodiment 32

The beta-herpesvirus according to any one of embodiments 1 to 31, wherein the beta-herpesvirus is deficient in at least one gene product encoded by an immune evasive gene.

Embodiment 33

The beta-herpesvirus according to embodiment 32, wherein the at least one gene product encoded by an immune evasive gene is selected from the group comprising gene products regulating MHC class I presentation and gene products regulating NK cell response.

Embodiment 34

The beta-herpesvirus according to embodiment 33, wherein the at least one gene product encoded by an immune evasive gene is a gene product regulating MHC class I presentation.

Embodiment 35

The beta-herpesvirus according to embodiment 34, wherein the gene product regulating MHC class I presentation is selected from the group comprising US6, US3, US2, UL18, US11, UL83 and UL40.

Embodiment 36

The beta-herpesvirus according to embodiment 33, wherein the at least one gene product encoded by an immune evasive gene is a gene product regulating NK cell response.

Embodiment 37

The beta-herpesvirus according to embodiment 36, wherein the gene product regulating NK coil response is selected from the group comprising gene products encoded by the genes UL40, UL16 and UL18.

Embodiment 38

The beta-herpesvirus according to any one of embodiments 1 to 37, wherein the beta-herpesvirus encodes a heterologous nucleic acid.

Embodiment 39

The beta-herpesvirus according to embodiment 41, wherein the heterologous nucleic acid is a functional nucleic acid, preferably selected from the group comprising antisense molecules, ribozymes and RNA interference mediating nucleic acids.

Embodiment 40

The beta-herpesvirus according to embodiment 38, wherein the nucleic acid is a nucleic acid coding for a peptide, oligopeptide, polypeptide or protein.

Embodiment 41

The beta-herpesvirus according to embodiment 40, wherein the peptide, oligopeptide, polypeptide or protein comprises at least one antigen.

Embodiment 42

The beta-herpesvirus according to embodiment 41, wherein the antigen is an antigen selected from the group comprising viral antigens, bacterial antigens and parasite antigens.

Embodiment 43

The beta-herpesvirus according to any one of embodiments 1 to 42 for or suitable for use in a method for the treatment of a subject and/or for use in a method for the vaccination of a subject.

Embodiment 44

The beta-herpesvirus according to embodiment 43, wherein the subject is a mammal, preferably a human.

Embodiment 45

The beta herpesvirus according to embodiment 43 or 44, wherein the beta-herpesvirus is human cytomegalovirus.

Embodiment 46

The beta-herpesvirus according to any one of embodiments 43 to 45, wherein the subject is suffering from a disease or is at risk of suffering from a disease.

Embodiment 47

The beta-herpesvirus according to any one of embodiments 43 to 46, wherein the vaccination is a vaccination against a disease.

Embodiment 48

The beta-herpesvirus according to any one of embodiments 46 and 47, wherein the disease is a disease or condition which is associated with beta-herpesvirus infection, preferably human cytomegalovirus infection.

Embodiment 49

The beta-herpesvirus according to embodiment 48, wherein the disease or condition is selected from the group comprising congenital inclusion disease.

Embodiment 50

The beta-herpesvirus according to any one of embodiment embodiments 43 to 49, wherein the subject is a pregnant female or female of reproductive age, preferably a pregnant woman or a woman of reproductive age.

Embodiment 51

The beta-herpesvirus according to embodiment 50, wherein the treatment is or is suitable for or capable of preventing the transfer of a beta-herpesvirus, preferably human cytomegalovirus, from the female to a fetus and/or to an embryo carried or to be carried in the future by the female.

Embodiment 52

The beta-herpesvirus according to embodiment 50, wherein the treatment is for or is suitable for the generation of or capable of generating an immune response in the female body or the immune response in the female body, whereby preferably such immune response confers protection to a fetus and/or to an embryo carried or to be carried in the future by the female against beta-herpesvirus, preferably human cytomegalovirus, and/or a disease or condition associated with beta-herpesvirus infection, preferably human cytomegalovirus infection.

Embodiment 53

Use of a beta-herpesvirus according to any of embodiments 1 to 47 for the manufacture of a medicament.

Embodiment 54

Use according to embodiment 53, wherein the medicament is for the treatment and/or prevention of beta-herpesvirus infection.

Embodiment 55

Use according to embodiment 53, wherein the medicament is for the treatment acid/or prevention of a disease or condition associated with beta-herpesvirus infection, preferably human cytomegalovirus infection.

Embodiment 56

Use of a beta-herpesvirus according to any of embodiments 1 to 47 for the manufacture of a vaccine.

Embodiment 57

Use according to embodiment 56, wherein the vaccine is for the treatment and/or prevention of beta-herpesvirus infection.

Embodiment 58

Use according to embodiment 57, wherein the vaccine is for the treatment and/or prevention of a disease or condition associated with beta-herpesvirus infection, preferably human cytomegalovirus infection.

Embodiment 59

Use according to any one of embodiments 56 to 58, wherein the vaccine is or is suitable for the administration to a subject, whereby the subject is selected form the group comprising a pregnant female, a female of reproductive age, a donor of a transplant, a recipient of a transplant and a subject being infected with HIV or being at risk of being infected with HIV.

Embodiment 60

Use according to embodiment 59, wherein the donor is a potential donor and/or the recipient is a potential recipient.

Embodiment 61

A nucleic acid coding for a beta-herpesvirus according to any of the preceding embodiments.

Embodiment 62

A vector comprising the nucleic acid according to embodiment 61.

Embodiment 63

A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 233681 of the nucleotide sequence according to SEQ.ID.NO:20 and wherein nucleotide 122630 of the nucleotide sequence according to SEQ.ID.NO:20 is covalently linked to nucleotide 123688 of the nucleotide sequence according to SEQ.ID.NO:20.

Embodiment 64

A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 233681 of the nucleotide sequence according to SEQ.ID.NO: 20 and a third nucleotide sequence comprising a nucleotide sequence according to SEQ.ID.No: 34.

Embodiment 65

The vector according to embodiment 64, wherein nucleotide 122630 of the nucleotide sequence according to SEQ.ID.NO:20 is covalently linked to nucleotide 1 of the nucleotide sequence according to SEQ.ID.No: 34 and wherein nucleotide 252 of the nucleotide sequence according to SEQ.ID.No: 34 is covalently linked to nucleotide 123668 of the nucleotide sequence according to SEQ.ID.NO: 20.

Embodiment 66

A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 233681 of the nucleotide sequence according to SEQ.ID.NO: 20 and wherein nucleotide 122630 of the nucleotide sequence according to SEQ.ID.NO:20 is covalently linked to nucleotide 123668 of the nucleotide sequence according to SEQ.ID.NO:20 and wherein the nucleotide 130670 of the nucleotide sequence according to SEQ.ID.NO:20 is covalently linked to the nucleotide 131243 of the nucleotide sequence according to SEQ.ID.NO:20.

Embodiment 67

A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 233681 of the nucleotide sequence according to SEQ.ID.NO:20, a third nucleotide sequence comprising a nucleotide sequence according to SEQ.ID.No: 34 and a fourth nucleotide sequence comprising a nucleotide sequence according to SEQ.ID.No: 35

Embodiment 68

The vector according to embodiment 67, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ.ID.NO:20, wherein nucleotide 130670 of the nucleotide sequence according to SEQ.ID.NO:20 is covalently linked to nucleotide 1 of the nucleotide sequence according to SEQ.ID.No: 35 and wherein nucleotide 67 of the nucleotide sequence according to SEQ.ID.NO:35is covalently linked to nucleotide 131243 of the nucleotide sequence according to SEQ.ID.No:20

Embodiment 69

A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ.ID.NO:20.

Embodiment 70

A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 233681 of the nucleotide sequence according to SEQ.ID.NO: 20 and a third nucleotide sequence comprising a nucleotide sequence according to SEQ.ID.No: 32.

Embodiment 71

The vector according to embodiment 70, wherein nucleotide 58442 of the nucleotide sequence according to SEQ.ID.NO:20 is covalently linked to nucleotide 1 of the nucleotide sequence according to SEQ.ID.No: 32 and wherein nucleotide 179 of the nucleotide sequence according to SEQ.ID.No: 32 is covalently linked to nucleotide 59623 of the nucleotide sequence according to SEQ.ID.NO: 20.

Embodiment 72

A vector comprising the nucleic acid according to embodiment 62, wherein the vector comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 233681 of the nucleotide sequence according to SEQ.ID.NO:20 and wherein nucleotide 62129 of the nucleotide sequence according to SEQ.ID.NO:20 is covalently linked to nucleotide 63261 of the nucleotide sequence according to SEQ.ID.NO:20.

Embodiment 73

A vector comprising the nucleic acid according to embodiment 62, wherein the vector comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 233681 of the nucleotide sequence according to SEQ.ID.NO: 20 and a third nucleotide sequence comprising a nucleotide sequence according to SEQ.ID.No: 33

Embodiment 74

The vector according to embodiment 73, wherein nucleotide 62129 of the nucleotide sequence according to SEQ-.ID.NO:20 is covalently linked to nucleotide 1 of the nucleotide sequence according to SEQ.ID.No: 33 and wherein nucleotide 38 of the nucleotide sequence according to SEQ-.ID.No: 33 is covalently linked to nucleotide 63261 of the nucleotide sequence according to SEQ.ID.NO: 20.

Embodiment 75

A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, third nucleotide sequence represented by nucleotides 63261 to 233681 of the nucleotide sequence according to SEQ.ID.NO: 20 and wherein nucleotide 58442 of the nucleotide sequence according to SEQ.ID.NO:20 is covalently linked to nucleotide 59623 of the nucleotide sequence according to SEQ.ID.NO:20 and wherein the nucleotide 62129 of the nucleotide sequence according to SEQ.ID.NO:20 is covalently linked to the nucleotide 63261 of the nucleotide sequence according to SEQ.ID.NO:20.

Embodiment 76

A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 63261 to 233681 of the nucleotide sequence according to SEQ.ID.NO:20, a fourth nucleotide sequence comprising a nucleotide sequence according to SEQ.ID.No: 32 and a fifth nucleotide sequence comprising a nucleotide sequence according to SEQ.ID.No: 33.

Embodiment 77

The vector according to embodiment 76, wherein nucleotide 58442 of the nucleotide sequence according to SEQ-.ID.NO:20 as covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ.ID.NO:20, wherein nucleotide 62129 of the nucleotide sequence according to SEQ.ID.NO:20 is covalently linked to nucleotide 1 of the nucleotide sequence according to SEQ.ID.No: 33 and wherein nucleotide 38 of the nucleotide sequence according to SEQ.ID.NO:33 is covalently linked to nucleotide 632161 of the nucleotide sequence according to SEQ-.ID.No: 20.

Embodiment 78

A host cell comprising a nucleic acid according to embodiment 61 or a vector according to any one of embodiments 62 to 77.

Embodiment 79

A pharmaceutical composition comprising a beta-herpesvirus according to any one of the preceding embodiments, a nucleic acid according to embodiment 61 and/or a vector according to any one of the preceding embodiments, and a pharmaceutically acceptable carrier.

The present inventors have surprisingly found that the infection of endothelial cells of a host organism such as man by beta-herpesvirus and more specifically CMV of the invention will result in eliciting an immune response against CMV. More specifically, the immune response is an anti-CMV response which comprises neutralizing antibodies against beta-herpesvirus and $CD4^+$ and $CD8^+$ T-cells directed against epitopes of beta-herpesvirus. Furthermore, the present inventors have surprisingly found that such immune response can be elicited by the beta-herpesvirus and more specifically the human cytomegalovirus of the invention being spread-deficient. It has to be acknowledged that any characteristic feature, embodiment of and any statement made in relation to beta-herpesviruses such as murine CMV equally applies to human CMV. Furthermore, it will be acknowledged that the beta-herpesvirus according to the present invention will, in a preferred embodiment, exhibit the following characteristics as observed for human and murine, respectively, CMV: multiple infections occur with mouse and human CMV, in mouse and human, respectively, (Boppana, S. B. et al., 2001. Intrauterine transmission of cytomegalovirus to infants of women with preconceptional immunity. N. Engl. J Med 344:1346-1371; Cicin-Sain, L. et al., 2005. Frequent coinfection of cells explains functional in vivo complementation between cytomegalovirus variants in the multiply infected host. J Virol 79:9492-9502.); an unusually high response of neutralizing antibodies against CMV is caused by infection with mouse and human CMV, in mouse and human, respectively (Farrell, H. E. and G. R. Shellam, 1990. Characterization of neutralizing monoclonal antibodies to murine cytomegalovirus. J. Gen. Virol. 71 (Pt 3):655-664; Farrell, H. E. and G. R. Shellam, 1991. Protection against murine cytomegalovirus infection by passive transfer of neutralizing and non-neutralizing monoclonal antibodies, J. Gen. Virol. 72 (Pt 1):149-156; Gerna, G., A. et al., 2008. Human cytomegalovirus serum neutralizing antibodies block virus infection of endothelial/epithelial cells, but not fibroblasts, early during primary infection. J. Gen. Virol. 89:853-865); memory inflation, which represents a very characteristic CD8+ T cell response, is caused by infection with mouse and human CMV, in mouse and human, respectively, and has almost identical kinetics (Karrer, U. et al., 2003. Memory inflation: continuous accumulation of antiviral CD8+ T cells over time. J. Immunol. 170:2022-2029; Karrer, U. et al. 2004, Expansion of protective CD8+ T-cell responses driven by recombinant cytomegaloviruses. J. Viral. 78:2255-2264; Klenerman, P. and P. R. Dunbar, 2008. CMV and the art of memory maintenance. Immunity. 29:520-522; Komatsu, H. et al., 2003. Population analysis of antiviral T cell responses using MHC class I-peptide tetramers. Clin. Exp. Immunol. 134:9-12). In connection with the present invention a person skilled in the art will also acknowledge that a murine CMV gene can replace a homolog of said murine CMV gene in a human CMV. (Schnee, M. et al., 2006. Common and specific properties of herpesvirus UL34/UL31 protein family members revealed by protein complementation assay. J Virol 80:11658-11666)

In a preferred embodiment the beta-herpesvirus according to the present invention is different from the Towne strain as described by Liu et al. in U.S. Pat. No. 7,407,744, i.e. a Towne strain where the genes UL133, UL134, UL135, UL136, UL137, UL138, UL139, UL140, UL141, UL142, UL143, UL144, and UL145 are deleted, preferably compared to wild type. A person skilled in the art will further acknowledge that the Towne strain is not endotheliotropic and has also a defective gH/gL complex.

In a farther preferred embodiment the beta-herpesvirus according to the present invention comprises a nucleotide sequence according to SEQ.ID.NO:23.

In still further preferred embodiment the beta-herpesvirus according to the present invention is different form the Toledo strain.

Spread-deficient as used herein, preferably means that the virus which is spread-deficient infects a cell and no viral particle is released from the infected cell, whereby the viral DNA is replicated, the viral proteins except those which are deleted in accordance with the present invention are expressed in the infected cell, preferably all viral glycoproteins are expressed, more preferably all viral glycoproteins are expressed, that mediate entry of the virus into a cell, whereby, preferably, the cell is an endothelial and/or an epithelial cell. The assay which is preferably used in accordance with the present invention so as to determine whether or not a virus is spread-deficient, is described herein as Example 1.

A wild type CMV strain as preferably used herein means that the virus is a beta-herpesvirus strain which has been isolated from its native host and which has maintained its ability to infect endothelial cells in tissue culture. More specifically the wild type human CMV strain as preferably used herein contains, among others, the genes UL133, UL134, UL135, UL136, UL137, UL138, UL139, UL140, UL141, UL142, UL143, UL144, and UL145 (Cha et al, supra) and more specifically the wild type CMV strain as preferably used herein is TB40/E and FIX-BAC (Sinzger et al. 1999 Journal of General Virology, 80, 2867-2877; Hahn et al, 2002 J Virol. 76(18): 9551-9555) and/or TB40E-BAC4-FRT (SEQ.ID.NO:20) (Scrivano, L. et al., 2011. HCMV spread and cell tropism are determined by distinct virus populations. PLoS. Pathog. 7:e1001256) for human CMV or Smith strain for MCMV (Rawlinson et al. 1996 J Virol 70:8833-8849). In a preferred embodiment of the present invention the wild type CMV strain as preferably used herein comprises a nucleotide sequence according to SEQ.ID.No:23. The sequence of the pTB40E-BAC4-FRT, which is the molecular infectious BAC plasmid according to TB40E-BAC4-FRT has the nucleotide sequence according to SEQ.ID.NO:20.

Said pTB40E-BAC4-FRT is consisting of viral sequences encoded by nt 1-181652 and by nt 189192-233681, as well as BAC sequences represented by nt 181653-189191. A person skilled in the art will acknowledge that a BAC plasmid such as pTB40E-BAC4-FRT comprising a virus genome such as the virus genome of TB40E-RAC4-FRT is circular in *E. coli* therefore the nucleotide 233681 of the nucleotide sequence according to SEQ.ID.NO:20 is covalently linked to nucleotide 1 of the nucleotide sequence according to SEQ.ID.NO:20. A person skilled in the art will know methods for reconstitute a virus from a BAC plasmid comprising the viral genome of said virus, for example for reconstitute TB40E-BAC4-FRT from pTB40E-BAC4-FRT comprising the viral genome of TB40E-BAC4-FRT. Such methods comprise among others transfection of cells, comprising complementing cells.

As used herein, the term “deficient in at least one gene product” preferably means that the at least one gene product which is a biochemical material such as a nucleic acid, DNA, RNA or a peptide, polypeptide or protein, resulting from expression of the gene does not show at least one of the functions displayed by said gene product in the wild type strain. Preferably, said at least one of the functions not shown is the function which is responsible for spread of the beta-herpesvirus. Also preferably, all of the functions of said gene product in the wild type strain are not shown. This may be the result of a complete or partial deletion or mutation of the gene coding for said gene product, of a complete or partial deletion of a mutation, of the nucleic acid controlling the expression of the gene coding of said gene product, of a truncation of said gene product, or of the inhibition of the otherwise compete gene product.

As used herein, the term “DNA is replicated” preferably means that the replication occurs like replication of a wild type virus.

As used herein, a wild type-like virion surface is preferably a surface displayed by a beta-herpesvirus of the wild type as defined herein, more specifically by a cytomegalovirus wild type strain as defined herein. The molecules which are used to define the surface displayed by a beta-herpesvirus of the wild type are glycoproteins expressed by said wild type virus mediating the entry of said wild type virus into a cell, preferably an endothelial cell. In other words, a virus according to the present invention having a wild type-like virion surface has a virion surface which, after infection of primary fibroblasts, displays or expresses the same glycoproteins identical to, essentially identical to or at least not significantly different from the wild type virus based on which the deletions were or may be made to generate the virus of the present invention. The determination of the expression of glycoproteins is known to the ones skilled in the art and may be performed by a quantitative RT-PCR or mass spectrometry (Britt et al. 1990. J Virol 64:1079-1085) although other methods suitable for such purpose are knoen to the person skilled in the art.

So as to determine whether the beta-herpesvirus of the invention and particularly the human cytomegalovirus of the invention is endotheliotropic, preferably, the assay as described in Example 2 is used.

So as to determine whether the immune response elicited by the beta-herpesvirus of the invention and particularly the human cytomegalovirus of the invention comprises at least neutralizing antibody, and whereby the at least neutralizing antibody is preventing said viruses from infecting endothelial cells and/or epithelial cells, the assay described by Cui et al. (Cui et al. supra) may preferably be used.

It will be acknowledged that viral DNA replication is abrogated in replication-defective virus mutants and therefore gene expression does not exploit the total set of viral epitopes. Especially glycoproteins and structural virion components are not expressed.

In order to further illustrate the present invention the biology of human cytomegalovirus will be outlined in the following.

Human cytomegalovirus is one of eight human herpesviruses, which are clustered in three subfamilies (alpha (α), beta (β), gamma (γ)) based on biological properties and molecular phylogenetic relationships to other herpesviruses. Cytomegalovirus belongs to the beta-herpesvirus subfamily and possesses the largest genome in the herpesvirus families: its genome of 240 kbp is capable of encoding more than 200 potential gene products (Murphy et al. supra).

The viral particle of cytomegaloviruses consist of three major constituents, namely the internal icosahedral capsid, which packages the double stranded linear DNA genome; the tegument which is a less organized protein meshwork surrounding the capsid; and the outermost envelop which is a lipid bilayer embedded with viral glycoprotein complexes. The infection of a host cell by the virus particles is mediated by the contact of the viral glycoproteins with the molecular structures of the host cell surface. CMVs can infect many different cell types and the mechanism of virus entry is known to be dependent on the specific cell type and can occur via two major routes: (a) the free, i.e. non-cell associated virus particles can encounter the host cell directly, or (b) the virus is transferred from the infected cell to a non-infected one by a preformed, i.e. non-virus-induced cell-cell contact, or virus induced cell-cell contact, the so called cell to cell spread.

After attachment with high affinity to a set of cellular receptors the viral glycoproteins induce fusion between the viral envelope and a host cell membrane. After entry of an CMV particle into the host cell the HCMV genome is targeted to the nucleus where it either establishes latency which is characterized by a symptomless maintenance of the more or less silent genome, or induces a lytic infection leading to propagation of new infectious CMV particles.

The lytic replication cycle of CMV is divided into three phases of regulated gene expression: immediate early, early, and late. The hallmarks of the replication stages are the specific gene clusters which are expressed with characteristic kinetics. Immediate early gene transcription occurs at first and leads to synthesis of viral master regulators that reprogram the host cell according to the needs of virus production. Following the synthesis of immediate early gene products, the early genes are transcribed. Early gene products include DNA replication proteins and regulators and enzymes which are important in nucleotide metabolism. Finally, the late genes are transcribed after the onset of DNA replication, and the gene products of said late genes are mainly structural proteins that are involved in the assembly of and egress of new infectious virus particles.

The late gene products comprise many viral antigens including the viral glycoproteins such as the gB and the gH/gL complex, which are the major targets of neutralizing antibodies against CMV (Schleiss et al. 2008 supra) and the major tegument protein the phosphoprotein 65 (pp65) and the immediate early 1 protein which are the major targets of the cellular immune response to CMV.

A further step in the lytic replication cycle of CMV is the maturation of novel infectious virus particles which comprises steps of envelopment of the pre-mature virus particle with membrane structures. The steps of envelopment comprise a primary envelopment, de-envelopment and secondary envelopment.

The primary envelopment at the membranes of the nucleus is crucial for the egress of virus capsids out of the nucleus. Proteins as part of the protein complex which is also referred to as nuclear egress complex (NEC) playing an essential role in this primary envelopment, were recently identified as M50 and M53 of mouse CMV (Lotzerich et al. 2006 J Virol 80:73-84) or as UL50 and UL53 being their homologs in human CMV.

A homologues gene as used herein is preferably the gene of one herpesvirus referred to be a homolog of the gene of another herpesvirus according to Possum et al. (Possum et al. PLoS Pathog. 2009 September; 5(9): e1000570) or Davison et al. (Davison et al. (2010) Vet Microbiol, 2010 Feb. 11. Herpesvirus systematics; and Davison et al. 2004 Compendium of Human Herpesvirus gene names; Reno).

Further, homologs of UL50 are listed in Mocarski (Mocarski Jr. E S.: Comparative analysis of herpesvirus-common proteins. In Human Herpesviruses: Biology, Therapy, and Immunoprophylaxis. Cambridge: Cambridge University Press; 2007. Chapter 4 Editors: Arvin A, Campadelli-Fiume G, Mocarski E, Moore P S, Roizman B, Whitley B, Yamanishi K, editors.)

The secondary envelopment occurs at the membranes of the Golgi-apparatus and/or the endoplasmatic reticulum. In connection with said secondary envelopment a protein complex which is also referred to as secondary envelopment complex (SEC), was identified comprising at least the gene product of M94 of mouse CMV or its homolog in human CMV, i.e. UL94. The gene UL94 of HCMV is conserved in all herpesvirus sub-families (Chee et al. 1991 Transplant Proc 23:174-80; Chee et al. 1990 Curr Top Microbial Immunol 154:125-169; Higgins et al. 1989 Comput. Appl. Biosci. 5:151-153) and was found only at a late stage of infection (Scott et al. 2002 Virus Genes 24:39-48; Wing et al. 1996 J Virol 70:3339-3345). It was recently shown that UL94 is part of the virion (Kalejta et. al. 2008 Microbiol Mol Biol Rev 72:249-65; Kattenhorn et al. 2004 J Virol 78:11187-11197; Wing et al. op:cit). UL94 is essential in the infection of the Towne strain of HCMV shown by transposon-mediated mutagenesis (Dunn et al. 2003 Proc Natl Acad Sci USA 100:14223-14228. That M94 is essential in mouse CMV infection is disclosed herein in the example part.

Homologs of UL94 are listed in Mocarski (Mocarski Jr. E S.: Comparative analysis of herpesvirus-common proteins. In Human Herpesviruses: Biology, Therapy, and Immunoprophylaxis, Cambridge: Cambridge University Press; 2007. Chapter 4 Editors: Arvin A, Campadelli-Fiume G, Mocarski E, Moore P S, Roizman B, Whitley R, Yamanishi K, editors.)

The high viral load of CMV in salivary glands indicates the transmission of CMV by direct contact via secretions. After initial replication in the first target cells at the entry site, CMV is disseminated through the body by blood and lymph. Most likely the virus is taken up by white blood cells which carry the virus from the primary infection site to almost every internal organ.

The interplay between the CMV and its host, i.e. humans or mice, is very complex. On the one hand, the immune response of the host is controlling the virus replication very efficiently. Therefore, most of the CMV infections are symptomless which means that virus replication is controlled before the tissue damage reaches an observable pathological level of local or systemic inflammation. On the other hand, the virus itself is controlling the immune response resulting in efficient clearance of the virus from the host. In almost all cases of immune competence natural CMV infection ends up with a situation where the virus is controlled by the immune system without being totally cleared from the host (Reddehase et al, 2002 J Clin Virol 25 Suppl 2:S23-S36).

In recent years an impressive body of knowledge was generated by studying the molecular mechanisms of immune suppressive functions of CMV. It is acknowledged that more than half of the CMV genes encode gene products interfering with different immune mechanisms at all stages of the immune system, the so-called immune evasive genes. There is evidence that neither the humoral nor the cellular immune response alone is sufficient to control CMV infection; a concerted action of both is needed to keep the balance with the viral immune evasion (Adler et al. 1995 J Infect Dis 171:26-32; Reddehase et. al. 1987 J Virol 61:3102-3108).

Diseases and conditions of a subject which is infected by beta herpesvirus and human CMV, respectively, are, among others, mononucleosis-like symptoms, splenomegaly, pneumonitis, blindness, hearing loss, congenital inclusion disease, and organ damage and organ failure, respectively, of the organ infected by HCMV. It is to be acknowledged that said diseases and conditions are diseases and conditions which can be treated and/or prevented by the beta-herpesvirus of the present invention.

Typically, human CMV infection becomes clinically apparent only if the host immune system is vulnerable or suppressed. There are several major risk groups of public health importance.

One situation where the host immune system is vulnerable, is where non-pregnant women of reproductive age or women being pregnant get infected by human CMV. If the human CMV infection is transmitted from the mother to the fetus and embryo, respectively, during pregnancy, due to the immature immune system of the fetus and embryo, respectively, direct cytotoxic pathology of the human CMV infection can develop which is called congenital inclusion disease (CID). The symptoms of CID are dominated by the cause that the human CMV infects the central nervous system comprising microcephaly, cerebral atrophy, chorioretinitis, and sensorineural hearing loss, which are typically combined with consequences of infection of other visceral organs including intrauterine growth retardation, hepatosplenomegaly, hematological abnormalities such as thrombocytopenia, and various cutaneous manifestations appearing as rushes, i.e. petechiae and purpura. CID is the most frequent infectious congenital disorder in developed countries. Furthermore, human CMV infection is the major cause of hearing loss acquired after viral infection.

A second scenario of clinically significant human CMV infection is formed by immunocompromised or immunosuppressed patients. This kind of patient is, e.g., a HIV-positive patient or a transplant recipient. In these patients the disease manifestations vary depending on the quality and the degree of immune dysfunction. Infection mostly occurs because of reactivation of latent viral infection, however, may be as well newly acquired via virus reactivation from organ or bone marrow transplant derived from an already infected donor in ease of a transplant recipient.

In the absence of sufficient immune control CMV infection leads to inflammatory diseases of various organs. In connection therewith the most frequent clinical manifestations consist of pneumonitis, gastrointestinal diseases, hepatitis, and retinitis. In bone marrow transplant recipients HCMV pneumonitis occurs with mortality rates of 90%. It is to be acknowledged that said diseases and conditions are diseases and conditions which can be treated and/or prevented by the beta-herpesvirus of the present invention.

In AIDS patients opportunistic human CMV infection is common and occurs at a frequency of almost 100%, if anti-retroviral therapy fails or not applicable/available. This is still the case in non-industrialized countries were an effective therapy is not yet available. Before the availability of highly active anti-retroviral therapy for human immunodeficiency virus (HIV) infection, HCMV retinitis was the most common cause of blindness in adult patients with acquired immunodeficiency syndrome (AIDS), with an overall lifetime prevalence of more than 90%.

In an embodiment of the beta-herpesvirus of the invention the beta-herpesvirus is used as a vaccine and/or vector. In a further embodiment thereof such beta-herpesvirus encodes for a heterologous nucleic acid. Preferably such heterologous nucleic acid codes for an antigen, more preferably an antigen of a pathogen. Because of this such vaccine and vector, respectively, is suitable for the treatment and/or prevention of a disease caused by or associated with said pathogen. Such pathogens preferably comprise viruses and bacteria. In an embodiment the antigen is NP-NT60 of Influenza, whereby the vector then is useful in the treatment of influenza. In a further embodiment the antigen is ORF Rv3407 from *Mycobacterium tuberculosis* strain H37Rv, whereby the vector then is useful in the treatment of tuberculosis.

In an embodiment the beta-herpesvirus of the present invention is a recombinant beta-herpesvirus.

In a further embodiment the beta-herpesevirus of the present invention is a human beta-herpesvirus, preferably a recombinant human beta-herpesvirus.

In a preferred embodiment the individual nucleotides of the beta-herpesvirus of the invention are linked, preferably covalently linked, through phosphodiester bonds. Such phosphodiester bonds are those phosphodiester bonds which are contained in nucleic acid molecules contained or produced in biological material such as cells.

It will be acknowledged that the beta-herpesvirus of the present invention is part of a pharmaceutical composition. Preferably, such pharmaceutical composition contains, a part from the beta-herpesvirus of the present invention and/or a nucleic acid coding for the same, a pharmaceutically acceptable carrier. The ingredients of such pharmaceutical composition and their respective contents are known to a person skilled in the art. It will be further acknowledged that such pharmaceutical composition is for or is for use in the treatment of the diseases and conditions as disclosed herein in connection with the beta-herpesvirus of the present invention.

It will be acknowledged by a person skilled in the art that the experimental evidence provided in the example part of the instant application is based on murine CMV, but that such evidence can be directly and immediately transferred to HCMV, so that the present invention is plausible to a person skilled in the art. The reason for this being that the genomes of different herpesvirus strains including CMV are linearly correlated and the mode of action of human CMV in a human host and of mouse CMV its a murine host are essentially identical.

The various SEQ.ID. Nos., the chemical nature of the nucleic acid molecules, proteins and peptides according to the present invention, the actual sequence thereof and the internal reference number is summarized in the following table. To the extent that the particular sequences are not displayed in this table they are contained in the attached sequence listing which is part of the instant specification.

| SEQ. ID. No. | Sequence | internal reference number |
|---|---|---|
| 1 | GTGGGATCCACCATGTACCCCTACGACGT<br>GCCCGACTACGCCACGTCCAGACTATCC | HAM94for |
| 2 | ACTCTAGAGTCGACTTCACATGTGCTCGA<br>GAACA | M94rev |
| 3 | AATTCATGATAACTTCGTATAGCATACAT<br>TATACGAAGTTATCCGGAGATATCCACCG<br>GTCTGGCGGCCGC | ATGlox1 |
| 4 | TCGAGCGGCCGCCAGACCGGTGGATATCT<br>CCGGATAACTTCGTATAATGTATGCTATA<br>CGAAGTTATCATG | ATGlox2 |
| 5 | CGT GGT CAA GCC GGT CGT GTT GTA<br>CCA GAA CTC GAC TTC GGT CGC GTT<br>GCT TAC AAT TTA CGC GCG GG | 5'-Δm157-pCR3-FRT-Kan$^r$-FRT |
| 6 | CCC CGA TAT TTG AGA AAG TGT ACC<br>CCG ATA TTC AGT ACC TCT TGA CTA<br>AGA AGC CAT AGA GCC CAC CGC | 3'-Δm157-flox-egfp |
| 7 | TGC TTC CCG GCG GCT TCT GCG CGA<br>CCT TCC AGC TGC AGG TAG ACC ACG<br>GCG ACG TCC AGA CTA TCC GTG AAA<br>AGT TTG AGA AGC ATC AGT AGC CGA<br>TTT CGG CCT ATT GGT T | 5'ΔM94-pO6-tTA |
| 8 | CAT GGA TGG GTT GGT TGA TTT GTA<br>TGT CTG TTG GCT ACT CAC ATG TGC<br>TCG AGA AGC CAG TGT GAT GGA TGA<br>TCC TC | 3'-ΔM94-pO6-tTA |
| 9 | SIINFEKL | OVA-MHC-I Peptide |
| 10 | TVYGFCLL | m139 MHC-I Peptide |
| 11 | RALEYKNL | ie3 MHC-I Peptide |
| 12 | SCLEFWQRV | M57 MHC-I Peptide |
| 13 | HGIRNASFI | M45 MHC-1 Peptide |
| 14 | FAM-AACGTACATCGCTCTCTGCTGGCCG-<br>TAMRA | Taqman-Probe M54 |
| 15 | Ttactgggtgctgccgggcggctttgccgtctcttcgcgcgtcactct<br>tcacggcctggcccagcgagccctgcgggaccggttccaaaacttc<br>gaggccgtgctggcccggggcatgcacgtggaggccggccggca<br>ggagcccgagacccccccgggtgagcggccggcggctgcccttcg<br>acgacctgtgatccggaggacgacggctcgtgtatcttgtgccaatt<br>gctgttgctctaccgcgacggcgaatggatcctctgtctttgctgcaa<br>cggccgttatcaaggccactatggcggggtctgacagttcacgggg<br>agaagaaacaagaaacaacaaaaaaaaaagaggagatctgcggc<br>cgctagggataacagggtaatcgatgttgacaattaatcatcggcata<br>gtatatcggcatagtataatacgacaaggtgaggaactaaaccatgg<br>caaaactgaccagcgcagttccggttctgaccgcacgtgatgttgcc<br>ggtgccgttgaattttggaccgatcgtctgggttttagccgtgattttgt<br>ggaagatgattttgccggtgttgttcgtgatgatgttaccctgtttattag<br>cgcagttcaggatcaggttgttccggataataccctggcatgggtttg<br>ggttcgtggtctggatgaactgtatgcagaatggtcagaagttgtgag<br>caccaattttcgtgatgcaagcggtccggcaatgaccgaaattggtg<br>aacagccgtggggtcgtgaatttgcactgcgtgatccggcaggtaat<br>tgtgttcattttgttgcagaagaacaggattaacctcgattaattaattgt<br>aacattaccctgttatccctaccggtgtcctaggcggggtctgacagt<br>tgtgttcattttgttgcagaagaacaggattaacctaggcggggtctgacagt<br>aacattaccctgttatccctaccggtgtcctaggcggggtctgacagt<br>tcacggggagaagaaacaagaaacaacaaaaaaaaaagagg | LIFdelUL94 |
| 16 | cgtgttagaccgttggagtcgcgacctgtcccgcaagacgaaccta<br>ccgatctgggtcgccaacagcgccaacgagtacgtcgtcagctccg<br>tgccccgccccgtcagtccgtagaagtaactcataaactttcaggtct<br>cgcgtacgattcgcgagtcgggaatgtagggataacagggtaatcg<br>atgttgacaattaatcatcggcatagtatatcggcatagtataatacga<br>caaggtgaggaactaaaccatggcaaaactgaccagcgcagttcc<br>ggttctgaccgcacgtgatgttgccggtgccgttgaattttggaccga<br>tcgtctgggttttagccgtgattttgtggaagatgattttgccggtgttgt<br>tcgtgatgatgttaccctgatattagcgcagttcaggatcaggttgttc | LIF-delUL99 |

-continued

| SEQ. ID. No. | Sequence | internal reference number |
|---|---|---|
| | cggataataccctggcatgggtttgggttcgtggtctggatgaactgt<br>atgcagaatggtcagaagttgtgagcaccaattttcgtgatgcaagc<br>ggtccggcaatgaccgaaattggtgaacagccgtggggtcgtgaat<br>ttgcactgcgtgatccggcaggtaattgtgttcattttgttgcagaaga<br>acaggattaacctcgattaattaattgtaacattaccctgttatccctaa<br>agtaactcataaactttcaggtctcgcgtacgattcgcgagtcgggaa<br>tg | |
| 17 | as contained in the sequence listing | pCB-Ubic-UL94-IRES-mChe |
| 18 | as contained in the sequence listing | pCB-Ubic-UL99-IRES-gfp |
| 19 | as contained in the sequence listing | pLV-Ubiqc-BLAs-IRES-Puro |
| 20 | as contained in the sequence listing | pTB40E-BAC4-FRT |
| 21 | as contained in the sequence listing | pBSK-OVA |
| 22 | as contained in the sequence listing | pTRE-HAM94 |
| 23 | as contained in the sequence listing | Unique\in\TB40\(UL133-<br>UL145) |
| 24 | MGSGIGAASMEFCFDVFKELKVHHANENIFYCPIAIMSAL<br>AMVYLGAKDSTRTQINKVVRFDKLPGFGDSIEAQCGTSVN<br>VHSSLRDILNQITKPNDVYSFSLASRLYAEERYPILPEYL<br>QCVKELYRGGLEPINFQTAADQARELINSWVESQTNGIIR<br>NVLQPSSVDSQTAMVLVNAIVFKGLWEKTFKDEDTQAMPF<br>RVTEQESKPVQMMYQIGLFRVASMASEKMKILELPFASGT<br>MSMLVLLPDEVSGLEQLESIINFEKLTEWTSSNVMEERKI<br>KVYLPRMKMEEKYNLTSVLMAMGITDVFSSSANLSGISSA<br>ESLKISQAVHAAHAEINEAGREVVGSAEAGVDAASVSEEF<br>RADHPFLFCIKHIATNAVLFFGRCVSP | OVA |
| 25 | MSGQGTKRSYEQMETDGERQNATEIRASVGKMIGGIGRFY<br>IQMCTELKLSDYEGRLIQNSLTIERMVLSAFDERRNKYLE<br>EHPSAGKDPKKTGGPIYRRVNGKWMRELILYDKEEIRRIW<br>RQTNNGDDATAGLTHMMIWHSNLNDATYQRTRALVRTGMD<br>PRMCSLMQGSTLPRRSGAAGAAVKGVGTMVMELVRMIKRG<br>INDRNFWRGENGRKTRIAYERMCNILKGKFQTAAQKAMMD<br>QVRESRNPGNAEFEDLTFLARSALILRGSVAHKSCLPACV<br>YGPAVASGYDFEREGYSLVGIDPFRLLQNSQVYSLIRPNE<br>NPAHKSQLVWMACHSAAFEDLRVLSFIKGTKVLPRGKLST<br>RGVQIASNENMDAMESSTLELRSRYWAIRTRSGGNTNQQR<br>ASAGQISIQPTFSVQRNLPFDRTTIMAAFNGNTEGRTSDM<br>RTEIIRMMESARPEDVSFQGRGVFELSDEKAASPIVPSFD<br>MSNEGSYFFGDNAEEYDN | NP-NT60 of Influenza |
| 26 | MRATVGLVEAIGIRELRQHASRYLARVEAGSELGVTNKGR<br>LVARLIPVQAAERSREALIESGVLIPARRPQNLLDVTAEP<br>ARGRKRTLSDVLNEMRDEQ | ORF Rv3407 from<br>*Mycobacterium tuberculosis*<br>strain H37Rv |
| 27 | MAWRSGLCETDSRTLKQFLQEECMKKLVGKSRKHREYRAV<br>ACRSTIFSPEDDGSCILCQLLLLYRDGEWILCLCCNGRYQ<br>GHYGVGHVHRRRRRICHLPTLYQLSFGGPLGPASIDFLPS<br>FSQVTSSMTCDGITPDVIYEVCMLVPQDEAKRILVKGHGA<br>MDLTCQKAVTLGGAGAWLLPRPEGYTLFFYILCYDLFTSC<br>GNRCDIPSMTRLMAAATACGQAGCSFCTDHEGHVDPTGNY<br>VGCTPDMGRCLCYVPCGPMTQSLIHNDEPATFFCESDDAK<br>YLCAVGSKTAAQVTLGDGLDYHIGVKDSEGRWLPVKTDVW<br>DLVKVEEPVSRMIVCSCPVLKNLVH | UL94 |
| 28 | VTLGGAGAWLLP | SSC cross-reactive UL94<br>peptide |
| 29 | MGGELCKRICCEFGTTSGEPLKDALGRQVSLRSYDNIPPT<br>SSSDEGEDDDDGEDDDNEERQQKLRLCGSGCGGNDSSSGS<br>HREATHDGPKKNAVRSTFREDKAPKPSKQSKKKKKPSKHH<br>HHQQSSIMQETDDLDEEDTSIYLSPPPVPPVQVVAKRLPR<br>PDTPRTPRQKKISQRPPTPGTKKPAAPLSF | UL99 |
| 30 | MATSRLSVKSLRSISRFVQWECCWMLVNKSARYREFRAVT<br>SQSPGLGKVSSTDDGRCLAASMMLFRRDGNFVLCLVVNKE<br>PVGQFGCSGMRREKMVIDGLQEPVYVMRLLAPLIPVKLGF<br>SPYMLPPKSIGGSGGLDPSVIYQNASVVTPEEAATVTMQG<br>SGIVTVGLSGVGSWVQIKDGGNMKLFVFALCFDVFTACCD | M94 |

-continued

| SEQ.ID. No. | Sequence | internal reference number |
|---|---|---|
|  | RLAFPSLAKIYSETVSCEADKCGFCRDSGRHVDPTGRFVG CVPDSGVCLCYSPCRGTDAAVSVRSWLPYLELEDGANTHS LFVRRYDGRKGLPATISDYLGARNSEGDEIPLRTEPWQLL KIEPTLSAMIIMACPLLKKIVLEHM |  |
| 31 | MYPYDVPDYATSRLSVKSLRSISRFVQWECCWMLVNKSAR YREFRAVTSQSPGLGKVSSTDDGRCLAASMMLFRRDGNFV LCLVVNKEPVGQFGCSGMRREKMVIDGLQEPVYVMRLLAP LIPVKLGFSPYMLPPKSIGGSGGLDPSVIYQNASVVTPEE AATVTMQGSGIVTVGLSGVGSWVQIKDGGNMKLFVFALCF DVFTACCDRLAFPSLAKIYSETVSCEADKCGFCRDSGRHV DPTGRFVGCVPDSGVCLCYSPCRGTDAAVSVRSWLPYLEL EDGANTHSLFVRRYDGRKGLPATISDYLGARNSEGDEIPL RTEPWQLLKIEPTLSAMIIMACPLLKKIVLEHM | HA-M94 |
| 32 | gaccgcgccacagcagagccagcaccagcagaagagccagcac cagcgggcccagagtcgcaaagcgcgcgggcagccacggccca gactgcggtcgcgatggcccggagcgcgctcgccaccacgatgac ggtgcccaacgataaccagtccgctcccgcaccgacgccaccgcc gat | delUL50S |
| 33 | atgtctagcgttttctcaacagcattcgtgcgccttga | delUL53S |
| 34 | cacggcctggcccagcgagccctgcgggaccggttccaaaacttc gaggccgtgctggcccggggcatgcacgtggaggccggccggca ggagcccgagaccccccgggtgagcggccggcggctgcccttcg acgacctgtgatccggaggacgacggctcgtgtatcttgtgccaatt gclgttgctctaccgcgacggcgaatggatcctctgtctttgctgcaa cggccgttatcaaggccactatgg | delUL94S |
| 35 | ctgggtcgccaacagcgccaacgagtacgtcgtcagctccgtgccc cgccccgtcagtccgtagaag | delUL99S |

It will be acknowledged by a person skilled in the art and is in so far also within the scope of the present invention that each and any of the above nucleic acid sequences can be replaced by nucleic acid sequences which, due to the degeneracy of the genetic code, code for the same or functionally homolog peptides and proteins, respectively, as the above indicated nucleic acid sequences.

The present invention is now further illustrated by the following figures and examples from which further features, embodiments and advantages may be taken.

More specifically,

FIG. 3A is a diagram indicating virus neutralizing antibody response as luciferase activity as a function of dilution of serum;

FIG. 3B is a diagram indicating the percentage of adaptively transferred T cells at various time points;

FIG. 3C is a diagram indicating the percentage of specific lysis of transferred cells loaded with various viral peptides by CD8$^+$ T-cells specific for the viral peptides;

Figure 7A:
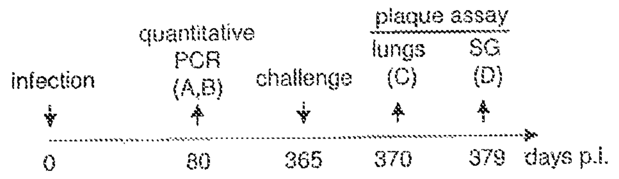
FIG. 7A is an agarose gel showing the result of a PCR detecting viral gene M54 in lungs of infected mice with either wild type or MCMV-ΔM94.
Figure 7B:
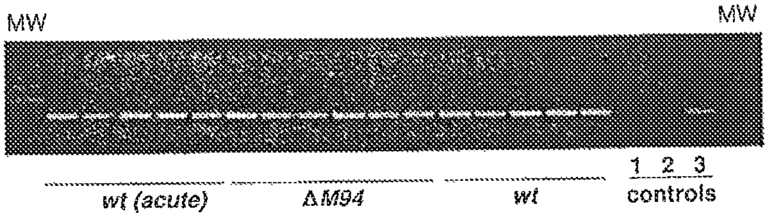
FIG. 7B is a diagram indicating the result of a quantitative PCR detecting viral gene M54 in lungs of infected mice with either wild type or MCMV-ΔM94.
Figure 7C:
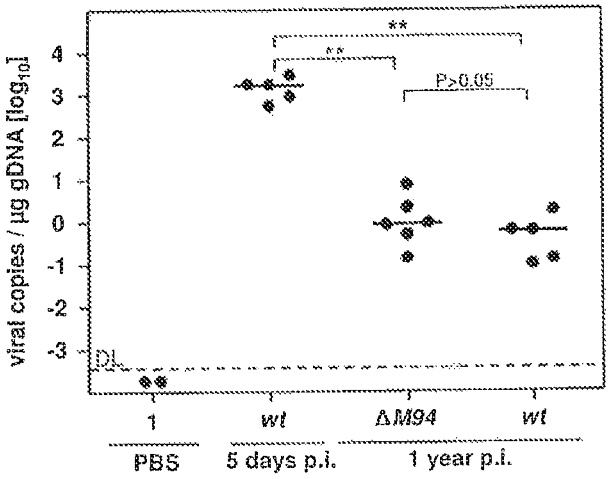
Figure 7C:
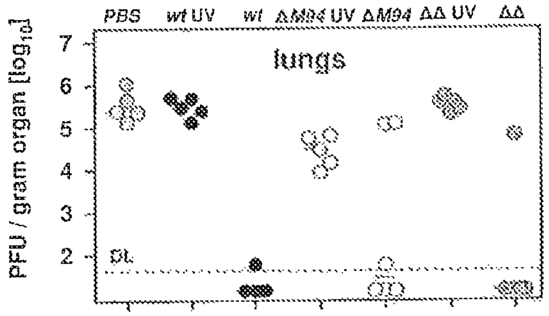
Figure 8:
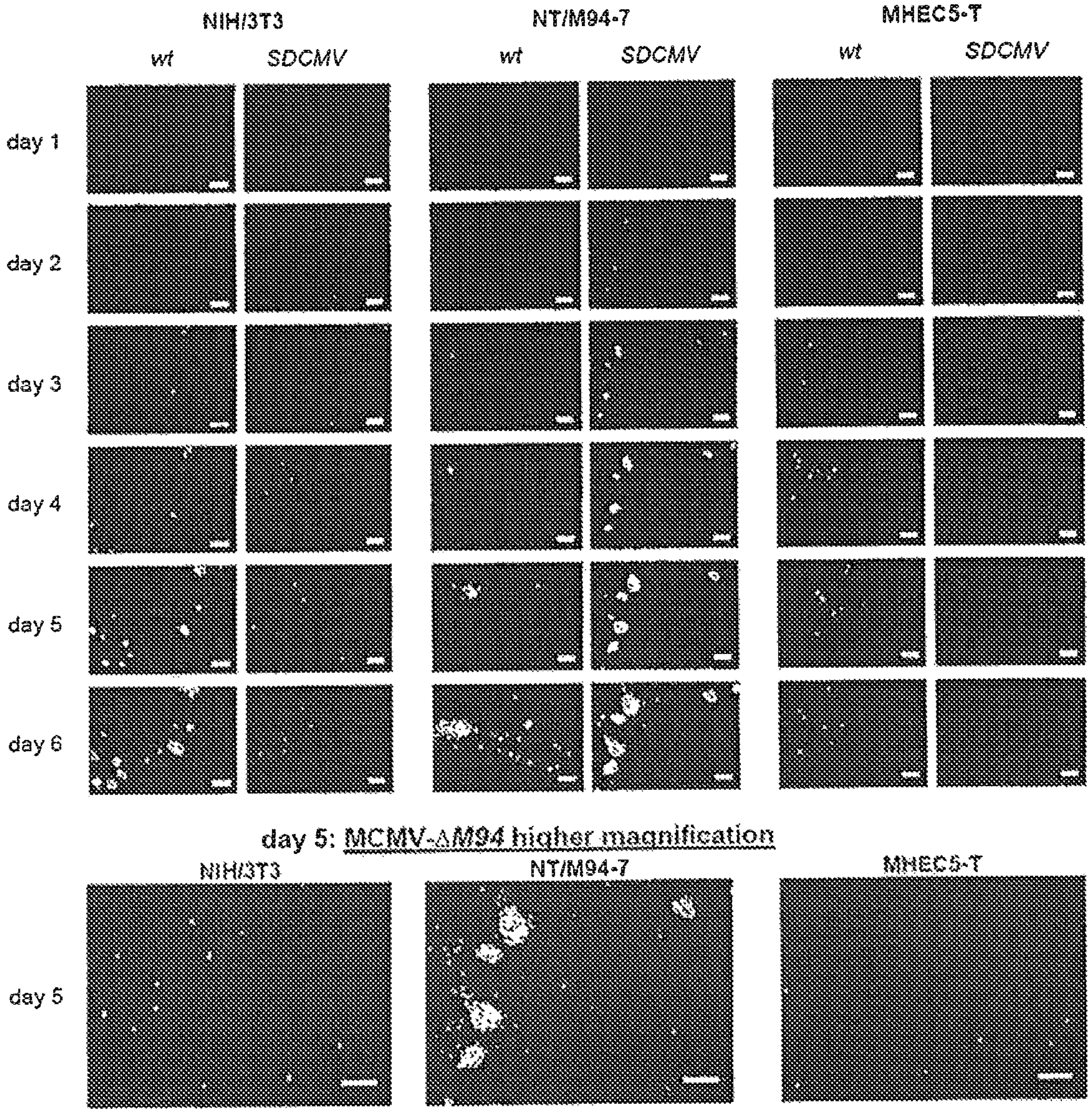

FIGS. 7C and D are diagrams indicating the challenge virus load in different organs of vaccinated mice;

FIG. 8 is a series of microphotographs of cells of different cell lines infected with and MCMV-Δm157-rec-egfp-ΔM94.

FIG. 9A is a schematic overview of a spread-assay

FIG. 9B is a series of microphotographs

FIG. 9C is a diagram showing the results of a spread-assay

EXAMPLE 1

Spread Assay

The spread assay described herein may be used in connection with the characterization of a beta-herpesvirus and a human cytomegalovirus so as to determine whether such virus is spread-deficient.

Primary fibroblast cell lines MRC5 for human CMV and NIH/3T3 for mouse CMV and complementing cell lines TCL94/99-BP and NTM94-7, respectively, are plated and infected at an MOI of about 0.25 for 1 h and then washed twice with D-PBS. Cells are incubated for 6 h and afterwards washed four times with D-PBS. Equal numbers of non-infected cells were stained with 5 μM CFSE for 8 min and blocked by 2% FCS/D-PBS, then washed twice with 2% FCS/D-PBS and subsequently seeded on top of the unstained but infected cells.

EXAMPLE 2

Assay for Determining Whether a Virus is Endotheliotropic

The assay described herein is used for determining whether a virus is endotheliotropic.

As to determine whether a human CMV is endotheliotropic a primary human fibroblast cell line, a complementing cell line which complements the product of the gene in relation to which the HCMV of the invention is deficient, and a human endothelial cell line are plated and infected at an MOI of about 0.1 with HCMV wild type or the virus of the present invention. 24 hours after infection immediate early staining is performed by incubating fixed cells with a monoclonal antibody against immediate early gene product of the beta-herpesvirus of the invention, more specifically CMV 1E ½ monoclonal Antibody CH160 (Plachter et al. supra), commercially available from Virusys Co. in 3% BSA/D-PBS. After three D-PBS washes, cells are incubated with an Alexa Fluor 555-coupled secondary antibody directed against the monoclonal antibody against human immediate early 1 of HCMV in 3% BSA/D-PBS. Finally cells are washed three times and imaged by UV microscopy. Cells infected with wild type HCMV are used as positive control and counted immediate early 1- and CFSE-positive cells using the ImageJ Cell Counter plugin (Rasband supra).

As to determine whether a mouse CMV is endotheliotropic a primary mouse fibroblast cell line, a complementing cell line which complements the product of the gene in relation to which the MCMV of the invention is deficient, and a mouse endothelial cell line are plated and infected at an MOI of about 0.1 with MCMV wild type or the virus of the present invention. 24 hours after infection immediate early staining is performed by incubating fixed cells with a monoclonal antibody against immediate early gene product of the beta-herpesvirus of the invention, more specifically Croma 101 designated as antibody 6/20/1 in Keil et al. (Keil et al., supra) in 3% BSA/D-PBS. After three D-PBS washes, cells are incubated with an Alexa Fluor 555-coupled secondary antibody directed against the mouse monoclonal antibody against immediate early 1 of mouse CMV in 3% BSA/D-PBS. Finally cells are washed three times and imaged by UV microscopy. Cells infected with wild type mouse CMV are used as positive control and counted immediate early 1 positive cells using the ImageJ Cell Counter plugin (Rasband supra).

EXAMPLE 3

Materials and Methods

Cells and Mice

The fibroblast cell line NIH/3T3 and BALB/c derived murine embryonic fibroblasts (MEF) were cultured as described in Cicin-Sain et al., (Cicin-Sain et al. 2005 J Virol 79:9492-9502.). C57BL/6 (B6) mice, B6.SJL-Ptpr$^c$ (Ptpr$^c$) mice and 129.IFNαβR$^{-/-}$ mice were purchased from Elevage Janvier (Le Genest Saint isle, France), Jackson Laboratories (Bar Harbor, Me., USA) and B&K Universal Limited (Grimston, England), respectively. 129.IFNαβR$^{-/-}$ mice (Muller et al. 1994 Science 264:1918-1921,) were backcrossed on the B6 background (B6.IFNαβR$^{-/-}$). T cell receptor transgenic mice OT-I (Hogquist et al. 1994 Cell 76:17-27.) and OT-II (Barnden et al. 1998 Immunol Cell Biol 76:34-40.) were backcrossed to Ptpr$^c$ (CD45.1) or Thy1.1 (CD90.1) congenic mice, respectively. Alb-cre (Postic et al. 1999 J Biol Chem 274:305-315.) and Tie2-cre (Constien et al. 2001 Genesis 30:36-44) were maintained on the B6 background. Mice were kept under specified pathogen free conditions. Animal experiments were approved by the responsible office of the state of Bavaria (approval no. 55.2-1-54-2531-111-07) or by the Ethics Committee at the University of Rijeka.

Generation of the Trans-Complementing Cell Line NT/M94-7

The conditional trans-complementing cell line NT/M94-7 was generated according to (Lotzerich et al. supra). Briefly, the M94 ORE was amplified from pSM3fr (Sacher et al. 2008 Cell Host Microbe 3:263-272.) using primers HAM94 for (SEQ.ID.No.1) and M94rev (SEQ.ID.No.2) thereby introducing an HA tag at the N-terminus. The PCR product was digested with BamHI and XbaI and inserted into the BamHI- and NheI-cleaved pTRE2Hyg vector (BD Biosciences Clontech, Heidelberg, Germany), resulting in pTRE-HAM94 (SEQ.ID.NO:22) putting HAM94 expression, the HAM94 protein is depicted in SEQ.ID.NO:31, under the control of the tetracycline (tet) inducible promoter. Stable NIH/3T3 transfectants harboring pTRE-HAM94 were selected with 50 μg/ml Hygromycin B. The deletion virus MCMV-ΔM94 was reconstituted by transfecting different NT/M94 cell clones with the respective BAC. The most productively infected trans-complementing cell line NT/M94-7 was subcloned using limiting dilution. The trans-complementing cell line was deposited under the Budapest Treaty with the DSZM, Germany on May 5, 2010.

Generation of Recombinant Viruses

Recombinant mouse CMV (MCMV) mutants were derived from the MCMV bacterial artificial chromosome (BAC) clone pSM3fr, originated from Smith strain (Messerle et al. 1997 Proc Natl Acad Sci USA 94:14759-14763). Nucleotide positions are given according to Rawlinson et al. (Rawlinson et al, supra). The 1.4 kilo base pair (bp) SmaI fragment of pCP15 carrying the FRT flanked kanamycin resistance gene (Kan$^r$) was introduced into the BssHII site of pCR3 (Invitrogen, Basel, Switzerland) resulting in pCR3-FRT-Kan$^r$-FRT. A fragment containing an ATG start codon and a loxP site was generated by annealing the oligonucleotides ATGlox1 (SEQ.ID.No.3) and ATGlox2 (SEQ.ID.No.4). This fragment was inserted into the EcoRI and XhoI site positioned between the major immediate early promoter of HCMV (IEP) and the polyA signal of the bovine growth hormone of pCR3-FRT-Kan$^r$-FRT to obtain pCR3-FRT-Kan$^r$-FRT-ATG-loxP. The ovalbumin gene (ova) was synthesized as contained in pBSK-OVA (SEQ.ID.NO: 21) introducing GGAA after nt position 9 resulting in a BspEI restriction site for further cloning. Ova was inserted in frame using BspEI and NotI of pCR3-FRT-Kan$^r$-FRT-ATG-loxP resulting in a full length ova with inserted loxP site after the initial ATG under control of IEP named pCR3-FRT-Kan$^r$-FRT-ATG-loxP-ova. To obtain a construct with Cre inducible ovalbumin (OVA) expression (SEQ.ID.NO: 24) a flox-stop cassette (Sacher et al. supra) was inserted into the EcoRI and BspEI sites of pCR3-ATG-loxP-ova resulting in pCR3-ATG-flox-step-ova. Using these constructs as templates and oligonucleotides 5'-Δm157-pCR3-FRT-Kan$^r$-FRT (SEQ.ID.No.5)(nt position 216243 to 216290) and 3'-Δm157-flox-egfp (SEQ.ID.No.6) (nt position 216885 to 216930) as primers a linear DNA fragment containing the IEP-ova cassette, the FRT flanked Kan$^r$, and the viral homology sequences to the MCMV genome target site m157 was generated. In a similar procedure the firefly luciferase gene (luc) was cloned under control of the IEP into pCP15 carrying the FRT flanked Kan$^r$. These fragments were introduced into m157 of pSM3fr as described (Sacher et al. supra) resulting in pSM3fr-Δm157-ova, pSM3fr-Δm157-flox-ova and pSM3fr-Δm157-luc. For excision of the FRT flanked Kan$^r$ FLP recombinase was transiently expressed from plasmid pCP20.

Generation of Spread-Deficient Virus Mutants

Figure 1:
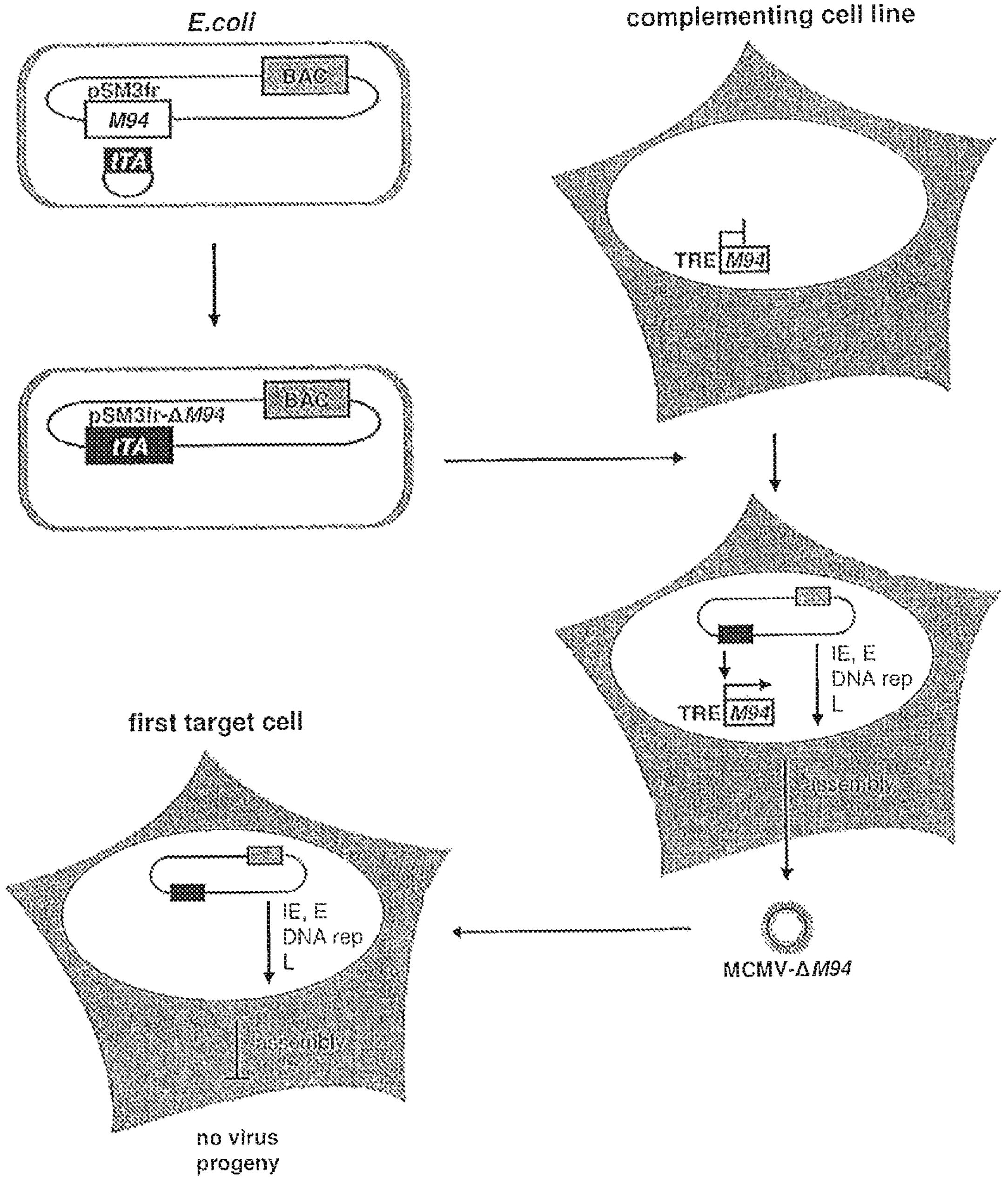
FIG. 1 is a schematic illustration of the concept of inducible trans-complementation.

As shown in FIG. 1 in *E. coli* the BAC pSM3fr-ΔM94 was generated by insertion of the tTA transactivator cassette into pSM3fr thereby deleting M94. The trans-complementing cell line NT/M94-7 expresses pM94 under control of the Tet inducible promoter. Upon transfection with pSM3fr-ΔM94 expression of tTA by the viral genome induces expression of pM94 by the cell leading to the production of trans-complemented MCMV-ΔM94. This virus is able to infect non complementing first target cells. Due to the lack of the essential gene M95 the release of infectious virus particles is impossible although immediate early (IE), early (E) and late (L) viral gene expression as well as DNA replication (DNA rep) occur.

For generation of the recombinant MCMV lacking the M94 sequence the parental MCMV BACs pSM3fr (MCMV-wt), pSM3fr-Δm157-ova (MCMV-ova) and pSM3fr-Δm157-rec-egfp (MCMV-Δm157-rec-egfp) (Sacher et al. supra) were applied to a second mutagenesis step. Therefore, the plasmid pO6-tTA-mFRT-Kan$^r$-mFRT was obtained by insertion of the Kan$^r$, on both sides flanked by mutant 34 bp FRT sites from pO6ic-F5 into pO6-tTA (Lotzerich et al. supra) to express the tTA transactivation gene under control of the IEP necessary for trans-complementation of pM94 (SEQ.ID:NO: 30). A linear DNA fragment containing the tTA cassette, the Kan$^r$ and viral homology sequences to the MCMV genome target site (MCMV upstream-homology: nt position 136189 to 136234 and MCMV downstream-homology: nt position 137256 to 137309) was generated using primer 5'ΔM94-pO6-tTA (SEQ.ID.No.7), primer 3'-ΔM94-pO6-tTA (SEQ.ID.No.8) and plasmid pO6-tTA-mFRT-Kan$^r$-mFRT as template. This PCR fragment was inserted into the different parental pSM3fr clones, hereby deleting the M94 gene. Since ORFs of M94 and M93 are overlapping 47 bp of homology had to be left at the 5'-end of M94 to keep the M93 ORF intact and 17 bp homology are still present at the former 3'-end of M94. Again FLP recombinase was expressed for excision of the Kan$^r$. Construction of pSM3fr-ΔM94, pSM3fr-ova-ΔM94, pSM3fr-flox-ova-ΔM94 and pSM3fr-Δm157-rec-egfp-ΔM94 was confirmed by restriction digest analysis and sequencing.

Viruses were reconstituted from BAC DNA, propagated on NT/M94-7 complementing cells and purified on a sucrose cushion as previously described (Sacher et al. supra). For analysis of virus replication supernatants from infected cells were taken every, 24 h. Quantification of infectious virus was done using $TCID_{50}$ (median tissue culture infectious dose) method on NIH/3T3 or complementing NT/M94-7 cells. For the determination of virus replication in vivo virus load was determined by standard plaque assay as plaque forming units (PFU) per gram organ as described (Sacher et al. supra). Spread-deficiency of each virus stock of M94 deficient mutants (MCMV-ΔM94, MCMV-ova-ΔM94, MCMV-flox-ova-ΔM94 and MCMV-Δm157-rec-egfp-ΔM94) was confirmed by the absence of plaque formation after infection of non-complementing MEF, although CPE of individually infected cells was detectable. The *E. coli* containing the pSM3fr-ΔM94 BAC of the spread-deficient MCMV-ΔM94 was deposited under the Budapest Treaty with the DSZM on Apr. 28, 2010 as DSM 23561.

UV Inactivation of Virus

For in vivo application, a fraction of the MCMV-wt virus preparation used for immunization was inactivated by exposure to 1.5 kJ/cm$^2$ UV light at a distance of 5 cm in a UV-crosslinker (Stratagene, Amsterdam, Netherlands) at 4° C. Viral infectivity was decreased by factor $2.4\times10^7$. The same treatment was sufficient to abolish viral gene expression when MCMV-Δm157-rec-egfp was subjected to different doses (0.5, 1.0 and 1.5 kJ/cm$^2$) of UV light and subsequently titrated on MEF. After 4 days post infection (p.i.) EGFP expression was monitored in single infected cells if virus was irradiated with low dose (0.5 kJ/cm$^2$) of UV and no EGFP expression was seen after strong irradiation (1.5 kJ/cm$^2$). Untreated MCMV-Δm157-rec-egfp formed EGFP plaques.

Immunization and Challenge of Mice 8 to 10 weeks old female B6 mice were immunized by intraperitoneal or subcutaneous (s.c.) injection of either MCMV-wt or mutant MCMV. Each mouse received 100 μl of virus suspension s.c. or 300 μl i.p. C57BL/6 mice were immunized with $1\times10^5$ $TCID_{50}$ MCMV-wt of MCMV-deltaM94, 129.IFNαβR$^{-/-}$ with $2.5\times10^5$ $TCID_{50}$ of MCMV-deltaM94 or UV irradiated MCMV-wt, and B6.IFNαβR$^{-/-}$ with $3\times10^5$ $TCID_{50}$ of MCMV-ΔM94 or MCMV-wt. Mock treated mice received same volumes of PBS. To boost mice, this procedure was repeated 14 days p.i. Sera collected from mice 12 weeks p.i. were used to determine amounts of virus specific antibodies by virus neutralization assay, as described below.

28 days or 20 weeks post priming, mice were challenged by intravenous (i.v.) injection of $10^6$ PFU of tissue culture derived MCMV-wt. Five days post challenge lungs, liver and spleen were collected under sterile conditions and stored at −80° C. Organ homogenates were analyzed for infectious virus load by standard plaque assay on MEF cells. Salivary glands derived MCMV (sgMCMV-wt) was generated as a homogenate of salivary glands from mice infected with tissue culture derived MCMV-wt as described in Trgovcich et al. (Trgovcich et al, 2000 Arch Virol 145:2601-2518). The isolated sgMCMV-wt is more virulent compared to tissue culture derived MCMV-Wt (Pilgrim et al. 2007 Exp Mol Pathol. 82:269-279). Vaccinated B6.IFNαβR$^{-/-}$ mice were challenged with $2\times10^5$ PFU sgMCMV-wt and 129.IFNαβR$^{-/-}$ mice were challenged with $2.5\times10^5$ $TCID_{50}$ tissue culture derived MCMV-wt.

Virus Neutralization Assay

Heat inactivated serum (56° C., 30 min) from 5 immunized mice 12 weeks p.i. were pooled and serially diluted 1:2 in DMEM containing a final concentration of 10% guinea-pig complement. Each dilution was mixed with 50 PFU of MCMV-luc and incubated for 90 min at 37° C. and subsequently added to NIH/3T3 cells in a 96 well format. After 1 h at 37° C. the virus inoculum was removed and NIH/3T3 medium added. The cultures were incubated for 24 h and luciferase activity was determined in cell extracts using the luciferase assay (Promega, Mannheim, Germany) in a luminometer (Berthold, Bad Wildbad, Germany) according to the supplier's and manufacturer's instructions, respectively.

In Vivo Cytotoxicity Assay

To evaluate CD8$^+$ cell effector function in vivo, splenocytes of congenic CD45.1$^+$ C Ptpr$^c$ mice were incubated with 2 μM of the indicated peptide and stained with 2 μM, 0.7 μM, or 0.1 μM carboxyfluorescein succinimidyl ester (CFSE) and PKH26 Red Fluorescent Cell Linker Mini Kit according to the manufacturer's instructions (Sigma-Aldrich). At day 6 p.i., labeled CD45.1$^+$ cells were transferred into B6 (CD45.2$^+$) recipients. After 16 h spleens of recipient mice were removed and flow cytometrical analysis of the target cells was performed. Specific cytotoxicity of target cells was calculated using the equation: % spec lysis=(1−ratio unprimed/ratio primed)*100; ratio=(% CFSE low/% CFSE high) (Lauterbach et al. 2005 J Gen Virol 86:2401-2410). The OVA derived class I peptide (SEQ.ID.NO.9) and MCMV specific peptides derived from m139 (SEQ-.ID.No.10), ie3 (SEQ.ID.No.11), M57 (SEQ.ID.No.12) and M45 (SEQ.ID.No.13) (Snyder et al. 2008 supra) were purchased from Metabion, Germany and were dissolved and stored according to manufacturer's device.

Adoptive Transfer and Flow Cytometrical Analysis

OVA specific $CD8^+$ T cells were isolated from spleen and cervical, axillary, brachial and inguinal lymph nodes of OT-I TCR transgenic mice backcrossed to congenic $CD45.1^+$ mice. OT-I cells were purified by negative selection via the $CD8\alpha^+$T Cell Isolation Kit (Miltenyi Biotec, Bergisch Gladbach, Germany). $3\times10^5$ transgenic T cells were injected i.v. into recipient B6 mice one day prior to i.p. infection with $10^5$ $TCID_{50}$ MCMV. To follow expansion of the transferred OT-I T cells 100 μl blood was taken 3, 6 and 8 days p.i., erythrocytes were lysed (PharmLyse, BD Biosciences, Heidelberg, Germany) and remaining cells were incubated with PE-TexasRed coupled α-CD8α (5H10; Caltag, Sacramento, Calif., USA) and PE coupled α-CD45.1 antibodies (A20, BD Biosciences Pharmingen). Flow cytometrical acquisition was performed using an Epics XL-MCL (Beckman-Coulter) and data were analyzed using FlowJo software (Tristar, Ashland, Oreg., USA).

OVA specific $CD4^+$ T cells were isolated from spleen and cervical, axillary, brachial and inguinal lymph nodes of OT-II TCR transgenic mice backcrossed to congenic $CD90.1^+$ mice. After lysis of erythrocytes $3\times10^5$ transgenic T cells were injected into recipient mice one day prior to infection with $10^5$ $TCID_{50}$ MCMV. Spleens were removed and splenocytes were incubated with Fc block (2.4G2; BD Biosciences) and subsequently stained with PE conjugated α-CD90.1 (HIS51; eBioscience) and PE-Cy5.5 coupled α-CD4 (RM 4-5; eBioscience). Flow cytometrical acquisition was performed using a FACS Calibur (BD Biosciences) and data were analyzed using FlowJo software.

Quantification of Viral Genomes in Organ Homogenates

Lungs were removed from mice twelve month after infection. Organs were homogenized and DNA was extracted using the DNeasy Blood & Tissue Kit from Qiagen (Hilden, Germany). Elution was done with 100 μl of the supplied elution buffer and genomic DNA concentration of each sample was quantified in duplicates using a NanoDrop ND-1000 UV-Vis Spectrophotometer. To quantify the viral DNA a quantitative realtime PCR specific for the MCMV M54 gene (Cicin-Sain et al. 2005 supra) was performed using a specific Taqman-Probe (SEQ.ID.NO.14) and the Taqman 1000 RXN PCR Core Reagents kit on an ABI PRISM 7700 Sequence Detector (Applied Biosystems, Carlsbad, Calif., USA). To calculate the viral genome copy number, a standard curve of the BAC plasmid pSM3fr containing the M54 gene was included.

EXAMPLE 4

MCMV-ΔM94 is Spread-Deficient

The HCMV virion protein pUL94 is essential for virus replication (Dunn et al. supra) and is expressed with late kinetics (Wing et al. supra). It has been found that pM94, the MCMV homolog, is also essential and plays a crucial role in a post nuclear step of virus maturation. In order to trans-complement the essential M94 gene product and reconstitute an M94 deletion mutant the NIH/3T3 derived complementing cell line NT/M94-7 harbouring the M94 gene under control of the TRE promoter was generated. The TRE promoter is only active in the presence of the Tet transactivator (tTA). To provide the tTA for trans-complementation of pM94 the tTA expression cassette was introduced into pSM3fr (Messerle et al. supra) disrupting M94 generating pSM3fr-ΔM94. MCMV-ΔM94 virus was reconstituted by transfecting NT/MN94-7 cells (FIG. 1). Next, multistep growth analysis infecting NT/M94-7 cells as well as parental NIH/3T3 fibroblasts with MCMV-ΔM94 or MCMV-wt were performed.

Figure 2A:
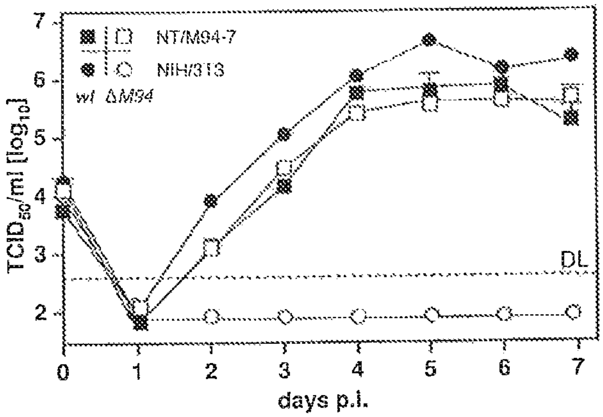
FIG. 2A is a diagram indicating TCID$_{50}$ as a function of time.

The results of this Example are shown in FIG. 2. In FIG. 2A Parental NIH/3T3 (circles) and NT/M94-7 fibroblasts (boxes) were infected at 0.1 $TCID_{50}$/cell with MCMV-wt (wt; closed symbol) or MCMV-AM94 (ΔM94; open symbol). At indicated days, infectious virus in the supernatant was quantified on NT/M94-7 cells by $TCID_{50}$ endpoint titration. Shown is the mean+/−SD of titrated duplicates. At day 5 p.i. supernatants were additionally titrated on MEF. No PFU was found within 1 ml supernatant of MCMV-ΔM94 infected NT/M94-7. p.i.=post infection; DL=detection limit.

Figure 2B:
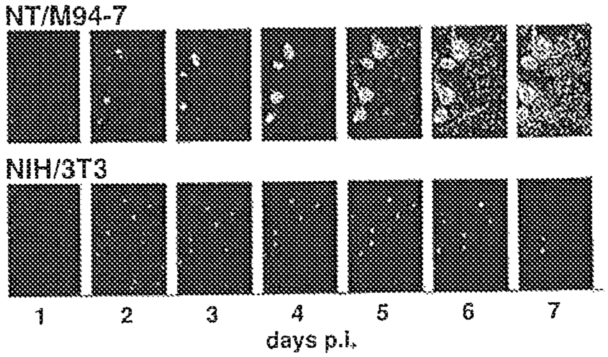
FIG. 2B is a series of microphotographs.

As shown in FIG. 2B Parental NIH/3T3 (lower panel) and NT/M94-7 (upper panel) fibroblasts were infected with MCMV-Δm157-rec-egfp-ΔM94. At indicated time points EGFP expressing cells were monitored. hpi=hours post infection.

Figure 2C:
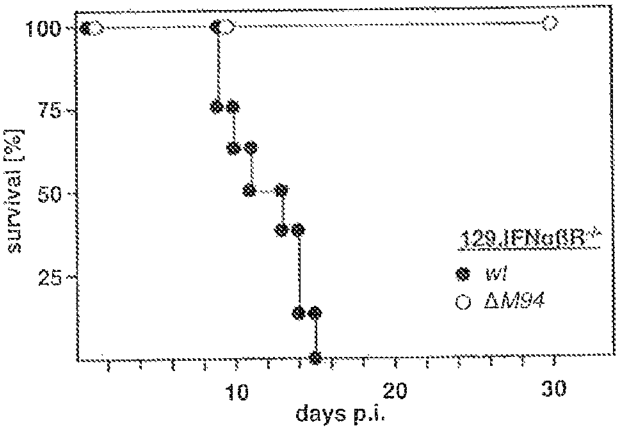
FIG. 2C is a survivorship curve indicating survival of mice as a function of time.

As shown in FIG. 2C 129.IFNαβ$R^{-/-}$ mice (n=15 for MCMV-ΔM94, open symbols; n=8 for MCMV-wt, closed symbols) were infected with $2.5\times10^5$ $TCID_{50}$ i.p. and survival was followed for 30 days p.i.

While MCMV-ΔM94 replicated to MCMV-wt-like titers on NT/M94-7 cells, no infectious virus was detectable in the supernatant of NIH/3T3 cells (FIG. 2A). As the defect of MCMV-ΔM94 to release infectious virus particles into the supernatant does not exclude cell-associated virus spread, a ΔM94 mutant expressing the enhanced green fluorescent protein EGFP (MCMV-Δm157-rec-egfp-ΔM94) was constructed. While MCMV-Δm157-rec-egfp-ΔM94 spread with kinetics comparable to MCMV-wt on NT/M94-7 cells, MCMV-Δm157-rec-egfp-ΔM94 remained strictly confined to the first infected NIH/3T3 cells (FIG. 2B). This result was confirmed also in endothelial cells (FIG. 8). In summary, M94 is essential and deletion abrogates virus release and cell-to-cell spread. In addition, MCMV-ΔM94 can be efficiently produced by trans-complementation.

Complementing NT/M94-7, parental NIH/3T3 fibroblasts and myocardium-derived endothelial cells MHEC5-T were infected with 0.1 TCID50/cell MCMV-ΔM94-Δm157-rec-egfp (MCMV-ΔM94) or MCMV-Δm157-rec-egfp (wt). At indicated time points EGFP expressing cells were monitored. Scale bar represents 100 μm.

EXAMPLE 5

MCMV-ΔM94 Does Not Revert to Replication Competent Virus

A major safety concern is reversion of vaccine strains to replication competent viruses during preparation (Roizman et al. 1982 Dev Biol Stand. 52:287-304) or in the vaccinated patient (Iyer et al. 2009 Ann. Emerg. Med 53:792-795). To exclude acquisition of the M94 gene through recombination via homologous sequences between MCMV-ΔM94 and the complementing cell line homologies were carefully avoided during virus construction. Replication competent virus indicative of recombination between the deletion virus and the M94 gene expressed by NT/M94-7 was never observed. In order to investigate the safety of MCMV-ΔM94 for vaccination studies in a highly susceptible mouse strain, 129.IFNαβ$R^{-/-}$ mice were infected with MCMV-wt or MCMV-ΔM94. While all IFNαβ$R^{-/-}$ mice died within 14 days upon infection with MCMV-wt, after infection with MCMV-ΔM94 all mice survived with no or only minimal weight loss (FIG. 2C). In conclusion, MCMV-ΔM94 could be safely produced and even immune deficient mice tolerated MCMV-ΔM94 infection.

EXAMPLE 6

MCMV-ΔM94 Induces Neutralizing Antibody and T Cell Responses

Poor induction of neutralizing antibodies that prevent viral entry is a problem in HCMV infection (Landini et al. 1991 Comp Immunol Microbiol Infect Dis 14:97-105). Therefore, the neutralizing antibody response to MCMV-wt and MCMV-ΔM94 was compared 12 weeks post immunization. Serial dilutions of sera were mixed with a luciferase expressing MCMV (MCMV-luc) prior to infection of NIH/3T3. The reduction of the luciferase signal reflected the neutralizing capacity of the antisera. Immunization with MCMV-ΔM94 induced a slightly lower amount of neutralizing antibodies than with MCMV-wt (FIG. 3A, $p<0.05$) whereas immunization with UV irradiated MCMV-wt abolished the induction of neutralizing antibodies confirming published observations (Gill et al. supra).

The results of this example are shown in FIG. 3. In FIG. 3A B6 mice were immunized i.p. with $10^5$ $TCID_{50}$ MCMV-wt (wt; closed circles), MCMV-ΔM94 (ΔM94; open circles) or mock infected (PBS; gray squares). Blood was collected 12 weeks p.i. and virus neutralizing capacity of the serum was determined using MCMV-luc. Neutralizing antibody levels of MCMV-ΔM94 immunized mice were significantly lower than antibody levels of MCMV-wt immunized mice using two-way ANOVA testing ($P=0.04$). Values represent the mean+SD of measured serum pools. RLU=Relative Luciferase Units, BG=background.

In FIG. 3B after adoptive transfer of $3\times10^5$ OT-I $CD8^+$ T cells (upper panel), B6 mice (n=5) were infected i.p. with $10^5$ $TCID_{50}$ MCMV-ova (wt-ova; closed bars), MCMV-ova-ΔM94 (ΔM94-ova; open bars) or PBS (gray bars). At day 3, 6 and 8 p.i. flow cytometrical analysis was performed on blood for the congenic marker CD45.1 and CD8. After adoptive transfer of $3\times10^5$ OT-II $CD4^+$ T cells (lower panel), B6 mice (n=5) were infected i.p. as above. At day 3, 6 and 8 p.i. flow cytometrical analysis was done on splenocytes for CD90.1 and CD4. Each bar represents the mean+SD of the indicated group; (**, $P<0.01$).

In FIG. 3C B6 mice (n=5) were infected i.p. with $10^5$ $TCID_{50}$ MCMV-wt (wt; closed symbols), MCMV-ΔM94 (ΔM94; open symbols) or UV irradiated MCMV-wt (wt UV; gray symbols). At day 6 p.i. in vivo cytotoxicity assay was performed using splenocytes labeled with carboxyfluorescein succinimidyl ester (CFSE) and the indicated viral peptides. Symbols represent the specific lysis activity against the indicated peptide in individual animals. The cross bar indicates the median of the analyzed group. The right panel shows an exemplary set of flow cytometric data.

Both $CD4^+$ and $CD8^+$ T cells play important roles in host defense against CMV. Antiviral $CD8^+$ T cells are effective in controlling MCMV during acute infection and mediate protection after immunization (Reddehase et al. supra). In addition, $CD4^+$ T helper cells are required for virus clearance in salivary glands (Jonjic et al. 1989 J Exp Med 169:1199-1212). In order to compare the level of $CD4^+$ and $CD8^+$ T cell responses induced by MCMV-wt and MCMV-ΔM94, OVA as a model antigen was chosen to be expressed by the vaccine. B6 mice were infected with MCMV-ova and MCMV-ova-ΔM94 one day after adoptive transfer of OVA specific $CD4^+$ or $CD8^+$ T cells. For MCMV-ova the expansion of OVA specific $CD4^+$ and $CD8^+$ T cells peaked at day 6 p.i., concordant with published data (Karrer et al, 2004 J Virol 78:2255-2264). Remarkably, MCMV-ova-ΔM94 also stimulated the proliferative response of OVA specific $CD8^+$ and $CD4^+$ (FIG. 3B) T cells to a degree comparable to the spread competent MCMV-ova. The amount of $CD8^+$ T cells was even slightly higher than with MCMV-wt ($P<0.01$).

This observation was to be confirmed for native MCMV antigens. B6 mice were infected with MCMV-ΔM94 or MCMV-wt. At six days p.i., target cells loaded with viral peptides derived from either m139, ie3, M57, or M45 (Snyder et al, 2008 supra) were injected and their cytolysis in vivo was analyzed (FIG. 3C). The cytolytic $CD8^+$ T cell response induced by MCMV-ΔM94 turned out to be comparable to MCMV-wt. In contrast, B6 mice injected with UV irradiated MCMV generated no or only poor lysis of targets. UV inactivation of MCMV-ΔM94 or MCMV-wt also abolished OVA specific. T cell expansion and the virus neutralizing capacity of sera. Thus, viral gene expression appeared to be crucial for the induction of the adaptive immune response. Altogether, spread-deficient MCMV induced an immune response comparable to MCMV-wt.

EXAMPLE 7

Role of Viral Target Cell Types in $CD8^+$ T Cell Activation

The strong adaptive immune response against MCMV-ΔM94 was surprising, since MCMV-ΔM94 gene expression is limited to the first target cells. Induction of a specific T cell response is dependent on antigen presentation by infected cells and by professional antigen presenting cells (Villadangos et al, 2008 Immunity. 29:352-361). In order to assess the contribution of infection of different cell types in the generation of an efficient $CD8^+$ cell response, the replication deficient MCMV was combined with conditional activation of a marker gene (Sacher et al. supra). MCMV-flox-ova-ΔM94 was constructed which expresses OVA only after Cre-mediated recombination.

Figure 4:
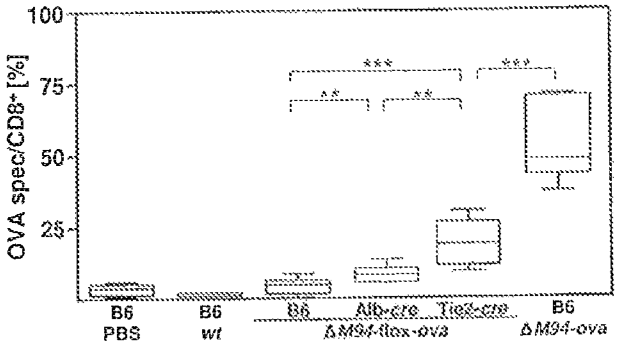
FIG. 4 is a Whisker blot indicating the percentage of adaptively transferred T cells in different mouse strains being infected with different virus mutants.

One day prior to i.p. injection of $10^5$ $TCID_{50}$ of MCMV-flox-ova-ΔM94 (ΔM94-flox-ova), MCMV-ova-ΔM94 (ΔM94-ova), MCMV-wt (wt) or PBS $3\times10^5$ congenic OT-I $CD8^+$ T-cells were transferred i.v. into B6, Alb-cre and Tie2-cre mice. At day 6 p.i. a flow cytometrical analysis was performed on PBL for the congenic marker CD15.1 and CD8. Boxes represent the ratio of OT-I cells per $CD8^+$ cells as a pool of 3 independent experiments and extend from the 25 to the 75 percentile. The lines indicate the median. Whiskers extend to show the extreme values. The P-values were obtained applying a two-tailed Wilcoxon rank sum test, (, $P<0.01$; *, $P<0.001$). The results are shown in FIG. 4

Endothelial cells (EC) and hepatocytes (H) are among the first target cells infected by MCMV in vivo (Sacher et al. supra). Whether these cell types contribute to $CD8^+$ T cell activation was addressed by infecting mice that express Cre recombinase selectively in vascular EC (Tie2-cre) or He (Alb-cre). One day after adoptive transfer of OVA specific $CD8^+$ T cells mice were infected with $10^5$ $TCID_{50}$ of spread-deficient MCMV-flox-ova-ΔM94. He are the main producers of infectious virus during the first few days of infection and are highly effective in activating a conditional marker gene by Cre recombinase (Sacher et al. supra). Yet, selective induction of OVA expression in MCMV infected He resulted in only weak proliferation of OVA specific $CD8^+$ T cells (FIG. 4). In contrast, a significantly ($P<0.001$) higher proliferative response of OVA specific $CD8^+$ T cells was observed upon OVA expression in EC. Therefore, infection of EC make a stronger contribution to the induction of an antiviral $CD8^+$ T cell response than infection of He. As infection of C57BL/6 mice with MCMV-ΔM94-ova that leads to expression of OVA in all infected cells induces a higher proportion of OVA specific $CD8^+$ T cells than expression selectively in EC (Tie2-cre mice infected with MCMV-ΔM94-flox-ova; $P<0.01$) additional cell types seem to be involved in antigen expression and T cell stimulation. In addition, the significant different T cell responses after cell type specific recombination in vivo prove that MCMV-ΔM94 is unable to spread from cell to cell.

The experimental details in connection with this example were, in addition to the ones outlined in Example 3, as follow and the results of this example are depicted in FIG. 5.

B6 mice (n=5) were immunized ($1^{st}$) s.c. or i.p. with $10^5$ $TCID_{50}$ MCMV-wt (wt; closed symbols), MCMV-ΔM94 (ΔM94; open symbols), Δm01-17+m144-158-MCMV (ΔΔ, gray symbols) or PBS (light gray symbols). Virus preparations were UV irradiated before immunization (UV) as indicated. Optionally, mice were boosted ($2^{nd}$) two weeks later with the same dose, route and virus. Challenge infection was applied i.v. 20 (A) or four weeks (B) post prime with $10^6$ PFU MCMV-wt. Five day post challenge plaque assay was performed. Horizontal bars show the median of each group. Each symbol represents one individual mouse. DL=detection limit.

EXAMPLE 8

MCMV-ΔM94 Protects Against Challenge with MCMV-wt

Figure 5A:
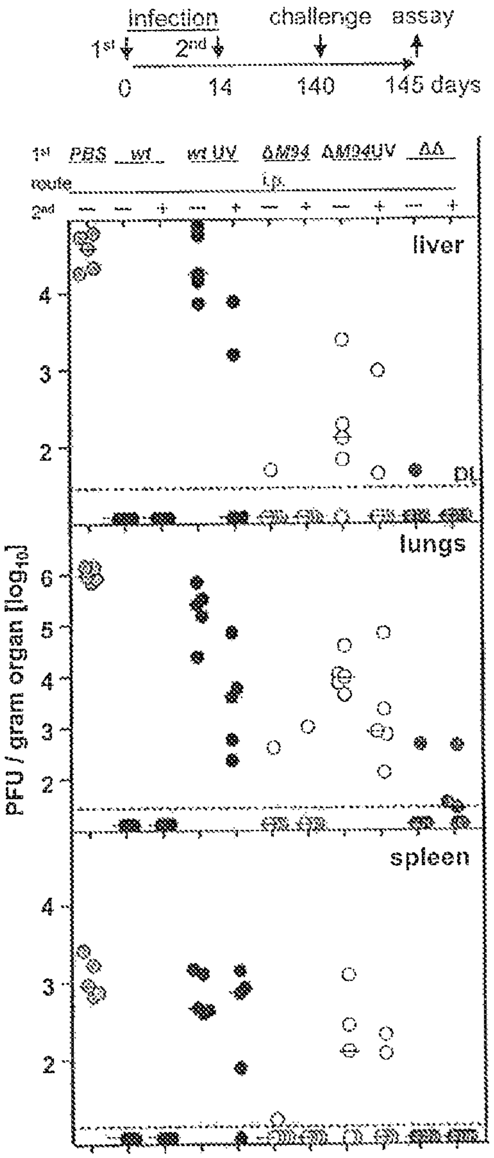
FIGS. 5A and 5B are diagrams indicating the challenge virus load in different organs of vaccinated mice.

In order to test protection of MCMV-ΔM94 against lethal challenge, B6 mice were infected with either spread-deficient MCMV-ΔM94, the attenuated strain Δm01-17+m144-158-MCMV (Cicin-Sain et al. 2007 J Virol 81:13825-13834) or MCMV-wt. A boost infection was applied 4 weeks later with the same dose. 20 weeks after priming mice were challenged i.v. with $10^6$ $TCID_{50}$ tissue culture derived MCMV-wt. Most remarkably, already a singular immunization dose of MCMV-ΔM94 was already sufficient to strongly suppress MCMV-wt replication by 10,000 fold in lungs, 1,000 fold in liver and at least 100 fold in spleen, whereas non-immunized controls had high virus loads in all organs tested (all $P<0.01$; FIG. 5A). Overall, the protection mediated by MCMV-ΔM94 vaccination was comparable to MCMV-wt or Δm01-17+m144-158-MCMV vaccination (all $P>0.05$). Due to the strong protection achieved already after one administration, a boosting effect could not be detected. However, there was weak protective effect after a singular dose when UV inactivated MCMV-wt or UV inactivated MCMV-ΔM94 virus was administered. Only after a boost with UV inactivated viruses the effect was slightly improved but still remained lower than that of a singular dose of MCMV-ΔM94 ($P<0.05$).

Figure 5B:
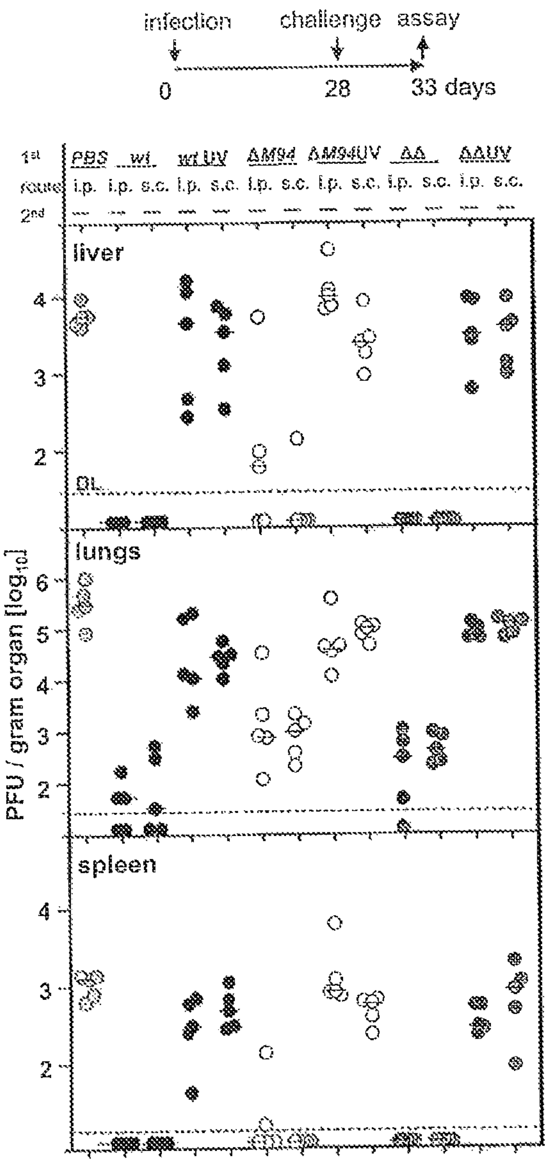

It was asked, whether the strong protection after singular administration of MCMV-ΔM94 could also be realized in a short-term vaccination protocol. In addition, the influence of two different application routes was tested. B6 mice were injected either i.p. or s.c. followed by challenge infection with MCMV-wt only 4 weeks later. Here, vaccination with MCMV-ΔM94 resulted in about 100 fold reduction of challenge virus load in liver ($P<0.05$), lungs ($P<0.01$) and spleen ($P<0.01$; FIG. 5B) comparable to immunization with Δm01-17+m144-158-MCMV. MCMV-wt vaccination resulted in reduction of challenge virus load by 1,000 fold ($P<0.01$). Generally, there was no significant difference between the i.p. or s.c. vaccination route although s.c. injection appeared to induce slightly better protection in spleen ($P>0.05$) FIG. 5B) and hearts.

Summarized, vaccination with the spread-deficient MCMV-ΔM94 was able to efficiently protect immunocompetent mice against challenge with MCMV-wt after vaccination with a singular dose. Remarkably, vaccination with MCMV-ΔM94 was as efficient as vaccination with MCMV-wt concerning long-term vaccination, whereas the use of UV inactivated virus could not compete even after a second application.

EXAMPLE 9

Protection of Severely Immune Compromised Recipients

Type I interferons are key cytokines in the immune response against CMV and deletion of their receptor results in a mouse ($IFN\alpha\beta R^{-/-}$) that is severely immunocompromised and at least 1.000-fold more susceptible to MCMV infection than the parental mouse strain (Presti et al. 1998 J Exp Med 188:577-588). Since spread-deficient MCMV-ΔM94 was proven to be well tolerated by $IFN\alpha\beta R^{-/-}$ mice (FIG. 2C), it was tested whether MCMV-ΔM94 could even protect $IFN\alpha\beta R^{-/-}$ mice against lethal MCMV-wt challenge (see FIG. 6A). B6.$IFN\alpha\beta R^{-/-}$ mice were immunized with MCMV-ΔM94 or a sublethal dose of MCMV-wt. Both groups survived and mice immunized with MCMV-ΔM94 showed no significant weight loss, whereas MCMV-wt infected mice lost approximately 15% of their body weight. Four weeks later, mice were challenged by infection with a lethal dose of more virulent salivary glands derived MCMV (as described in Example 3). Most strikingly, the vaccination with both, MCMV-ΔM94 as well as MCMV-wt was protective and all animals survived (FIG. 6A).

The results of this Example are shown in FIG. 6.

Figure 6A:
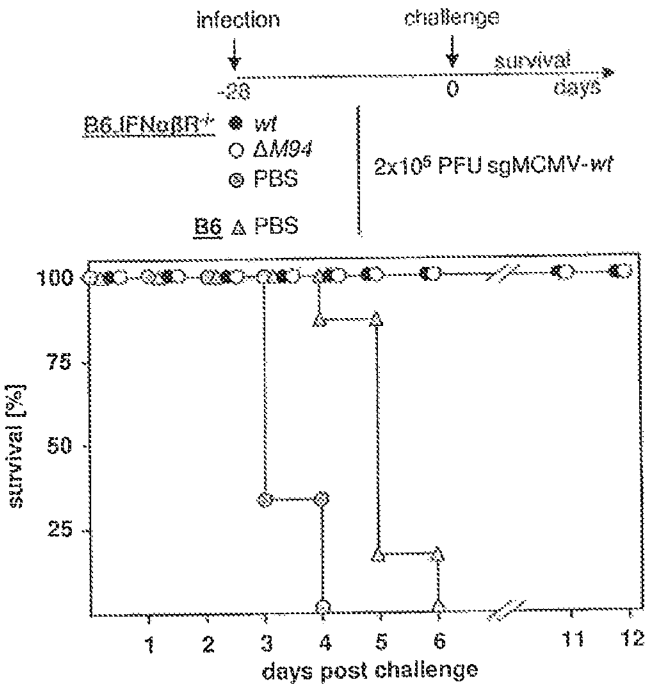
FIGS. 6A and 6B are survivorship curves indicating survival of vaccinated mice as a function of time.

In FIG. 6A B6.$IFN\alpha\beta R^{-/-}$ (n=6) mice were immunized i.p. with $3\times10^5$ $TCID_{50}$ MCMV-wt (wt; black circles) or MCMV-ΔM94 (ΔM94; open circles). Control groups of B6.$IFN\alpha\beta R^{-/-}$ (gray circles) or B6 (gray triangles) were treated with PBS. Four weeks later challenge infection was performed by i.p. injection of $2\times10^5$ PFU salivary glands derived MCMV (sgMCMV-wt) mice and survival was monitored.

Figure 6B:
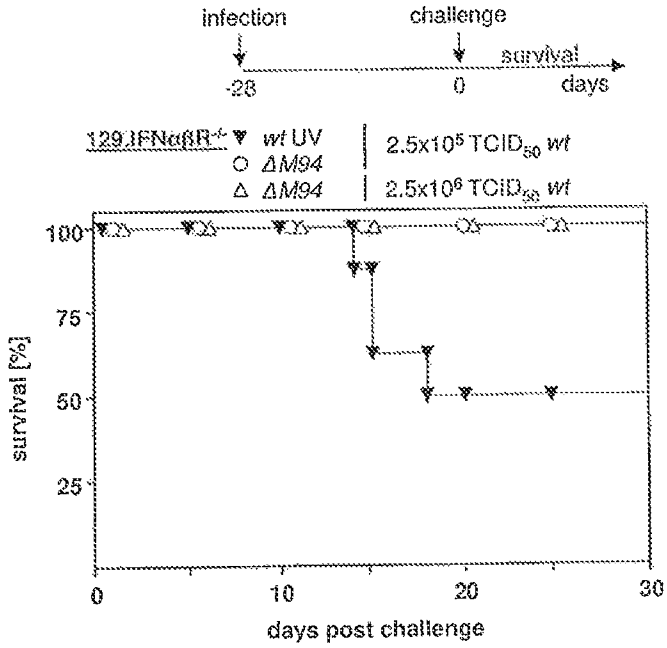

In FIG. 6B 129.$IFN\alpha\beta R^{-/-}$ mice 4 weeks previously immunized with $2.5\times10^5$ $TCID_{50}$ of MCMV-ΔM94 (ΔM94; open circles, n=8), or UV irradiated MCMV-wt (wt UV; closed triangles down, n=8) were challenged with a lethal dose of MCMV-Wt (see FIG. 2C) and survival was monitored. A 10 fold higher dose of MCMV-wt was applied to mice immunized with MCMV-ΔM94 (n=7) (open triangles).

B6 mice profit from an Ly49H-dependant activation of natural killer cells resulting in a strong innate immune response stimulated by the MCMV protein encoded by m157 (Sun et al. 2008. J. Exp. Med. 205:1819-1828.). 129.IFNαβR$^{-/-}$ mice do not express Ly49H and are even more susceptible to MCMV infection than B6.IFNαβR$^{-/-}$ mice. 129.IFNαβR$^{-/-}$ mice were vaccinated with MCMV-ΔM94 and challenged 4 weeks later with a dose of $2.5\times10^5$ TCID$^{50}$ tissue culture derived MCMV-wt (FIG. 6B). In line with the earlier data (Cicin-Sain et al. 2007 supra), vaccination with UV inactivated virus mediated only partial protection and could delay death for a short period. MCMV-ΔM94 vaccinated mice survived the lethal challenge even with a dose of $2.5\times10^6$ TCID$^{50}$. In summary, vaccination with MCMV-ΔM94 is able to protect even highly susceptible immune compromised mice against lethal MCMV challenge.

EXAMPLE 10

Maintenance of the MCMV-ΔM94 Genome In Vivo

One argument against the application of attenuated life vaccines is their ability to establish a latent infection that bears the risk of reactivation (Iyer et al, supra). On the other hand non-productive reactivation episodes might result in endogenous boosts of the antiviral immune response (Snyder et al, 2008 Immunity 29:650-659). Thus, it was intriguing to test whether MCMV-ΔM94 genome is maintained in vaccinated hosts. Quantitative PCR analysis on total DNA extracted from lungs, a key manifestation site of CMV disease (Balthesen et al. 1993 J Virol 67:5360-5366), was performed. Twelve months p.i. genomes of MCMV-ΔM94 could be detected in all mice tested (FIGS. 7A and B) proving that the genome of MCMV-ΔM94 is maintained. Interestingly, the genome numbers detected in lungs one year after infection with MCMV-ΔM94 and MCMV-wt were not significantly different (P>0.05). This finding proved that at least some of the first target cells are not lost after infection either due to virus-induced cell death or elimination by the immune response. In summary, these data also provide first evidence that virus spread is not necessary for long-term genome maintenance and that first target cells of MCMV-ΔM94 may be able to contribute to a more sustained immune response.

The results of this example are shown in FIG. 7.

B6 mice were infected i.p. with $10^5$ TCID$_{50}$ MCMV-wt (wt) (n=5) or MCMV-ΔM94 (ΔM94) (n=6). Twelve months p.i. total DNA was extracted from lungs. (FIG. 7A) PCR analysis was performed obtaining a specific 246 bp fragment of the polymerase gene M54. As controls DNA from lungs five days after infection with $10^5$ TCID$_{50}$ MCMV-wt (wt acute) (n=5), PBS (1), no template (2) or the BAC plasmid pSM3fr (3) were used. (FIG. 7B) Quantitative realtime PCR analysis was performed and viral M54 gene copies were calculated per μg genomic DNA. Each symbol represents one individual mouse. Horizontal bars show the median of each group. Genome copy numbers of MCMV-wt (wt) and MCMV-ΔM94 (ΔM94) are not significantly different (P>0.05). Both groups are significantly different compared to acutely infected lungs (wt acute) (**, P<0.01). MW=molecular weight marker; DL=detection limit. (FIG. 7C and FIG. 7D) B6 mice (n=5) were immunized i.p. with $10^5$ TCID$_{50}$ MCMV-wt (wt; closed symbols), MCMV-ΔM94 (ΔM94; open symbols), Δm01-17+m144-158-MCMV (ΔΔ; gray symbols) or PBS (light gray symbols). Virus preparations were UV-irradiated before immunization (UV) as indicated. Challenge infection was applied i.v. one year post prime with $10^6$ PFU MCMV-wt. Plaque assay was performed (FIG. 7C) five days post challenge with lungs and (FIG. 7D) 14 days post challenge with salivary glands (SG). Horizontal bars show the median of each group. Each symbol represents one individual mouse. DL=detection limit.

EXAMPLE 11

Figure 7D:
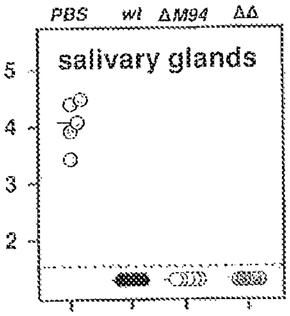

Vaccination with MCMV-ΔM94 Prevents Replication of Virus in the Respiratory Tract From epidemiological studies it was suggested that saliva is an important route of transmission of HCMV (Pass et al. 1986 N. Engl. J Med 314:1414-1418.). To test whether the vaccine MCMV-ΔM94 is able to block virus replication in salivary glands and lungs C57BL/6 mice were immunized with MCMV-ΔM94 or control viruses and received twelve months later a challenge infection with $10^6$ PFU MCMV-wt i.v. (FIGS. 7C and D). A single application of MCMV-ΔM94 was sufficient to suppress challenge virus replication by more than factor 1,000 in lungs in 4 out of 6 animals (FIG. 7C). Further, no challenge virus could be isolated from salivary glands 14 days after challenge (FIG. 7D). This implies that shedding of virus from the respiratory tract via saliva and therefore horizontal transmission via this route is abrogated by vaccination with spread-deficient MCMV.

EXAMPLE 12

Discussion

It is reported herein on the vaccination against a beta-herpesvirus using a spread-deficient vaccine. The vaccine induced a strong adaptive immune response comparable to MCMV-wt conferring protection even in highly immune compromised mice. This means that infection of the first target cells is sufficient for successful vaccination.

An intact immune system usually protects against HCMV disease. Hence, the antigenic capacity of the wild type virus is sufficient for the induction of a protective immune response. The inability of UV inactivated virus to protect efficiently against challenge infection demonstrated the need for viral antigen expression including nonstructural antigens (Cicin-Sain et al. 2007 supra; Gill et al. 2000 J Med Virol 62:127-139). As a consequence an ideal vaccine should exploit the full immunogenic but avoid the pathogenic potential of the wild type virus.

The alpha-herpesvirus field has pioneered the use of replication defective viruses as vaccines (Dudek et al. supra). These vaccines were generated by the deletion of genes essential for virus replication and are thus apathogenic (Dudek et al. supra). Now, to construct a spread-deficient beta-herpesvirus vaccine deletion of M94 was chosen for the following reasons. First, M94 is essential for spread of MCMV and inferred from studies of HCMV it should be expressed with late kinetics during virus replication (Scott et al. supra; Wing et al. supra). Second, pM94 does not belong to the group of glycoproteins which comprise major targets for the neutralizing antibody response of HCMV. Third, M94 of MCMV is the homolog of UL94 in human CMV (Wing et al, supra) that in principle allows translation to the human pathogen. Finally, the deletion of UL94 of HCMV might even be of advantage because pUL94 induces autoreactive antibodies that are associated with systemic sclerosis (Lunardi et al. 2000 Nat Med 6:1183-1186). The SSc cross-reactive UL94 peptide is depicted in SEQ.ID.:NO: 28. Interestingly, genomes of the spread-deficient MCMV-ΔM94 were detected in lungs after i.p. infection, showing that virus can disseminate either as free particles (Hsu et al. 2009 J Gen Virol 90:33-43) or associated to cells. Monocytes and macrophages were shown to be attracted to the peritoneal cavity after infection and transport the virus in blood (Stoddart et al. 1994 J Virol 68:6243-6253; van der Strate et al. 2003 J Virol 77:11274-11278). These cells could also release virus at distant sites to infect EC or other cell types, a process called trans infection (Halary et al. 2002 Immunity 17:653-664).

The spread-deficient betea-herpesvirus vaccine presented here, has a strong protective capacity similar to wild type CMV infection. The immune response of the vaccinee controls virus replication in all analysed organs preventing overt CMV-disease. The absence of detectable amounts of infectious virus in salivary glands of long-term vaccinated mice two weeks after challenge implies that also horizontal transmission to other individuals via saliva is abrogated. Because of this it is plausible that such an equivalent vaccine will protect against HCMV-disease, similar to the protective effect of a pre-existing infection. This is supported by the observation that women who were exposed to HCMV were at lower risk to give birth to children with symptomatic disease compared to non-infected women (Fowler et al. 2003 JAMA 289:1008-1011.). The seropositivity of the mother could not prevent infection but pathogenesis of the children. In addition, frequent exposure to different CMV strains could further increase immunity against reinfection (Adler et al. supra). It is therefore again plausible that a spread-deficient human CMV vaccine induces an immune response equal to natural infection which will protect against symptomatic human CMV infection without the risk for reactivation and pathogenesis.

The immune response to MCMV-ΔM94 reached a level comparable to MCMV-wt. Protection was similar to the recently generated vaccine Δm01-17+m144-158-MCMV (Cicin-Sain et al. 2007 supra) which lacks 32 viral genes but which is not spread-deficient in vitro. In Δm01-17+m144-158-MCMV immune evasive genes were deleted to increase the antiviral immune response and thereby to attenuate the virus (Scalzo et al. 2007 Immunol Cell Biol. 85:46-54.).

It is within embodiments of the present invention that (a) at least one essential gene and (b) at least one immune evasive gene is deleted, whereby it is preferred that the deleted at least one immune evasive gene is selected from the group comprising genes encoding gene products affecting antigen presentation, interaction with cytokines, the complement system and humoral immunity. More preferably, the deleted at least one immune evasive gene is selected from the group comprising genes encoding gene products that down-regulate MHC I to avoid CTL response, gene products that evade the NK cell response, gene products that interfere with MHC II presentation, down-regulate adhesion molecules, gene products that interact with IL-1, gene products that activate TGF-β.

Infection of susceptible IFNαβR$^{-/-}$ mice with spread-deficient MCMV proved the safety of the vaccination concept. Furthermore, IFNαβR$^{-/-}$ mice were protected against otherwise lethal challenge, similar to other infection models (Calvo-Pinilla et al, 2009 PLoS One. 4:e5171; Paran et al. 2009 J Infect Ibis 199:39-48). Although recent work revealed the capacity of MCMV to efficiently induce type I interferon (Hokeness-Antonelli et al. 2007 J Immunol 179: 6176-6183), the efficacy of the spread-deficient MCMV vaccine in IFNαβR$^{-/-}$ mice implies that type I interferon-dependent immunity is not essential in the protection conferred by short term vaccination.

Interestingly, the spread-deficient MCMV induced an adaptive immune response with similar efficiency as MCMV-wt. The CD4$^+$ and CD8$^+$ T cell response was on the same level as MCMV-wt and the neutralizing antibody response was only marginally reduced. This slightly lower neutralizing capacity might be caused by the smaller number of infected cells and by the therefore reduced amount of antigen that is released after infection with MCMV-ΔM94. A lower number of antigen-antibody complexes might lead to less efficient affinity maturation creating antibodies of lower neutralizing capacity. Nevertheless, the neutralization of virus appears sufficient to control virus replication.

Why did the adaptive immune response to the vaccine reach a level near to MCMV-wt infection despite the inability to spread? MCMV-ΔM94 was able to establish viral genome maintenance as efficient as MCMV-wt. The classical definition of herpesviral latency includes the potential for reactivated gene expression with subsequent release of infectious virus (Roizman et al. 1987 Annu Rev Microbiol 41:543-571.). Although the term “latency” is formally not applicable to the situation with MCMV-ΔM94 in the absence of productive infection, there is no evidence that pM94 affects reactivation of gene expression. Because the protective effect of MCMV-ΔM94 rather increased than faded over time, the inventors believe that periodic restimulation of the immune response due to reactivation of gene expression contributed to the sustained protection induced by MCMV-ΔM94. Interestingly, virus infected cells are not eliminated by the activated immune response. This means that the first target cells that are infected by the spread-deficient vaccine are resistent to elimination. Similarly, cells infected with a spread-deficient mutant of the gamma herpesvirus MHV-68 were not attacked by the adaptive immune reponse (Tibbetts et al. 2006 Virology 353:210-219). For MCMV-wt it was shown that T cells are activated against a highly antigenic virus epitope of M45 presented by professional APC but the activated T cells did not eliminate infected target cells in organs of C57BL/6 mice (Holtappels et al. 2004 J Exp Med 199:131-136). This protection was caused by m152, that is known to downmodulate MHC class I. The target cells that are protected from CD8$^+$ T cell elimination were not identified and it could be shown that at least some of these protected cells are first target cells of MCMV.

Endothelial cells (EC), hepatocytes (He) and macrophages are first target cells for HCMV and MCMV in vivo (Hsu et al. supra; Sacher et al, supra). In addition, EC have recently been identified as sites of virus latency (Seckert et al. 2009 J Virol 83:8869-8884), and at least liver EC are able to directly stimulate a cytotoxic T cell response (Kern et al, 2010 Gastroenterology 138(1):336-46). Using MCMV-ΔM94 constructs for conditional gene expression, substantial differences were noticed in the ability of EC and He to activate a CD8$^+$ T cell response. In contrast to EC, He one of the most important first targets for MCMV during acute infection (Sacher et al, supra), induced only a poor CD8$^+$ T cell response. This lack of stimulatory capacity is apparently not compensated by cross presentation through professional antigen presenting cells. Cross presentation was shown to be important for the induction of a T cell response against fibroblasts infected with a single-cycle MCMV (Snyder et al. 2010 PLoS One. 5:e9681). On the other hand, bone marrow derived APC, that are thought to be important cross presenting cells, seem not to be necessary for the activation of a CD8$^+$ T cell response via cross presentation against MCMV infection (Kern et al. supra). In addition to EC also other cell types seem to contribute to CD8$^+$ T cell stimulation as antigen expression in most infected cells led to a stronger T cell response than expression in infected EC only. Infected dendritic cells and macrophages were described to activate a T cell response against MCMV in vitro (Mathys et al. 2003 J Infect Dis 187:988-999) and are infected in vivo (Andrews et al. 2001 Nat Immunol 2:1077-1084). Therefore, it suggests itself that infected professional APC contribute to immune stimulation against MCMV in addition to EC. It appears noteworthy that the attenuated human CMV strains such as Towne and AD169 which are characterized by a 20-fold reduction of immunogenicity and the inability to confer immune protection (Adler et al. supra) accumulated mutations resulting in their inability to infect EC, epithelial cells, smooth muscle cells and macrophages (Hahn, G. et al. 2004 J Virol 78:10023-10033). Thus, it appears likely that the restricted cell tropism may in fact represent the cause for their failure as human CMV vaccines.

EXAMPLE 13

Spread-Assay of MCMV-ΔM94

The phenotype of MCMV-ΔM94 was analyzed in cell-to-cell spread. This was investigated by an in vitro spread assay as essentially described herein in Example 1 with the following mo modifications The results of this Example are shown in FIG. 9.

NIH/3T3 and NT/M94-7 cells were plated and infected with MCMVΔ1-16-FRT (del1-16) and MCMVΔM94tTA (Δ) at an MOI of 0.25 for 1 h and then washed twice with D-PBS. Cells were incubated for 6 h and afterwards washed four times with D-PBS. Equal numbers of non-infected cells were stained with 5 μM Carboxyfluorescein succinimidyl ester (CFSE) for 8 min and blocked by 2% FCS/D-PBS, then washed twice with 2% FCS/D-PBS, and subsequently seeded on top of the unstained but infected cells. Cells were fixed 48 hours post infection with 4% PEA in D-PBS for 10 min at 37° C. and washed and permeablized with 0.1% Triton X-100 for 10 min. After triple washing cells were blocked with 3% BSA/D-PBS for 1 h. Staining of immediate early gene products was performed by incubating fixed cells with a monoclonal antibody to MCMV immediate-early 1 in 3% BSA/D-PBS. After three D-PBS washes, cells were incubated with an Alexa Fluor 555-coupled anti-mouse secondary antibody (Invitrogen) in 3% BSA/D-PBS. Finally, cells were washed three times and imaged by confocal microscopy using a LSM 510 Meta (Zeiss). Virus transmission was determined by counting immediate-early 1- and CFSE-positive cells using the ImageJ Cell Counter plugin.

FIG. 9 shows that infection of NIH/3T3 and NT/M94-7 (NTM94) cells with MCMVΔ1-16-FRT (Mohr C A et al., Engineering of cytomegalovirus genomes for recombinant live herpesvirus vaccines; Int J Med Microbiol. 2008 January; 298(1-2):115-25. Epub 2007 Aug. 16, Review) and MCMV-ΔM94, followed by removal of excess virus by extensive washes after infection. Next, CFSE stained NIH/3T3 were added and virus replication was permitted. After additional 48 h the culture was fixed and stained for immediate-early 1. This resulted in cells which were either immediate-early 1-positive, CFSE-positive or positive for both stains (FIG. 9A). Stained cells were counted and cell-to-cell spread was determined by calculating the ratio between immediate-early 1-positive/CFSE stained cells to immediate-early 1-positive/CFSE-negative cells (FIG. 9C). The spread rate of the MCMVΔ1-16-FRT was set as 100%. MCMVΔ1-16-FRT infection spreads rapidly throughout the cell culture as indicated by the large number double stained nuclei (FIG. 9B). In contrast, the M94 deletion mutant did not infect the newly added cells. Only one double stained nucleus was seen after counting 416 immediate-early 1+/CFSE negative cells. Its ability to infect fresh cells was, however, restored to a transmission rate of 97% when the mutant was grown on complementing NT/M94-7 cells. It is thus evident that the effect of the M94 deletion on secondary envelopment of mouse CMV also resulted in a deficiency of cell-to-cell spread.

EXAMPLE 14

Propagation of Spread-Deficient Human CMV

Generation of the Trans-Complementing Cell Line TCL94/99-BP

Recombinant lentiviruses expressing a) UL99 coupled with EGFP (encoded by pCB-Ubic-UL99-IRES-gfp; SEQ-.ID.No:18), b) UL99 coupled with UL94 mCherry (encoded by pCB-Ubic-UL94-IRES-mChe; SEQ.ID.No:17) and c) beta-lactamase coupled with puromycine resistance gene (encoded by pLV-Ubiqc-BLAS-IRES-Puro; SEQ.ID.No:19) were constructed and propagated by Sirion GmbH using ViraPower lentiviral packaging mix (Invitrogen) in 293FT cells (Invitrogen). $2\times10^6$ MRC5 fibroblasts (ATCC CCL-171) were transduced by 5 TDU/cell (transduction units/cell) of each lentivirus by spin infection according to the manufacturer's protocol. The transduced cells were plated out on a 10 cm dish and were selected for 5 days with 20 μg/ml puromycin in OPTI-MEM 5% FCS. The tranduced cells were passaged (1:2) one time in the presence of 20 μg/ml puromycin and the double positive (mCherry+EGFP) cells were purified by fluorescence associated cell sorting and re-plated at density of $2.5\times10^4$ cell/$cm^2$. 48 h after confluency the cells were passaged (1:5) two more times in the presence of 20 μg/ml puromycin and re-sorted as above. After one more passage in OPTI-MEM 5% FCS+20 μg/ml puromycin the cells were aliquoted to $0.7\times10^7$ cell/vial and were deep frozen OPTI-MEM supplemented with 10% PCS and 10% DMSO.

Construction of Spread-Deficient Human CMV

To generate a non-functional UL94 locus pTB40E-BAC4-FRT; SEQ.ID.No:20 (Serivano L, et al., 2011. HCMV spread and cell tropism are determined by distinct virus populations. PLoS. Pathog. 7:e1001256; Sinzger, C. et al., 2008. Cloning and sequencing of a highly productive, endotheliotropic virus strain derived from human cytomegalovirus TB40/E. J. Gen. Virol. 89:359-368.) was introduced in GS1783 *E. coli* strain (Tischer, B. K. et al., 2010. En passant mutagenesis: a two step markerless red recombination system. Methods Mol. Biol. 634:421-430.). (a) Red-recombination was induced by electro-transformation of the synthetic DNA fragment LIFdel94; SEQ.ID.No:15 according to the standard protocol (Tischer, B. K. et al., supra) resulting in pTB40E-BAC4-delUL94-SZeo. Recombinants were selected by picking single clones after plating the transformants on LB agar plates in the presence of 25 μg/ml chloramphenicol and 30 μg/ml zeocin. The correct replacement of the BAC sequences from nt122630 to 123668 reffering to SEQ.ID.No:20 with LIFdelUL94, SEQ.ID.No: 15 was confirmed by restrictions pattern analysis and sequencing. (b) To remove the zeocin cassette from the UL94 locus, a second round of Red recombination was induced in liquid culture of pTB40E-BAC4-delUL94-Szeo according to the standard protocol (Tischer, B. K. et al., supra) in presence of 25 μg/ml chloramphenichol and 2% of L-arabinose. Recombinants, which were coined pTB40E-BAC4-del94, were selected by picking single clones after plating of the recombinants on LB agar plates in the presence of 25 μg/ml chloramphenicol 1% of L-arabinose. The correct removal of the operational sequences were confirmed by restrictions pattern analysis and sequencing. (c) A next red-recombination was induced by electro-transformation of the synthetic mutagenesis fragment LIFdel99, SEQ-.ID.No:16, as described above (see a) herein) resulting in pTB40E-BAC4-delUL94-del99-SZeo. Recombinants were selected by picking single clones after plating the transformants on LB agar plates in the presence of 25 m/ml chloramphenicol and 30 μg/ml zeocin. The correct replacement of the sequences from nt 130670 to 1:31243 (according to the numbering of the BAC referred to herein as SEQ-.ID.No:20) was confirmed by restrictions pattern analysis and sequencing. (d) To remove the zeocin cassette from the UL99 locus, a final round of red-recombination was induced in liquid culture of pTB40E-BAC4-delUL94-delUL99-Szeo as above (see b) herein). Recombinants, which were coined pTB40E-BAC4-del94-del99, were selected by picking single clones after plating of the recombinants on LB agar plates in the presence of 25 μg/ml chloramphenicol 1% of L-arabinose. The correct removal of the operational sequences from the UL99 locus were confirmed by restrictions pattern analysis and sequencing. 1. The description of the BAC modifications in the new way are the following:

M1) To generate a non-functional UL94 (or inactivate the UL94 gene) the nt sequence of pTB40E-BAC4-FRT (SEQ-.ID.No:20) between nt 122630 and nt 123668 is replaced by the synthetic fragment delUL94S (SEQ.ID.No:34).

M2) To generate a non-functional UL99 (or inactivate the UL99 gene) the nt sequence of pTB40E-BAC4-FRT (SEQ-.ID.No:20) between nt 130670 and nt 131243 is replaced by the synthetic fragment delUL99S (SEQ.ID.No:35). For the double mutant of UL94-UL99 this has to be done in addition to modification M1.

M3) To generate a non-functional UL50 (or inactivate the UL50 gene) the nt sequence of pTB40E-BAC4-FRT (SEQ-.ID.No:20) between nt 58442 and nt 59622 is replaced by the synthetic fragment delUL50S (SEQ.ID.No:32).

M4) To generate a non-functional UL53 (or inactivate the UL53 gene) the nt sequence of pTB40E-BAC4-FRT (SEQ-.ID.No.:20) between nt 62129 and at 63261 is replaced by the synthetic fragment delUL53S (SEQ.ID.No:33). For the double mutant of UL50-UL53 this has to be done in addition to modification M3.

Reconstitution of Spread-Deficient Human CMV.

$0.7\times10^7$ frozen TCL94/99-BP cells were plated on a 10 cm dish in OPTI-MEM 5% FCS containing 0.2 μg/ml puromycin and two days later the adherent cell were split and plated on 6 cm dishes at densities of $2\times10^6$ cells per dish. On the next day two 6 cm cultures were transfected with 2 μg of purified pTB40E-BAC4-FRT-del94-del99-DNA each by Lipofectamin 2000 (Invitrogen) according to the manufacturer's protocol. 24 h later the two culture were combined and plated on a 10 cm dish in OPTI-MEM 5% ECS. After 10 days the reconstitution of the recombinant TB40E-BAC4-FRT-del194-del99 virus was evident by plaque formation. After 14-16 days the most of the cells in the transfected cultures showed CPE the entire culture was harvested. The amounts of the viable viruses was determined by limiting dilution on sub-confluent TCL94/99-BP cell in 96 well plates using TCID50 (median tissue culture infectious dose) method as described in Mohr et al (Mohr, C. A. et al., 2010. A spread-deficient cytomegalovirus for assessment of first-target cells in vaccination. Virol. 2010 August; 84(15):7730-42. Epub 2010 May 12.). The spread-deficient human CMV reconstituted from TB40E-BAC4-FRT-del94-99, can be propagated using TCL94/99-BP cells after infection with 0.1 MOI per cell using standard protocols for propagation of human CMV as described by Scrivano et al. (Scrivano et al., supra), HCMV lacking secondary envelopment complex, i.e. UL99 and UL94, is spread-deficient.

The phenotype of the UL94-UL99 double deletion CMV reconstituted from TB40E-BAC4-FRTdel94-99 was tested in cell-to-cell spread. This was investigated by infection of MRC5 and TCL94/99-BP cells as essentially described in Example 1 herein, with CMVs reconstituted from TB40E-BAC4-FRT-de194-del99 and TB40E-BAC4-FRT, respectively, followed by removal of excess virus by extensive washing after infection. Next, CFSE stained MRC5 cells were added and virus replication was permitted. After additional 72 h the culture was fixed and stained for immediate-early 1 expression as described in Example 1 herein. This resulted in cells which were either "immediate-early 1"-positive, CFSE-positive or positive for both stains. These cells were counted in each preparation. The missing increase of double positive cells in MRC5 after infection with TB40E-BAC4-FRT-del94-del99 is conclusive to a deficiency in cell-to-cell spread.

EXAMPLE 15

Immunization with Spread-Deficient Human CMV

After primary immunization with an additional boost with spread-deficient human CMV the human sera exhibit at least 64-fold higher neutralizing potency against endotheliotropic a human CMV strains such as TB40E or VR1814 assayed on endothelial-or epithelial cells (such as HUVEC [ATCC CRL 1730] or ARPE-19 [ATCC CRL2302], respectively, than against the same virus assayed on human fibroblasts cell line (such as MRC5, ATCC CLL-171). In addition, specific antibody response is detectable against the gene products of UL130, UL128, or UL131A by Western blot (whereby it is sufficient that at least one specificity is seen).

The following deletions of the indicated genes result in recombinant human beta-herpesviruses which are spread-deficient:

| Effector complex | UL50 gene | UL53 gene | UL94 gene | UL99 gene |
|---|---|---|---|---|
| NEC | + | | | |
| NEC | | + | | |
| NEC | + | + | | |
| SEC | | | + | |
| SEC | | | + | + |

The features of the present invention disclosed in the specification, the claims, the sequence listing and/or the drawings may both separately and in any combination thereof be material for realizing the invention in various forms thereof. It has to be acknowledged that the sequence listing is part of the instant specification.

We claim:

1. A method for the vaccination of a human or for the treatment of a disease of human comprising administering to the human a human beta-herpesvirus, wherein the beta-herpesvirus is spread-deficient and wherein the beta-herpesvirus us endotheliotropic and/or has a wild type-like virion surface, wherein the beta-herpesvirus is deficient in at least one gene product involved in primary and/or secondary envelopment, wherein the at least one gene product involved in primary involvement is encoded by a gene selected from the group consisting of UL50 and UL53 and homologs of each thereof, wherein the at least one gene product involved in secondary envelopment is encoded by a gene selected from the group consisting of UL94 and UL99 and homologs thereof, and wherein the beta-herpesvirus is human cytomegalovirus.

2. The method of claim 1, wherein the beta-herpesvirus is endotheliotropic and has a wild type-like virion surface.

3. The method of claim 1, wherein the beta-herpesvirus induces and immune response, wherein the immune response comprises neutralizing antibodies against beta-herpesvirus and $CD4^+$ and $CD8^+$ T-cells directed against epitopes of beta-herpesvirus.

4. The method of claim 3, wherein the immune response comprises induction of neutralizing antibodies against a wild type beta-herpesvirus, wherein said antibodies are capable of inhibiting said wild type beta-herpesvirus from infecting endothelial cells and/or epithelial cells.

5. The method of claim 1, wherein the beta-herpesvirus comprises a deletion of nucleotides 122631-134667 and 181653-189191 of SEQ ID NO: 20, and wherein SEQ ID NO: 34 is inserted into said virus to replace deleted nucleotides 12263-123667 from SEQ ID NO: 29.

6. The method of claim 1, wherein the beta-herpesvirus further comprises a deletion of nucleotides 130671-131242 of SEQ ID NO: 20.

7. The method of claim 1, wherein SEQ ID NO: 35 is inserted into said virus to replace deleted nucleotides 130671-131242 from SEQ ID NO: 20.

8. The method of claim 1, wherein the beta-herpesvirus comprises a deletion of nucleotides 58443-59622, 181653-189191 of SEQ ID NO: 20, and wherein SEQ ID NO: 32 is inserted into said virus to replace deleted nucleotides 58443-59622 from SEQ ID NO: 20.

9. The method of claim 1, wherein the beta-herpesvirus comprises a deletion of nucleotides 62130-63260 and 181653-189191 of SEQ ID NO: 20 and wherein SEQ ID NO: 33 is inserted into said virus to replace deleted nucleotides 62130-63260 from SEQ ID NO: 20.

10. The method of claim 9, wherein the virus further comprises a deletion of nucleotides 58443-59622.

11. The method of claim 10, wherein SEQ ID NO: 32 is inserted into said virus to replace deleted nucleotides 58443-59622 from SEQ ID NO: 20.

12. The method of claim 1, wherein the beta-herpesvirus comprises the nucleotide sequence of SEQ ID NO: 23.

13. The method of claim 1, wherein the beta-herpesvirus is deficient in at least one gene product encoded by an immune evasive gene, wherein the at least one gene product encoded by an immune evasive gene is selected from the group comprising gene products regulating MHC class I presentation and gene products regulating NK cell response.

14. The method of claim 13, wherein the gene product regulating NK cell response is selected from the group comprising gene products encoded by the genes UL40, UL16 and UL18.

15. The method of claim 13, wherein the gene product regulating MHC class I presentation is selected from the group consisting of US6, US3, US2, UL18, US11, UL83 and UL40.

16. The method of claim 1, wherein the beta-herpesvirus encodes a heterologous nucleic acid, wherein the heterologous nucleic acid is a functional nucleic acid selected from the group consisting of antisense molecules, ribozymes and RNA interference mediating nucleic acids, or a nucleic acid a nucleic acid coding for a peptide, oligopeptide, polypeptide or protein.

17. The method of claim 1, wherein the disease is a disease associated with human cytomegalovirus infection.

18. The method of claim 17, wherein the disease comprises congenital inclusion disease.

19. The method of claim 1, wherein the vaccination is against a disease, wherein the disease is a disease associated with human cytomegalovirus infection.

20. The method of claim 19, wherein the disease comprises congenital inclusion disease.

* * * * *

SEQUENCE LISTING

<160> NUMBER OF SEQ ID NOS: 35

<210> SEQ ID NO 1
<211> LENGTH: 57
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNA

<400> SEQUENCE: 1
gtgggatcca ccatgtaccc ctacgacgtg cccgactacg ccacgtccag actatcc 57

<210> SEQ ID NO 2
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 2
actctagagt cgacttcaca tgtgctcgag aaca 34

<210> SEQ ID NO 3
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 3
aattcatgat aacttcgtat agcatacatt atacgaagtt atccggagat atccaccggt 60
ctggcggccg c 71

<210> SEQ ID NO 4
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 4
tcgagcggcc gccagaccgg tggatatctc cggataactt cgtataatgt atgctatacg 60
aagttatcat g 71

<210> SEQ ID NO 5
<211> LENGTH: 68
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 5
cgtggtcaag ccggtcgtgt tgtaccagaa ctcgacttcg gtcgcgttgc ttacaattta 60
cgcgcggg 68

<210> SEQ ID NO 6
<211> LENGTH: 69
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 6
ccccgatatt tgagaaagtg taccccgata ttcagtacct cttgactaag aagccataga 60
gcccaccgc 69

<210> SEQ ID NO 7
<211> LENGTH: 112
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 7
tgcttcccgg cggcttctgc gcgaccttcc agctgcaggt agaccacggc gacgtccaga 60
ctatccgtga aaagtttgag aagcatcagt agccgatttc ggcctattgg tt 112

<210> SEQ ID NO 8
<211> LENGTH: 77
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 8
catggatggg ttggttgatt tgtatgtctg ttggctactc acatgtgctc gagaagccag 60
tgtgatggat gatcctc 77

<210> SEQ ID NO 9
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: PEPTIDE
<222> LOCATION: (1)..(8)

<400> SEQUENCE: 9

Ser Ile Ile Asn Phe Glu Lys Leu
1 5

<210> SEQ ID NO 10
<211> LENGTH: 8
<212> TYPE: PRT
<213> ORGANISM: Artificial
<220> FEATURE:
<223> OTHER INFORMATION: synthetic
<220> FEATURE:

<221> NAME/KEY: PEPTIDE
<222> LOCATION: (1)..(8)

<400> SEQUENCE: 10

Thr Val Tyr Gly Phe Cys Leu Leu
1               5

<210> SEQ ID NO 11
<211> LENGTH: 8
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(8)

<400> SEQUENCE: 11

Arg Ala Leu Glu Tyr Lys Asn Leu
1               5

<210> SEQ ID NO 12
<211> LENGTH: 9
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(9)

<400> SEQUENCE: 12

Ser Cys Leu Glu Phe Trp Gln Arg Val
1               5

<210> SEQ ID NO 13
<211> LENGTH: 9
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(9)

<400> SEQUENCE: 13

His Gly Ile Arg Asn Ala Ser Phe Ile
1               5

<210> SEQ ID NO 14
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 14
aacgtacatc gctctctgct ggccg                                            25

<210> SEQ ID NO 15
<211> LENGTH: 940
<212> TYPE: DNA
<213> ORGANISM: artificial
<220> FEATURE:
<223> OTHER INFORMATION: synthetic

<400> SEQUENCE: 15
ttactgggtg ctgccgggcg gctttgccgt ctcttcgcgc gtcactcttc acggcctggc 60
ccagcgagcc ctgcgggacc ggttccaaaa cttcgaggcc gtgctggccc ggggcatgca 120
cgtggaggcc ggccggcagg agcccgagac cccccgggtg agcggccggc ggctgccctt 180
cgacgacctg tgatccggag gacgacggct cgtgtatctt gtgccaattg ctgttgctct 240
accgcgacgg cgaatggatc ctctgtcttt gctgcaacgg ccgttatcaa ggccactatg 300
gcggggtctg acagttcacg gggagaagaa acaagaaaca acaaaaaaaa aagaggagat 360
ctgcggccgc tagggataac agggtaatcg atgttgacaa ttaatcatcg gcatagtata 420
tcggcatagt ataatacgac aaggtgagga actaaaccat ggcaaaactg accagcgcag 480
ttccggttct gaccgcacgt gatgttgccg gtgccgttga attttggacc gatcgtctgg 540
gttttagccg tgattttgtg gaagatgatt ttgccggtgt tgttcgtgat gatgttaccc 600
tgtttattag cgcagttcag gatcaggttg ttccggataa taccctggca tgggtttggg 660
ttcgtggtct ggatgaactg tatgcagaat ggtcagaagt tgtgagcacc aattttcgtg 720
atgcaagcgg tccggcaatg accgaaattg gtgaacagcc gtggggtcgt gaatttgcac 780
tgcgtgatcc ggcaggtaat tgtgttcatt ttgttgcaga agaacaggat taacctcgat 840
taattaattg taacattacc ctgttatccc taccggtgtc ctaggcgggg tctgacagtt 900
cacggggaga agaaacaaga aacaacaaaa aaaaaagagg 940

<210> SEQ ID NO 16
<211> LENGTH: 719
<212> TYPE: DNA
<213> ORGANISM: artificial
<220> FEATURE:
<223> OTHER INFORMATION: synthetic

<400> SEQUENCE: 16
cgtgttagac cgttggagtc gcgacctgtc ccgcaagacg aacctaccga tctgggtcgc 60
caacagcgcc aacgagtacg tcgtcagctc cgtgccccgc cccgtcagtc cgtagaagta 120
actcataaac tttcaggtct cgcgtacgat tcgcgagtcg ggaatgtagg gataacaggg 180
taatcgatgt tgacaattaa tcatcggcat agtatatcgg catagtataa tacgacaagg 240
tgaggaacta aaccatggca aaactgacca gcgcagttcc ggttctgacc gcacgtgatg 300
ttgccggtgc cgttgaattt tggaccgatc gtctgggttt tagccgtgat tttgtggaag 360
atgattttgc cggtgttgtt cgtgatgatg ttaccctgtt tattagcgca gttcaggatc 420
aggttgttcc ggataatacc ctggcatggg tttgggttcg tggtctggat gaactgtatg 480
cagaatggtc agaagttgtg agcaccaatt ttcgtgatgc aagcggtccg gcaatgaccg 540
aaattggtga acagccgtgg ggtcgtgaat ttgcactgcg tgatccggca ggtaattgtg 600
ttcattttgt tgcagaagaa caggattaac ctcgattaat taattgtaac attaccctgt 660
tatccctaaa gtaactcata aactttcagg tctcgcgtac gattcgcgag tcgggaatg 719

<210> SEQ ID NO 17
<211> LENGTH: 9048
<212> TYPE: DNA
<213> ORGANISM: artificial
<220> FEATURE:
<223> OTHER INFORMATION: synthetic

<400> SEQUENCE: 17
actagtcggg gtcattagtt catagcccat atatggagtt ccgcgttaca taacttacgg 60

-continued

```
taaatggccc gcctggctga ccgcccaacg acccccgccc attgacgtca ataatgacgt    120
atgttcccat agtaacgcca atagggactt tccattgacg tcaatgggtg gagtatttac    180
ggtaaactgc ccacttggca gtacatcaag tgtatcatat gccaagtacg ccccctattg    240
acgtcaatga cggtaaatgg cccgcctggc attatgccca gtacatgacc ttatgggact    300
ttcctacttg gcagtacatc tacgtattag tcatcgctat taccatggtg atgcggtttt    360
ggcagtacat caatgggcgt ggatagcggt ttgactcacg gggatttcca agtctccacc    420
ccattgacgt caatgggagt ttgttttggc accaaaatca acgggacttt ccaaaatgtc    480
gtaacaactc cgccccattg acgcaaatgg gcggtaggcg tgtacggtgg gaggtctata    540
taagcagagc tggtttagtg aaccgggtct ctctggttag accagatttg agcctgggag    600
ctctctggct aactagggaa cccactgctt aagcctcaat aaagcttgcc ttgagtgctt    660
caagtagtgt gtgcccgtct gttgtgtgac tctggtaact agagatccct cagacccttt    720
tagtcagtgt ggaaaatctc tagcagtggc gcccgaacag ggacctgaaa gcgaaaggga    780
aaccagagga gctctctcga cgcaggactc ggcttgctga agcgcgcacg gcaagaggcg    840
aggggcggcg actgcagagt acgccaaaaa ttttgactag cggaggctag aaggagagag    900
atgggtgcga gagcgtcagt attaagcggg ggaaaatagc ggccgccaca attttaaaag    960
aaaagggggg attggggggt acagtgcagg ggaaagaata gtagacataa tagcaacaga   1020
catacaaact aaagaattac aaaaacaaat tacaaaaatt caaattttcg gggatcccca   1080
tggtggccct cctatagtga gtcgtattat actatgccga tatactatgc cgatgattaa   1140
ttgtcaacac gtgctgcagg tccgaggttc tagcgcgtgg cctccgcgcc gggttttggc   1200
gcctcccgcg ggcgcccccc tcctcacggc gagcgctgcc acgtcagacg aagggcgcag   1260
cgagcgtcct gatccttccg cccggacgct caggacagcg gcccgctgct cataagactc   1320
ggccttagaa ccccagtatc agcagaagga cattttagga cgggacttgg gtgactctag   1380
ggcactggtt ttctttccag agagcggaac aggcgaggaa aagtagtccc ttctcggcga   1440
ttctgcggag ggatctccgt ggggcggtga acgccgatga ttatataagg acgcgccggg   1500
tgtggcacag ctagttccgt cgcagccggg atttgggtcg cggttcttgt ttgtggatcg   1560
ctgtgatcgt cacttggtga gtagcgggct gctgggctgg ccggggcttt cgtggccgcc   1620
gggccgctcg gtgggacgga agcgtgtgga gagaccgcca agggctgtag tctgggtccg   1680
cgagcaaggt tgccctgaac tgggggttgg ggggagcgca gcaaaatggc ggctgttccc   1740
gagtcttgaa tggaagacgc ttgtgaggcg ggctgtgagg tcgttgaaac aaggtggggg   1800
gcatggtggg cggcaagaac ccaaggtctt gaggccttcg ctaatgcggg aaagctctta   1860
ttcgggtgag atgggctggg gcaccatctg ggaccctga cgtgaagttt gtcactgact   1920
ggagaactcg gtttgtcgtc tgttgcgggg gcggcagtta tggcggtgcc gttgggcagt   1980
gcacccgtac ctttgggagc gcgcgccctc gtcgtgtcgt gacgtcaccc gttctgttgg   2040
cttataatgc agggtggggc cacctgccgg taggtgtgcg gtaggctttt ctccgtcgca   2100
ggacgcaggg ttcgggccta gggtaggctc tcctgaatcg acaggcgccg gacctctggt   2160
gaggggaggg ataagtgagg cgtcagtttc tttggtcggt tttatgtacc tatcttctta   2220
agtagctgaa gctccggttt tgaactatgc gctcggggtt ggcgagtgtg ttttgtgaag   2280
ttttttaggc accttttgaa atgtaatcat ttgggtcaat atgtaatttt cagtgttaga   2340
ctagtaaatt gtccgctaaa ttctggccgt ttttggcttt tttgttagac gctagcctag   2400
```

-continued

```
cggatccgaa ttctgcagat atcaacaagt ttgtacaaaa aagcaggctt aatggcttgg   2460
cgcagcgggc tttgcgagac cgattccaga actttgaagc agttcttgca agaggaatgc   2520
atgtggaagc tggtcggcaa gagccggaaa caccgcgagt atcgggccgt cgcttgccgt   2580
tcgacgatct ttagtccgga ggacgacggc tcgtgtatct tgtgccaatt gctgttgctc   2640
taccgcgacg gcgaatggat cctctgtctt tgctgcaacg gccgttatca aggccactat   2700
ggcgtgggcc acgtacatcg gcgtcgtcga cgcatctgtc atttacctac cttgtaccaa   2760
ctgagcttcg gaggtccttt gggtccagcc agcattgatt tcttgccaag ctttagccag   2820
gtgaccagca gtatgacgtg cgatggtatt acgcccgacg tgatttacga ggtctgcatg   2880
ttggtgcccc aggatgaagc caagcgcatc ctggtcaagg gtcacggtgc catggacctg   2940
acctgtcaga aggcagtgac gctaggcggc gccggcgcct ggttgctgcc gcgtcccgaa   3000
ggctacacgc ttttctttta cattctgtgc tacgacctgt ttacctcatg cggcaatcgg   3060
tgcgatatcc cttccatgac gcggctcatg gcggcggcca cggcctgcgg gcaggcgggt   3120
tgcagctttt gcacggatca cgagggacat gtagatccca ctggcaatta cgtgggttgc   3180
acccccgata tgggccgctg tctttgttac gtgccctgtg ggcccatgac gcagtcgctc   3240
atccacaacg atgaacccgc gactttttc tgtgagagcg atgacgccaa atacctatgc   3300
gccgtaggtt ctaagaccgc ggcgcaggtc acactgggag acggcctgga ttatcacatc   3360
ggtgtcaagg attctgaggg ccgatggttg cccgtcaaga ccgatgtgtg ggacctggtc   3420
aaggtagagg aacctgtgtc acgtatgata gtgtgttcct gtccggtgct taagaaccta   3480
gtgcactaaa cccagctttc ttgtacaaag tggttgatat ccagcacagt ggcggccgct   3540
cgagtctaga gggcccgcgg ttcgaaggta agcctatccc taaccctctc ctcggtctcg   3600
attctacgcg ccgcggccgc tacgtaaatt ccgcccctct ccctaacgtt actggccgaa   3660
gccgcttgga ataaggccgg tgtgcgtttg tctatatgtt attttccacc atattgccgt   3720
cttttggcaa tgtgagggcc cggaaacctg gccctgtctt cttgacgagc attcctaggg   3780
gtctttcccc tctcgccaaa ggaatgcaag gtctgttgaa tgtcgtgaag gaagcagttc   3840
ctctggaagc ttcttgaaga caaacaacgt ctgtagcgac cctttgcagg cagcggaacc   3900
ccccacctgg cgacaggtgc ctctgcggcc aaaagccacg tgtataagat acacctgcaa   3960
aggcggcaca accccagtgc cacgttgtga gttggatagt tgtggaaaga gtcaaatggc   4020
tctcctcaag cgtattcaac aaggggctga aggatgccca gaaggtaccc cattgtatgg   4080
gatctgatct ggggcctcgg tgcacatgct ttacatgtgt ttagtcgagg ttaaaaaacg   4140
tctaggcccc ccgaaccacg gggacgtggt tttcctttga aaaacacgat gataatatgg   4200
ccacaaccat gaccgagtac aagcccacgg tgcgcctcgc cacccgcgac gacgtccccc   4260
gggccgtacg ggatcccgcc accatggtga gcaagggcga ggaggataac atggccatca   4320
tcaaggagtt catgcgcttc aaggtgcaca tggagggctc cgtgaacggc cacgagttcg   4380
agatcgaggg cgagggcgag ggccgcccct acgagggcac ccagaccgcc aagctgaagg   4440
tgaccaaggg tggccccctg cccttcgcct gggacatcct gtcccctcag ttcatgtacg   4500
gctccaaggc ctacgtgaag caccccgccg acatccccga ctacttgaag ctgtccttcc   4560
ccgagggctt caagtgggag cgcgtgatga acttcgagga cggcggcgtg gtgaccgtga   4620
cccaggactc ctccctgcag gacggcgagt tcatctacaa ggtgaagctg cgcggcacca   4680
acttcccctc cgacggcccc gtaatgcaga agaagaccat gggctgggag gcctcctccg   4740
agcggatgta ccccgaggac ggcgccctga agggcgagat caagcagagg ctgaagctga   4800
```

aggacggcgg ccactacgac gctgaggtca agaccaccta caaggccaag aagcccgtgc 4860
agctgcccgg cgcctacaac gtcaacatca agttggacat cacctcccac aacgaggact 4920
acaccatcgt ggaacagtac gaacgcgccg agggccgcca ctccaccggc ggcatggacg 4980
agctgtacaa gtaagtcgac ccggaccgcc acatcgagcg ggtcaccgag ctgcaagaac 5040
tcttcctcac gcgcgtcggg ctcgacatcg gcaaggtgtg ggtcgcggac gacggcgccg 5100
cggtggcggt ctggaccacg ccggagagcg tcgaagcggg ggcggtgttc gccgagatcg 5160
gctcgcgcat ggccgagttg agcggttccc ggctggccgc gcagcaacag atggaaggcc 5220
tcctggcgcc gcaccggccc aaggagcccg cgtggttcct ggccaccgtc ggcgtctcgc 5280
ccgaccacca gggcaagggt ctgggcagcg ccgtcgtgct ccccggagtg gaggcggccg 5340
agcgcgctgg ggtgcccgcc ttcctggaga cctccgcgcc ccgcaacctc cccttctacg 5400
agcggctcgg cttcaccgtc accgccgacg tcgaggtgcc cgaaggaccg cgcacctggt 5460
gcatgacccg caagcccggt gcctgagttc gcgtctggaa caatcaacct ctggactcga 5520
caatcaacct ctggattaca aaatttgtga aagattgact ggtattctta actatgttgc 5580
tccttttacg ctatgtggat acgctgcttt aatgcctttg tatcatgcta ttgcttcccg 5640
tatggctttc attttctcct ccttgtataa atcctggttg ctgtctcttt atgaggagtt 5700
gtggcccgtt gtcaggcaac gtggcgtggt gtgcactgtg tttgctgacg caacccccac 5760
tggttggggc attgccacca cctgtcagct cctttccggg actttcgctt tccccctccc 5820
tattgccacg gcggaactca tcgccgcctg ccttgcccgc tgctggacag gggctcggct 5880
gttgggcact gacaattccg tggtgttgtc ggggaaatca tcgtcctttc cttggctgct 5940
cgcctgtgtt gccacctgga ttctgcgcgg gacgtccttc tgctacgtcc cttcggccct 6000
caatccagcg gaccttcctt cccgcggcct gctgccggct ctgcggcctc ttccgcgtct 6060
tcgccttcgc cctcagacga gtcggatctc cctttgggcc gcctccccgc ttagtactgg 6120
tacctttaag accaatgact tacaaggcag ctgtagatct tagccacttt ttaaaagaaa 6180
aggggggact ggaagggcta attcactccc aacgaagaca agattccgga atttatttgt 6240
gaaatttgtg atgctattgc tttatttgta aaccggtgca gctgcttttt gcctgtactg 6300
ggtctctctg gttagaccag atctgagcct gggagctctc tggctaacta gggaacccac 6360
tgcttaagcc tcaataaagc ttgccttgag tgcttcaagt agtgtgtgcc cgtctgttgt 6420
gtgactctgg taactagaga tccctcagac ccttttagtc agtgtggaaa atctctagca 6480
tctagagtat gcaaagcatg catctcaatt agtcagcaac caggtgtgga aagtccccag 6540
gctccccagc aggcagaagt atgcaaagca tgcatctcaa ttagtcagca accatagtcc 6600
cgcccctaac tccgcccatc ccgcccctaa ctccgcccag ttccgcccat tctccgcccc 6660
atggctgact aatttttttt atttatgcag aggccgaggc cgcctcggcc tctgagctat 6720
tccagaagta gtgaggaggc ttttttggag gcctaggcta gagatcataa tcagccatac 6780
cacatttgta gaggttttac ttgctttaaa aaacctccca cacctccccc tgaacctgaa 6840
acataaaatg aatgcaattg ttgttgttaa cttgtttatt gcagcttata atggttacaa 6900
ataaagcaat agcatcacaa atttcacaaa taaagcattt ttttcactgc attctagttg 6960
tggtttgtcc aaactcatca atgtatctta tcatgtctgc tagccgggct ttttttttctt 7020
aggccttctt ccgcttcctc gctcactgac tcgctgcgct cggtcgttcg gctgcggcga 7080
gcggtatcag ctcactcaaa ggcggtaata cggttatcca cagaatcagg ggataacgca 7140
ggaaagaaca tgtgagcaaa aggccagcaa aaggccagga accgtaaaaa ggccgcgttg 7200
ctggcgtttt tccataggct ccgcccccct gacgagcatc acaaaaatcg acgctcaagt 7260
cagaggtggc gaaacccgac aggactataa agataccagg cgtttccccc tggaagctcc 7320
ctcgtgcgct ctcctgttcc gaccctgccg cttaccggat acctgtccgc ctttctccct 7380
tcgggaagcg tggcgctttc tcatagctca cgctgtaggt atctcagttc ggtgtaggtc 7440
gttcgctcca agctgggctg tgtgcacgaa ccccccgttc agcccgaccg ctgcgcctta 7500
tccggtaact atcgtcttga gtccaacccg gtaagacacg acttatcgcc actggcagca 7560
gccactggta acaggattag cagagcgagg tatgtaggcg gtgctacaga gttcttgaag 7620
tggtggccta actacggcta cactagaaga acagtatttg gtatctgcgc tctgctgaag 7680
ccagttacct tcggaaaaag agttggtagc tcttgatccg gcaaacaaac caccgctggt 7740
agcggtggtt tttttgtttg caagcagcag attacgcgca gaaaaaaagg atctcaagaa 7800
gatcctttga tcttttctac ggggtctgac gctcagtgga acgaaaactc acgttaaggg 7860
attttggtca tgagattatc aaaaaggatc ttcacctaga tccttttaaa ttaaaaatga 7920
agttttaaat caatctaaag tatatatgag taaacttggt ctgacagtta ccaatgctta 7980
atcagtgagg cacctatctc agcgatctgt ctatttcgtt catccatagt tgcctgactc 8040
ctgcgcagtc caaaaaaaaa ggctccaaaa ggagccttta attgtatcgg tgggccctta 8100
gaaaaactca tcgagcatca aatgaaactg caatttattc atatcaggat tatcaatacc 8160
atatttttga aaaagccgtt tctgtaatga aggagaaaac tcaccgaggc agttccatag 8220
gatggcaaga tcctggtatc ggtctgcgat tccgactcgt ccaacatcaa tacaacctat 8280
taatttcccc tcgtcaaaaa taaggttatc aagtgagaaa tcaccatgag tgacgactga 8340
atccggtgag aatggcaaaa gcttatgcat ttctttccag acttgttcaa caggccagcc 8400
attacgctcg tcatcaaaat cactcgcatc aaccaaaccg ttattcattc gtgattgcgc 8460
ctgagcgaga cgaaatacgc gatcgctgtt aaaaggacaa ttacaaacag gaatcgaatg 8520
caaccggcgc aggaacactg ccagcgcatc aacaatattt tcacctgaat caggatattc 8580
ttctaatacc tggaatgctg ttttcccggg gatcgcagtg gtgagtaacc atgcatcatc 8640
aggagtacgg ataaaatgct tgatggtcgg aagaggcata aattccgtca gccagtttag 8700
tctgaccatc tcatctgtaa catcattggc aacgctacct ttgccatgtt tcagaaacaa 8760
ctctggcgca tcgggcttcc catacaatcg atagattgtc gcacctgatt gcccgacatt 8820
atcgcgagcc catttatacc catataaatc agcatccatg ttggaattta atcgcggcct 8880
cgagcaagac gtttcccgtt gaatatggct cataacaccc cttgtattac tgtttatgta 8940
agcagacagt tttattgttc atgatgatat atttttatct tgtgcaatgt aacatcagag 9000
attttgagac acaacgtggt ttaaacaaat agtcaaaagc ctccggcg 9048

<210> SEQ ID NO 18
<211> LENGTH: 8455
<212> TYPE: DNA
<213> ORGANISM: artificial
<220> FEATURE:
<223> OTHER INFORMATION: synthetic

<400> SEQUENCE: 18
actagtcggg gtcattagtt catagcccat atatggagtt ccgcgttaca taacttacgg 60
taaatggccc gcctggctga ccgcccaacg acccccgccc attgacgtca ataatgacgt 120
atgttcccat agtaacgcca atagggactt tccattgacg tcaatgggtg gagtatttac 180

-continued

```
ggtaaactgc ccacttggca gtacatcaag tgtatcatat gccaagtacg ccccctattg    240
acgtcaatga cggtaaatgg cccgcctggc attatgccca gtacatgacc ttatgggact    300
ttcctacttg gcagtacatc tacgtattag tcatcgctat taccatggtg atgcggtttt    360
ggcagtacat caatgggcgt ggatagcggt ttgactcacg gggatttcca agtctccacc    420
ccattgacgt caatgggagt ttgttttggc accaaaatca acgggacttt ccaaaatgtc    480
gtaacaactc cgccccattg acgcaaatgg gcggtaggcg tgtacggtgg gaggtctata    540
taagcagagc tggtttagtg aaccgggtct ctctggttag accagatttg agcctgggag    600
ctctctggct aactagggaa cccactgctt aagcctcaat aaagcttgcc ttgagtgctt    660
caagtagtgt gtgcccgtct gttgtgtgac tctggtaact agagatccct cagacccttt    720
tagtcagtgt ggaaaatctc tagcagtggc gcccgaacag ggacctgaaa gcgaaaggga    780
aaccagagga gctctctcga cgcaggactc ggcttgctga agcgcgcacg gcaagaggcg    840
aggggcggcg actgcagagt acgccaaaaa ttttgactag cggaggctag aaggagagag    900
atgggtgcga gagcgtcagt attaagcggg ggaaaatagc ggccgccaca attttaaaag    960
aaaagggggg attggggggt acagtgcagg ggaaagaata gtagacataa tagcaacaga   1020
catacaaact aaagaattac aaaaacaaat tacaaaaatt caaattttcg gggatccca    1080
tggtggccct cctatagtga gtcgtattat actatgccga tatactatgc cgatgattaa   1140
ttgtcaacac gtgctgcagg tccgaggttc tagcgcgtgg cctccgcgcc gggttttggc   1200
gcctcccgcg ggcgcccccc tcctcacggc gagcgctgcc acgtcagacg aagggcgcag   1260
cgagcgtcct gatccttccg cccggacgct caggacagcg gcccgctgct cataagactc   1320
ggccttagaa ccccagtatc agcagaagga cattttagga cgggacttgg gtgactctag   1380
ggcactggtt ttctttccag agagcggaac aggcgaggaa aagtagtccc ttctcggcga   1440
ttctgcggag ggatctccgt ggggcggtga acgccgatga ttatataagg acgcgccggg   1500
tgtggcacag ctagttccgt cgcagccggg atttgggtcg cggttcttgt ttgtggatcg   1560
ctgtgatcgt cacttggtga gtagcgggct gctgggctgg ccggggcttt cgtggccgcc   1620
gggccgctcg gtgggacgga agcgtgtgga gagaccgcca agggctgtag tctgggtccg   1680
cgagcaaggt tgccctgaac tgggggttgg ggggagcgca gcaaaatggc ggctgttccc   1740
gagtcttgaa tggaagacgc ttgtgaggcg ggctgtgagg tcgttgaaac aaggtggggg   1800
gcatggtggg cggcaagaac ccaaggtctt gaggccttcg ctaatgcggg aaagctctta   1860
ttcgggtgag atgggctggg gcaccatctg ggaccctga cgtgaagttt gtcactgact    1920
ggagaactcg gtttgtcgtc tgttgcgggg gcggcagtta tggcggtgcc gttgggcagt   1980
gcacccgtac ctttgggagc gcgcgccctc gtcgtgtcgt gacgtcaccc gttctgttgg   2040
cttataatgc agggtggggc cacctgccgg taggtgtgcg gtaggctttt ctccgtcgca   2100
ggacgcaggg ttcgggccta gggtaggctc tcctgaatcg acaggcgccg gacctctggt   2160
gaggggaggg ataagtgagg cgtcagtttc tttggtcggt tttatgtacc tatcttctta   2220
agtagctgaa gctccggttt tgaactatgc gctcggggtt ggcgagtgtg ttttgtgaag   2280
ttttttaggc accttttgaa atgtaatcat ttgggtcaat atgtaatttt cagtgttaga   2340
ctagtaaatt gtccgctaaa ttctggccgt ttttggcttt tttgttagac gctagcctag   2400
cggatccgaa ttctcactat agggagaccc aagcttggta ccgagctcgg atccaccatg   2460
ggtggcgaac tctgcaaacg aatatgttgt gagttcggta ccacgtccgg tgagcccctg   2520
```

-continued

```
aaagatgctc tgggtcgcca ggtgtctcta cgctcctacg acaacatccc tccgacttcc   2580
tcctcggacg aaggggagga cgatgacgac ggggaggatg acgataacga ggagcggcaa   2640
cagaagctgc ggctctgcgg tagtggctgc gggggaaacg acagtagtag cggcagccac   2700
cgcgaggcca cccacgacgg ccccaagaaa aacgcggtgc gctcgacgtt tcgcgaggac   2760
aaggctccga aaccgagcaa gcagtcaaaa aagaaaaaga aaccctcaaa acatcaccac   2820
catcagcaaa gctccattat gcaggagacg gacgacttag acgaagaaga cacctcaatt   2880
tacctgtccc cgcccccggt ccccccgtc caggtggtgg ctaagcgact gccgcggccc   2940
gacacaccca ggactccgcg ccaaaagaag atttcacaac gtccacccac ccccgggaca   3000
aaaaagcccg ccgccccctt gtccttttaa agtcgactct agagggccct attctatagt   3060
gtcacctaaa tgctagagct cgctgatcag acgcgccgcg gccgctacgt aaattccgcc   3120
cctctcccta acgttactgg ccgaagccgc ttggaataag gccggtgtgc gtttgtctat   3180
atgttatttt ccaccatatt gccgtctttt ggcaatgtga gggcccggaa acctggccct   3240
gtcttcttga cgagcattcc taggggtctt tcccctctcg ccaaaggaat gcaaggtctg   3300
ttgaatgtcg tgaaggaagc agttcctctg gaagcttctt gaagacaaac aacgtctgta   3360
gcgacccttt gcaggcagcg gaacccccca cctggcgaca ggtgcctctg cggccaaaag   3420
ccacgtgtat aagatacacc tgcaaaggcg gcacaacccc agtgccacgt tgtgagttgg   3480
atagttgtgg aaagagtcaa atggctctcc tcaagcgtat tcaacaaggg gctgaaggat   3540
gcccagaagg taccccattg tatgggatct gatctggggc ctcggtgcac atgctttaca   3600
tgtgtttagt cgaggttaaa aaacgtctag gccccccgaa ccacggggac gtggttttcc   3660
tttgaaaaac acgatgataa tatggtgagc aagggcgagg agctgttcac cggggtggtg   3720
cccatcctgg tcgagctgga cggcgacgta aacggccaca agttcagcgt gtccggcgag   3780
ggcgagggcg atgccaccta cggcaagctg accctgaagt tcatctgcac caccggcaag   3840
ctgcccgtgc cctggcccac cctcgtgacc accctgacct acggcgtgca gtgcttcagc   3900
cgctaccccg accacatgaa gcagcacgac ttcttcaagt ccgccatgcc cgaaggctac   3960
gtccaggagc gcaccatctt cttcaaggac gacggcaact acaagacccg cgccgaggtg   4020
aagttcgagg gcgacaccct ggtgaaccgc atcgagctga agggcatcga cttcaaggag   4080
gacggcaaca tcctggggca caagctggag tacaactaca acagccacaa cgtctatatc   4140
atggccgaca agcagaagaa cggcatcaag gtgaacttca agatccgcca caacatcgag   4200
gacggcagcg tgcagctcgc cgaccactac cagcagaaca cccccatcgg cgacggcccc   4260
gtgctgctgc ccgacaacca ctacctgagc acccagtccg ccctgagcaa agaccccaac   4320
gagaagcgcg atcacatggt cctgctggag ttcgtgaccg ccgccgggat cactctcggc   4380
atggacgagc tgtacaagta agtcgacccg gaccgccaca tcgagcgggt caccgagctg   4440
caagaactct tcctcacgcg cgtcgggctc gacatcggca aggtgtgggt cgcggacgac   4500
ggcgccgcgg tggcggtctg gaccacgccg gagagcgtcg aagcgggggc ggtgttcgcc   4560
gagatcggct cgcgcatggc cgagttgagc ggttcccggc tggccgcgca gcaacagatg   4620
gaaggcctcc tggcgccgca ccggcccaag gagcccgcgt ggttcctggc caccgtcggc   4680
gtctcgcccg accaccaggg caagggtctg ggcagcgccg tcgtgctccc cggagtggag   4740
gcggccgagc gcgctggggt gcccgccttc ctggagacct ccgcgccccg caacctcccc   4800
ttctacgagc ggctcggctt caccgtcacc gccgacgtcg aggtgcccga aggaccgcgc   4860
acctggtgca tgacccgcaa gcccggtgcc tgagttcgcg tctggaacaa tcaacctctg   4920
```

```
gactcgacaa tcaacctctg gattacaaaa tttgtgaaag attgactggt attcttaact   4980
atgttgctcc ttttacgcta tgtggatacg ctgctttaat gcctttgtat catgctattg   5040
cttcccgtat ggctttcatt ttctcctcct tgtataaatc ctggttgctg tctctttatg   5100
aggagttgtg gcccgttgtc aggcaacgtg gcgtggtgtg cactgtgttt gctgacgcaa   5160
cccccactgg ttggggcatt gccaccacct gtcagctcct ttccgggact ttcgctttcc   5220
ccctccctat tgccacggcg gaactcatcg ccgcctgcct tgcccgctgc tggacagggg   5280
ctcggctgtt gggcactgac aattccgtgg tgttgtcggg gaaatcatcg tcctttcctt   5340
ggctgctcgc ctgtgttgcc acctggattc tgcgcgggac gtccttctgc tacgtccctt   5400
cggccctcaa tccagcggac cttccttccc gcggcctgct gccggctctg cggcctcttc   5460
cgcgtcttcg ccttcgccct cagacgagtc ggatctccct ttgggccgcc tccccgctta   5520
gtactggtac ctttaagacc aatgacttac aaggcagctg tagatcttag ccacttttta   5580
aaagaaaagg ggggactgga agggctaatt cactcccaac gaagacaaga ttccggaatt   5640
tatttgtgaa atttgtgatg ctattgcttt atttgtaaac cggtgcagct gctttttgcc   5700
tgtactgggt ctctctggtt agaccagatc tgagcctggg agctctctgg ctaactaggg   5760
aacccactgc ttaagcctca ataaagcttg ccttgagtgc ttcaagtagt gtgtgcccgt   5820
ctgttgtgtg actctggtaa ctagagatcc ctcagaccct tttagtcagt gtggaaaatc   5880
tctagcatct agagtatgca aagcatgcat ctcaattagt cagcaaccag gtgtggaaag   5940
tccccaggct ccccagcagg cagaagtatg caaagcatgc atctcaatta gtcagcaacc   6000
atagtcccgc ccctaactcc gcccatcccg cccctaactc cgcccagttc cgcccattct   6060
ccgccccatg gctgactaat tttttttatt tatgcagagg ccgaggccgc ctcggcctct   6120
gagctattcc agaagtagtg aggaggcttt tttggaggcc taggctagag atcataatca   6180
gccataccac atttgtagag gttttacttg ctttaaaaaa cctcccacac ctccccctga   6240
acctgaaaca taaaatgaat gcaattgttg ttgttaactt gtttattgca gcttataatg   6300
gttacaaata aagcaatagc atcacaaatt tcacaaataa agcatttttt tcactgcatt   6360
ctagttgtgg tttgtccaaa ctcatcaatg tatcttatca tgtctgctag ccgggctttt   6420
ttttcttagg ccttcttccg cttcctcgct cactgactcg ctgcgctcgg tcgttcggct   6480
gcggcgagcg gtatcagctc actcaaaggc ggtaatacgg ttatccacag aatcagggga   6540
taacgcagga aagaacatgt gagcaaaagg ccagcaaaag gccaggaacc gtaaaaaggc   6600
cgcgttgctg gcgtttttcc ataggctccg cccccctgac gagcatcaca aaaatcgacg   6660
ctcaagtcag aggtggcgaa acccgacagg actataaaga taccaggcgt ttccccctgg   6720
aagctccctc gtgcgctctc ctgttccgac cctgccgctt accggatacc tgtccgcctt   6780
tctcccttcg ggaagcgtgg cgctttctca tagctcacgc tgtaggtatc tcagttcggt   6840
gtaggtcgtt cgctccaagc tgggctgtgt gcacgaaccc cccgttcagc ccgaccgctg   6900
cgccttatcc ggtaactatc gtcttgagtc caacccggta agacacgact tatcgccact   6960
ggcagcagcc actggtaaca ggattagcag agcgaggtat gtaggcggtg ctacagagtt   7020
cttgaagtgg tggcctaact acggctacac tagaagaaca gtatttggta tctgcgctct   7080
gctgaagcca gttaccttcg gaaaaagagt tggtagctct tgatccggca aacaaaccac   7140
cgctggtagc ggtggttttt ttgtttgcaa gcagcagatt acgcgcagaa aaaaaggatc   7200
tcaagaagat cctttgatct tttctacggg gtctgacgct cagtggaacg aaaactcacg   7260
```

-continued ttaagggatt ttggtcatga gattatcaaa aaggatcttc acctagatcc ttttaaatta 7320
aaaatgaagt tttaaatcaa tctaaagtat atatgagtaa acttggtctg acagttacca 7380
atgcttaatc agtgaggcac ctatctcagc gatctgtcta tttcgttcat ccatagttgc 7440
ctgactcctg cgcagtccaa aaaaaaaggc tccaaaagga gcctttaatt gtatcggtgg 7500
gcccttagaa aaactcatcg agcatcaaat gaaactgcaa tttattcata tcaggattat 7560
caataccata tttttgaaaa agccgtttct gtaatgaagg agaaaactca ccgaggcagt 7620
tccataggat ggcaagatcc tggtatcggt ctgcgattcc gactcgtcca acatcaatac 7680
aacctattaa tttcccctcg tcaaaaataa ggttatcaag tgagaaatca ccatgagtga 7740
cgactgaatc cggtgagaat ggcaaaagct tatgcatttc tttccagact tgttcaacag 7800
gccagccatt acgctcgtca tcaaaatcac tcgcatcaac caaaccgtta ttcattcgtg 7860
attgcgcctg agcgagacga aatacgcgat cgctgttaaa aggacaatta caaacaggaa 7920
tcgaatgcaa ccggcgcagg aacactgcca gcgcatcaac aatattttca cctgaatcag 7980
gatattcttc taatacctgg aatgctgttt tcccggggat cgcagtggtg agtaaccatg 8040
catcatcagg agtacggata aaatgcttga tggtcggaag aggcataaat tccgtcagcc 8100
agtttagtct gaccatctca tctgtaacat cattggcaac gctacctttg ccatgtttca 8160
gaaacaactc tggcgcatcg ggcttcccat acaatcgata gattgtcgca cctgattgcc 8220
cgacattatc gcgagcccat ttatacccat ataaatcagc atccatgttg gaatttaatc 8280
gcggcctcga gcaagacgtt tcccgttgaa tatggctcat aacacccctt gtattactgt 8340
ttatgtaagc agacagtttt attgttcatg atgatatatt tttatcttgt gcaatgtaac 8400
atcagagatt ttgagacaca acgtggttta aacaaatagt caaaagcctc cggcg 8455

<210> SEQ ID NO 19
<211> LENGTH: 12088
<212> TYPE: DNA
<213> ORGANISM: artificial
<220> FEATURE:
<223> OTHER INFORMATION: synthetic

<400> SEQUENCE: 19
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggacccg acaggcccga aggaatagaa gaagaaggtg gagagagaga 1980
cagagacaga tccattcgat tagtgaacgg atcggcactg cgtgcgccaa ttctgcagac 2040
aaatggcagt attcatccac aattttaaaa gaaaaggggg gattgggggg tacagtgcag 2100
gggaaagaat agtagacata atagcaacag acatacaaac taaagaatta caaaaacaaa 2160
ttacaaaaat tcaaaatttt cgggtttatt acagggacag cagagatcca gtttggttag 2220
taccgggccc gctctagtcc ggaatcagtc ctgctcctcg gccacgaagt gcacgcagtt 2280
gccggccggg tcgcgcaggg cgaactcccg cccccacggc tgctcgccga tctcggtcat 2340
ggccggcccg gaggcgtccc ggaagttcgt ggacacgacc tccgaccact cggcgtacag 2400
ctcgtccagg ccgcgcaccc acacccaggc cagggtgttg tccggcacca cctggtcctg 2460
gaccgcgctg atgaacaggg tcacgtcgtc ccggaccaca ccggcgaagt cgtcctccac 2520
gaagtcccgg gagaacccga gccggtcggt ccagaactcg accgctccgg cgacgtcgcg 2580
cgcggtgagc accggaacgg cactggtcaa cttggccatg gtggccctcc tatagtgagt 2640
cgtattatac tatgccgata tactatgccg atgattaatt gtcaacacgt gctgcaggtc 2700
cgaggttcta gcgcgtggcc tccgcgccgg gttttggcgc ctcccgcggg cgcccccctc 2760
ctcacggcga gcgctgccac gtcagacgaa gggcgcagcg agcgtcctga tccttccgcc 2820
cggacgctca ggacagcggc ccgctgctca taagactcgg ccttagaacc ccagtatcag 2880
cagaaggaca ttttaggacg ggacttgggt gactctaggg cactggtttt ctttccagag 2940
agcggaacag gcgaggaaaa gtagtccctt ctcggcgatt ctgcggaggg atctccgtgg 3000
ggcggtgaac gccgatgatt atataaggac gcgccgggtg tggcacagct agttccgtcg 3060
cagccgggat ttgggtcgcg gttcttgttt gtggatcgct gtgatcgtca cttggtgagt 3120
agcgggctgc tgggctggcc ggggctttcg tggccgccgg gccgctcggt gggacggaag 3180
cgtgtggaga gaccgccaag ggctgtagtc tgggtccgcg agcaaggttg ccctgaactg 3240

-continued

```
ggggttgggg ggagcgcagc aaaatggcgg ctgttcccga gtcttgaatg gaagacgctt   3300
gtgaggcggg ctgtgaggtc gttgaaacaa ggtggggggc atggtgggcg gcaagaaccc   3360
aaggtcttga ggccttcgct aatgcgggaa agctcttatt cgggtgagat gggctggggc   3420
accatctggg gaccctgacg tgaagtttgt cactgactgg agaactcggt ttgtcgtctg   3480
ttgcgggggc ggcagttatg gcggtgccgt tgggcagtgc acccgtacct ttgggagcgc   3540
gcgccctcgt cgtgtcgtga cgtcacccgt tctgttggct tataatgcag ggtggggcca   3600
cctgccggta ggtgtgcggt aggcttttct ccgtcgcagg acgcagggtt cgggcctagg   3660
gtaggctctc ctgaatcgac aggcgccgga cctctggtga ggggagggat aagtgaggcg   3720
tcagtttctt tggtcggttt tatgtaccta tcttcttaag tagctgaagc tccggttttg   3780
aactatgcgc tcggggttgg cgagtgtgtt ttgtgaagtt ttttaggcac cttttgaaat   3840
gtaatcattt gggtcaatat gtaattttca gtgttagact agtaaattgt ccgctaaatt   3900
ctggccgttt ttggcttttt tgttagacgc tagcctagcg gatccgaatt ctcgaaactt   3960
aagatgcacc cagaaacgct ggtgaaagta aaagatgctg aagatcagtt gggtgcacga   4020
gtgggttaca tcgaactgga tctcaacagc ggtaagatcc ttgagagttt tcgccccgaa   4080
gaacgttttc caatgatgag cacttttaaa gttctgctat gtggcgcggt attatcccgt   4140
attgacgccg ggcaagagca actcggtcgc cgcatacact attctcagaa tgacttggtt   4200
gagtactcac cagtcacaga aaagcatctt acggatggca tgacagtaag agaattatgc   4260
agtgctgcca taaccatgag tgataacact gcggccaact tacttctgac aacgatcgga   4320
ggaccgaagg agctaaccgc ttttttgcac aacatggggg atcatgtaac tcgccttgat   4380
cgttgggaac cggagctgaa tgaagccata ccaaacgacg agcgtgacac cacgacgcct   4440
gtagcaatgg caacaacgtt gcgcaaacta ttaactggct ccggaggcgg cggctccggc   4500
ggcggcggct cgagcggcgg cggcggatcc ctacttactc tagcttcccg gcaacaatta   4560
atagactgga tggaggcgga taaagttgca ggaccacttc tgcgctcggc ccttccggct   4620
ggctggttta ttgctgataa atctggagcc ggtgagcgtg ggtctcgcgg tatcattgca   4680
gcactggggc cagatggtaa gccctcccgt atcgtagtta tctacacgac ggggagtcag   4740
gcaactatgg atgaacgaaa tagacagatc gctgagatag gtgcctcact gattaagcat   4800
tggtgagcag atctgcccac tagtgagtcg tattacatcc atcacactgg cggccgcaaa   4860
ttccgcccct ctccctcccc ccccccctaac gttactggcc gaagccgctt ggaataaggc   4920
cggtgtgcgt ttgtctatat gttattttcc accatattgc cgtcttttgg caatgtgagg   4980
gcccggaaac ctggccctgt cttcttgacg agcattccta ggggtctttc ccctctcgcc   5040
aaaggaatgc aaggtctgtt gaatgtcgtg aaggaagcag ttcctctgga agcttcttga   5100
agacaaacaa cgtctgtagc gaccctttgc aggcagcgga acccccccacc tggcgacagg   5160
tgcctctgcg gccaaaagcc acgtgtataa gatacacctg caaaggcggc acaaccccag   5220
tgccacgttg tgagttggat agttgtggaa agagtcaaat ggctctcctc aagcgtattc   5280
aacaaggggc tgaaggatgc ccagaaggta ccccattgta tgggatctga tctggggcct   5340
cggtgcacat gctttacatg tgtttagtcg aggttaaaaa aacgtctagg ccccccgaac   5400
cacggggacg tggttttcct ttgaaaaaca cgataatacc atggccaccg agtacaagcc   5460
cacggtgcgc ctcgccaccc gcgacgacgt cccccgggcc gtacgcaccc tcgccgccgc   5520
gttcgccgac taccccgcca cgcgccacac cgtcgacccg gaccgccaca tcgagcgggt   5580
caccgagctg caagaactct tcctcacgcg cgtcgggctc gacatcggca aggtgtgggt   5640
```

```
cgcggacgac ggcgccgcgg tggcggtctg gaccacgccg gagagcgtcg aagcgggggc   5700
ggtgttcgcc gagatcggct cgcgcatggc cgagttgagc ggttcccggc tggccgcgca   5760
gcaacagatg gaaggcctcc tggcgccgca ccggcccaag gagcccgcgt ggttcctggc   5820
caccgtcggc gtctcgcccg accaccaggg caagggtctg ggcagcgccg tcgtgctccc   5880
cggagtggag gcggccgagc gcgctggggt gcccgccttc ctggagacct ccgcgccccg   5940
caacctcccc ttctacgagc ggctcggctt caccgtcacc gccgacgtcg aggtgcccga   6000
aggaccgcgc acctggtgca tgacccgcaa gcccggtgcc tgagttcgcg tctggaacaa   6060
tcaacctctg gattacaaaa tttgtgaaag attgactggt attcttaact atgttgctcc   6120
ttttacgcta tgtggatacg ctgctttaat gcctttgtat catgctattg cttcccgtat   6180
ggctttcatt ttctcctcct tgtataaatc ctggttgctg tctctttatg aggagttgtg   6240
gcccgttgtc aggcaacgtg gcgtggtgtg cactgtgttt gctgacgcaa cccccactgg   6300
ttggggcatt gccaccacct gtcagctcct ttccgggact ttcgctttcc ccctccctat   6360
tgccacggcg gaactcatcg ccgcctgcct tgcccgctgc tggacagggg ctcggctgtt   6420
gggcactgac aattccgtgg tgttgtcggg gaagctgacg tcctttccat ggctgctcgc   6480
ctgtgttgcc acctggattc tgcgcgggac gtccttctgc tacgtccctt cggccctcaa   6540
tccagcggac cttccttccc gcggcctgct gccggctctg cggcctcttc cgcgtcttcg   6600
ccttcgccct cagacgagtc ggatctccct ttgggccgcc tccccgcctg gaattaattc   6660
tgcagtcgag acctagaaaa acatggagca atcacaagta gcaatacagc agctaccaat   6720
gctgattgtg cctggctaga agcacaagag gaggaggagg tgggttttcc agtcacacct   6780
caggtacctt taagaccaat gacttacaag gcagctgtag atcttagcca ctttttaaaa   6840
gaaaagaggg gactggaagg gctaattcac tcccaacgaa gacaagatct gctttttgct   6900
tgtactgggt ctctctggtt agaccagatc tgagcctggg agctctctgg ctaactaggg   6960
aacccactgc ttaagcctca ataaagcttg ccttgagtgc ttcaagtagt gtgtgcccgt   7020
ctgttgtgtg actctggtaa ctagagatcc ctcagaccct tttagtcagt gtggaaaatc   7080
tctagcagta gtagttcatg tcatcttatt attcagtatt tataacttgc aaagaaatga   7140
atatcagaga gtgagaggcc ttgacattgt ttaaacccgc tgatcagcct cgactgtgcc   7200
ttctagttgc cagccatctg ttgtttgccc ctcccccgtg ccttccttga ccctggaagg   7260
tgccactccc actgtccttt cctaataaaa tgaggaaatt gcatcgcatt gtctgagtag   7320
gtgtcattct attctggggg gtggggtggg gcaggacagc aagggggagg attgggaaga   7380
caatagcagg catgctgggg atgcggtggg ctctatggct tctgaggcgg aaagaaccag   7440
ctggggctct agggggtatc cccacgcgcc ctgtagcggc gcattaagcg cggcgggtgt   7500
ggtggttacg cgcagcgtga ccgctacact tgccagcgcc ctagcgcccg ctcctttcgc   7560
tttcttccct tcctttctcg ccacgttcgc cggctttccc cgtcaagctc taaatcgggg   7620
gctcccttta gggttccgat ttagtgcttt acggcacctc gaccccaaaa aacttgatta   7680
gggtgatggt tcacgtagtg ggccatcgcc ctgatagacg gtttttcgcc ctttgacgtt   7740
ggagtccacg ttctttaata gtggactctt gttccaaact ggaacaacac tcaaccctat   7800
ctcggtctat tcttttgatt tataagggat tttgccgatt tcggcctatt ggttaaaaaa   7860
tgagctgatt taacaaaaat ttaacgcgaa ttaattctgt ggaatgtgtg tcagttaggg   7920
tgtggaaagt ccccaggctc cccagcaggc agaagtatgc aaagcatgca tctcaattag   7980
```

-continued

```
tcagcaacca ggtgtggaaa gtccccaggc tccccagcag gcagaagtat gcaaagcatg   8040
catctcaatt agtcagcaac catagtcccg cccctaactc cgcccatccc gcccctaact   8100
ccgcccagtt ccgcccattc tccgccccat ggctgactaa ttttttttat ttatgcagag   8160
gccgaggccg cctctgcctc tgagctattc cagaagtagt gaggaggctt ttttggaggc   8220
ctaggctttt gcaaaaagct cccgggagct tgtatatcca ttttcggatc tgatcagcac   8280
gtgatgaaaa agcctgaact caccgcgacg tctgtcgaga agtttctgat cgaaaagttc   8340
gacagcgtct ccgacctgat gcagctctcg gagggcgaag aatctcgtgc tttcagcttc   8400
gatgtaggag ggcgtggata tgtcctgcgg gtaaatagct gcgccgatgg tttctacaaa   8460
gatcgttatg tttatcggca ctttgcatcg gccgcgctcc cgattccgga agtgcttgac   8520
attggggaat taattcagcg agagcctgac ctattgcatc tcccgccgtg cacagggtgt   8580
cacgttgcaa gacctgcctg aaaccgaact gcccgctgtt ctgcagccgg tcgcggaggc   8640
catggatgcg atcgctgcgg ccgatcttag ccagacgagc gggttcggcc cattcggacc   8700
gcaaggaatc ggtcaataca ctacatggcg tgatttcata tgcgcgattg ctgatcccca   8760
tgtgtatcac tggcaaactg tgatggacga caccgtcagt gcgtccgtcg cgcaggctct   8820
cgatgagctg atgctttggg ccgaggactg ccccgaagtc cggcacctcg tgcacgcgga   8880
tttcggctcc aacaatgtcc tgacggacaa tggccgcata acagcggtca ttgactggag   8940
cgaggcgatg ttcggggatt cccaatacga ggtcgccaac atcttcttct ggaggccgtg   9000
gttggcttgt atggagcagc agacgcgcta cttcgagcgg aggcatccgg agcttgcagg   9060
atcgccgcgg ctccgggcgt atatgctccg cattggtctt gaccaactct atcagagctt   9120
ggttgacggc aatttcgatg atgcagcttg ggcgcagggt cgatgcgacg caatcgtccg   9180
atccggagcc gggactgtcg ggcgtacaca aatcgcccgc agaagcgcgg ccgtctggac   9240
cgatggctgt gtagaagtac tcgccgatag tggaaaccga cgccccagca ctcgtccgag   9300
ggcaaaggaa tagcacgtgc tacgagattt cgattccacc gccgccttct atgaaaggtt   9360
gggcttcgga atcgttttcc gggacgccgg ctggatgatc ctccagcgcg gggatctcat   9420
gctggagttc ttcgcccacc ccaacttgtt tattgcagct tataatggtt acaaataaag   9480
caatagcatc acaaatttca caaataaagc atttttttca ctgcattcta gttgtggttt   9540
gtccaaactc atcaatgtat cttatcatgt ctgtataccg tcgacctcta gctagagctt   9600
ggcgtaatca tggtcatagc tgtttcctgt gtgaaattgt tatccgctca caattccaca   9660
caacatacga gccggaagca taaagtgtaa agcctggggt gcctaatgag tgagctaact   9720
cacattaatt gcgttgcgct cactgcccgc tttccagtcg ggaaacctgt cgtgccagct   9780
gcattaatga atcggccaac gcgcggggag aggcggtttg cgtattgggc gctcttccgc   9840
ttcctcgctc actgactcgc tgcgctcggt cgttcggctg cggcgagcgg tatcagctca   9900
ctcaaaggcg gtaatacggt tatccacaga atcaggggat aacgcaggaa agaacatgtg   9960
agcaaaaggc cagcaaaagg ccaggaaccg taaaaaggcc gcgttgctgg cgtttttcca  10020
taggctccgc ccccctgacg agcatcacaa aaatcgacgc tcaagtcaga ggtggcgaaa  10080
cccgacagga ctataaagat accaggcgtt tccccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
```

gattagcaga gcgaggtatg taggcggtgc tacagagttc ttgaagtggt ggcctaacta 10440
cggctacact agaagaacag tatttggtat ctgcgctctg ctgaagccag ttaccttcgg 10500
aaaaagagtt ggtagctctt gatccggcaa acaaaccacc gctggtagcg gtggtttttt 10560
tgtttgcaag cagcagatta cgcgcagaaa aaaaggatct caagaagatc ctttgatctt 10620
ttctacgggg tctgacgctc agtggaacga aaactcacgt taagggattt tggtcatgag 10680
attatcaaaa aggatcttca cctagatcct tttaaattaa aaatgaagtt ttaaatcaat 10740
ctaaagtata tatgagtaaa cttggtctga cagttaccaa tgcttaatca gtgaggcacc 10800
tatctcagcg atctgtctat ttcgttcatc catagttgcc tgactccccg tcgtgtagat 10860
aactacgata cgggagggct taccatctgg ccccagtgct gcaatgatac cgcgagaccc 10920
acgctcaccg gctccagatt tatcagcaat aaaccagcca gccggaaggg ccgagcgcag 10980
aagtggtcct gcaactttat ccgcctccat ccagtctatt aattgttgcc gggaagctag 11040
agtaagtagt tcgccagtta atagtttgcg caacgttgtt gccattgcta caggcatcgt 11100
ggtgtcacgc tcgtcgtttg gtatggcttc attcagctcc ggttcccaac gatcaaggcg 11160
agttacatga tcccccatgt tgtgcaaaaa agcggttagc tccttcggtc ctccgatcgt 11220
tgtcagaagt aagttggccg cagtgttatc actcatggtt atggcagcac tgcataattc 11280
tcttactgtc atgccatccg taagatgctt ttctgtgact ggtgagtact caaccaagtc 11340
attctgagaa tagtgtatgc ggcgaccgag ttgctcttgc ccggcgtcaa tacgggataa 11400
taccgcgcca catagcagaa ctttaaaagt gctcatcatt ggaaaacgtt cttcggggcg 11460
aaaactctca aggatcttac cgctgttgag atccagttcg atgtaaccca ctcgtgcacc 11520
caactgatct tcagcatctt ttactttcac cagcgtttct gggtgagcaa aaacaggaag 11580
gcaaaatgcc gcaaaaaagg gaataagggc gacacggaaa tgttgaatac tcatactctt 11640
cctttttcaa tattattgaa gcatttatca gggttattgt ctcatgagcg gatacatatt 11700
tgaatgtatt tagaaaaata aacaaatagg ggttccgcgc acatttcccc gaaaagtgcc 11760
acctgacgtc gacggatcgg gagatcaact tgtttattgc agcttataat ggttacaaat 11820
aaagcaatag catcacaaat ttcacaaata aagcattttt ttcactgcat tctagttgtg 11880
gtttgtccaa actcatcaat gtatcttatc atgtctggat caactggata actcaagcta 11940
accaaaatca tcccaaactt cccaccccat accctattac cactgccaat tacctgtggt 12000
ttcatttact ctaaacctgt gattcctctg aattattttc attttaaaga aattgtattt 12060
gttaaatatg tactacaaac ttagtagt 12088

<210> SEQ ID NO 20
<211> LENGTH: 233681
<212> TYPE: DNA
<213> ORGANISM: artificial
<220> FEATURE:
<223> OTHER INFORMATION: synthetic

<400> SEQUENCE: 20
catgcacacc aataaacttt tgcttttctt tttagccaat aatatgtttc cgtgtggttt 60
ttataggtta accacttatg gtgtaaagta ggatattcat agttattgaa aacatgggta 120
cacaatgtaa cactaaacta ctatccgcac taatagcaac tgcaatcatc ctaactgcca 180
ttctagctcc ggtactttta catgaacaag aaaaggcatt ttaccgacaa ctttttgcgc 240
aaagtcaaca tgtaaaaaca cccatcacgg tagttcaggg agatacagtt taccttaacg 300

-continued

```
ctagtaataa cccctgcaac tattccagct tctggaacta tggcgattgc gaactttgtg    360
gatggaacgg atacatacaa agacaatatc acgaaaacaa atcgtgctct ccacgattta    420
catgttttaa tgacaccaaa ggtcttagac tacataacgt tacgtttagc gattcaggaa    480
catacacaga atacatgtac gactgtgatt ttccatgtaa cacgagtgac tatgaatatg    540
acatactaaa ctattttgac aattgtacta ctaccataaa cagtaccaat tatattatca    600
ccgtattgtc tccacgtcat tctaaacaca ccgatttgca cgtatccgct cacgccggtt    660
tggcagctgc catggtgaca gtaattataa tttgcgtttt gatctacttt aacgttccgg    720
caacccggag acacagacta cgaactagaa ataacgttaa ccacatactg taattacaaa    780
gtatcgacgc tagtttattc aggataaatt tgtgctactt tgtgtagctc tcaaaaattg    840
taaggcccca cttttccact ccgtcatgaa agatcgtaat aagctactca tatgtattat    900
ccttattttc accatgtgcc tcatctgtct ttattttaaa cgccgttgta ttcctactcc    960
atctccagac aaggcagatc tgcgagtgga atttccttcg ttatctccgt gtgtcggcat   1020
acaatgcgct tcacgggaag atgcgtgata catagcgtac ccccagacgg tacggcttat   1080
gagaacacaa ttgaaggaaa gtacaggttc ctgttgatat gttattacag aaggtcacgg   1140
aacacaaacg ttttctgcgt gtgtttttat aaaagagcgt ctcgaagcag cttgagccac   1200
actacggtcc agatgacgag cgtgatcaaa aatatgccgc gcagtagtcg aaagccgtac   1260
tgagcgtgcg aggcgggtag ggtgccgaac gacggatatg cgtcgtcatc atctttgact   1320
ataaggatcg cgaccgaatc ttcggacatg gtaaaagcca cccactgtgg ctggtatgta   1380
gcgtatccgg tttggaatcg ttcggctccg gctcggggga tagtgaggaa ttctcagggg   1440
acgatatggg acccaatgac tggataaaag aagggttttt cccagtaaga tgatccccgt   1500
atcacatgag atctggatat gtataaatga ggagtgaaat aggcaaaggg tatcagacac   1560
cggccccgtc atgcagccgc tggttctctc agcggaggaa ctatcgtctc tgctgatttg   1620
caaatacatc ccaccttaag cgacgagtcc ataaagcatc gttatccggg tacggtgaaa   1680
gtgacccgga ttgcaccacg tccctttttt gtttttgcat cgtttatcgt caccactagt   1740
gcaatatttt tatcgtaagg ctgaaagagt atcgttatga tgcttagaat gtggagatta   1800
ttacagatgg tactgcttgc cacgtactgt tattatgttt ttgcgaattg ttcaatcagc   1860
acgacgactg ctcctgtgga atggaagtct cccaaccgtc agattcccaa gaatattacc   1920
tgcgctaatt actcagggac cgtcggcggt aacgttactt ttcagggtct caagaataaa   1980
acggaagact tttatcttgg gctactcggg tctggctata agtctatttg ctcgttcttc   2040
ccacaactcc ctggtgattc taatgagcag cattacagat atgaagtaac caacctcacg   2100
tacaattgta cctatgaccg cctaacgtta ctgaatctaa cgatggaaaa cagcaggaat   2160
tactatttca gaagagaaga tgcgaattcc accttctact actcttgtta caacctgacc   2220
gtgtcctaga gaacgcacgt gaagttccac agagccgcgt ggctgtagct attgtttacg   2280
ttgcttttga aatgttaagc gtccctacga cgctaactcg gggggagtcca gggttttccc  2340
agtcacgacg ttgtaaaacg acggccagtg aattcgagct cggtacccgg ggatcttgaa   2400
gttcctattc cgaagttcct attctctaga aagtatagga acttcagagc gcttttgaag   2460
cttggcgtaa tcatggtcat agctgtttcc tgtgtgaaat tgttatccgc tcacaattcc   2520
acacaacata cgagccggaa gacacaagac tgccactcca catacaacgt ggatcatacc   2580
cctggttatc attataacaa tcatcatttt aatttgtttc aaatttcccc agaaagcttg   2640
gaataaattc acacaatacc gatacagcga tatgctcgcc gctgcttaaa gaatcaacgt   2700
```

cgaggaaacc aaaacgcaaa cataatggat atgtacgtgt atttttcagc tcactgtttg 2760
aataccgtaa gaaaaatgac gtacatatac gtaataatac aacagttgct catgttatgc 2820
ggcgcctgat taactatatc gtgagtcatg gcctttttcc atggtccgtc atgaccgcaa 2880
tgatacttta caggtattcc gaaacctgta tggaggtcac cgttaaagta ggtgatccgg 2940
tcaccctcgg aagtggacac ggttatcatc ctggccaaag agtacactgg tataatcatt 3000
catgtgtcgg catcggtaac ggcgaaaatg cgcatcctat ctgtacctac gaccctccta 3060
aacctggtaa acataagacg atgaaaacca ctccgccgcc attaccgccg ttgtacgaat 3120
gtcataattc tacattaagt atccttcatg taaacgtttc agatcccaaa aactactgca 3180
gacgaaaatg tccatcaaat ggtaataact gtgagtttcc cacgtgtttt cagttatcgc 3240
ttatttatag aacgacgacc accaaaaaac ccggacaaaa aactacgtca ccgagattaa 3300
gaaccacgcc aaagaaacat acacagcaca aaagatccac aggaagaacg tcacctaaag 3360
attataatgt tacaggtctg ccaaaaggct ttgcggactc gtttaccggt aacgcagagg 3420
cacatagagc caaagatgcc gcacacagcg catggattat cattgtcatc atcattatca 3480
tagtcgtcat tttatttctc ttcaagattc ctcaaagact ccgagaaaaa tgggacacca 3540
ggggatactt ttacaaagga accgacggcc tgcccactac ggactaattg tcgtgagcgg 3600
atggatatct ccggtttcaa acccactgtt tgaatatagg gacagtccct acggaacctg 3660
agaacatgtg gaaattacct gtggtagaat gctgttcagg tacatcacct ttcatcgcga 3720
aaaggtactt tacctaacgg ctgcatgcat ctttggtggc tacatcagcc tccacgatgc 3780
ctgcataccg gtggttggca aaataggtac caacgtcacg ttgaacgcgg tagattttca 3840
tcccggtgat cacgttcgct ggtcttacgg tcccggtggg gcaggctaca tgctatgtgt 3900
ttacactggt agttggacag aatacaaaaa gccagacatc atttttaagt gtttatcaaa 3960
taacagtctt cttttaatta acgtaactgt aaattatacc aacacttacc gtaccttgac 4020
atcgttaaac aattgggttc acaatcaaca tcaccataaa tttcccggat ggaacttgga 4080
cacatgttac agtctcacag tgaacgaaaa cggtacattc cccactacca ccaccaaaaa 4140
acccactacg accacgagaa cgacaactac caccacaaca aagaaaacaa ccaccacgag 4200
aacaaccacc gccgccaaga agacgacgat aagcactacc catcataaac actccagtcc 4260
caaaaaatcc agcaccccta acagtcacgt agaacatcac gttggttttg aagccacagc 4320
agcggaaaca ccgttacaac caagcccaca gcaccaacac gtggctacac acgccctctg 4380
ggttttagcg gtcgtaatcg ttattatcat cattatcatt ttctactttc gaataccgca 4440
aaagctgtgg ctgctctggc agcatgacaa gcacggcatc gtgctcatcc ctcaaaccga 4500
tctgtgagca agtcgcgtag gaaatgattg catgaaatca ctgtgaaacg ccaactccgt 4560
gccagctggc gcggcggaca ggcctttgac gtatttgaag ccaggcgcgc tctcgatacc 4620
gaaaggatcc gagggggctt tccaaagccg acgtccctga ttcccttcat aaagctgttg 4680
accggcccta gaaagaccaa gagcatgctg tgggcccact gcggtcgctt cttgcgttat 4740
catctgctcc cgctgctgct gtgtagactg ccattcttac tccttttcca gcggccgcag 4800
tgggcccacg gcttggacat tgtcgaggag gacgagtggc tacgggagat acaaggagcg 4860
acgtaccagc tgtccatagt gcgccaagcc atgcagcacg ccggattcca agtcagagca 4920
gcgtcggtca tgacgcggcg aaacgccgtt gacctggacc gaccgccgct ttggtcggga 4980
tcgctcccgc atttgcccgt ctacgatgtg cgttccccgc ggccgttgag accgccgtca 5040

-continued

```
tcacagcatc acgccgtatc acccgaactg ccgtcgcgag acgggatacg ttggcagtac   5100
caagagctgc agtatctggt ggaagaacaa cggcggcgaa atcagtcgcg caatgcgatt   5160
ccgagaccct cgttcccccc tccggatcca ccatcgcagc cggcagagga tgcacgagac   5220
gcggacgcag aacgtgccga atcaccacat agtgcagaaa gcaccgtcag gcacgacgcg   5280
agtgagaacg cagtgcggcg acggcacgaa agacggcgct ataacgctct gacggtccgc   5340
agccgggact cgctgctcct gacgcgaata cgcttctcca accaacggtg tttcggacgc   5400
gggcgtctga gacatcccgc gggaagcggt cccaacaccg gcggaccgcg acccggcggt   5460
gcgggactcc gtcaactacg ccaacaactg acggtccgct ggcagctgtt ccgcctacgg   5520
tgccacggtt ggacacagca ggtctctagc cagatcagaa cccgctggga ggaaagcaac   5580
gtcgtgagcc agacggccac gcgagtacgt acgtggttcg tgaaaagaac cacgttttgg   5640
cgtcgcacgt gggttccggg acagaacccg gcggccgaag cgcaagaact ggccgtcata   5700
ccgccggcac ccacggtgct ccggcagaac gaggaaccac gtcaacagct tacgggagag   5760
gagacaagaa attcaacgca cactcaacgt gaagaagtgg aggacgtttc gagagagggc   5820
gcgagagaag ggaatgatgg gagccgagca agtggaaacg acgagagaag gaataatgcg   5880
ggaagatatg atgatgatca tgaggttcaa gagccgcagg tcacttatcc agcgggacaa   5940
ggagaactga ataggaggtc acaggaggag aacgaggaag gtggaccgtg tgaatcgccg   6000
ccaatgacga caaatacgct gaccgtggcc tgtccgcccc gagaaccccc gcatcgtgcc   6060
ctgtttcgtc tatgcttagg actgtgggtc tcgagctacc tggttcgacg gcccatgacg   6120
atttagaata caccgagcca ttcctttatt tccccccatc cccggtcgct tatgcgtgtt   6180
aaacactacc aataaagata atctgccaat cgcaccttat atataatatg tggtcgcgtg   6240
tggtcttttt aaggagctct gaaacacaga caggtatggg cggtggtcgg ctgccgccgc   6300
tgtggctgcc gctactgatc gcctggagcg agtggggcaa ctgctgcctc gatgcgcctc   6360
cggtggtgcg ttcgccctgt ctgcagccgg tgcgcgaccg caaccgcgag cggaacccgg   6420
gctcaccgca gttgctgcct tacggcgacc gtctggaggt ggcctgcatc ttccccgcgc   6480
acgactggcc agaggtctct atccgagtcc acctctgcta ctggcccgag atcgtgcgtt   6540
cgctggtggt ggacgcacgc agcggtcagg tgttacacaa cgacgccagc tgttacatcg   6600
ccggcgggcg ctggcgcttc gaggacggcg gcgcggcgca gcggctgagc ctctcgtttc   6660
ggctcatcac cgagaccgcg ggcacctaca cctgcgtgct gggcaacgag acccacagcc   6720
tggcgaccga gaccacggcg ctggtggccg acatgcacga cctgcgccac tcggaccgct   6780
cctgcgacct ggctttcgga tcgcgctcac agacgcggta cctgtggacg cccgatccct   6840
ccaggttgcg cagtataaac tgcggttggg agggtgaacg gcaccgcgta gtccactaca   6900
tccccggcac ctcgggtttg ctgccctcgt gcgaggagga cgagcgcgaa ctgtgcgtgc   6960
ccttcatcag ccagagcatt gcggacaaca actgcagccg ccggcatcga gttgacggcg   7020
ctaggcggcg ctatcatcta cggagggatt actggctgac ggatccgaag atcgggttgc   7080
tggccgcggg atcggtggcc ctgacctccc tctgccacct gctgtgctac tggtgttccg   7140
aatcgtaccg gcgtctgaac accgaggagg aaagcgaggc ggcggaggaa actgccgcgg   7200
gagaagcctc tgcggtagcg gcggcggccg tctctgagga agagcagcgg cgggagtaaa   7260
cgaggagagc catgaagcgg atgattcgca gtcacggcag gaaaacggaa tgtcagatga   7320
cgggcgccgg cgagcgacgc ggctccgccg tcggtgcgcc catctgcggc agcggtaccc   7380
gacgcggcag cggcgccaac gaacgccgcg actccgacgt cggtcccatc gcccacagta   7440
```

-continued

```
gcggtaccag acgcggttcg gcgaatgaaa cgtccgcctg tacgcggacc gatcaccaga   7500
aggcggacat tgggctgtgg ttcatgtttc tggtttttgg actgtgttcg tggttggcga   7560
tgcggtatcg cgcacaataa attttgaatc gatgtcaagg aacgcgtgtt ttgtatttta   7620
ttgggaatat tggcggggat aaaccggttt cggatgttta cccttaatct taccggggac   7680
ctcgttgtcc tctcctcctt cttcctcgga caccgggctc catgctgacg taggtaccga   7740
ctggggtcaa aagcctgggt acttatgagg agcgcgcaca aaggaccgtt aggcgccggc   7800
atggagcgtc gccgaggtac ggtaccgctg ggatgggtgt tttttgttct ttgcttatct   7860
gcctcttcct cgtgtgctgt tgacctgggt agcaagtcct ccaactcgac ctgccgcttg   7920
aatgtgacgg agttggcctc gatccatcct ggggaaacgt ggacgttaca cgggatgtgt   7980
atttctatct gctactacga gaatgtgacc gaggacgaga tcatcggcgt ggcttttact   8040
tggcagcata acgagtctgt ggttgacctg tggttgtacc agaacgacac ggtgatccgc   8100
aatttcagcg acatcaccac taacatcttg caagacggac tgaaaatgcg aaccgtccct   8160
gtgactaaac tgtacaccag ccgcatggtc actaatctta ccgtgggccg ctatgactgt   8220
ttacgctgcg agaacggtac gacgaaaata atcgagcgcc tctacgtccg attgggctcg   8280
ctatatccga gaccgcccgg atccgggctc gccaaacacc cctccgtaag cgccgacgag   8340
gaactgtccg cgaccttggc gagagacatc gtgttggtct cagccatcac tctgttcttc   8400
ttcttgttgg ccctacggat cccccagcga ctgtgtcagc ggctgcgcat tcgcctgccg   8460
catcgatacc agcggttacg caccgaggac tgaacggata accgcaaagg ccacgtgcaa   8520
cgttcacgct gctataagaa ggccatgtcc cccgtggacg ggtctctttg acacgagcgc   8580
ggcacgccgt tgccacgagc atggatcacg cgctcttcac acacttcgtc ggccgacccc   8640
gtcactgtcg gttggaaatg ttgattctgg acgaacaggt gtctaagaga tcctgggaca   8700
ccacggttta ccacaggcgc cgcaaacatc tacctcgacg tcgcgctccg tgcggccccc   8760
agaggcccgc cgagattccc aaaagaagaa aaaaggcggc cgtccttcta ttttggcacg   8820
atttgtgctg gctgtttcga cgacttttct ttcctcggga ggactcagag ccactgatgt   8880
cggatccggc acggtctccc gaagaggagg agtaaacaac acacggctaa gaggatacat   8940
catcaaagaa gataggaggg gtcaaaacgc ggactgaaag tatataacgc cgatcatgtc   9000
cgaggaactg ttaataaaac gccatgatga caatgtggtg tctgacgttg tttgtgctgt   9060
ggatgttgag agtggtggga atgcacgtgt tgcgttacgg gtacacgggg attttcgatg   9120
atacatcgca tatgacgttg accgttgtgg ggatttttga cgggcaacac ttttttacct   9180
atcacgttaa ttccagcgat aaagcgtcaa gtcgggccaa cggtaccatt tcttggatgg   9240
ctaacgtctc ggcggcctac ccccacctacc tggacgggga aagagccaaa ggtgacctta   9300
tttttaacca aaccgagcaa aacctgttag agctggaaat tgcgttgggt taccggtcac   9360
agagcgtgct gacgtggacg cacgagtgta ataccacgga aaacggtagt tttgtagccg   9420
gttacgaggg atttgggtgg gacggggaaa ctttaatgga gctcaaggat aacctgacac   9480
tatggacggg ccccaattac gaaattagtt ggttgaagca aaacaaaacg tacatcgacg   9540
gtaaaattaa aaacatcagc gagggggata ctacaataca aaggaactat ctcaagggta   9600
attgcactca atggtccgtc atttatagcg ggtttcaaac ccccgtcacc cacccagtgg   9660
taaagggcgg tgtccgaaac cagaatgaca acagagctga agcattctgt acatcttacg   9720
ggttctttcc aggggaaatt aatattactt ttatccatta cggtaataag gcgcccgatg   9780
```

-continued atagcgagcc tcaatgcaat ccgctacttc ccaccttgga tgggactttc catcagggat 9840
gttacgtagc catcttttgc aatcaaaact acacctgccg cgttacacac ggtaattgga 9900
cggtggaaat ccccatcagc gttacctcac ctgacgacag ttcctcgggg gaggtccccg 9960
atcacccgac agctaacaaa cgctataaca ccatgaccat cagcagtgtc ctcctagccc 10020
tgcttttatg cgctttgcta ttcgcgttcc tgcactactt taccaccttg aaacaatacc 10080
tacgtaacct ggcctttgcg tggcgctatc gcaaggtccg gtcgtcatga ccagcaacgc 10140
cctgtatgag ctgtttcgac gtcggttacc gcgtgccccc gtcaacacgg tcatgtttct 10200
cacgcgacgc actcgtgatg ggttctgcgg tcggttgacg tccatcgcca cgaattccca 10260
ctacactatg ttcgtgttgg atcacgggtc cgtgcgcatc gagcgaccga gtcagtcaga 10320
agtggattgc gccagtttaa tggaaacgct gaagcggatt cggttacgaa attcgtgggt 10380
agcgtcagaa gacgagctag atgggagtcg cagggacgcg tgacacgaaa cgcgttcagg 10440
attaacgtag gttttcaaaa taacctacgt ccgtgagtga cgcggtttcg tgttgaaacc 10500
cgcgcccggt tcccacggtg gtttatgatg aaaccggcgt tggggatcta cgcgggttcc 10560
tcattcaacc tgcgaaaaga ggaagttgcg gtaaaaccac gtcaataaag acgtcaatga 10620
cacctcaatg ttgcgttgga acggtcttta tatatacaaa cgccgttatg ctcagtgtcc 10680
ggcaagatgc tcgggataca tgctatgctg gtgatgctga attaccactg ggcacaggtg 10740
acaacgaaca atgacgcccg aaataataat acagatacca tctttgtatc tctccttacc 10800
gggcccaacg gaattacccg cacagccgtt ggaggtttgt attcaaacta caccgaccta 10860
accgggacat tcaatttcat ccaaggcaac atatcagcta atgcgtccag tggagataat 10920
tggagcgtag ctaacctgac aaaaaactgc atcaaccgcg gtgagtctta cctgactacc 10980
ctctggcttt tgaactgtac tcaaaacgat acttattggt actctggaaa tgcttacaac 11040
tatacaaata acacctgtgg aagtacagtc tcgggatatc ttttgggcat gtgcgaacta 11100
tggaaaaagt gggtcggtaa tgatacttct cataacacca ccagaatcga gttgttaaaa 11160
aatgaaacac gctgcacgct gcccgctaaa cagtatatcc tcaacgccac ggtggaatgg 11220
tacaacaaat ctgaaggtga cataccaaag gaattcatga gttatgctat cctgagttcc 11280
gtggcggtgc ttacatgcgg acttcaggaa gcttatatac tcgacatgac tcgcagaatc 11340
acgtacttgt tctccatgtc ctgcatagga atcacaagta taatatccat catactcgcc 11400
tccttatcgc tgcttatcct catctgttac tatcgctgtg gccgacttct gatatgccca 11460
cgcggctttg aacgcttgcc agaattcacc gaggaagagg aggaaaaaga aaacttgtta 11520
acgcacaagg acattgaagt ccaggtgcct atccgcacgc ggcgactgct cgtcccttgg 11580
atccgggaaa gcaaaatgtg gacattacca cctccacttc ctccacgacc tcctcactta 11640
atagaattcc caccgtctcc tccgtcgtcg cctgagccca cgcacatggt aatctgcata 11700
ccatcatgac ggactttgga ctgagcccca agcggtacgg actatatatt ttccacaagt 11760
ctacactgaa cttgagcaca caaatactga caatagactg gatatataga cttttatatg 11820
atccctgtac agatgtaaat aaaatgtttt tatttaaaac tggtcccaat gttcttcggg 11880
aatcatgggg tggggacggg ggacgcggta gggagcaaaa ccgggtacat ggggggggaac 11940 atcgtccagc aatagcacca gcggattggg taggggttgc tgcggaggtc ggtcgatgac 12000
gatgtcgatc tccatcggca gatccggcaa catctcttcg tctccctcac cgaccagcac 12060
tcggcgctgt tctggatgta tatgattctg gaaaagcctc cgacgagctc gcggcgcgta 12120
gaaagccaag cggcgcaagg gccggcgagc ccgaaagtcc atgcgcacag atggcatgag 12180
tccttgagtg acggtggtga gctggggaac agggctacct cccatcgcga cggtgacagt 12240
ggatccatga gagaggcgcc gcacgctgca tgactaaata ccgtgaatcc cctgacgtcg 12300
tctttcgtcc agaacgcgtc atgttggggg cgaggcgtaa accgtcgagg ttgaaaaacc 12360
gcgtatctgc gacccgtccg gactacgttg tttttcagaa gcggccacat gacctcgaga 12420
tgtcgtcacc caaggtattt aacggcacac agccagacgc gttcgtcagc agcgacgccg 12480
acaagacctc agcatggctc ggaggctatg gatcttgagc ttactagccg tgaccttgac 12540
ggtggctttg gcggcacctt ctcagaaatc gaagcgcagg taaacggaat ctggggaatt 12600
caacacaggt aagaaataca aaaaaataac gtgattgtga acgcggttat cgtgtttttg 12660
cagcgtgacg gtggaacaac ccagtaccag cgctgatggt agtaatacca cccccagcaa 12720
gaacgtaact ctcagtcagg gggggtccac caccgacgga gacgaagatt actccgggga 12780
gtatgacgtt ttgattacag acggagatgg cagcgaacat cagcaaccac aaaagactga 12840
tgaacacaaa gaaaatcaag ccaaagaaaa tgaaaagaag attcagtaac agcagacccc 12900
aagggttaac gattatgttg actaccttgt tttttattaa aaagctgtaa ggttttgctc 12960
taaaaacacc ccgcctccgg tctttttttct tttgtattcg gcacgcgaaa cacggtttct 13020
tcccatagcc tgtctaacta gccttcccgt gagagtttat gaacatgtat ctcaccagaa 13080
tgctagtttg tagaggctat gcgggatgct gcggcggcgc gaccttccct ctccacccag 13140
ccccgtcaaa acacacgcga ctcgagcggt tcgtatgaaa aataaaaaac agctttttat 13200
ttacaggaac ggggaaaaaa aaaggcacac ggtccgtggg agacgcgggt tcacgcgtcg 13260
tcaaaaagtt ggtggtccac tccgtaagga caggtaggct tatttagctt ccgcatgctc 13320
ctggttccgt aataaatgcc gttttcgtgg cagcgtgtca tgccgcgagt cacaaactcc 13380
atcaaactgt cggccacgat gcaaacgtgc tgattgttgg cagcaaagac gcgcatacag 13440
tcgtccacga agaggttgat cacgtcgtag ggctcacca accagcctaa aggttccacg 13500
tggttactgc cgaccatgac cctccagtcg ttaatctcgc tccagtcgta cagccgaatc 13560
gtggagacgc gaatgacgct gtaatcaccc atgaccatga gtcggccgcg atacgtagca 13620
cgccactgcg cgaacgcgtg gatgtgcatg cagccggcca gcgctctaag cgaggcggtg 13680
tgcggcagct cctctgggac ggtgatgaag ttgcagcgtc gcaaaccgat gttgagaaat 13740
tcagtgatgc tctcggccac aaaggtcaac gagtcagagt agatgtggtc ggtccacagg 13800
tacatggcgc ccgaggcgcc caggtacagt tcagacggca cgttgtgatc gcccttgtgt 13860
ttaagaaagt tgtaggtgca gatgctgccg acgaaacgca gcggctcggg gcagcagagg 13920
tagctggcca gacgctgtgc atcccgtcct tcgtcgcgca ccaagcgcca gcgacgccgg 13980
ataacgaggc agcggtcttt gggccagacc agggccacgc gttgcccggg tttccacggt 14040
cgcgacgtct taggaggcct ccagcggtcg agcagattga gaaaacagtc cttgattacc 14100
gacatcgcgg tcgcgcgtcg gtggacaaaa agaaatcggg ccgatccgga aaaaaaaaaa 14160
aaacgacggc aaaacaccgc cgtgctcgag cgaagggtgg cggagggcca gaagaggcgg 14220
ccttgacggc gttggcagcg aaaaaattgg cacgcgagtc aaacgggaag tagcgtcggt 14280
gttttatgcc ccaagcagcg tcgtcgtcac tcgtggcgtc acagtcaacg gtgctgacgt 14340
cctttggggc agtcgggcac gcgatcgtag atgccgttgt ggccgctgaa acgtcggttt 14400
tcaaacagca ggttaagtcc cagacacatg aacgtgttga gattatctcc cacccggatg 14460
tagcggtcgt cgcgcacgtc gcaggcgtag acggccccgg tataggcgac gacgatgggg 14520

```
ataaggtcga cgggccagcg caagtgagga aagggcgcgt tctcgccctt gaggctgacg  14580
gttcccaggc cgagaacgcg cattccgaaa gcggttttga tgttgcgcag caagtgaccg  14640
ccttccacgc tgttttcgaa acacctgagg ttgcatagac gcagttccgt tcccggcggg  14700
tacgtcaacg gcatgaactg cccgtggtgg cggatgatga atcgcgccat ggtatccaaa  14760
ccgaggctcc aggcgcgcaa cagcgggcga aagtagcgct taaccaacga cgaggtcagg  14820
tagcgcatgc agtgcagggt ctcgacggcg cgcagcccga cgcgcgcaaa ctccatgagg  14880
ttgcgggcca ggtagtagac ggcggtgtcc tcgcgtacat agcaaaagac atagccctcg  14940
tccgagatga ggcacacggc ggtcttcttc tgctgatccg gcgacaacac ggcctcgttc  15000
acgaagcgac ccacgaaggc caggcgcgtc tcgcagcaca ggtagtgact ccaagctttc  15060
acgtcctccg gtttgaagtc ctcgtccgtc tcgatctcct gcagcactag gttccagccc  15120
ggcggccaga ccacgggcaa cacctggcct gcgttgatgc gcacgtaagc ttccagacag  15180
cccaggccga actcggccgt gagcgccagg ctagccagat cgctcatgtg acgcgccgag  15240
tcagtgggcg agcccggggg cccgtcgcac accacgctcc gtcttcttgt cctcaccgcg  15300
gccagcgtgg cgaggacact ttccgcgccc gaggctgtat cttcggtttg cccgccggag  15360
ccggccctca ctatataacg tcccgcccgg gtctcctcca tgtatgcagg taagcaactg  15420
agccgaacgc acctcagcag acgagaggat gtcgtcgcgg cgtcgcagct cgtcacgtcg  15480
ctctggcgaa ccctcgacgg tgatttatat cccctcgagc aacgaggaca cgccggcgga  15540
tgaggaggcg gaggacagcg ttttcacgag cacgcgggcg cgcagcgcca cggaagatct  15600
ggatcgcatg gaggccggtt tgtcgcccta cagcgtctcc tcggacgctc cgtcgtcctt  15660
cgagctcgtg cgcgagaccg gcggcaccgg cgccgccaag aaaccgagcg aaaagaaacg  15720
atcgtcgtcg cgtcggcaac cgcagatcgc agcgggcgcg cctcggggct cgccggcgac  15780
acccaaggcc ggcaagtcgc ctaaagtctc gcgaccgcct agtgtgccct cgctgcccga  15840
gaacggcgcc ggcggcggtg gcgacgataa cagcagcagc ggcggtagca gcagtcgcac  15900
caccagtaac agtagcagaa gtaccagtcc cgtggcgcca ggtgagccgt ccgctgccga  15960
gggcgatgag ttttccttct gcgacagcga catcgaagac tttgagcgcg aatgttaccg  16020
ggtcagcgtg gccgacaatc tgggcttcga gcccagcgtg gtcgcgccgc agcacgtcga  16080
gtatctcaaa ttcgtgctgc aagactttga cgtgcagcac ctccgccgcc tcaacgaatg  16140
catacccatg ccggccttcg cgctcaccag cctcgtcgac cccgtcttaa acaacgtagc  16200
gcctggcgag cgcgatctca cgcgtcggat aatcacgcac gcggtgatca tcaactatta  16260
ctacgtggcg caaaagaaag cgcgccacat ggtggaggcc atacggacca ccgtgcgggg  16320
cgacacggta cgccgggtag ccgcgcaggt caacaaccag agccgttcgg ggcgtgcggc  16380
cgcgctagcg cttcactttc tcacgtcacg aaaaggagtg acggacggcc agtacgccac  16440
gtctctgcgg cggctggacg aagagctgcg gcatcgcggc acgcccgaat cgccgcggct  16500
caccgaggtc taccagacgc tacgcgatta caacgtgctc ttctataccg cccactacac  16560
ctcgcgcggc gcgctctatc tctatcggca aaacctgcag cggctcaacg agaaccaccg  16620
gggcatgctc cggctgcttt cggtcgaaga gatatgtgaa gagcacacgc tcaacgatct  16680
ggcgttccta gtaggcgtcg agcttatgat cacgcacttt caacgcacca ttcgcgtgct  16740
gcgctgctat ctccagcacc agctgcagag catctcggag ctgtgttacc tcatctatgt  16800
acaactgccg tcgttgcgcg aagactacgc gcagcttagt gacgtgatct actgggccgt  16860
cagtcaaaac tacgactacg cgctctacgc gagcacgccg gcgttgtttg actttttacg  16920
```

cgtcgtgcgt cagcaggacg ccttcatttg caccgactac gtgtactgcg ccctgcgtct 16980
gctggcctgt cccgacagac ctattatcgg tgacaccggc ggcagcagta gctcccaacg 17040
cctcgtaggc gagtttatgg tgcgcgatcc gctgttgcgc gacccgcgcg ccacccacct 17100
gcgccagaaa ctcatcaccc gcgacatatg cgtggcgcgg ttgcaagcgc agccctcgag 17160
tcgacacatt ccggtcgaac acacgggtgt ctcctccgtc accctgctca aaatctttag 17220
ccaggtcccc cccgacgaac gcgaagaaga cacgttacgc gagatggctc ttaaagcgtt 17280
tatggaagcg aacggtaatc accccgaaca aatctgccga tccccaccac ccccgctgcc 17340
accgcgcgac tatcctcaac gcgacgagcg ggaccgtcac cgtcgcgacc gccgcgacag 17400
cggggaatac tgttgctgat ggtgggacga aacagcaggg cggaacagtt tatgatagaa 17460
agtcacagga aagtatgtgt tgtttttttt ttaatgtacc aagaataaaa agtgcgtcta 17520
cgaccaaagc ggtgtgtgga cgctcgtcct ctgtcttctc cggttttttt ttatgtgtgt 17580
gtttttcttt tccttcctat tttgttacgg caacagcgct gatggcacgt tgccggcttc 17640
gaacatcgcg tcggtgattt cttgcttgcc cggcgtcaca cggtgacgca gcagcgcgcg 17700
gctcacgtag caggccgact cgcggatgac ctggccgtcg gcgtcgcgtc gcaggcccga 17760
gcggttgccg tgacgcagtc ggccctgcgc ggcgcgctcc acgtcttcaa agtagctgtg 17820
tagcaggccg cgctccagca gctgcggcag cgagtcggcg gcgcgcacca caaagttctc 17880
acggctgatc tcgtagcaca gcacgctgcc gtcggctgcc acgccggcca cgctgcggtc 17940
ccaactgaag aggttggcga gtccgatggt gccgatgacg cgcaactgac cctgggtcac 18000
caccagcagc ttccagtatt ctacgtcgcg cggggtgagg atggtctcct ccacgtcgca 18060
gacaaacaac gtgtagccgc gcggataggg cagatccagg tggcgaccgc gctggcggcg 18120
cataaaatcg tctaaattca aaccgccgtc gggtgcgcgc ctgctcgtca tcgccgcgcc 18180
tcgtcggtcg atgaccccac ggtgcttata acgcgccgcc gcggcttcat gtggcgtgac 18240
ctccgacctc gtgaggccga aaacggcgta catgaagacg ctcaaacttt tgaatgtggg 18300
cccggtagcg caccgagggc cccggggcgg cgacgacggc gggtccgagt tccagcgggg 18360
ccttgcggcg gcagcggttg gcgtggttgc tcagctcggc gtccgagagc gccgagctga 18420
actgcggcag ccgcgtgcga tcctgcggcg cgtccccgtg tcgcagcgag tgccagagca 18480
ggcgctggac gcgcgccgtc tcgggcgtcg gcggcgcgcg acagccccgg cgcagcttga 18540
aaacgtgcag gcacagcagc tcgcgcttga tgcgcagcga cacgctgcgg tagtcgggaa 18600
tccgctgcac cagctcgaga aagtcgcaga aggtctccac gaacgtgtcc tcggtgaagc 18660
gaatgcgctt cagatcgtgg acgtgtttgc gaaaccgcga cagttctcga cgttgcacgg 18720
ggttctgagc gagtcccttg cgcagcagcg cagcctcgcc tttaaacagc ctgatgagcc 18780
gctgcacgtc cccgctcaac atacgtatac acgccgtgta ctcgtgacgt atactggcgc 18840
gcagcagccg aatgatacgc agggccagca cggcgttgga ggccaggtac atggcgtagc 18900
cgcgacgcgg gttggcacag gcccagcccg cggggagcag aaagtagtcg tcgaccagcg 18960
tctgcgacca gtcggcgaag cccaggtcac gtgatacgct gtcctggacg cgggccacgt 19020
cgccggctgt gaggtggcgg atcgccggca ggtgaaacgc gcccaggtgt cgattgcgct 19080
ccagcctcag ctcggcgtgc tccaaacggg aatggtggga cgccaccgcg gagggcgaca 19140
aagaggagtg gtcgccgccg ccgtagttac cgttgtgatt accgccgtcg tcgcgcccgt 19200
cgccgcactc gcaaaaggcc gcgtagaggt ccttcaacgc cgcttcggct cgcgccataa 19260

-continued

```
acgtggcgtg gaaaaaaacg gcggcgcggt gcgtccggta cttgacgggc aacccgcggc  19320
acagggccgc cggcaggcag cggccgatga gttcgcgctc ctcgggctcc agaaacaggc  19380
acagggtgcc gtccaggcgc aggtacagct cctcggtcat cgagcatagc tgccgcaagt  19440
aatgggtgcg cgtcccaaag gtcttgtaat cgagcaacgt gcacaccacg tattgccccg  19500
tggccacggc cagagcgatg cgtttggcgg cgcgactgat ctctggcaag tactgcgcct  19560
cgtgcaccag acggcggaaa gcgccggcgt tgagccagcg aaaatgctgc ggatcgggcg  19620
gcaagggcac gcctcgaagc gcggcccaga cagcgaggtc cgactcgagc gtcagaccgc  19680
ggatgtcgta cttgccgtgc gccgtagcgc aggctgaatg gacaagacag ctgcggcgaa  19740
tgtacaccat ggcgtgcttg ggatgtttgg gcgccggcgt tttctttttc tgaccgccgg  19800
cggccgccag atcctcgggc gtgcgacaca acaggccggc gcgcacagcc tcctgtcgat  19860
tacgaatcgg cgtcaggtag gcgcgcagga actggtgaca aaactcctca tcatcacgac  19920
agtcgtcgag atactcgtac gtggtgagcg gatcgcgaaa taggcgctcg tcaccgtcgt  19980
catggtcttc tttagcctgc tcctccggct gctgggttgg cggtggaggc ggcggctgat  20040
ccacggggtt catgactgag aggaagaaga aggtggcggc gaagcgacgc ggagcgacgg  20100
cggtaaagcc agacaccggc tatatagcta gtcatcacag tctcctcctt cacgacgccc  20160
ccgtgccgct cacgctatcc agcacgctac ggcccgaaaa cacgtactcg ctgacgtcgt  20220
acgcgggcga tgtatggctg ctcaccggtt tcgcggcgac ggttgcgctc gagtccaacg  20280
gcgagaagca aaaacgccgt gggcaacgaa accagaagga gccctgacgg ataaaaccgc  20340
gcagcgtctc ggccaactta accagcatcg taccgtacag cagtacgtga atgccgccat  20400
gcgcgtccat aaatacggct ttgttcacgg gttccatcca tccgatgact acaaaatggg  20460
cctgttctag cacgccgatc acgaaattgt tggcctcgtc ggcctcggcc acgttccacg  20520
agccgaaagt gaaagtacaa gcgggcgagc cgcccaggcg gatcttgcta ccggcgtgga  20580
gctgacatac gcgcagcaga ttggcgcggt cgtgcagtat ctgggagagt tcgtacatgc  20640
ccgcaaaggt gtgcttaaac cacgcgccct ctacgatctc atccacgtag tcgcgctcaa  20700
agaagctgta cacggcaaag aggccgttct caaaaaactc gccgaacgag agccccagca  20760
cgtacacctt gtcctcgccg ggcaggtacg caaaggcgtg cccgtgcccg gagacccaga  20820
tctcgggcgc cgtgtttgcg tccggcacgc attcgtacac actgacgagg ccgataaagt  20880
acaagcggcc agcctggcgc aggcacgaga agcgccggta ggtcttgtga tcgcgcacca  20940
ccccaaagta ctgagtgtcg cccagcatga tgccgtgcag cggcggccag cacagcggga  21000
gccaacgacc cgccgtggcg cgcacgtagc gctgcaggtg aaccccgctc gcacgctcgc  21060
gcggcttcgg gcgcttgtgg gtccaggcat cacgcaggcc gcgccagatg ctgctgaact  21120
tgggctgccc gcgcagatag agcgacgaga gcgagtcaaa gtagcccacg acgagcctgt  21180
cgggagacac aagagcgcga aaatcaaacc tagaacgaca acggtgaaaa aaccgaccag  21240
aagcgcgtgt ctcaaacacg ctactttcgg ttataaaaac accgtcgccc tatttctggg  21300
cgtgtgtaca ctgatgactc acctacgctt tttgaacggc agtctcagct cgggattggc  21360
ctcgtacagc gagctgcggt ccacggggcc gatgctctcg taacgaaagt cgtcgatgag  21420
cagcgccagc cccacgcgca cgaagcccct gaggtcgcgc gccagccgca ccaacttatc  21480
ctgccccacc agcgccgcgt acacggtgcc cgtatcaccg cagagaatcc gcacgcggtg  21540
aaagaaggtc ttgtcctcgg cgccctcgat ttcgcccagc ggcatgacgg gctcgcgcgt  21600
gtacaacgaa cgttgaaagc ggcgcagcat cgaggccgag agccccagat cgcgcgccgt  21660
```

gcgcagcacc agggaatgct tctcgggcca gatgaggatc agttgcgcct cgcggtgcgc 21720
ctctacgtag gcgcaacgag cggcggtgtc ctcgcaggcc agcaactcgc ggaaagccag 21780
cagcgaacgt aggtagcggc cgcgagcgga ggcgcgcgag cggcggcaca gctcagcccg 21840
atggtcggga tgcaccaagg gcacgttggg ttgcagacgc gcgcagatgg attcgtgcac 21900
cgggtcgcag cgaatcatgc ccttggcaaa aaatccggcc agatccgagg ccaactcgta 21960
caggcagtcc tcttgcgcgt cgtaggcgaa cacggagccg tacgcgtcca cgaacacctg 22020
gtaccggcag gtggcgtgcg agaccgtgcc aatgagatgc agagctcgga attcgccgaa 22080
aaagtcgttc tggcagtgct ccagatcgat ctcggtcagc gagtgcggcg aatgctcacc 22140
cccgaccacg tagatgcact gcgagggcca gcccagcgat acgcacgaac cctcgaagcg 22200
ccgcaagtaa cgccgcaggc cctcatagtc gcgtcgcacg cacaggtcgg ccaagtcgcg 22260
cgtgcaaaag acctcgggta ccaagcagcg tttgcgacgc ggccgacgcg cgtgcccggg 22320
cagaggagga aggcgcgacg gcggcgacga cgaggaggaa gacgccgtgg ccgccgagca 22380
gcccttgcga cggccagaca tgccggcagt ccgcgacgat ccacaggaga caaaaaagca 22440
gaagcagcag tagtctcgac gacccgctcc accccgtcct ccacacgctc agccgcgact 22500
gagcgccggg gcgcgccgct acttgggttt ttatagccat ctgccccccg tctcgggcac 22560
ccgggagcga tctacggaga cctgacagca cttgggcaac acaagacagg gaaatacaaa 22620
gacactttta ataaaaaacg agactacttt gtgtgtgtgc tccgtaaact gtttattctc 22680
cccctccgtc tcgctctgga tgggctccgg gtccgtcaac acgcgacccg cgtggcaaaa 22740
ggcacgctgt tgacggcgcg agagcccgtc atgatagtcc atcatgcccc ggagatcgtg 22800
cacaaagcag ctgtcgccgc gcagaaaccg acgcagcgtc tccacgtgct gcagctgtcg 22860
gcgcgtatca ggagccgtca tcgctgatgt cgtcatcgcc ctgacaggcg cgtagatggc 22920
tccgcgagat catgcgcgtt ttcaaccgcc gtgacacatc aggtccatct tgagctggcg 22980
ccgggcctcg cgcaggtctc gcacgcgttg tgagcgggag gcgagttcgg cttcttgctc 23040
gaactcctgc tgctcactgt ccgagagggt gcgataaaag gcggcaaagt cctccaagtc 23100
ggctacatgc gccctgggtc tgacgctcca aagcgtacgc agtctgatga agcggaccca 23160
tcgagcgtca cggcacgccg tcttgaacgc agggcccggg aagagattct tctccccggc 23220
gcgctcgggc cggcgaggcc gacgcggttt atatacaccg tctcggacgg cgggacgccg 23280
agcccgcgcc gcggccgctc atccggagac ggcggaaacc gcggcgccgg aggaaacggg 23340
gaccggcaac gacggcggtg gcggcgacca gattatgggg gacaagccca cgcttgtgac 23400
cctgttgacc gtcgccgtgt cgtcgccgcc accgtcgtcg ccgctgccgc tcgtcagctt 23460
cacggagctg ctgttaccgc cgccgtccgt cgccgccgct gcggtggcgg caacagcgac 23520
gagcgaggtg ggcgagaaaa ccgcggagca agaggtagcg gctgcgggtc cggagaccgg 23580
gaatgagaga agagaaaaca gggaggacga aggaggggag acgaggacga cgggcaccac 23640
cgcggtcaaa aggtcgcacg acggtatccc tcgccaactg gcagagcgcc tgcggctgtg 23700
ccgccacatg gaccccgagc aggactatcg tctgccggcg caggacgtgg tgacctcgtg 23760
gatcgaagcg ctacgcgacg cggaccgcga caactacggt cgctgcgtgc gccacgccaa 23820
gattcaccgt tcggcctcgc acctgacggc ctacgagtcg tacttggtgt ccatcaccga 23880
gcagtacaac acggcctcga acgtgacgga gaaagcttcg tacgtgcagg gctgcatctt 23940
tctctcgttt cccgtcattt acaacaacac gcagggctgc ggctacaagt acgactggtc 24000

-continued

```
caacgtggtg acgcccaagg cggcgtacgc cgagctcttc tttctgctct gctccaccag  24060
cgagagctcc gtggtgctgc aaccgctcat caccaagggc gggctctgct cgtccatggc  24120
ggtttacgac gaggaaacca tgcggcagtc gcaggcggtg cagatcggtt ttctgcacac  24180
acaactggtc atggtgccct tcgtgccgca cgcctgcccg cattacgccg tgcctttcac  24240
gacgccggga aagccgggct gcggcggtgc tccgagcggc gttgcggggt tggaggaggc  24300
ggcgcccttt ggacgggtca gcgtcacgcg gcatggcgcg acgctgctgt gtcgcgtgga  24360
ccatctgacc tggatcagta agcgcgtaac cacgtacgga cacaaaaaaa ttacgcgcta  24420
cctcgcgcag ttccgcggca cgatggacga cgacgaggcg gcgctacccg gcgaggacga  24480
ggcgtggatc gcgtccaaaa acgtgcagta cgaattcatg ggtctcattt tcaccgtcaa  24540
cgtggattca ctatgcgtgg acgcggaaca gcgccaactg ctgggcaccg tggccacctc  24600
cttctgtcac cgcgtctcgg acaagatcac agcgcgcaac atgccgcgcg ccttttcctt  24660
ctacttgcta acgagcgcgc agcgcgggta cgacctgcga tttagccgca acccgtcact  24720
ctttttcagc ggcgacgcgc tcaactgtcc gcttctcaac gagcccaacg tgttttcgct  24780
cacggtgcac gcgccttacg atatccactt cggggtgcaa ccgcggcaga cggtggagtt  24840
ggacttgcgc tacgtgcaga tcacagaccg gtgtttcttg gtggccaact tgccacacga  24900
ggacgccttt tacacggggc tcagcgtgtg gcgcggcggt gagccgctca aagtcacgct  24960
gtggacgcgc acgcgttcca tcgtgatccc gcagggcacc cccatcgcca cgttgtatca  25020
aatcaccgag ggcgacggta acgtgtactc gtacaatcac cacacggtgt ttcggcagat  25080
gcacgccgcc ggagcaacca cgttctttct gggcgacatg caattgcccg cggacaactt  25140
tctcacgtct ccccatccct gaccctccgt ccgtcctcct ttcccgacac gtcactatcc  25200
gatgatttca ttaaaaagta cgtctgcgtg tgtgtttctt aactattcct ccgttttctt  25260
aatcttctcg atcttttgga ggatgttctg cacggcgtcc gacggcgttt tggcgccccc  25320
catgccggca gaacccggtt gcggccccgt accgctcttc tggggcgacg ataggtcgaa  25380
agccaccgtt ttcatgcccg tcgtgctctt gacgggggaa cctacggcgg cggtccccgt  25440
cgagcggcgt gattgcaaag ccgcgctcgc ccccggtttc aggatggagg gggaggccac  25500
aggcggcgca ttcgatacgc tgcttttggc cgtagacgac ggtgggtaaa cggtagttac  25560
tgcgggatac gtcggcgtgg tcgaggcggc ccggctggtg ccggacaggc gacccggcgc  25620
gctaccgctc acggggaccg agggcggtcg acctaccacc gccttgccgc ccaaagtagg  25680
tttcaaggaa ggaacaacac cgacgcggct gccccggcct ttcaccggag acggggggc  25740
actcttggcc ggggacggag aggctgacga aagcatggac agcggcgatg tggcggggga  25800
cacgatatca tcctccgtgg gcgataaaac ggacgccgaa gctgacggct gtcgagccga  25860
agaagcggaa gaggttcccg cgccagaagt cacgttcctt gatgacgtcg ttttagacga  25920
agccggttga ggttgcaaca gcgtggcggg taccgtcgac ggcgtgcccg acacctgttt  25980
ctctagcctt ccctgaaccg gtgtcgacgt caccgtctgc gctcgggcgg acgcgtgcgg  26040
cgtcgcgact cgcttgccca gcaccggttt ctggctcgtg gatgtcgtcg tcattggaga  26100
cgataactta gctttacgta ttctggacgg cgtcgactgc tcgggcgtct gactgggagg  26160
cgaaatgacg tcgttgtaat cggacgacgg tgttgtgtgt cccaggctga cgacggagcc  26220
ggtgtccgag gagtcgtcgt cttcctcctc gctgtcttcg accggtgact ctgcagtttg  26280
gtcccttaaa gcccaaacct catcagcggt gttctgagac gctgtttgtg tcaccgcggc  26340
gcgtggagtc gacggcctcc gaggggtggt ggacacggtg ttttgagaag ccgtggaagt  26400
```

cgtaggcatc ctgaagggat tgtgagccag gtgaggattc ctgagggccc acgcgcgttc 26460
gcgcggccag ttggcggggt tcatatcccc gggcaacggc gccgtcggag cccagggcga 26520
gttaccgttg accggggttt gggtacccgc gaaggtaggt gtcggggccg gagcgggggc 26580
cgtagaagga ttgacaggcg tcggcgtgag gatggcagcg ccggcgccag cagggacgtt 26640
aactccggcg ccgaacgtca acgtcggttg ctcgaacttg tacgcggtgg tgacgggcgg 26700
tttggcgctc gtctcggtat ccgtgatgtc caccagcgtg tcggtgaaac gcggatcttg 26760
acggttgggg ggatagccat ccgagctgtc ggaatcctcg tcgcccgaga aaagatcccc 26820
tctggtctcc gtgagcggcc tcacgtccca cgcgctgtcc cgacggaccc ttcccgggct 26880
ggccttggtc acctgcgggg agacgagact gaaagccgcg tgacgctgtt gttgctgcgg 26940
gatgttcaag ggaccactgg tcggtttctg actgcccgag gataacaggc cgctgaaaat 27000
gctggaaaca ccgccaccac tagcggcgcc cttgccgcta gttcccggtt tcttgatggg 27060
cgtaaagatg tttttctcgt catcatcatc gtcgtcgtcg tcctcatcgg cactggagcc 27120
aaagagcctc cgggaggcgc tcggtttacg tgccgggggc ggtggttgct gctgacgttg 27180
ctgcaggttc tgctgcctct cctcccaagc cttcagctgc tgtttctcac gctgcaccac 27240
ctcgtcgtcc acccgtttct gccgctcgcg acgcttttcc tcttcgtcgt aatagccgac 27300
ggccgccgaa cgggcagcgt gggcgtcggc ggccggtgcc agagaaccat gggcctcgaa 27360
gcggaacggt ttgtgtccct tccagggact agcgatccag ctccagccgt ccagcggctg 27420
cgtggggaca tgtttcttgg gtaccgacga gaaggctgaa ccgccgccga gcgagaggag 27480
attggcgtca tcatcaaact ccaacgacgg cgagcgcgcg cccaaaaagg tgtgcgccga 27540
ctgcgggaag ctgtccacgt agatatcaaa gtcctcgatg agcagctcca gcagcgtgtc 27600
ggccgagtcg ccgttttcca cggcgtgctt gaggatattg cgacagtagt tggaatcaaa 27660
ggaaaggcac atgcgcagct ccttgaccag cagcttgcag cgctcttgaa tgcgcgccag 27720
acatttgcgc tccagctcct cccaagacct tcgcacgttc atgatgagac ggcccgtgta 27780
cacgagcttg ttgacggcgt tgaccagcgc cgtgttggcg tgccggtcca ggttaaggtc 27840
gagcggtttc acacagaaca tgttacggcg cacaccctcc aggttttctt caatgcgctg 27900
cacctccgta tctttgaggt gcacaaaggc gatgggttcc gtctggccga tggctgtgac 27960
cagcgtctcg cgcaccgaca tcttggccag aatgaccgcg cttacgagcg cgcgctccac 28020
gatctcggca tcgtggcgca cgtccgtatc gaattcggta cggtctagca cagccaggtg 28080
gtcacgcgcc ttaccacgat caccgaacgg gtaagtgtag ccgcgacgcg ccacggccgc 28140
gcaacgcacc tcgaactcct cgagcaccga ggagaggtcg ggattgtgga aacgcagctc 28200
gcggtagtat cccaaccaaa gcatgagctc gttgaacagc accgtacgcc ggtgcaggcg 28260
tttttcgcca catttttca ggatcttggg gtgtgcctcg agatccacgt cgggcttttg 28320
cgtgagatgg cgcagaaagt tgaccagggc caccacatcg cgccgctgta gaccgataaa 28380
ctgcaaactc atgctggctt ttctccagaa cccggaagcg tcgtcgcccc ggactgcgcc 28440
cgcggtctgc tattcgccca cgatggacac catcatccac aactcggtga gcgccccacc 28500
tagagggagg gggggtagtt taatagcgga ggcggatacg cggttttctt ttaagcgccg 28560
ctgacttgtt tcttctgttt tttcgccccg tgtgctgttc cgcccagacc cgcaacaaca 28620
ctcctccgca catcaatgac acttgcaaca tgacagggcc gctattcgcc attcgaacca 28680
ccgaagccgt actcaacaca ttcatcatct tcgtgggcgg tccacttaac gccatagtgt 28740

```
tgatcacgca gctgctcacg aatcgcgtgc ttggctattc gacgcccacc atttacatga  28800
ccaacctcta ctctactaat tttctcacgc ttactgtgct accctttatc gtactcagca  28860
accagtggct gttgccggcc ggcgtggcct cgtgtaaatt tctatcggtg atctactact  28920
caagctgcac agtgggcttt gccaccgtag ctctgatcgc cgccgatcgt tatcgcgtcc  28980
ttcataaacg aacatacgca cgccaatcat accgttcaac ctatatgatt ttgctattga  29040
catggctcgc tggactaatt ttttccgtgc ccgcagctgt ttacaccacg gtggtgatgc  29100
atcacgatgc caacgatacc aataatacta atgggcacgc cacctgtgta ctgtacttcg  29160
tagctgaaga agtgcacaca gtgctgcttt cgtggaaagt gctgctgacg ctggtatggg  29220
gtgccgcacc cgtgataatg atgacgtggt tctacgcatt cttctactca accgtacagc  29280
gcacgtcaca gaaacaaagg agtcgtacct taacctttgt tagcgtgcta ctcatctcct  29340
tcgtggcgct acagactccc tacgtctctc tcatgatctt caacagttat gccacaaccg  29400
cctggcccat gcagtgtgaa cacctcacac tgcgacgcac cattggcacg ctggcgcgtg  29460
tggtgcccca tctacactgc ctcattaatc ccatcctgta cgcgctgctg ggtcatgatt  29520
ttctgcaacg catgcggcag tgtttccgcg gtcagttgct ggaccgccgc gctttcctga  29580
gatcgcagca gaatcagcga gctacagcgg agacaaatct agcggctggc aacaattcac  29640
aatcagtggc tacgtcatta gacaccaata gcaaaaactg caatcagcac gccaaacgca  29700
gcgtgtcttt caattttccc agcggtacgt ggaaaggcgg ccagaaaacc gcgtccaacg  29760
acacatccac aaaaatcccc catcgactct cacaatcgca tcataacctc agcggggtat  29820
gagctttcct gttactttat tcagaaagca ccagaacccg tcgccatttc ccctcatata  29880
cggtacacgt ccccctgatc tgtcatcacg gtacacagat ttcgcccgac tgcggacgcc  29940
gacggccaat cgcgtggcgt aggagtggcg ccccggcttc attataacgc cacgtcggag  30000
cccctgcgcg ccacaacgcc gtccggcgca acttctgtct cggcacggta cgataaaaac  30060
aacgtccccc ctcgacgttg ttttctccga gcggtgatcg ttcccgtccc tctcctccct  30120
ccgcggcccc cacggcggcg gcctgctcgc acggacctat actattaccg ccccaccgcc  30180
gtcgtcgtca tgaacttcat catcaccacc cgagacttct ccaacgacga ttcagtcctg  30240
cgagccgccg agatgcgtga caacgtggca ggctcgattt ccaaagcgta caagggcacg  30300
gtacgcgccg aaggcaagaa gaagctgctg ctgaagcact tgcccgtgcc gcccggcggc  30360
tgctcgcgcc gcaacagcaa cctcttcgtt ttctgcaccg agcgcgacta ccgcaagttc  30420
caccagggca tcgcacagct caagcgcgcg ccggccgaac tggacccccca cgagatccag  30480
caagtcacgg ccagtatccg ctgccgcctg cagcccagtc tccgcgagcc gcccacgccg  30540
gccgacgagc tgcagacggc tgtgtcgcgc gtgtgcgcgc tcttcaacca gctggttttc  30600
acggcccagc tgcgccacta ctgcgagcac caggacaagg tggtgagcta cgcgcgcgac  30660
gagttgacca aacgctgcgg cgaaaaatcg gcgctgggcg tggaggtgca tcaactggta  30720
gccttgctgc cacacgagcg ccaccgcgaa ctgtgccacg tcctcatcgg cttgttgcac  30780
cagacgccgc acatgtgggc gcgctccatc cgtctcatcg gacacctgcg ccactacctg  30840
cagaacagct tcctacacct gttgatgaac tcaggtttgg atatcgcaca agttttcgac  30900
ggctgttacc acagcgaggc ctaccgcatg ctcttccaga tcggtcatac ggactcggtg  30960
tcggcggccc tggaactctc acacagcgca gcggccgggc cgcccgaggc cgatgagaac  31020
aacgacgagg gagaggagga cgacgacgag ctccgtcaca gcgacccggc gccgcttcac  31080
gagtccaaga agccccgcaa cgcccgccgt ccccgcacac gcatgccgcc tcacgagcaa  31140
```

```
aagcccgaag aaaacgagga ggaagaagag gagctgtttc cctcctgcaa ggcaaccgca  31200
gcattcctgc gggcagaacc ctccgtctcc aacgacgacg gcaacggcgg cgaacgctgc  31260
gacacgctag cgaccgccct gcggcattgc gccgacgaag aagacggacc tctagccagc  31320
cagaccgctg tgcgggtcgc cgcgaccccc tcaccttcag tcaccccagc ccttaccccc  31380
gtcacgtccc ccataacccc gttgtgtatt taacgtcact ggagaacaat aaagcgttga  31440
tttctcaagt tccgctctgg ttttggtttc gttttcaaag ggagccccat catggcccaa  31500
ggatcgcgag ccccatcggg cccgccactg cccgttctcc ccgtggacga ctggctcaac  31560
tttcgggttg acctgtttgg ggacgagcac cggcgcctgc tgctcgaaat gttgacccag  31620
ggctgctcca actttgtggg gctgctcaac tttggcgtgc ccagccccgt atacgcgctg  31680
gaggccctgg tggacttcca ggtgcgcaac gcttttatga aggtaaagcc cgtggcccag  31740
gagattatcc gtatctgcat cctcgctaac cactaccgca acagccgcga cgtgttgcgg  31800
gacctgcgca cgcagctcga cgtgctgtac tcggagccgc ttaagacacg gctgcttaga  31860
gggctcatcc ggctctgccg cgctgcgcaa accggcgtca agcccgagga catcagcgtg  31920
cacctgggcg ccgacgatgt gacattcggc gtgctaaaac gagcgctggt ccggctgcac  31980
cgggtacgcg acgcgctggg gctgcgcgcg tctcccgagg ccgaggcgcg ctatccgcgc  32040
ctcaccacct acaacctgct gttccaccca ccgcccttca ccacggtcga ggcggtggat  32100
ctgtgcgccg agaacctgtc cgacgtaaca caacgtcgca accgaccgtt acgctgcctc  32160
acctccatca aacgcccggg ctcacgcacc ttggaggacg cgctaaacga tatgtatctg  32220
ttgttgacgc tgcgacactt gcagctgcga cacgcgctgg agctacaaat gatgcaggac  32280
tgggtggtgg aacgctgcaa ccggctttgc gacgcgcttt acttttgtta cacgcaagcc  32340
cccgagacgc ggcagacttt cgtcacgctg gtgcgtgggc tggaacttgc gcggcaacac  32400
agcagtccgg ccttccagcc gatgctgtac aatctgttgc agctactgac gcaactgcac  32460
gaggccaacg tgtacctctg cccgggatat ttacatttca gcgcgtacaa gctgctgaaa  32520
aagatccaat cggtctcgga cgcccgcgag cgcggcgagt tcggggacga ggacgaagag  32580
caggagaacg acggcgagcc gcgcgaggcc cagctcgatc tcgaagccga tcccacggcg  32640
cgcgagggcg agctcttttt cttctccaag aacctgtacg gcaacggtga ggttttccgc  32700
gtgccagaac agcccagccg ctacctgcgc cgacgtatgt tcgtggaacg gcccgaaacc  32760
ctgcagatct tctataactt ccacgaaggc aagatcacca ccgagacgta tcacctccag  32820
cgcatctata gcatgatgat cgagggcgcc tctcggcaga cgggcctgac acccaagcgc  32880
ttcatggaac tcctcgacag agcgcctctg ggccaggagt cggaacccga gatcacagaa  32940
catcgcgatt tatttgccga tgtttttcgc cgtcctgtga ccgacgcggc ttcttcgtcg  33000
tccgcgtctt cgtcgtcgtc ctcagcatct ccgaattctg tttcgctgcc gtctgccagg  33060
tcgtcatcca cacgaaccac cacgcccgcg tccacgtaca cctcggccgg gacttcttct  33120
accacgggtc tcttgctctc ctcttcttcc ttgtcggggt cacacggcat tagctccgcg  33180
gacctggagc agccgccccg gcaacgacgc cgcatggtca gcgtgaccct cttttcgccc  33240
tactcggtag cctacagcca ccaccgacgt caccgaaggc gacgcagccc accacccgca  33300
ccccgagggc cagcccacac acgcttccag ggacccgaca gcatgccgag cattagctac  33360
ggcagcgacg tcgaagaccc gcgggacgat ctggccgaaa acctacggaa tctctgaacg  33420
cggtttttcc tctttttcta cgtgtctgtc tcaggacgag atgtcgatat caataaaaat  33480
```

-continued accgtcgacg tggttttcta acagtgtggt tttctttatt gaccagcgga gtacacagtt 33540
tacgagtaaa aaagacaggg aaaggttata taaaatgctg tattatatac aaaaacatgc 33600
acatagacaa acgggaccac cgtgctcgtc atcccctcct taatcagtta ttcatgtagg 33660
cgtgtggcgg ggtgaggggc ggcatgccgt tggcggcgcc aggaataatg tgccgtcgac 33720
cgacgtcgca caccttgaaa cgccgtcggc gcacgcagcg gtcgcaggac gggatatccc 33780
agaggaagcc catgtaagtt tcggggtcct cgtcgtgaaa gcggtaggag agttcaaagt 33840
ggtgcaacga gcccgtccga gctcgcagct tctggcgaac accctccacg tcatcggtgc 33900
acagcgacag tgctgggctg tcacacaggg cctgaagctc ctgcggccac aggtgcgtgg 33960
ccaggggcga gtccgtcgtc accagtttga cgcagtgcat caggttctcg gtgatggcgt 34020
cgtacaggcg actctcggcc tcctcgtgcg tcatcacgtt tcgaggcagc gacagctcgt 34080
cgtcgtcatc ctcgtcaaac atgatcatgg ggtcaggggt ttttttggga tgttgacagg 34140
tgggtgtctt ttccagacgc acgatggcct cacgccggcc gctgaaacgg tggtttcggt 34200
gtcccttctt tcccatgacg caggtgaaca taaccacgtc ctcggccaaa cggtagacgg 34260
cgtccatggc ggggtcgtag ccgtagacga cgccgaaagt gtccaccaag acgtactggc 34320
gtacgaggaa ctctttgcgt tctggcacct cgtggcccag cgcgcccaac aactggtggt 34380
aacaggtgat gcgcggcacg gtacggatca tgagctccat ggtctggatg ctgccgcccg 34440
cgcggacgac gctgaaggat gtttccttga acttcataac ctctgtgttg tgggtccaga 34500
aggcgaaatg ggtgtcggga cactcatcga aagggtcgtc gatgctgtag gaagcgtagc 34560
cccgcttggt cacctcggcc gacaggctct ccacgtcacc gcggtagagc atgacggcgt 34620
tccagtagtc gtcgtactgc accatgggcc gctggtagtc gcgcatagtg tggaagtggt 34680
cgcagtgacg aaagccatgc cgcagaaagt ccttcatggt ggccgccagc tcgtagacgc 34740
agtcgcgcag gtcatcgtag cagtagatgc caccgcgctg cccgatgagc acgatgagtt 34800
ggtaacgcat aaagcccgga ccctcgacga aaccaaaggg gtgcaggtac tcctgacagc 34860
agacgtaagc acctggtgga gaaatgagaa aaatccacgc acgttgaaaa cacctggaaa 34920
gaacgtgccc gagcgaacgt cctctttcca ggtgtcttca acgacgtggg gcttaccttg 34980
cgaacagacg gtgcccatct tgcccacgaa gggccccagg gcgctgcgcg aacggagctg 35040
gatgaagcag cgttcgggcc aggccacgtg cagccgggtg ccgcattcct gctccagaaa 35100
gtcgttgaga ccgttaaagt ccccggctcg gatggcgatg cagccgtagg ccatcagcgt 35160
gtcccgtagg tcgtccatga cggactcctc taccttcgct cgccgacgct gcgcttctcc 35220
agccaccgct gcggtcgaca gactccttcg tccgccttcg gagaactacg gcgcggcggc 35280
acggccttta tagacactat cagcgttgac gtcagacgat ccgatgaacg tcgtttttttg 35340 tgctggaact tccctcgtcc cgacaaatgt agcggaaatc ttcaagcaaa tcgcgacgaa 35400
gtccgatgag gaggatgcaa aagaggctga gcaacgcgat gctgcccgcc gccacagtac 35460
atatgctcaa caacgcccag tgtcccaacg cgcgactttt ggctcggagc agagccgaac 35520
ggcggtttct ccacatcgtg gatagcgtga tccaatactt ccatccttca cattccggtg 35580
tccacatggg aagcgacgtc acgttagttc ccgtaaacgt tgagtttctt tttttgtttt 35640
tcgtaagctt aagggttctc ctaagaaacc gcgggcacat gtcttgtaga aagatgtaat 35700
cactttccgc gtattttgtc agtattaaca tcacagtggt agtgttttcc aaagaagtga 35760
cgttactagt aacgttggtt tcctcccaat gtacgtatga ttcaaacgga ctcgtatgtg 35820
ctaccgcttg caacacgtaa ctgtggccgg tgaagttgag catcaattgt cccacggtaa 35880

```
cattggtgtc atttgtaaaa cacgcgattt ctccgcgaac ttccgtgacg ttggtctcac  35940
gactctcgtt caacacacgc aggggaaacc agccttccag gtgatactga aaaccaaatt  36000
taagcatgac gctgtgccat tgccgtcgtg attggttaaa cgttacattc aagggtagtc  36060
tggcttcggt cccgacacag gggccgttgt agatttgcgt attattgcac gtgcagttta  36120
actgacagtt catactcgta gtgttggaag tgacgttaat gtccgtgccg tggtacgtac  36180
agcggaccga aacaccgtgt cccgtgctcc aaaacagcgt caacaacagc cacacagaca  36240
cctacgtggg gacgatacgg gactttttat tgacggagac tcacgtttct accctcccct  36300
ttcccgtagg taaaaaccca cgtttatcac acacgttgtt tttacctgaa acccgcgcag  36360
cccgtggacg cgacaaaaaa ccgcggcact agaaagaaaa tgaaacaagt atgtttatta  36420
agcagcatgt ggggctaata ggggggataa ctgaggtata gcaactatga aaaaatacta  36480
caaaaaaaaa agctgaacat ggtcatctag cagcaaagtt ctccttctag accacgacca  36540
ccatctgtac cacgtcgccc tccccggccg tgtacacgac atccttcacc acgaccggcg  36600
gcagcggcgg cgacgaggac aactcgctct cgatggaggc cgggacgaca gaggacgggg  36660
gggtggtggc ggcggaggac gaaggggtgg cggcggcagc ggggtcttct tccgacacgg  36720
gcgacggcag gctcggcggc gcggacagca cccgttgcgc cggggcgtga gaaggctgag  36780
ccccggtggc ctggatgtgg gccaacgaat tggctcgcag cgagtcgcga tccacgaagg  36840
tcataggaat cttcccttcg cggatccgcc gctcagattc caggatggcg cgcacgtagc  36900
tgttcaccga tttggcaaaa gtgcgcggcc cctccgtatt cttgtcgcga cgcgcttcca  36960
gcacttgctt ttcgtagtcc agctggtgga agaccatcac cagatcgtcc atagtgtgcg  37020
cgtgctgacg gacgtgggaa cgcacctcca ccgggaacaa agcgttccaa tactccagca  37080
cgatggcacc gtgccagaac tgcgccatgc tgggcgccag gaaaaacagg ataccggagt  37140
cgtaggcgaa cacgtcccac ttgggcgtca tgaacaacac cagctgacgc gtgggccgca  37200
ccgaagcttc ctcccaggcc tcgatgaccc cgaacatgat gagctcctgg tccaacgggg  37260
ggcagtgtcg ctccagccaa ctgatcttgc tcaggttcat ctgcaaaaac tcgtaagagg  37320
ggtcgcagat gcacacgtag agacccgagt cgtgccgcag cctggctccg cgcttcatca  37380
gtttcctcac cgcgtagcga agcgccacct tgcccaacgc cgacgcctgg atcagtcccc  37440
ccacgtccat ctgcgtctgt cgccactcgg cctcgtccag caggctcatg atagcggcgg  37500
tgctatgcgt ggtcgtagtc atcctttcta tccttctcta tgaatagcag caatagcggt  37560
aaagtccctt cttatactat cccggagtct gtggtttttt tgtttacccc tgcttactgg  37620
tgagactgct gggggccgtt gtgctgcagc agccgagctc gtcgccgccg ttgccacagg  37680
aaccggtgcc tccgcagggc ctttttgagg gcctcgcagg cttctcgcgc aagtcctgag  37740
aggccctcgg cgtcgatggg gttcacctcg ggcgtccgag cctcgttttc ttcttcttca  37800
tcctcccttt cctcctccgt gtcctcccgc tctgtgtcct ccgttacgct ctcctccccg  37860
gcctcggcca agagcgcggc caccaagtcc acggaccgct cggtctccga gttctcaccg  37920
tcaattacgc catgttggcg gcgtaaccgg tgccgagaac gccgggtgag cgcacatgct  37980
tttttctttc ttaaccaagg cgggagagga tcttcaaggc gttttcgctg gatccagcgg  38040
tagctaaagt accaaaaggc cagcaggccc acgctaccta acagattcac gtagactgga  38100
gacataatta aagaaagaag tgaaacccgc gtgtgggtct cacgtcgtct tgaaacaccg  38160
tcttatatac atgaagatgc cggacatgac gcgcccaaga cacgtggggt tttcccctta  38220
```

```
ggcgacccgg tttcttaaga tgtttttcat cttcgcacgc gatgtactac atcaaagggt  38280
cggctgaccg accgcattga cgcagtttcc gagtacgcgc gtctcggagc acctgacggt  38340
gagccaccca gctcacgcgg ataggggaca acactgacgt gaggggcgat tcccgtcact  38400
gacgggtgac aggaataaga cgggtgagga atttccacct ttttcttaag tgtgactctc  38460
cttacggtaa atcgcacctg tgacctctta acccctcctc cctggtaccc aataacagtg  38520
aaaaacacac accacacgtc acgacaccga tcgattttct ttattcttag tgtgatgata  38580
ggtaagggca ctcgtgagga tgtgcaatta tcattatcaa gcctttttca aggcgtagtg  38640
atgatcgttg ggcagaaccc ccaggctcct agcgatctgg gaatagaagg aggagaacga  38700
ccccagggcc agaatgccca cagtgtacat ggcccaggtc tccagaccga acgtggcggg  38760
tcgcagcttc agatggtagg ccacccgctc cgagagttgt gaatgctcgt tcaggcaaca  38820
ggactgcaga tgggtgagtc caaaagcgct ttcgtttacg ccgcgcacgt gcaccgtctg  38880
ggccgggcaa tcctggtgtt gcgcgcgaaa atggtccagg caggagactc cgtctgcacg  38940
gcggcgagtg ttgttaccca cttcgatcaa cagcgtgtta acggcaagat gacgcgagaa  39000
cgcgacggcg gtgttgttgg aggtctggcg gcagcagtac acgtcgagtg tcatgagggc  39060
catgtcgcct tggtggtaca cggcgtacgc ccaaccctgg aacacgagcg gacataacgg  39120
accgtgagcg gacgtcacgc cggcggttgt taccgtcgtc tcggcaggag aagataataa  39180
actcctgatc ctcatacaca ggagtccaag cgtcagaatt aaagtccgcg gagccacaac  39240
cgcgcaagtg aagccgatac gagtgttgct gaatttgttc attctgccga ctgttgccca  39300
cgagcgttcg gaggcggtgc cacaggctgt tggccattaa aaagtcctgg cccgaatgac  39360
gacgagacag agcccgaggc gaagaaaaag acgcccgtca tgaagacgta ggcaggggaa  39420
ttcccatatt tttatggctt cttttaaaag tctgtatccg actccatccg gcgcttttcc  39480
caaaccgtgg tctcctcgtc gtccgactcg gtacccagga ggtggtaagt cttttgccgc  39540
acgtagaaag ctttcaacgt ggagcaaaag atgagaataa agaccccaaa aacgaaacaa  39600
accacgccga tcatgccgat gcagacgttc atgtcgacgt agccggcggt gctgttggca  39660
gtgcggcaaa agagtgtcat gtcgtacgtg cacaaaaaac aacacacacc acaggccagg  39720
tcgtagcgta gttattattc cgtagcagca atgatagtac agtcaagcac atgctctatc  39780
cccgttaccc cgatgatgag gaaacccccg ttgttgtatt ggcactgtcc cggttaatca  39840
ccacggtgaa caccacggcc aagaaaatga tccctaatat agcgaccact aagagagcaa  39900
aagtccattt ccagccgttg tcaaagtacg cccccgtggt gggatgcatg gtggcgggca  39960
tttccatcat atccatgtcg aacgtgtgtc gcggcgacgg cgaactaacc aggcagtacg  40020
ggggtcgata gggcggtggg ctgcagtcgg gtggtggcgg cggtggcgtg gaaaccgtcg  40080
tcgggcacag acccatggcc tgctcgtagg tggggggcgc gtcgtcgtga tcccggtcgc  40140
ggagcatcgg cgtgggctcc atgtcggtgg cagtgacggc gacggtggta actgtggtgg  40200
agacggtacc gacggcgtcc gcggttcacc ttcgagcaaa gagccccttc tttttgcgca  40260
aacgacggca aaacagttct ctgggacagc cggtggcgcg gtaagcgggt gccacgcttt  40320
cagggtgggt aaaacagtcg cgggcaaagc agtaattgtt gcagaaccgc aagaacccga  40380
cgcgaaagaa gcccaggagt ccgcgcgcca gaaagtgcgc ctgccgcgtc tcgggatgca  40440
cgccgaagac ggcgccgctc tcgttcacca gtatggagat gtccaggcgc tgctgcgact  40500
ccaccggcac ggcccgcacc acaaatacct gcagcacgtt cagcgagcac gtctctttta  40560
accagttgcc gtgggccgga tcctcgtaag tctggctccc gttcaagacg accgtcgtca  40620
```

-continued

```
gcgcctcatt accgtctcgc cagctgaaga tggaaccctc gcgcttcatg cacaggcgcc  40680
acagggccag caggtcgcgc gccaacatga actcgcgacc cacgtcgccg ccggtctcga  40740
agcggacata gcccagttct tcgcgcagcg gcgcgtagtt gcgcaggccc tcctgcacga  40800
agccgcggaa accggaccgc gacaccaggt acagcgattc caccacgggc gagtagacgt  40860
agacgcgacc gccttcgccg atgagtacgg gtagcggtgg gcggccgatg gcttcgcaac  40920
gactcacagt gcccaccggc agcaggaact tgtcgcagca caggaaggtc ttctccaaac  40980
ctttaatatt gagatgtcca aagtaaccaa cgcgtaacag gtcgcagtag gtgaagaacc  41040
aaccgtttgg ccagctgaga cgcagcaccg tgccgctgac gcgacgaacc agcttctgca  41100
ggtccttgcg agcgtcggag gtgacagaac agcggaaggt ctcgttgacc agctcgacag  41160
ccagcgcgtc ctccagcgtg cgttccttca tctcgtcgtt gatgctctgg cggcgccgcc  41220
ggatttcgtc gaaacgggcc gcggaggcgg cgaccgacgc ggaggtcgtc cgaacgccct  41280
ctgtgacgct accgtccggc cagtcaagaa agctaaggct ggcgctgcgc cgcctaaagt  41340
gtccgatccg cgcgggacgt cgctgaggga cggtggctgg tctgctgggg cgggtacggc  41400
cgcgggtgtc cgcggacacg ttagttatac acggaattga gtcacgtggc acgttgccag  41460
ctgaaaccgc cgtcgtctcc gccggcgttt tctccatcac gggaccgcgc cgtgcgcgcg  41520
ttcccaggca cgcggcccgc gctctagccg cacttttgct tcttggtgtt agggacgaac  41580
tcgaacgtta cagaatcctc gctgtcgctc tcctctttcg cgtcgttgaa gtaattgccg  41640
gagttgcgat ccaaaccgcc gcctcctcct cctccgccgc cgcccgatcc acctttggac  41700
gtcaggtagc tggtgatctt gtgctgctcg tatttttcct tggaggaaag accgtggtcg  41760
tgatcaccgc cgccgccacc gctgctcatt ttccgcgtac cggaaccacc gccgccaccg  41820
cggtcgtgct tcttgccgcc accgccgcca cctcctccca gaccgccgag acccatgggc  41880
tcgttcatga gatcgttatc cagacccggg ccgtcgtcat gcagaccgcc ggcattggcc  41940
agcgaagaga ggctgccgcc accaccgccg ccgccacgcg acttgccgct gttcccgacg  42000
taatttttat cgaagggatc gccacgctgg aaaggttcct cggtgagaaa attctccacg  42060
gcgaacagac cgttgcggct ggccacgtac aacagcgtgt cgtgctccgt aactatacgc  42120
aacgtgcacg gcagtttggt gacggcgcaa ttgagcagcg tctggtagaa gttcttcagc  42180
tgcacgttga tacgcatgtt tttcacgccg tggaaactga cgcggttatt ggccgtgaat  42240
tccagctcgc tgccgtttgt caggatgaac ttgatggccg gcggaccggc gtgcaccaga  42300
atctgcacgg tgcccgtagg gcagggcgct tttttaacgt tacgcttgac gcgagtatgc  42360
ggcccgatcc acttaagcag gtcggccacc acgccgaaat ctagatccac gtgcacggcc  42420
gaattctcgc tttcgcgcac aatgtcttgg ccgtgcacac aggccgagct gaactccata  42480
ttgaaatcgg gcgcgcacat ggagatcttg gccgaaaggt ccgaaatgtc ctgcacgtag  42540
aacttggtca ggtccttgct ggaagtcagg tacatgaaat taccgagcag cggcgtggaa  42600
ttgttaatgg tcttgggctg aaacgacttg tcagtgatgt agaggcatga gctgttaaaa  42660
gtgatttttg acacgcagtg actgcgtacc gtttgcaaga taagcgacgg cgtgggcaag  42720
aaggtaaccg tggtgttctc cttgagcgca cggatcacag atcgcagctg ctggatagcc  42780
gtcttgtacg gcttcagccg cagcgccagc gtcggtggct ccgagagacg cgtcttgcga  42840
tccatcccgg acagcgtgca agtctcgact aaggagcggg cgcgagcgag cgaaagtttt  42900
atagagagca cacacgacga ccgggaacgc tgcgaagacg cccggcgtct aataatacag  42960
```

-continued

```
ccgcgccgag ccagcgggcc cccgactaag aggcacagta cttatatact ccgaccttaa  43020
agcgccagtg gtaccacttg agcatcctgg ccagaagcac gtcgggcgtc atcccagagt  43080
catagtagaa aaccagggcc acgcactggt ccacaaacac gctcaggttc acggccgcca  43140
tttccacgtc gttttggatc gccggcgccg cctggaacag acactgcgtc gccttgccct  43200
cctcctggtg ctgctccaac cacgcgtaat tcaccacggg cacgcgcaac ggcctccgca  43260
ccacggtggg gaagtaacac tcacggttgg gcgggcacaa tgaccacacc gtctcctcct  43320
cgaacacggt gccgcgcgaa gcccatactg acggcgtcac gccccacaga tgcgccacct  43380
cgtcgtcggg acccaccgcc agaaactgac agttgcgcaa tccgaactcg agcatgtcgg  43440
cgcgcagcgc ttcccagcgc gcgctggcga tggagagccg cggcaaccga tacaattcga  43500
aaatgaattt gccctcttga tagatggtgc gttcgaacca ttcgcagcgt ggcaaacccg  43560
acttgcacaa atcgacgcta gcgcgcaccg cggcaaagta catgtgctca aagatgcgct  43620
cgatcaagtc ccaagaggca aagtacgtaa accctaaccg cataagcgcc gtgtgcaggc  43680
cagccacgcc gatgtgcagc ggacgcagtt tttccagcgc gctctctacc caccattcgg  43740
acgccgacat tagcgcgtcc aagcgcgcgt tgccccaaac caccgcctcg gtcaccaact  43800
cacgcagcac gctcaaatca aagtaacgtc gcgtgttccc caaaaccacg tcgggtagat  43860
gcagcttctg ctcgtcgcta cgcgcaaaca cgcagcgagc cacgttcacc gtcagccgct  43920
gcaccggcat gtcacactcg ccaaagtggc acgacgccat atcgggactc aagcacggcg  43980
gcaggcacac gctgtcggcc ataatcgagt acttgactac gtgatggaca aagaccaccg  44040
aggcacggcc cttgagcgcg cacagcaaca tctttttcag aaaatcgtcc gtgttcacga  44100
ccaccttggg gcacgattgc tcgcagcgcg aatactcttt ctcgaaagcc gactcctgac  44160
ccaggtccga gagccgccgg gagacaggcc gcccgaacag cgagtagcgc tgctcacgcg  44220
cacggtagcg cttcattaac acgctaggca cgttgaaagc gtagcaaacc cccgtcaact  44280
ccgacgtgct ttctttgaga ataaagttga tcacgcggat agcagccacg tcccacatgt  44340
ccacaaacac acgtaccacg ggtcgatgca cctccttctc gcgtatcaaa tcgcagtatc  44400
cccccagaca acgaatcacg ctgttcacat cggcgttaag tcgcgttacg ttcaccgaca  44460
cagaaacgcc gcaactcaag gtgctcatcc atttgcacat agccgcccaa ctggcgtcac  44520
gcgaaaaagg gtcggccgag atcagaaagt cgtactgcgg cacgcgatcg aaacccacgg  44580
tagacatggt gaaggtggac agcgacagct gcccatcgcg acagcgcttc aacaccgatt  44640
ccaacacctc gccctcgaaa cgcgcatcca gatggaaacg atagatgcgc gagtgcctac  44700
tgttctcgat agccgccgtc aacgccacgg cgatgcgcaa aaacacgccg cccggactct  44760
cgtcctgtcc gtgcagttgg cgacacacct tatccaaaca caaaatggcc gcgtacaagc  44820
cccagcaacc ggccaattcc acaaaacgcg ccgtctcttc ggccagcttg ggtagatcct  44880
ccatgtgacg cagcacaaaa cggcgcaccg actcatcgca cagctccgaa gcgtaacaca  44940
gtggcgtgcg gctttcgcgc gcccagttgg ctttgaaata aaagcgaccc aacagcagat  45000
cgcaacgcgg cgagtgacga atcagacagg gaccgtggcg catgatgagc tgaaacagcc  45060
tgaaactgcc caaaccggca ctgtgtcgcg acacggtgtc catctcgcgc cacaacgcgt  45120
tcctgtcaga cggcagctcc cgcgccggct cctgtacgcc acaaaagcga aacttgcccc  45180
aatagccgtg acaatgacac tttttgccca tcaacatgcg cgtagcctgt atcggcggcg  45240
acactttgca gagcgaagcc ccgaaatcgt cctcctcctc gacactgtcc agctccatcc  45300
tggtcgcgcc ggtcggattg aaggtgctca gaccgctact cacgcgtcca ccacgactgg  45360
```

gcacggcggg accgctatca cgcgtcaacg acagcacaga cggcgtgccg tcgggagacg 45420
gcgactcggg acgccaactg acgacgccgc caccactcgt aaaacccgct acacacgcta 45480
cgccgctcga cacgttggta ttttcagcgg acgcttcctt gtcacccccg ggcagcggcc 45540
cttcctcgag ctcgctgtca tctcccccgg tagtatcagc gacggcctct gccgacgatt 45600
cctccgtctc gatttccgcg ccgcggctcg gaatcctacc tggccggcac cgatacacgg 45660
gcaccgagga cacccgctgt tcctcgtccg cgtcagccgg agtcataagt ttacgaggaa 45720
aagaacaaag aaatcaggta gatttcaata aagtgtgtct atatggcacc gataactacg 45780
gtttataaag tctgtgtgcg ctgtgtttat tttttcttct gtgtctcctc ctcgtatgct 45840
gtcagcgccg ctcagacgaa ttctcgaaag tctcccaatt cgacgctaaa gttgtccaaa 45900
cggacgacgg acagtttgag ttctttgtgt accaggaacg aggtgtgaat gtcgtcagcc 45960
aggcaccagc ccagcttttg tataaccccg gtacacagag ggatctggcg tgggcgcgtg 46020
atgcgacggt tgacaaagct acagcgctcg cgggcgaact ttccgcgtgc aacgtcgacc 46080
agggtctgcc aatgtgcgat gctggaggtg agcacgtaga tgccgggacg tgtttcgggc 46140
ccgtcatagt catagacgat gattaaatac acgtattgca gccgtccccg ggtctcttcc 46200
cacgtcaggt acatgtcttt cggtatcatc aacgcgaaca cctccgtttt gagcgtgttg 46260
taaaggtagc cgcgcatgac gcaggtgagc aacgaggtga tgcccagcga gacggtcttg 46320
acgcagccca gcgtctcgag gcggcggtgc agcagatgcg ggcccaggtc cagccactgc 46380
agcgcggcgc gcgcggccga ggccgtgtac acgctttcga gcaggcagcg cgtgctggcc 46440
gagacgttgg aggcgcgaat gcctaacagg tagaggctaa tgtagaggtg tcgcggcgag 46500
tcgcaacccg tctccatgcg gatgagcagc gcgcccggct gcgcctcgaa ctctaccagg 46560
ccctcgggca cgaagaaacg cgccgtgagc gcctggtgat cggcgtggta gaggtagcgc 46620
accgatatag tatttacctc gcgtttggct ttgagcgccg tcactagttc attgtcctcg 46680
tcggccgggt cgcgcggccg tttggccacc gcgcgcgcgt ccatgatggc aaggcgcacg 46740
gtagatttca aaaagttgat agagcagctg cgggcacggg ccacggacaa agcggaggcg 46800
ttaaataccg tgagccaatt ggagatcggc gcggtggatg cccaggacgt gaccgcgagc 46860
gccgtgcgcg ccttcgtggg tgcgttgccg agctcgggtt accactttgg cttcgtgcgt 46920
cagaacgtgg tcttttacct cctaagccac gccacggtac agacggcgcg cgacccgctg 46980
tacgccgccg agcagttgca cgaacagctg gaccgcttcc tgcgacacca gcacgacggc 47040
ggcggagacg aggaccggtt gccgttctac cacaacgggg ccacgctgac ggctttccag 47100
aagctgttgc agaccctgcg cgagatccag accgtaatag ccgaacagag cggcggcacc 47160
gcggcggcgg cggacttgat cgccagtaac aacgcgtcga ccgagcgccg cggcaagaag 47220
ggcggttcga gttccggggg ccagcagccg ctggttcgcc gggtgatcac gcagctggaa 47280
acggctgcca cggaggcgcg gccctacatc aattgtcgcg ccgtggccga actcctggac 47340
ctgacctacc agcggctcat ctactgggcc tgcacgctca tgccctacgt gttgtttcgg 47400
cgcgacaccg acaccgaact ggacacggtg cttctgatgc attttttta cacacactac 47460
cgttcggtta acggcgattt ggccgtggag tttcaaaact acgtcaagaa cagcgtgcgg 47520
cacatgagct ctttcgtcag ttccgatatc gacggcgacc agaagcccgg tgccgaacac 47580
atgcgtgacg tcagctacaa gctgttcgtg ggtaatctgc aggcgcgtga cgccagcggc 47640
ctcatgtttc ccattattag cacgcgcatc tccaccgtga acctttacct gtcgcccgaa 47700
cgtatgtttt tccacccggg tctgatctcg cgtctgttga gtgaggaagt ttcgccgcgc 47760
gccaacctag acgcttacgc gcgcgtgtgc gatcgcgtgc tggaagacca cttgcatacg 47820
ccgcgacgcg tgcagcggct actggatctg acgcagatgg taacgctact ggtggaactg 47880
ggtttcaatc acgatacctg cgcggcctac gcacaaatgg cgctgatcca gccggccagt 47940
cagaagagct cgctctttgt cagcgagatt cgcgagaaac tcatacagat tatctacaat 48000
ttttacacgt ttttcatgtg cctctatgtg tacagcccca cgttcctgtt cgaccaccgg 48060
cggcggttga ttttggagca gcatcgatcc acgttgatcg gctccaagga ggaactacag 48120
cacgtctgga gcaacgtgac gctgaacgtc aatacgcact ttgcggttca gtacacggaa 48180
gaagactttg aggcacatac gaagggtgcc acggaggcag agcgcgagta cctgtatcgg 48240
gacctgcaca gcaagtgggg cgtgcacctg tttaccttgc gtccgtctcg cggcgcggcc 48300
ggcgcggcct cgcctttgcc tccgcttgac ggcgtcacac gctccgacat cttacgcgaa 48360
tgcgcgctcg ttaatctgaa cgaaggccgc gtcaactacg cctccctgct agccttcagc 48420
catcatcccg agttccccag catcttcgcg cagttggtgg tggtaactga attttcggag 48480
atctttggta tcccgcaggg cctgtttcaa gccgtgggtt cgccgcgtct tttcgcgctc 48540
attcagctgt gtcgtgtatt gttgcccgag caggtgacgc tgtaccagaa cctggtctcc 48600
atttacaacc tgaccacctt tgtcaagcac atcgacgccg cggtttttaa gacggtacgc 48660
gattgcgtct tcgacatcgc cacgaccctc gagcacctca gcggtgtacc cgtcacgccc 48720
aatgtggacc tgctggccga gctcatggcg cgctccgtag cgcataacct gtacaccacc 48780
gtcaacccgc tgatagagga cgtgatgcgc agcagcgccg gcagtctgag aaactatctg 48840
cgacacacgc gactctgttt cggtctggcg cgcggccggg cgcgcctctc ggaggacggc 48900
gtgacggtgt acgtggaggt acagggtcag tacggactgc gcgtacctac cacgcgtttc 48960
gtagaacagt tgcgcgaact ggttcgccgc gatcggctgt tggccgagaa tctgcgcggc 49020
ttaaacgagc gcctgctgag tgttcgcgtg cgcgtacgtc agatcagcag cgacacagag 49080
gaagtaagcc gacacgccaa gggtcaccgc acggtggccc agatgagcaa ggcgctcaaa 49140
aagacggcct ccaaaatcaa agtgttggaa acacgcgtga cattggcgct cgagcaggcg 49200
caacgttcca atggcgccgt cgttaccgcg gtgcaacgcg cgctagccgt ctttgacgta 49260
ctaagtcgcg agaacttgga acgccgcggc gcacagctct gtctgacgga agcgacgagc 49320
ctactgcacc gacatcgcgc gctagcgccg atgacctggc ccgcgggcac gggcgttgcg 49380
gcggcggccg aagcggatcg cgccttacgc gagttcttgg aggcgccctg ggaatcggcg 49440
ccccaaccgc cgcgactccg catgacgccc gacaccgatc acgaagaatc gacggcaggc 49500
gcgacgtccg taccggaggt cctgggtgcg cgctacgaac ccgcacacct ggccgcgagc 49560
gacctattaa actggtacat cgtccccgta agccaggcgc agcaggacat cttgtcttcg 49620
atcgacccgc ccgccggctc gacatcggtg tccctgccgc cggcctcgcc atgaaagtca 49680
cgcaggccag ctgccaccag ggcgacatcg ctcgctttgg agcgcgagcg ggcaatcaat 49740
gcgtctgcaa cggcatcatg ttcctacacg ccttgcacct gggtggaacg agcgccgtcc 49800
tgcagaccga ggcgctggac gccatcatgg aagagggcgc gcgtctggac gcgcggctag 49860
agcgcgagtt gcaaaagaag ctgcccgccg gcgggcggct gccggtctac cgactgggcg 49920
acgaagtgcc gcgccgcctg gagtcgcggt tcggccggac cgtgcacgcg ctctcgcggc 49980
ccttcaacgg caccaccgag acgtgcgacc tggacggcta catgtgtccg ggcatctttg 50040
actttctgcg gtacgcgcac gccaaaccgc gtcccaccta cgtactcgtc accgtcaact 50100

```
cgttggcgcg cgccgtggtc ttcaccgagg accacatgtt ggtctttgat ccgcacagct  50160
ccgcggaatg tcacaacgcc gccgtgtatc actgcgaggg tctccatcag gtgctgatgg  50220
tgctcacggg cttcggcgtg cagctatcgc ccgctttcta ctatgaggcc ctttttctct  50280
acatgctgga tgtggcgacc gtgtcagagg ctgagatcgc cgcacgtttg gtctccacct  50340
atcgcgaccg cgatatcgac ctcaccggcg tcgttcgaga aagcgcggac acggcggcga  50400
caacgaccac cgccgcacct tccttacctc cgctgcccga ccccatcgtc gacccgggct  50460
gccctcctgg cgtggcgccc agcattcccg tctacgatcc ctcgtcctca cccaaaaaaa  50520
cacccgagaa acgccgcaag gacctcagcg gtagcaaaca cggaggcaaa aagaaacccc  50580
cgtccacgac gtccaaaaca ctggccaccg cctcctcctc ctcagcgata gcggcggcct  50640
cttcttcgtc cgcggtacca ccgtcctaca gctgcggcga aggggccctg ccggccctgg  50700
gccgctacca acagctggtc gacgaggtag agcaggagtt gaaggctctg acgctgccgc  50760
cgttgcctgc caacaccagc gcctggacgt tgcacgcggc gggtaccgaa agcggcgcta  50820
acgcggcaac ggccacggcg ccgtccttcg acgaagcttt cctcaccgat cgtctccagc  50880
agctcatcat ccatgccgtc aatcagcgct cgtgtctgcg tcgcccctgc ggtccgcaat  50940
cggcggcgca gcaggcggta cgcgcctatc tgggcctatc caagaaattg gatgcctttc  51000
tgctcaactg gctgcaccac ggcctggatc tgcggcgcat gcacgactac ctgagccaca  51060
agaccaccaa aggcacgtac tcgacgctgg atcgcgcact gctggagaag atgcaagtcg  51120
tcttcgatcc ctacggacgt cagcacggcc cggcgctcat cgcctgggtg gaggagatgc  51180
tacgctacgt ggaaagcaag cccactaacg aactgtctca acgactgcaa cgtttcgtaa  51240
ccaagcgacc gatgcccgtt agtgacagct tcgtctgcct gcgacccgta gactttcagc  51300
gtctgacgca ggtcatcgaa cagcgacgtc gggtgttgca acgtcaacgc gaggagtacc  51360
acggcgttta cgagcacttg gccggcctca tcaccagcat cgacattcac gacctagacg  51420
ccagcgatct gaaccgacgc gaaattctga aagcgctgca gccgttggac gacaacgcca  51480
agcaggaact ctttcgcctg ggcaacgcca aaatgctaga gttgcagatg gacctggacc  51540
gtctgagcac gcagctgcta acgcgcgtgc acaatcacat cctcaacggc tttttgccgg  51600
tagaggacct gaagcagatg gaacgcgtcg tcgagcaggt actgagactc ttttacgacc  51660
tgcgcgacct gaaactgtgt gacggcagct acgaagaggg atttgtcgtc atacgcgaac  51720
aactgagcta cctcatgacg ggcactgtgc gcgacaacgt accgctactg caagagatcc  51780
tgcagctgcg acacgcgtac cagcaagcca cgcagcaaaa cgagggtcgc ctcacgcaga  51840
ttcacgacct gcttcatgtc atcgagacgc tggtgcgcga cccgggcagc cgcggctcgg  51900
cgctgacact ggccttggta caggagcagc tagctcagct ggaagcgcta ggcggcctgc  51960
agctacccga agtgcagcag cgcctacaga acgcgcaact cgcgctaagc cgcctctacg  52020
aagaggaaga ggaaacgcag cgtttcctcg acggactctc gtacgacgat ccgcccaccg  52080
aacagaccat caagcgacac ccacaattac gcgagatgtt acgtcgcgac gaacagacgc  52140
gtctgcgact catcaacgcc gtactgagca tgttccacac attagtgatg cgactggcgc  52200
gcgacgagtc gccgcgaccg acgtttttttg acgccgtcag tttgttgttg cagcaactgc  52260
cacccgactc gcacgaacgt gaggatctgc gtgccgccaa cgccacgtac gcgcagatgg  52320
tcaagaaact ggagcagatc gagaaagccg gtaccggcgc atccgaaaaa cgtttccaag  52380
cgttacggga gttggtttac tttttccgta atcatgaata tttctttcaa catatggtcg  52440
```

gacgactggg cgtcggacct caggtaacgg aactctacga gcgatatcaa cacgagatgg 52500
aagaacagca cctggaacgg ctagaacgtg aatggcaaga agaggccggc aagctcacgg 52560
taacttctgt ggaggacgtg cagcgtgtct tggcccgggc accgagccat cgtgtcatgc 52620
atcaaatgca acaaacgtta accaccaaga tgcaagactt tttagacaag gagaaacgta 52680
aacaggaaga acagcaacgg cagctactgg acggctacca aaaaaaggtg cagcaggatt 52740
tgcaacgcgt ggtggacgcc gttaagggcg agatgctctc caccatcccg caccaaccac 52800
tggaggccac actcgagctg ctcttgggcc tagatcaacg cgcccaaccg ctactagaca 52860
agttcaacca ggacttgctg tcggcgctgc agcagctgag caaaaaacta gacgggcgaa 52920
tcaacgagtg tctgcacggc gtgctgacgg gtgatgtaga gcggcgctgt cacccgcacc 52980
gagaagcggc tatgcaaacc caagcctcgc taaaccactt ggaccaaatt ttgggtccgc 53040
aacttctgat ccatgagacg cagcaggccc tgcaacacgc cgtccatcaa gcgcagttca 53100
tcgagaagtg tcaacagggc gatccaacta cagccatcac gggcagcgag ttcgagggcg 53160
actttgcacg ctaccgcagc agtcaacaga agatggagga acaattacaa gagactagac 53220
aacagatgac cgagactagc gagcggctag atcgctcgct gcgccaggat cccgggagca 53280
gctccgtcac gcgtgtaccc gagaaaccct tcaagggtca ggagctggcg ggtcggatca 53340
cgcccccgcc cgccgacttc cagcagcccg ttttcaaaac gctgctagat cagcaggccg 53400
acgcggcccg gaaagcgctc agcgacgagg ccgatctgct gaatcagaaa gtacagacgc 53460
agttgcgaca acgcgacgag cagctgagca cggcgcagaa cctgtggact gatctggtca 53520
cgcgccacaa aatgagcggc ggactggacg tgaccacccc cgacgccaag gcgctgatgg 53580
aaaagccgct ggagacactt cgcgagctgt tgggcaaagc cacgcaacaa ctgccgtacc 53640
tgtcggcgga gcgcacggtg cgctggatgc tggcttttct ggaggaagcc cttgcgcaaa 53700
tcaccacgga ccctacgcac ccgcatcacg gaagcaggac ccactaccgg aacctgcaac 53760
agcaagccgt cgagagcgcc gtgacgctag cgcatcaaat cgaacaaaac gcggcctgtg 53820
aaaattttat tgcacagcat caagaggcga ctgccaacgg cgcgtccacg ccgcgggtcg 53880
acatggtcca ggcggtggaa gcgatctggc agcgactgga acccggacgc gtagccggcg 53940
gcgccgcgcg tcatcaaaaa gtgcaggaac tgttgcagcg cttgggtcag acgctaggcg 54000
acctagaact gcaggaaacg ttggcgacgg aatactttgc gctgttacac ggcatccaga 54060
ccttcagcta cgggctggac tttcggtcgc agttggaaaa gatccgcgat ctgcggactc 54120
gttttgcgga actggccaag cgacgcggta cacgtctctc caacgaggga gccctgccca 54180
acccacggaa accgcaggcg acgacttcgc tgggcgcctt tacacgcggg ttgaacgcac 54240
tggaacgaca cgtccagctg ggtcaccagt atctgctcaa caagctcaac ggctcatcgc 54300
tagtctatag gctggaagac attcctagcg tgcttccgcc aacacacgag accgaccccg 54360
cgctgatcat gcgcgaccgc ctgcgtcgtc tatgcttcgc gcgtcaccac gacacctttc 54420
ttgaagtggt agacgtcttc ggcatgcggc aaatcgtcac gcaggccggc gagcccattc 54480
acctggtcac cgattacggc aacgtagcct ttaagtactt ggcgctgcga gacgatggcc 54540
gacccctggc atggcggcgc cgctgtagcg gcggaggact caagaacgtc gtcaccacac 54600
gttataaagc catcacggta gccgtggccg tctgtcagac attgcgcact ttctggccgc 54660
agatctcgca gtacgaccta cggccctacc tcacgcagca tcagagccac acgcaccccg 54720
cggagactca cacgttacat aaccttaagc tcttttgtta tctggtgagc accgcctggc 54780
accagcgcat cgacacgcag caggagctga cggccgccga tcgcgtaggc agcggcgaag 54840

-continued gtggtgacgt aggggaacag agaccgggcc gcggcaccgt gctgcgtctg agtctccaag 54900
agttttgtgt actcatagca gctctgtacc ccgagtacat ctacaccgtc ctcaagtacc 54960
cggtgcagat gtcgctaccc tccctcacag ctcacctaca tcaggatgta atacacgcgg 55020
tagtcaataa cacacacaaa atgccccccg accacctccc cgaacaggtc aaggctttct 55080
gtatcacccc cacccaatgg cccgccatgc agctcaataa actgttttgg gaaaataaac 55140
tggtgcagca actgtgccag gtaggcccgc aaaaaagcac accatcccta ggcaagctat 55200
ggctctacgc catggccacg ctggtctttc cacaagacat gctgcagtgt ctgtggctag 55260
aactgaaacc ccagtacgcc gagacctacg cctcggtgtc cgaattggta cagacgctgt 55320
ttcagatttt cacgcaacaa tgcgagatgg tgaccgaggg gtacacgcaa ccgcagctcc 55380
ccaccggaga gccggtgctt cagatgatcc gcgtgcgacg ccaagacaca accaccacag 55440
acacaaacac gaccacagag ccaggacttt tagatgtttt tattcaaaca gaaaccgccc 55500
tagactacgc gctgggctcc tggcttttcg gcatacccgt gtgtctcggc gtgcacgtag 55560
ccgacctgct gaaaggccaa cgtgtattag tagcgcgcca cctcgaatac acgtcgcgag 55620
accgcgactt cctccgcatc caacgctccc gggacctcaa tctcagtcaa ctgctccagg 55680
acacgtggac cgaaacgccg ctggagcact gctggctaca agcccaaatc agacggctac 55740
gcgattacct gcgtttcccc acccgcttag agtttattcc cctagtcatt tacaacgcac 55800
aggaccacac cgttgtacgc gtgctgcgac cgccctccac gttcgaacag gaccacagtc 55860
ggctggtgtt ggacgaggcc ttccccacct tcccgctgta tgaccaagat gataacacat 55920
ccgcggacaa cgtcactgcg tctggcgccg ctccaacacc gccggtacct ttcaaccgcg 55980
taccagtcaa tattcagttt ctgcgtgaaa acccgccacc catcgcacga gttcagcaac 56040
cgccgcgccg acatcgtcat cgagcggccg cggccgcaga cgacgacgga cagatacatc 56100
acgtacaaga cgatacatca aggacagccg actctgcatt agtctccacc gcctttggcg 56160
ggtccgtctt tcaagaaaac cggctgggag aaacaccact atgtcgagat gaacttgtgg 56220
ccgtggcacc cggcgccgcc agcaccagtt tcgcctcgcc gcctatcacg gtgctcacgc 56280
agaacgtcct cagtgctcta gaaatattgc gactagtgcg attggacctg cgacaactgg 56340
cgcaatccgt acaggacact attcaacaca tgcggtttct ctatcttttg taaccgacac 56400
tgacagtagc gggcaataaa aacaagagga ttgttatggt tttttgatat aaaacaacgt 56460
gtcactttca cggtgattta ttcttgctat tacttttccc catgggctgt cagcgtcggg 56520
tgcgcgacac ggctaccatg cgcaacaggt ccagcttaaa ggcgcacttg tcgttaaaca 56580
gactggacat gcgcgtatac ttgctcagca tggtggccag taccgggtgg gtggcctctg 56640
agatctcggt cggcaactcc aaaacgacgt tgacgacgtg acggtgtttt tcgtcccgct 56700
tgttggccac cgtgggtccc ggcgcggtgt tagacatggg gcaggccgtg gggggaggac 56760
gaggaggaaa tcgctgctaa accgccgcgc gcctgctgca caatgtggcc gccgacgtgg 56820
caggcggtct gtttaaccag cgcgcagccc cgacacagcg gggcgccgtc ttcgctttcc 56880
aaacagctgt cgcggtactc gcccgtctga cagcgcgcgc acagcaggcc gtgcccgtgc 56940
gaagtgaggc gcaggagacg cgggaccgtc acgccgcgta ccaccacagt ggagtcgcag 57000
gtgcgtgccg cgcagggcag aatgacgtcg aaagccagcc ggtgatcgta cacggcacaa 57060
gccgcgttga ggcccagcac ggctttccag cccacgcgta cgcagcgctg tccaaagagc 57120
gtctcggaga cgagctcgta gacgcgctgc cgcaccaccc gctgactgcc gcagagcgag 57180
cagtgtacga gctcggcgtg cgtgttgaag atgacgctct tttcttgacg gtcccgataa 57240
tagaacatcg agttgagcgg aaaattttgc tggcagtgta gcttttcctt acccaggttg 57300
aggcagtgtc cgcactgccg acagaccacg gccaccagcg agcgcgcgtc cagatggcgc 57360
tcgcacttga gtcgacacag acaccagagc ggcaggtcga tgacgctgcc gatgaggccg 57420
ccgcgcagcg cggcgctgag tgcaaagagg acgatcttgg tgggctctac gtgacgcgcc 57480
tgctgtccgg cgcccgcgtg tcctaccgcc gcagctgccg ccgtcgagcc tcctccgcgc 57540
gtctcgtcgt gcagacccag tgcccgcaac ggcaccaggt atcgcggaca cgtgtcgcaa 57600
aacgtctgca ccgcttgtcg ggccagtacg tagagcgggt ttccgcaggg taccttcccg 57660
gcgtgccggc gcaaggctgc gatgaggccc cgcagctgcg gcgaccgcgg ctgccgttgg 57720
tgacaccact ggttacggtg gtatacggcc aaatcagcgc gggcgtcgaa gcgcttggcg 57780
cgtagtagtg ctaggcacgg cgagctggtg gggtgaagca cgggcagccg aaggtccacc 57840
ccgaaaagga aacggtgaag gtcacctagc agcgaggcgg tgacaccgtc caacaacgcg 57900
tgcagccgct cgggcgggta gagccgcaga cggcgcagca ggtagtcggt gttgtagcgt 57960
tcgaaacgca gaaaagccat cgtgcggacg gccacggtgt gcagacagtc catgctgtag 58020
acgtaagcga gaaacacaaa gtagggcttg gtcataacca tacgctgaaa gagcgccgtc 58080
accgcctccc gctcggcctg ccgacacacc agccattcgc gcaggaagcg ttggtagaga 58140
cggtcgccca gctcgcgatt caaaaagcgc ttatccgtca cgaagagatg aaggacgcaa 58200
gaacgtggca cgtgatgcac cagctgctgc tggaggaccg ccgacgtctg cgccgcaaac 58260
tgcgccggtg gctgcgacgt ttctaccgcc gcttcctccg gctgcagcgc accgcggccg 58320
atcaccagct gcacatggaa atggtcctcg tgaacgcaga ggggcgcgaa gagacggcac 58380
agagcctggt ggaactcatc agtcgcggtg tgcggagcgt gtcggagacg acgattggcc 58440
atgaccgcgc cacagcagag ccagcaccag cagaagagcc agcaccagcg ggcccagagt 58500
cgcaaagcgc gcgggcagcc acggcccaga ctgcggtcgc gatggcccgg agcgcgctcg 58560
ccaccacgat gacggtgccc aacgataacc agtccgctcc aaggacggcg cgcacggcgg 58620
agacggcgga tgacggtgat gggtcgacac ccctcgccga cgactcacgt gctcctccag 58680
aggccgacgc gcggaccctc cgacgtcctg gcccgccgct gccgctgccg ccttcccttc 58740
tcccgccaga gccagcaact cctcctcctc ttcatcagcg tctccctcgc ttgcgcatcc 58800
gcatcgtccc atacaggcct cacaacgaca caaccgccac gaccccgccg ccatgggtgg 58860
cggcggcggc cgaggcccgg cagcggcgcc gccagcggcg accatggtgg gagagcaact 58920
cggatgacga ggaggaggag gaggaggagg gggagatgcg ctccgagagg accgctttcc 58980
cgccgttcgc gtgagcgcgg ccgacatgcg ggcgcgccac agggacggac cgctgccgct 59040
gtgactgctt acggtgacgt ggttccggac cgccaacgac gtcgacgcgg ctttcttggc 59100
gtacagctcg cgcagcagat tctcgtactc gccctcgttt tcgggtccga aggcgataag 59160
ctcgatgttg aagaccgacg ctgaattgga tttgcgcacc acgcacttcg tcagcactcc 59220
gtaggccgag ggcttgatct cctcgatgtc cttgagcgtg acgatgagcg actcgttcac 59280
cttaagcaca ttgaactcac ctacgtggcg cgccggcgaa acgagcttga cgggcgctcg 59340
cacaaaacag cagagggaga cggcgcagcc agtgttttta aagataaaac aaggcacgtg 59400
gtctgtgcgg ctctcccagt agctgagcag atactcgaca caatagaccg tgtctgtctt 59460
gagcatggcg tcgcacaccg agtaattggg gtttttacag atgaggccgg catcggtgac 59520
gcgcagctcg ctgggaccca acttgaggat acgccgcgtg gcctgcacca gatcctgatg 59580
gagaaccttg ttcatctcca tcgcaccgac gccaccgccg atttatttac ccggcgccgg 59640
ctcgtctttt ccctccagga ttccgttaat gtccataagc ttgctgacga tcgccgttaa 59700
tagttgcgtc ttctcacgga ggatctctcc gtgactgcag gtcgcgcagt cgccgtgcac 59760
gtacttgagg aaggcggcgt acttctgacc cgcgttcacg aaatttaagc gcgcgtccag 59820
agagggcagc aacagatcgt agacgcgcgg cagcatcggc tcgaactgta atagcagatc 59880
gtcgtcaaga tcgggtagcg cgtgtccgtc ttcaccgtcc tcgtcgtcac cacctccccc 59940
ctcgagccca ccgctcgtac cagccgcggg ctccgcgtcc tcgtcgatca ccagcggtcg 60000
cgtcggcacc ggagaatcca cgtcatcctg cacgtcgttt tcctcctctc cgtcgtcatc 60060
gtccagaaac ggcacccgct gcttagtcca ggacattctt tctccgcgtc ctcaatcagc 60120
ggcgccgatc gccatgaatc cgagtaccca cgtgagcagt aacggcccaa cgactccccc 60180
tcacgggccc cacaccacgt ttcttccccc gaccagcccg gccccgtcca ccagctccgt 60240
cgccgccgct accttgtgca gtccgcaacg acaggccgtt tcgcgttaca gcggctggag 60300
caccgagtac acccagtggc actcggactt gacaactgag ctgctatggc acgcgcaccc 60360
gcgtcaagta cctatggacg aagcgctggc cgccgcggcg gccgcctcat accaggtgaa 60420
tcctcaacac cccgccaacc gttaccgtca ttacgaattc cagacgctca gcctcggcac 60480
ctcggaggta gacgaactgc tcaactgctg tgcggaagaa accacgtgcg gcggcacgca 60540
atccaccgta ctcaccaatg cgaccaacac cactagctgc ggcggagccg tcgccggcag 60600
tagtaacgca ggacccgccg gcgcttcggc cgcctgcgac ctagatgcag aactggccgg 60660
cctcgaaacc tcggcggccg actttgaaca actgcggcga ctgtgcgcgc cgctggccat 60720
cgacacgcgc tgtaacctat gcgccatcat cagcatctgc ctcaaacagg actgcgacca 60780
gagctggctc ctcgagtaca gcttgctgtg cttcaaatgc agttacgcgc cccgtgcggc 60840
gctcagcacg ctcatcatca tgtccgagtt tacgcatctg ctgcagcagc acttttccga 60900
tctgcgcatc gacgacctgt tccgacacca cgttctcacg gtcttcgatt tccacctgca 60960
ctttttcata aatcgttgct ttgaaaaaca agtgggcgac gcggttgata acgagaatgt 61020
caccctaaac catctagccg tggtgcgggc catggtcatg ggcgaagaca cggtgcctta 61080
caacaagcct cggcgccacc cgcaacagaa gcaaaaaaac aaccccttatc acgtcgaagt 61140
gccacaagaa ctgatcgaca actttctaga acacagctca cctagccgcg accgctttgt 61200
gcagctgctt ttctatatgt gggccggcac cggcgtcatg agcaccacgc cactcacgga 61260
acttacgcac actaagttcg cgcgactaga cgcgttatcc acggcctcgg aaagagaaga 61320
cgcaaggatg atgatggaag aagaggagga tgaagaagga gaaaaaagag gtgacgatcc 61380
gggccgtcac aacggcggtg gcaccagcgg ggggttcagc gagagcacgc taaaaaagaa 61440
cgtgggtccc atttacctat gtcccgtacc cgcctttttt accaagaacc aaaccagtac 61500
cgtgtgtctg ctgtgcgaac tcatggcctg ctcctattac gataacgtcg tcctgcgcga 61560
gctgtaccgc cgcgtcgtct cgtactgtca gaacaatgtg aagatggtgg accgcattca 61620
gctggtattg gccgacctgt tgcgcgaatg cacgtcgccg ctcggcgcgg cgcacgagga 61680
cgtggcgcgc tgtggactcg aagcgcccac ctcgcccgga ggcgactcgg actatcacgg 61740
cctgagcggc gtcgacggcg cactggcgcg acccgacccg gtattttgcc acgtcctgcg 61800
tcaggcgggc gtcacgggca tctacaagca ctttttctgt gacccgcagt gcgccggcaa 61860
catccgcgtc accaacgagg ccgtgctctt cggacgcctg cacccccacc acgtccagga 61920
ggtgaaactg gccatctgtc acgacaatta ctatataagt cgacttccgc gacgtgtgtg 61980
gctctgcatc acactcttca aggcctttca gattacaaaa cgcacctaca aaggcaaagt 62040
gcacctggcg gactttatgc gcgatttcac gcagctgttg gagagttgcg acatcaagct 62100
ggtggacccc acgtacgtga tagacaagta tgtctagcgt gagcggcgtg cgcacgccgc 62160
gcgaacgacg ttcggccttg cgctccctgc tccgcaagcg ccgccaacgc gagctggcca 62220
gcaaagtggc gtcaacggtg aacggcgcta cgtcggccaa caaccacggc gaaccgccgt 62280
cgccggccga cgcgcgcccg cgcctcacgc tgcacgacct gcacgacatc ttccgcgagc 62340
accccgaact agagctcaag tacctcaaca tgatgaagat ggccatcacg ggcaaagagt 62400
ccatctgctt acccttcaat ttccactcgc accggcagca cacctgcctc gacatctcgc 62460
cgtacggcaa cgagcaggtc tcgcgcatcg cctgcacctc gtgcgaggac aaccgcatcc 62520
tgcccaccgc ctccgacgcc atggtggcct tcatcaatca gacgtccaac atcatgaaaa 62580
atagaaactt ttattacggg ttctgtaaga gcagcgagct actcaagctc tccaccaacc 62640
agccgcccat cttccaaatt tattacctgc tgcacgccgc taaccacgac atcgtgccct 62700
ttatgcacgc cgaggacggc cggttgcaca tgcacgtcat cttcgaaaac cccgacgtgc 62760
acatcccctg cgactgcatc acgcagatgc tcacggcggc gcgcgaagac tacagcgtca 62820
cgctcaacat cgtgcgcgac cacgtcgtta tcagcgtgct gtgtcacgcc gtctcggcca 62880
gcagcgtcaa gatcgacgtg actattttgc aacgcaagat tgacgagatg gacattccca 62940
acgacgtgag cgagtccttt gagcgctaca aagagctcat tcaggagctg tgtcagtcca 63000
gcggcaacaa cctatacgag gaggccacgt cgtcctacgc gatacggtct cccttaaccg 63060
cgtcgccgtt gcacgtagtt tccaccaacg gctgcggccc ctcctcctcg tcccagtcca 63120
cgccgcctca tctccacccg ccgtcgcagg cgacgcagcc ccaccactac tctcaccacc 63180
agtctcagtc tcagcagcat catcaccgtc cccagtcacc accgccgccg ctgtttctca 63240
acagcattcg tgcgccttga cactgtacgg cagaaaagcc ggctccaagt gcaagcgccg 63300
cggcagcacc atgtgcaaaa acttgtcctt gcgcgcagtt tcgccgccgg gaaagacggg 63360
cgacagcacg ttggttacag ccttgagaac ctgctcaaag tacttgtcgg cgtgaatggg 63420
cacgccgtgc tcgcgcacgt agctcggatc ttcggctacc tcgtagttgc acacgaccga 63480
cggtggtttc cgcgccctct tctttgccgg ctctcctcct ctcctgttgc tctcctctac 63540
cccgccgccg tcagcgtcgt cgtccgtgcc atcaatcgcg tccgaccggg aaaccacgcc 63600
ggtggttaca gaatcaccgt tgtcggagga accctgcggc gccgtccgga caccgggcgc 63660
cgtcaggacg taaaagaccc gatccccgac cgagggtagc tcctcagaac gggccgccag 63720
tcgcttaatg acggcaatgt gcggcaagtt agattgacgg tacaacgaga tgtccttaga 63780
aagcaccgac gaaagcacca ggtcctcgac acgcacacgg tgcaggtaca gatcgtcgcg 63840
agcctgcacc agacggcgca agatacgcca gaaaccgcgt ggcacgccgt atttcttgac 63900
ttcatcgagt gagaggcgcg acaggcgcac ggctgcttcc gagacctcgc gatcctcaaa 63960
gagcagcgag aggacgtcac gcgtgacgcc cttgacgaac tcgcaagccg tcttgcgcac 64020
caaatccacg cccttcatgc tcaggcccga ggcgccctcc actttgccga tgtaacgttt 64080
cttgcagatc atcataagag agacgaagac cttttcaaac tccagcttga cgggctccac 64140
aaaaagacag gccgtcacgt agtgcgccag gctgggccca cgcgccacca gagcctgcgg 64200
cgtcaggcca cgaaagcgga caaacacgct gtccgtgtcc ccgtagatga cccgcgcctc 64260
cacccgccgt tcgtccgagc cccctgacga tgtttcgagc ccctccggta acgtgctgct 64320
ctcctccgaa tccccctccc gcgttcccac tacatagtct tcctgattaa aaaaattgtg 64380
caaaaaacac ggctctgaaa agttgtcttt gatgaaccgc gccgtgcgct ctagcatgtc 64440
gcgaccgatg cgcgtgatgc tggcggcgat gggcagacac ggcatcatgc cgttgaccac 64500
gcctgtaaaa ccgtagaaag cgttacacgt tactttgagt gccatctgtt ccttgtcgag 64560
cagcatacgg cgcacggggt cttgacactc gcgcatgcat tcgcgcacgg cacggcgctg 64620
cgaaacccac ttgttgagca gttccgaaag caccgagacg cgcaccgaag cacgcacaaa 64680
gcggtgagtc acgccgttct ctagcgtgac gctgtataca tcggcggggt ccacggggta 64740
ctcgccaccc ggcaccagca gggtggagta gcaaaggttg tgagccatga tgatggaagg 64800
atagaggctg gcaaagtcaa acacggccac ggggtcgttg taataaccca cctcgggctc 64860
aaacaccgtg gcaccctggt acgaaaccgc cgcagtaccg ccggcgccgt gactgtcgtt 64920
ggaaacgccg acgccgccac tactgccgga gccgacgctg aaaacgccga cgctgctact 64980
actgttactg ccagagccgg gtaaaacgcc gtcctgactc gacggcgcag attgcaaggg 65040
cggcgacatc tgaaacatag ccgccacaga acccgcgtcg ccgggcacgg cggcggtaga 65100
gatgatagcg gcgttaggtg acacggcaac actattcgtt tcgggcaccg tcgtaccttt 65160
gctgtagtgg ttgggcagga taaaatcgcg gcaggcgcac tcgtccagca gcgaggtgta 65220
gatacggatc tgctgtccgt caaagatgac acgccgcaac ggaattttag ccagccgcgc 65280
gatggccccg gcctcgtagt gaaaattaat ggtgttgaac agatcgcgca ccaatacggc 65340
gtcctgcaga cagtaacggc ctacctgggc gcggccctcg gcattagcca cgaaacaacg 65400
cgggatgtcc ttgtaggaca ggtcatcctt gcgttgccgc aggtaaagct cggccatagt 65460
gttgagctta tagttgggcg agttagtctt ggccatgcat acggggtaca tgtcgataac 65520
caccgaaccc gcaatataca ccttggtggc ggccgtgctg gccggattgt tgtgagaagc 65580
cgagggaaag gcggcggcgt actgccgctt aaaacccacg gcggggctgt gtaaaaagaa 65640
acggccgccc tgcgccgtag gcaacttgca gaagcgctgc gagtccacct tatacaggta 65700
ctcgaggcgc gtgaggatgt acttcaagtc aaaagagttg atgttgtaac cggtcacaaa 65760
ggccggcgcg taccgttgaa agaaaagcat aaagcccagc agcagctcgt attcggaagg 65820
gaactcgtag acgtccacgt ctgggcccac ctgcccgcag gtgccgatcg tgaagagatg 65880
aagacccgag tgcccaaaga tcacaccctc cgaagtgcag ccccggccat cgttcccgtt 65940
tgggatcccc tgatccacgg cggtgtttcc ccccgtctcg tagcacacgc acgagatctg 66000
aatgacaatg tcatcggact tctcggcgca gggaaaacca ccctcgccgc tcatgcactc 66060
gatatcgaag gacaggcatc gatagcgcgg ccacgagctg tcgtcgggca cggccaccag 66120
gtcagagaca tcgcagtcga cctcgatatc acaagtcgac gcgcgaccct gctgccgcca 66180
gtcgtaacga ttcacggagc accagccgaa cgtggtgatc cgccgatcga tgaccaaacg 66240
cgtcagcgga tccacacgga cctcgtacac gggaaaaccc tgctccagca gatactcgcc 66300
gatttttctg gccatggtcc agttgctgat agacacacac tgcaaatcgg gcacgggtcg 66360
cgtcccgtac ccgtagatcg aggttttggt ggccggcgtg acagacacgg cgtatggcgt 66420
ccgcggttcg ggcactagtt cgcccacgct ggcaatgacc tcacgcagcc tatcggtgtc 66480
gctgtactca cagtaaaagt agctgcgctg cccgaaaacg ttgacgcaga tactgtagcc 66540
gtgttctgtg gccccgaaga aacgcaacac gttccccgaa ggcaccagat gctgacgata 66600
gcgcggcgac acgttttcgg gcgagtcgaa gaagagcacg gcgtccgtct gatcgtaggt 66660

```
gtgaaaacga ataggtccca ccacgcgacc caccagggtc tcgcgccaag gacacggcca  66720
aaccatgtca tgactcaaca aatgtttaat ctctcgatag aacatgagag gcagccgtcc  66780
cgtcttatgc ttgatcaacc ccgtctgacc gtcgaacatg acgcctcgcg gcacgatctg  66840
caaaaactgt ttctgtggcg gccgcttgcc cgagccctgc gcggagccgg gctgcgaacg  66900
ctgacgccgg ccacccgcga ccgcaccgcc ggtcacgccg ccgctcagat acgggttgaa  66960
aaacatagcg gaccgtgaga ggctgacagc ttacgaagca aaatcacaaa gaaaatacac  67020
atgcagcacc tagatatcca gtttaacccc gtatatcaca agtctctgtg tcactttttt  67080
tgtctgtttt ttttttcttc tcctggttca gacgttctct tcttcgtcag agtctttcaa  67140
gtgtcggtag ccgtttttgc gatgtcgcag tcggtctagt aggttgggct tctgtccctt  67200
gtcctgcgtg ccagtctgtc cgtccaaaga atctgtaccg ttctgctgcg ctcgctgctc  67260
tgcgtccaga cgggccaggg ccagaagcat ctggtaagcc tgctcgttgg tgtaaggcgg  67320
agccgccgtg gatgcatcag acgacggtgg tcccggtcct ttgcgaccag aattataaac  67380
actttcctcg taggaaggcg gagcctgtaa cgacgtgtct ttggtgctgc ccgacgtcac  67440
ggtggtcccg tcggcggaca ccagataggg aaagaggttc tgcagcggct gcgtgcacaa  67500
acgccgctgt cgagtataga tcaaataagt gataatgact acggctatgg ccacgaggat  67560
gatggtgaac gctccgaagg ggtttttgag gaaggtggca acgccttcga ccacggaggc  67620
caccgcgcca cccacggccc caatggctac gccaacggcc tttcccgcgg cgcccaggcc  67680
gctcatgagg tcgtccagac ccttgaggta gggcggtagc gggtcgacta ccttgtcctc  67740
cacgtacttt acccgctgct tgtacgagtt gaattcgcgc atgatctctt cgaggtcaaa  67800
aacgttgctg gaacgcagct ctttctgcga gtaaagttcc agtaccctga agtcggtatt  67860
ttccagcggg tcgatatcca gggcgatcat gctgtcgacg gtggagatac tgctgaggtc  67920
aatcatgcgt ttgaagaggt agtccacgta ctcgtaggcc gagttcccgg cgatgaagat  67980
cttgaggctg ggaagctgac attcctcagt gcggtggttg cccaacagga tttcgttgtc  68040
ctcgcccagt tgaccgtact gcacgtacga gctgttggcg aaattaaaga tgaccacggg  68100
tcgtgagtag cagcgtcctg gcgactcctt cacgttcata tcacgcagca ccttgacgct  68160
ggtttggttg atggtcacgc agctggccag gcccaagaca tcacccatga aacgcgcggc  68220
aatcggtttg ttgtaaatgg ccgagagaat ggctgacggg ttgatcttgc tgagttcctt  68280
gaagacctct agggtgcgcc gttgatccac acaccaggct tctgcgattt gcgccagcgc  68340
ccggttgatg taaccgcgca acgtgtcata ggtgaactgc agctgggcgt agaccagatt  68400
gtgcaccgat tccatgttgg ataaatgagt tgcattgttg ccatctgtac ttcttttggt  68460
tctattatga gtaagattca gactggagcg gttggccaaa cgttcgagtt ctaccagaga  68520
tttttgcttg ataccttgcc agaacactac caaaccacca gtggtttcaa agacggacac  68580
gtttccatat ttttcatatg tttgattgta tgaagtattg aaaatctgct gtaacttatt  68640
tatagcctca tcacgtacgc agtccagcgc agagtcggac atgttcacct cttgcttctt  68700
agataagaaa gtggcggtca ttttggcaga agaaaagtga tacgagtcct cggcttcgga  68760
acgaatggtg cgttccgagg cttcccagaa agtgagttga caagtgacat tcttttcgtc  68820
ctgtatatcc caggagatca ccgagtccgc acgttcaaga aaagccacca acctgtgggt  68880
ctctaacgca gaattcggtc ttccaaagtc ggagacgata gtgtagttcg gaaaaatgaa  68940
aaacttgtcg gcgttttctc caaagtagct ggcattgcga ttggttccgt tgtagaaagg  69000
agaaatgtca accacgttac ccgtggaagt ggcgaaaaaa tgataaggat atttggagcg  69060
```

cgcagtagtg atggtcacca tacaattcag attacaggtc tcacgataga gccaggtgct 69120
gccgcggctg tgccattgat ccttgaccgt cacgtaacgg gtactgtggg tgttggaata 69180
atcgtcgggc attaattgca tggttttgtt ttcatagctg tccctatgat aagccacgaa 69240
aaccgtgcct gctataacgc ggctgtagga actgtagcac tgactgtggc tgttgatatg 69300
atgaatctcc cacataggag gcgccacgta ttccgtgttg ctgcccagca gataagtggt 69360
gtggatgtaa gcgtagctac gacgaaacgt caaaaccttc tggtagactc gtaccttaaa 69420
ggtgtgcgcg acgatgttgc gtttgtagac caccatgatg ccctcgtcca ggtcttcatt 69480
gatgggcttc atcgaggtgc agacgatatt acgttcaaag cgaataagat ccgtaccctg 69540
ggccatagaa cacacgcgat aggggtactt ggtggtattg acccccacca catctccgta 69600
cttgagggta gtgttgtaga tggtctcgtt aacaccatgg ctgaccgttt gggaagaagt 69660
tacgcgttga gagactgaac cggatcgaga gtgagcagca gacgtcgtac gagaggaatg 69720
gtgactgtga gtagcagaag ttccacgagt agaagatgag gaaaccgcag cacccagacg 69780
gacgatacac aagttaacgc agactaccag gcaccagatc ctggattcca tgttcgtcgc 69840
gggccaaatc cagcagcgat gaggcgcgtc gtggtctctt gcgtgttgcg cggaccctcc 69900
gggaaacgcc cgcggtcgag gaggaggggt acggacttgg cagccaaagt cggtccggct 69960
ccctgaaggc acccgagacg gccgcggcgg ccgtcagggt ggagggcttg gccacgggag 70020
ctgttggcac gtcgccactc tcatccggtc tggacagatg cctgtagagg aggagatata 70080
gatctttgga cttataaaga cttccttcgt gacgaagcag cagcggccac tctttgttat 70140
acgtgagaat cacatctctg tccgggtgca gttcgtcgcg caggcacgcg atcgagagtt 70200
gtttcccgaa agtttcatta tatagtgcga cggagagcac gagctcccgc acgtgcatcc 70260
acatctcctt ctgcagcacg tttaggtcct gacagtccga aaaattgaaa aaacccatgt 70320
acttcaccac catccactca ctgggataca cggtaccttc cgcgcatttg accaaatcgt 70380
ccttgacgtg gggtagtacg cccgcgttgt cgcaggcata ggccatgtcc acattgtgag 70440
agaggggata gcgatcggta cagtgtgtga agaggggccc gttacacaac tcgtagatct 70500
gctgacccag tagcgggagg gattccacag gcagactctt gtggatcagg ttattgacca 70560
catacaggtg ctcatcgtac gtgaactgat cccccacgtc caccacgtct tgatcctggt 70620
ggtattggct gcggtataga aacccattca tgagcttaga gataaagtcc agacacaagg 70680
gccccactag gttgacatcg atgagtttgc tagtcagacg ctcctgcgtt ttgatgcaac 70740
ggatcacctt gccatagccc acctctgaga ccttctgcag gtaggcgcgt ttgcgcacgt 70800
tcacctcgcg ggtgacgttg tggatgcggg aacgcgcgtc caccaagtcg agagcctcgt 70860
gttcgtcgca gttgcgcacc cgtaagccgt tctcgctgcc gtcgccgtcc tgcccattcg 70920
cccctccccc tacagctttc ttgcctcctc cacgggcccg gccgccgcca ccgttattcc 70980
tctgactgtg agtactgctg ttgctgctgt tgctggccgt catcaaagtc gtacccgtcc 71040
ccgacatcgc ctcccgtcca cgcaggtgaa tagcctcgcc ctcggggccg tcgccccccg 71100
tgccatcggg cagcggacgt cgaatctcct cgagaatatg cttgattttg gtgtacatct 71160
cgttgctttc gtggagcttg ttgaacaccg gattgtcctc gaaagcttga atgctgaggg 71220
atgtgatgag gtcgatgatc ctgttggggg cggcaaagac cgaccccacg aacatgcgct 71280
cctccccgtc caacgccttt tccccgagca cgaagatgtc ctccacgtcc tccccgtaca 71340
gatggcgact gatgccgttc atgagcgccc ggcacagctg gtgatacaca tttagctgct 71400

-continued

```
ggatggtgat gcccacccgc ttgacgataa cctccgaggt acgggaccag taggtaaaat  71460
ccgacaagga atatattcgt tccggtatat ccgtaaacag gttgtactcc ctcagcgcct  71520
cctccgcctc ctggatgtag ctgtggtagg ccgatgaaga agagaatagg cttttgaggg  71580
ccgaaaggac tccagccaag tgggggatgc gcgttgtcag gtccagcagg tcctgctcca  71640
ccgtctggat attcacatcg gactggcttg acggacggtg gaccgctata tggttgcaca  71700
gcaagccctg cagccgcttg ttcagcgagc ggccctgatt cgggatgatg gtcaactcct  71760
cgtagcattg ggcgcatgtc gtcccttcga cgtacacttc ctgacgcgcc accggcgaga  71820
tgccgcatag gcgacggagg agctccagca gctgcgcgca gacctccagg ccggcctccg  71880
gcgccaggat cccgtacacg tagttcattt tgcacaggaa gcgctcgatg tcgttgagtg  71940
tggccagact gacgctgaaa cggacgttgt ccgtaaactg gagctccacg gtgtgatggc  72000
gatcgcagcg atccaaacgg aggacggtac ggtagaaggc cgcccggtcc ggctggcgcg  72060
agtaggccat cagcgcccga tccagcaaag ccgtatcctc gtgcagcgcc ttcagcagca  72120
tctccagata gagcgtcagc agcgaactct gcgtacgatt ctgcgccacc acctccgggt  72180
agatcttccg gtacagatac actatagccg ccgcgtttct cttgaacggc gtggactccg  72240
ccagtaacac gttcggatcg cagtacttta gacactccag ctccatggcg tattcgttgc  72300
atttcgaaca cactacgcat agtttctgta acaaattcat ctccatgact cgactcgctc  72360
acgtacgaga cgctgtcgtc cggtctggcg ccggccagag acatggagtc ggtgcacaaa  72420
taactcgcgg gccgctcgct atgccgactg acgttgacgt taatatataa cgacgtcgtc  72480
gacgagggtt ctgctcccga agctgttgcc gccgcttgcg gcgcaacctc ctccaccacc  72540
gccgccgccg gctcctccgc ctcgggcgac gggggctcgg agatgaccgg ctgtgtctga  72600
cactcctccc cttcctcagg cggcccgggc gccgacgcga atgtcggagt ttgccagcgc  72660
ggcggcggtc tctgtctctg gtgccgcggc gctaatcttc ggggctgttg ctgctgttga  72720
tgatgcgacg ccgtctgtcg ccgctgttgc ggcggtagct gatacggtgt cgcctggtgc  72780
tgctgtgtcg gtggctgctg ttgctgctgt tgttgcggtc tgaaaagcgg ccacgggggc  72840
tgcgactgtt gctgctgttg ttgcgatgct cgtgactgcg gcggccgttg tcgcggcgtt  72900
tgctggcggt tacaaccggc tgcgtttggc cggcaataac ccgctgcccc cgccgccccc  72960
gctgctcccg ccgacgccgc cagcctcgtc ttcgccggcg ttcacgagaa agcagccacc  73020
tcccgtctcg ccgggcacgc cgaagcaaat ggagttgccc gcgacggact cgccgagaag  73080
aagaccgcca cccccgacgc cggacgccgc gccgacgcca ctgggcgcga agagcgccga  73140
caggtcgtgc acctcccccc cggcggcgtc cgttaatcgc tgggcgtcgg cgtccagcac  73200
gcgtcgcaag ttctccagcg aaaagtcctc cacgccctgc tcctgcaacg cggcaaactt  73260
gtccatcagc gacgcggcca gcgcctcgca gccatccacg aagaagagca catcgtcgga  73320
cgcggggatc tcctcgcgca cgctcagaat ctcgtacacg gccatcactt cggggtcgca  73380
atccaagttc tcggcgtcca gcgccagcat gacgcggttt tttataagat ccgcgtcaaa  73440
aagcacgttc tcgcggcgcg agcgtttgat gagcacgtcg gccagacgcg tagccaagag  73500
gtaacgctgg cgcatgaaac gataatcttg accgctcata gagctcacgt taaggctgcg  73560
ttccacaccg ttgcccgaaa agtagccgat ctgcccaaac tgatagatct ccttgctgtt  73620
gttgataccg gcatattttt ccacgctcac gggcacggtc accaaggaac gatgctcaaa  73680
aacgctccgt accaacgatt cacgcgccac agtagcggcc atgggcgccg gcacgcctgc  73740
ggtcttcaag cccttgacat gcaacgcaaa ttcggcgggc gacgagaaac gcggactagc  73800
```

acctaacacg tgaggaaact gcgcgtggtt ctgcgtcgtt aagcgcgtcg ttaacccgtg 73860
cagcgagcca atgtagtctt tgaagccgta gtagcagagg aatttgttat ggaaacggct 73920
ttccacgtaa ctcagcacac agtctggcgc cacatccagc agatcgtgct cctgatagtc 73980
agccgtcaca gccaccagaa atttgacgaa agcattgaac tcgcccatgt cacctatggg 74040
cacattcttg ggcaacgcgt tggaacagac cttctgccaa aactgtaagc aggggagacc 74100
acattcagga aagagtcgct cgtgatgtcg atacagcaga aatcccaagc agcccttagc 74160
cggattacga cgcggaacgt gatcgcggcg aaaaaacacg ctacccgcgt tgcccttgcc 74220
cgcgcggtag atgggtcggt ttttcacccg caccatgatc aacgtgggta ccgacagccg 74280
cgagagcttg atctccatgg gcaccacggc gtacgtaccc tgcgcgtaca gcctaaagtc 74340
cagcaggcgg tcgtgatccg aattcttgga cgacttgatc tgcttggtga agagaaagcc 74400
cttgcgcgac gacgtggtgg agaacgcgcc gtgaatggat tgaaaatgct gcgtcatcca 74460
tttggatacc aagttggtgg tcaacggatt gtccacaatg tatgaggtag cggtaataag 74520
cgccacgttc tggatcacgt aaaagacgga tctgaaatag gcgtaggcca gcagcggctg 74580
gaaagccacg gcgtagggat tcagatccag gttgaaggcc tgcgtggcgc ccgccacctc 74640
gtcgcggctg ctcttgaggc gcacctccga aacgaaaccc agggcctcgt cgtccacaaa 74700
cttgttgagc gccgaaaaga cggccacaaa gtcgcttttg ccgtgcgcgc taaaggtatc 74760
ctcgcccgtc acggggtcga tgagccgcat cttgcggcag taatccaaga tgcgattgag 74820
ccgataggta cggtccacac tagcgcccag catgcgaccg ccgcgcccca tcattccccc 74880
ggaatccccg ccaccccac caccacgacc gccgcccaga ccgtcgctcg ggccccccgct 74940
cacgtctcgt ccaccacccc cgccagcacc gccgcccgga accccgtcgt cacctttgcc 75000
gtccaaaccc ccgtccttgg cgtcgacgtt gtaacgccga ccgaagctgc ccaaaatatc 75060
cacgtcgttg agaaaacgcg actgcacggt gatcacgcag ggctccttct tgggctgctt 75120
gggcaccacg ggcaagcggg tgcgcacccg cacgaaggcc gtctgataac acgtgtggca 75180
acaagtaccc ccacaggcct cgcacagccc cgcggcgcag cccaccaggt gattcgtgag 75240
cgtcgacgaa cccgacaagc ccgtgttata caccgagaca cgatttagat accagacgaa 75300
gcccgaaact agctgcggac acgtgccaca caccaacgcc aaatgctgcg gcccatagcg 75360
ttcgtccttg agcggcgcgc cttgaaactt gagcaccttg cgcgcgtcgt tgtagacgtc 75420
ttcgcaggcc gccgacaacc cgttggtgaa ctgaatagcc ttgagcaacg tctcctgact 75480
ggccgtaccg ccggcgctgg gatgccgcgc agacgactga agatacacca gcctgtgctg 75540
gtagagcacc gaattagcgc tgaagaccaa ggcggccacg tgcgtcgaga gatgcaactt 75600
gagctcggtc agcgcgcgga tcagatcgcg gtgatcggtt gcgttggtca ctaaaggcca 75660
ctcggaaaag agcatagact cggcaggttg gtaggccgaa tcgaaaaata ccgaggcaaa 75720
actgaaggcc aactcacaaa ccaccgcgtc actcagcatc agatgatcct tttccagact 75780
gctgagtcgc tggctcatgt accccaagta gcgcttatgt ggcgccagct tcaccgactg 75840
ctgactgtcg tgcacaaact gccgcaacgc cgcctcgatc agcacacgcg gctccgagaa 75900
gcgcagcgat tgacaccatg acgtgtacac gtagtagaaa agcgtctcgc ttacggccgg 75960
cacgtagagc cctcgcgcct ccacaaaagc gctgcgcgca tccagcgaga cctcgtcggc 76020
ttcggcgtca agctgcagcg aattaaagag cgtaggcggg tacaacggca cgcgcaccgc 76080
ctcgccgccg tgcagtcgca ccgtggtcgc ctcctccacg catggaatca gctgaccggc 76140
aaagagaaac tccttcaagc cgttgcccac caccacgtgc acagtcgtct cggacgcctg 76200
acagcccact gccgcgcaca acgccgccag atcggtaggc acgcgatccg cctcgggcgt 76260
gtaggcctcc aacgcgtact tctggcgggc gtcctcgcac agccgatgca cgtctccgtg 76320
atcctcggta aaagccacga tgccttgcgt atgatgaaag tagagcgcaa aaggacaaaa 76380
ggacgtgact ttcgtgagca ccccgccgtc gtaacaaagc acaggcgtgc gcacagagac 76440
gccgaaatcc gcctccaccg tgagccccgc caacagagga gcgatcacca cgctcgagga 76500
acggtcgcat agcgagagag tggccagaat ctcctgcgtt tctgcgttca acctgctgaa 76560
gtagagaaaa gccgcgggcc ccaccggcgc tagcgcggtt agttcctcgt ggctcatggt 76620
ggatgaacgg aagacaatgg ctacgccgcc actgagtgaa ttttatacca aggaaaagtt 76680
cagcacgtca tgtttgacgc acgacgtctg atacaccacc gtggccacca ctgcggtctg 76740
gctgcggttg cggaccacca aaggcgacaa ccgcaacgat cccagcaatt cgtaagaaaa 76800
gctaaccgtt acggtcgggc agcctctcgc agccagaccg ctagccgacg cacccgcccg 76860
cgaaaatagc gtgatgttcg ggacggcttc gcgtcaccgc aaactaacgt cggtagtcgc 76920
gcacgtcgtt tatcatcagc acaccgtccg atcacaaccc gttttcccac tcagtcgcac 76980
aagcagcaca taaaaacccc acacagggca catgaaaaca acgtccctag aaaacggtgt 77040
tttctgtcct accgtcaccg ggccacacag gcaaatcccg agcccgatcc ccgaaaacac 77100
cgtacggtgt ttgtggcctc caaaatcaca tcagctaaca aaccgtgaaa agtcacgttt 77160
cacgaacacg gtgtttctaa atcacaaaga accgcctgac ggtttacaag cagaaacacc 77220
gcaccacggt ggtacaagcg cggtggatct ggtctcgcaa cctcaatcgc cgctatcacc 77280
accgactttc gctgcgctcc gccgacaaaa cgccgtacaa gttacacacc ccaaaaacct 77340
gcgcgcctat gggcgccaaa cgtgtgtatt atctcaacgt cacaacacga cacaaaccgc 77400
gtaacgtggt ttcccgaaca cgtacgcggc acagaccccc gacacgtact cgaagacctt 77460
acagtttacg agtcaataaa acaggaaaag atccgaactt taaaattgtg tatttttatt 77520
ttcccatccc cctcttttta ccaaaaaaca catttttcgt cttgtaaaaa gtaactttcg 77580
cccattgcca tgaaacaccg tgatggggaa cggtgttgtg tgtcgactga cgtcactacg 77640
gcgatcagta tcgacgtcgt gtatacataa cggtgcccgg tgtttttatt cggggcgttg 77700
tcgcgtcttg atgtaatgta acctgaaacc gccgtgccta agaatgcgga agccagcgtg 77760
taatcataac ggggttttgg gtacaatctg acgacatctg gcggcgagcg tacaccatcg 77820
aatgtggcga tcgccggctc tacgtcacaa tgacgcaaaa acacactgta aaacccgcgt 77880
agacagcttt cctggtcaat gagcgccatc tggtgtcggc ataagaacag gcatcaaccc 77940
cgtggccggc gaggcggtga gcacttttgt tggtcacgtg accatccgcg caggaagcga 78000
ggcccgtaga accgcccaag aggcggtgcc agatgccaac gtcataatca caaggtgatt 78060
tgttacgtca cgcgcacacg cacgcgcgcg cgcggtagaa tacagcgatc catagtgaag 78120
ccacacccat tacgtgtagc catatccgct tacgtataca gacacacccc taggtacgcc 78180
accttatcta ccaatcacag aaacggatat aaaatgaccc ctccctagac tccacccctt 78240
gtacggaaat ttcagatagg tggaacccgt tagggttcca ccgtcctcgg tgtacgtaca 78300
ggcttctccg tctaccggaa atatacacat gctgacgtag acgctactcc cggatacgcg 78360
tcataagcta ctggacccta ggggggggagt gtctacaggg ctacgtgcac gccccttac 78420
ttagggtatc cgcccctttc ctctgttttg gcctagtaaa cttaacgccg ccgcttctca 78480
cgtgacccct gacaagccta cgtcacactc gcgtgaccac acccactccg gatatacgtc 78540

-continued

```
atcccgtgga ttccggacat acggtgacgt agcgagcgta gcgagctacg tcacgtatgc  78600
atgcgtcatc tccggcggaa atcatctctg atgacgtagc gagcgaagcg agctacgtca  78660
tcagtccgtt ttacgtatac cggatgctag gcgacgcccc gtaggggcgg agcctagctt  78720
ccacccctag gatgcatacc ctatatagca taattcttct aacgaaacgt tctacgaaaa  78780
cggactggcg gaacgggaac caccgtaacc ccccccctc acccccccc ttctcctccg  78840
gaaccggggg gggcaaattt ttaccaaatt tgggcaacca tgatttccaa tgggacggcg  78900
tttccgtgcg catgcgcagt cggggcgagt ttttggttgt cagggcgttg ccacgcggat  78960
tatgggatgg tgactcgagt gcgcatgcgc cggggatgcc gcatggaaaa cctatatata  79020
aggaggggtg aaccaggggc cccggtgcgc atgcgcgggc cagggcccgc gggagggtcg  79080
ccctgcgcat gcgccggtaa aattccagtg tgtgtgtcgt gcgcatgcgc cagtattttt  79140
ccactagagg cagtcagtgc gcatgcgtcg gtaaaattcc actagatgtg cgccgtgcgc  79200
atgcgccggt atttttccac tggcggccg cacctaggga gcgcgagccc cgtgccgggc  79260
atgggccgcg gcggtggaaa attaccgctc cgcccaccta ggcggggcat ctgaaaacct  79320
ataaaacccg gcgtgcccgc cgccccccgg cgcagtccgc ggcagggttc cggccgtgct  79380
gcggtccgca cgctgcgccc gctcccgcct gcctcccgcc ctaccccca ccctccccgg  79440
ccgaggcccg gcgccggtcc gtccgcgggc ccgtcccacc gccctggagc accatccggg  79500
gccgtgggcc gggcaccggg cgcggcccgc tccggacctc ggccgggggt ccctcccctc  79560
cccccgctcg accccccatc cgacggcccg gccgggctgg gacccccgca ccggggtccc  79620
ggttcccgtc cgcggcccgg ggggacccga gcgggggctt cccaccccca ccccgctcct  79680
ccccgggctc cggcccggga tccctcgctg ctcccggcga cctccgccgg cttcccggtc  79740
cacccgccgc ggaacggacg ggacccgggg tccgcgccct tcccctcccc ccacgggggg  79800
ctgggtcgcg gaccccggtt cctaggctcg ttccgcggtg ggcgaccggg gatcccccac  79860
ccagctcccc ttcccggccc gccccgctgg cttttgggcc cctccgggct ttttttttcc  79920
ggctgggtgt cgcggcggtc ggccgacgac gacggtaggt gggccgggtg gacggtggtg  79980
gggacgggcg acgccccggc tcgacggcag tcggtcccgg aaggttgggg gctgggggcc  80040
cggtcaggag cttcgggagc ggggtcgacc gcgacggctt ccgggtctcg cggcggctcc  80100
ctctcggcgg ctccggttgg gctcccctcc cccctctcga gggtccggcc gccagtcgtg  80160
accgggggtc cctcggccta gccgccggct ctcggtccgc cttatcctgg gcgttggccg  80220
gtcccgtgac gctcccctcc cccactgctc cccaaaaaaa ctccgcccga accgtcgcgg  80280
cttgctggcc ctgggcgtgg tcccccactc ccctcccccc atcggccgcc cagccggggt  80340
cggcgcctcg gaccccacca ggctgtggcg tgtgtgctgg ccgatgcggc ggcgaggttg  80400
ggtgtggccg gaagcgctcg gggtcgacgg tgggccgcca tgacacctca attgccgtca  80460
gtacgccctt ccacaatcac cgtccccaca cgatgggccc ggcaggtcac ccaacgttgg  80520
ttcaggccca gtcgagtttt tccccggcac gaacgcacgt ccccgtgggc tccacgcgtt  80580
ttccaccctt tcctggaggg gtccggaaca ccgtgaatcc acggggaggg tcccggcacg  80640
ggccgaggag accacgaccg tcccacccgg cgtgtcgact cgtccgagac ccgggaaggg  80700
aacaggcccc accatttttt ttttcccttc tccgatttgc cgtggaaaac ccgtgaaccg  80760
atacgggtac agacggccga aaaaaaaatt cgagacaata cgacggcagg gcgtgatttt  80820
ctcccccatc cgacaaaacc gtgtccctca aaattcccca cctttctctg ctcaaatggc  80880
```

```
cccgaaactg taaaacaccg tttgaccgca ccccaaccgg cgccatcttg gtgaccttct  80940
cgacggttct ctcgctcgtc atgccgttct gagctccgac atggcggacg agagaaaatg  81000
gcgtcgagag cctaggagcg ttttcgctcc aggcgggtaa aaaaatagca cgataacttt  81060
tctgtgcttt ttttgagacg ttttagaaga gctttttttct gctcagcgaa aaaatgatag  81120
ccctgaaaat ctcgacgagt ctggccgagc ggcgccatct tggaggaggg gcgagtcgcg  81180
ggcaccgcct cggtaccccc tggccgaggc gagtccgcgg tcgccgcctg ttccgtgatg  81240
ctacctagag ggcgctgtcg aggcgactct tcctgttttc gccctgaggg ctaacggtcg  81300
ctgacgtcaa accatctcgt gctcgctgag tcacatccgg ttgttgacaa gcgatggagg  81360
accgcaccca aagtgcgccc tctagtcatc gcgcctgacc ccttttataa actgctcgaa  81420
gaaaagaaca ccttatgtga aaaaatacag aatgatgaca agttcatcca acacaaccgc  81480
tcaacaacgc catatctatc agtgtccaaa aactatcttc tatcctttga aactataaat  81540
gctgcctata tacatattta gtatccaaga ctcttaccac gtagacgaaa agaagtgata  81600
caatgatctt gacgtgtatc gtctatatcg tgctagatat attcagataa gacgcgcaaa  81660
ccatagattt ctcatcagta tcatgaaaga cctatagctc tatatacgaa cctagtcatt  81720
ttaggacagc cgccggagaa gccgacgagg gatcgggcgg gtgcagccag aacctcacgc  81780
ccgatcccgc ctccggtagg cgatttgcat ctgtttggta aaaagctcat aagtctgtat  81840
gtgacctata tatatattat acgctatgta caccgaactg tcgctgttgt ataagaagaa  81900
aaaactctcc atatttatat cgtctgaatt tttgcttgat agacacgtgt ttggaactct  81960
gtccccccac gttttcactg tgtataacaa aaatatgtgt ttctcaaaag atcttgaggt  82020
gtttgaaaac gggggaaacc tgcgtttggg tgcgctaagc cccggactgg gacgtagccg  82080
gcgtccggca cctatatttt tctatttttt tacaaaatat atgatgaacc aagaataaaa  82140
ctctagctct cgtctatttt taatatgctc tacttagaac ctttttaatg acagaatgaa  82200
ctccatgtta tacgctcttt atatagtttc tctgcactaa cctttaaaac cgtatccttc  82260
cctgttgtac aaatcatctt ttgatacaca atgatgacct gatatccctc catatatatg  82320
atcggatatt attccgttag acttgtcctc cttttttttc ctcatctcct atatctggag  82380
atatatgttg accaccaccg ccatgaccac caaaaagcta gccgtcacga ctagaaatgt  82440
gtaggattcg gactttccgt tcgagaagaa agagaccgcg tctctggacg ctctttttgt  82500
cggtctgaat cgacccggga tacgtaagag agcggcccta catcgggggg cgctcgagac  82560
cgacgacgtt ccatctgacc agaaaaaaaa aaggcacccc tcggtagcga cctctcacca  82620
tcgtttgccc gtccgcccgt ccttcgtagc catcatcatc atctcaggct ctatcggtac  82680
catcgttgtc atctgaaaaa aaaaactgcc tcacccacct gcgtaaaaac accatctttc  82740
cggaggtgcg gtaagacggg caaatacggt cgtgccgagg caaaaaaaaa cgcaccatcg  82800
acaccacacc ctcatgagca ccacctgtcg gtgttggtcg tcctccatcg ttctctacga  82860
acatctcgac gcccgggtga cggacgacgg caagacgtcc cggagaagac ggtgttctct  82920
cgggcggtac gctctctgga tctataatat ctatagtagc taaacgagac tgtgagtacg  82980
acgaaccaca tcatcttttt tttatgttgc ttctttagaa aatgacttat gtcgacgaca  83040
ctcggcatca gccatctcgt gaaacacgct cgcttttcgt ctctccaagg aacactgggt  83100
ccgctgaaag ggaccgtgta ccgaccaaag caaaaaacac acacgtagta acatgatcaa  83160
ccacgtctga atgacacgaa aacacaatcg tataacgctc tattcatgga acgaacttgg  83220
aataaaaaaa accatcgcag gccagaggct aagccgaaac cgtccgggga agcgggcgcg  83280
```

agttttccga cttagccttt ggtgctcgtt gagcctcttt ttttttttct gattctctga 83340
agaatcaccg tcacagccct atgacgcgaa atcaattgct agaacataaa cgttctcaac 83400
aggtatgaaa tgaacaaact agatgatgct ataaccttat attgtgtgta tatagatagg 83460
tgtgaaattt gtaggataaa aagtgtcgtt gtatgatgca caacgatcgt gaaactggag 83520
actgtagctc tctaccgaat gcaaatacac aaatgacatc gattcccgtc cccacataaa 83580
gaaatgtgct ttactgtgaa agaatgaaga agattcttgt tcctcgtacg acggggccct 83640
cgctcgtcgt gcctcttccc ccctccggga gaggggacgt cggggccctc cgtcgcaccg 83700
ggccgaagcc agtgaaatgt ttactacact gtcatcagaa tatatgatgt atattatttc 83760
ctccaaactc ctcaccatag ccaccaattc gcatcactta agaaagtagt agcaaccgcg 83820
gcggcggcga ccggccggtc gtcgtctcct cgtcctcaaa tgttgtacat gtgcagaaaa 83880
atgtgtaaat acgtgttatt tatcccatgc gtcttgtaca tagatatatg tttttatata 83940
cgctatttat actttatata tccttttgca taaccataga cagtcaagga ttttaatgat 84000
ttgctcatcc gcctttgagc catcgcttag gagttagttc ctctatgttc tcggcccacc 84060
ttttcgacta cagtagcaaa cccttgtact accaccccga taaaaaccac atcatcatcg 84120
tcaccacgac ctggaaacga cacacgttcc cccccaatct tgggcatgtg tatatataaa 84180
gaatgggagg gagaggacgt ggggctcgag aagaaataaa cgccaagctc gattcgaacc 84240
aaaaaaccac atgtgtattg tgctttgttt tttttttac ggtgggggaa aaggaggggg 84300
ccgtcattaa cggaaaccgt gtatggggtc cggacacgaa cagtacacag cttatgggga 84360
aaaaagctca cagagagaaa aaaaacacca agctcaggca cgcgtacatc attatcatca 84420
tcggatatct caccacgggt catagtagta ccaaggagtg tgtgtaacac catttttttct 84480
tttctttgta acgggataag ggacagcaat catcacgcac aacacccttc acttttttttt 84540
ttagtcatcc atatcatcgc tgtaacacag catgtcctcg taatcgggcg tctggcaacg 84600
cattaccacc gagtcgtctt cttgcggtac cggtggtggt ggcggcggcg gctgctgctg 84660
ggttgccgtc gtactgtgat taccgttggc ggactgcacc gggatgatgg gctgcttgtg 84720
gggaacctgg ggtggactgc cgccgtgaga aggcgacggc gtcatcaagt taagctcacc 84780
acggtgactc cggacaccgg cgaggggcgc cgggggactg ggagggaccg cggtcgtctt 84840
gtagacgacg gtgtccccgt gccgatccgt ggctcgtacc agatcttgac tgctagcgtc 84900
gtcactgtct tcgtcctctt ccagctcgcc ctcagagtag tgctgctgtg gttgcgacgg 84960
tggctgggcg ggaggagcgg cggcgatcat tggagaggga tgtcgatgac tcccttctct 85020
gtccttttta tcgtaggctg tcagcgttgc tgggtccgtc ctgctttcca tatttgcgca 85080
ttgctcatcg gtgggatgaa tttggtctcc tccccgctgt tgtccgccgg cagtggcgtg 85140
gttgctggcg gttgtcgttg tcgtaccggc aaagacggtg agatccaata gcgactgctc 85200
gtcgaaggga cagtacgcta tcatgaaacg atagggtgcc aacgcgcgtt ggatgcgcag 85260
ttcgcacatc tcgttctgac actcgtggca ctgcagggcg cctaggatca ggtccgagac 85320
agcgccgcag cggtaggtac ccatggcgtt gttagtatcg aactggtcaa aaaattgggg 85380
cgtaccggtg acttgcaacg cgcgacggcg tagcgagacg gccacgcgcg agaaagagca 85440
cacgtaggcc atggcgcggt gcatgggttg cgagaaggtc tcgggcggac gcttctgcag 85500
atcgcagacg tcgtcgcgta gccaggcgct catttgaccg ggcttcttga ctaaccgttt 85560
gagcgtgctg caatggtcgc cccagccgtc ctggtggtcc aggatgcagc ccaggtccag 85620
gttgttgagt ttgttgaaga gcagctgacg catgccgccc accgtctcca gatagggatc 85680
gtgcgggttg acgggtagcc cgtgcaagtg gtggtacttc atgtagctga gcgtttcgtc 85740
gatgatggcc agcaacgtgt gcaagttggg agcgttgtac acggcgaaga tcttttccac 85800
caccagcttg cgcagcaacg gttcctccag ccaatcgaac tgttgacgga tgtgcaacag 85860
gtagtcggtg tgcatgagct cgtcgtgtga cagcaggatg cgaccgcgcg gctgatgatc 85920
ttgcgggaag gcggtgggga ccttgagatc ggcggggtag ggtgccagac gtagactctc 85980
ggccgtgtag cgctgaaggt cgtagacggg cgaggtagaa ctcggtgagg tacccgacga 86040
ggcggcgccg cgctgcagac gcgctctttt tttcttttcg atcaaacggc tgagttgctg 86100
tagttcgtcc tcgtccatgg cgtccagttc gtcgtcaata agcgccagca tctgttgttg 86160
ttgcggtccg gcggacgatc cgtgatgatt attggctgag gaggggtgag aagaaccgaa 86220
agtcgtagga caactgggaa ctcggcgacg aagatgcgtc gaatcgccgc cgtgatggtg 86280
cggttcgccg tcatcgttgt cgtaagactt accgtagtgg gggtgaaggg gcaccgaggc 86340
ggacgcggcc acgcgtcgct tgaaagagga ggacgcccta tgtccgccac ggaagcccgc 86400
ggtgcccatg atgatgtgtc cgccggtgcc cccgagtgcg tggcgggagg agggtggaag 86460
gggaggagga tagtggtccg gatcgccttc ggtatcatcg tctttgctgt agcggggtcg 86520
tcgtgcgggg acgcagggtc ggtgatgatg cgaggcggcg ccgacggtat cttccgcgag 86580
atggtattcg ctggcggctg ctccgttccg tgtcgacggc gaggttggac ttcgctcgcg 86640
tcggaacttc cgtggcacgg gttcgtaatc cagacagaag cgccgtgcgc gacgggcgcg 86700
gcgttcgcgc tcgctcaggg aagataacga cggagcgtcg tgacggccgc gtgagtgcag 86760
ctccatggcc gccgtcgcta ggaaggtcac gttcgggcac gctgatgtat atatagatga 86820
gaccgctgcc ggggggcggg tcaccggcgc cgtggaaagt gaggctcaga cggcggtcgc 86880
cggcggcacg ggcgcgtcgg gcggtctgat tttgatggaa atgtggacgt ttttggcgtt 86940
ggagtgacac tttttggtga aacagcggct ccagaggctg gcccagagcg cgtagctgtg 87000
ctcggtgcgc aggtcgatga acacttgcac ggtctcttgc gggttgcggt gcgtgtagtt 87060
gagacagcga aaatcccgcg tgcgcgcgcc gtcgcgccgc ttgacggcca cgcagcaggc 87120
gccgtggggc tgaaagagga ggacgtgggg cgcagtaaac tgctcgctga cgtgcggctc 87180
gtagtgttgc gtgaggtgct cgagcagtgg cggccacacg cgggtgacga cgagccgctg 87240
caagtccgtg tcggaaatcg cagcggcagt ggcgccgtcg ccaccgtaca ggtgataggc 87300
gagcacctcg gtgagaccgc ggcgtcgata acgcgtcacg ttaagcgagc gcgtctcgat 87360
aaagttggct tcggtcgagg ggcagatttt gtcatgtacg ctgagaatga cgcgtggcgg 87420
cggcgacagg ggcaacgcgg gcaggtcgtg cggcgggtgg tggtgaagca ggttacgcag 87480
atccagttgg gcgcgcacaa agcctagcgg gtgttcgcgg taggcgtcgg gcacgatgaa 87540
cagcggcaac agacggcgat gcatgaaata gccgtcgtct tggtccattt tatacatgta 87600
gggcagacgt acagagcgtc catggtggta gatgcctgtg tctaggctgc tctcgggatg 87660
cgagatgggg tccagcagcg tgtgcagttc ggcgtcgaga cagacggcgt gattgagcac 87720
ctgcgccacg gcgcgtaaaa cgctgggatg tacggcgacg gtgcaggcgg ggaacggcgt 87780
gatgatgcgc agccccagtt tgcccttgca gcggcagtaa gggggtgacg tgtcaacgga 87840
agacgttgtt ttttgaaaaa cgccgttatc tgggacgtta tttttgtcct ctttcccgtc 87900
ttcgtcttcc tctgtgtcgc gctcgtcccg gtaatcgaga tagtcgtcgt catcgaaagg 87960
cgcgccggcc gcgtccacgg gcacgctgtt gggtgggcac gcgcttttga agaaatagac 88020
cgggtgccgg tcggggtgcg tgtagccaaa gaggctcgcc catacggtca tccagacgcg 88080
tcgtagtccg cgacataact caaagacggt gtgtcgcgcc agaccggaga cgccgtcgcg 88140
cagccgtaaa tcaaagtcgg ccacaaaatt gaagacgggc agacgttcgt tgaagacttc 88200
gtgtcgcgtg tagtagaact gtgtctcggg gctggtgctg gccacgtcgt cgtcgtgtag 88260
ccacacggtc tcggtcaggg cctcgtccga gaaacggctg tcgggtacgt gacggagcag 88320
gtcgcgcgga aagaggctgc gatgccaggt ttcggaggcc acggcgcaga agacgtgctg 88380
gtcattgggc aggtgtacgc ggtagacggg cagcggtcgc tccagcagcg gtgccagcgc 88440
gggctcgggt agcaggtagc gacgttgcga gtaacgcgtt agcgtgccgg tggtgtaggt 88500
ctgggctgtg cgcagcgagg cgcagagacg taataagccg gacagggagc gttccagcgg 88560
ggagaagaca gactcggaaa gcgtgttgat gcgttcgagc tggcgcgcca gctgcgtgga 88620
ggtgccgaag aagcccgcca ggtgcgtgcc gtcgatgcgg ccgccgtagc cggccagccc 88680
caggccgtgc gggctggtcg ccgagtgggg ggattcgtcg agacgcagta ggtgcgtctc 88740
cacgtagtcg tgtagaaagt tgtcgagcga gaagtatttt tgcatgacgt ccagcagctc 88800
ggtggaaagc cggcggccca gaaaacccgg ttcgcgcgtg cactgcgctt cgggcgccgc 88860
gtcagcgtcg taagccacca cgcgccggta ctcgagcaac cgcgcgcgtg ccagcgccgt 88920
gcggtaggcc aggtagacgt agtgcacgca gaccgtgtcg ggcagacgcg cacgttcgcg 88980
gaacgcgttg atctgcgtgt ccacctgctc tagctcggtg tagtcgcggc ggttgcgcgc 89040
tacggcgtac gccacgaaag cggacacgcg ctgacggaag ggcgagccaa gtagcagacg 89100
cgcgaactcg cccatggagg cgtgcgtggg gatgatggtg ccaaggtcgc gcgtgcagaa 89160
gctgcgcacg tactcctcca cggtggagat ggtgctgtac tggccctcga ataggtagta 89220
ggccatggtc agcagcacct ggccctcggt gtgcccgaag acgctgatga accacgaggg 89280
cgaggtgggg cagaggaaga cctggttgag atgacgtagc acggccgcgt ggtgaaagta 89340
caccaggtgc ttgaattcgc gcacctcgcc gccgtgttcg ggcgagagca cgggcgtgcg 89400
gaagagatgc cggtagagcg gttgcgtctc ggcctcgtcc agactggcga tgagcgccga 89460
gagggggatg ggctggcgcg cggccaggta gcgcgagagc tgcagcgttt cgttgttcac 89520
ggcgaagacg ggcgccaccc gccgcgagtc cgagcacttt tgcgtctgta ggcagaaata 89580
aacacgtcgc gagacctggt gtttgaccag caggggggaag acgcagtggt ccgtcggtgt 89640
ctgcgagagt acgttggcga ctatatgagc agaatcatac tctgttgcga acagaacgag 89700
cgtcatcgtc gcgccggcac gatgcagctg gcccagcgcc tgtgcgagct gctgatgtgc 89760
cgtcgcaaag ccgcgcctgt ggccgattac gtgctgctgc agcctagcga ggacgtggag 89820
ctgcgcgagc tgcaggcgtt tctggacgag aactttaagc agctggagat caccccggcc 89880
gatctgcgaa ccttttctcg cgacacggac gtggtgaacc acttgctgaa gctgctgccg 89940
ctctataggc aatgccagag caagtgcgcg tttctcaagg gctatctctc ggagggctgt 90000
ttgcctcaca cgcggccggc ggccgaggtg gagtgcaaga aatcgcagcg tatcctggag 90060
gccctggaca ttcttatcct caaactggtg gtgggcgagt ttgccatgtc cgaggccgac 90120
agcctggaga tgttgctgga caagttctcc acggatcagg cctcgctggt ggaggtgcag 90180
cgcgttatgg gcctggtgga catggattgc gagaaaagcg cgtacatgct cgaggccggc 90240
gcggctgcga cggttgcacc accgacgcca ccggcggtcg ttcaggggga aagcggcgtc 90300
cgcgaggacg gggaaacggt cgccgccgtg tcggcctttg cctgtccctc ggtttcggac 90360

-continued tcgctgatcc ccgaggaaac gggggtcacg cgtcctatga tgagtttggc tcacattaac 90420
accgtctcct gtcccaccgt tatgaggttc gatcagcggc tgctggaaga gggcgacgag 90480
gaggatgaag tgaccgtgat gtcgccgtca cccgagcccg tgcaacagca gccgccggtc 90540
gagcccgtgc agcagcagcc ccagggacgc gggtctcacc gtcggcgcta caaggagtcg 90600
gcgccgcagg agacgctgcc tacgaatcac gaacgcgaga ttttggatct catgcgacac 90660
agccccgacg tgcctcggga ggcggtgatg tcaccgacca tggtcaccat acctcctccc 90720
cagataccct ttgtgggttc cgcgcgtgaa ctcaggggcg tgaagaaaaa gaaacccacg 90780
gcggcggcct tgctgtcctc cgcgtgaaca gcctggcacg ttttggaaaa cgtacgtgat 90840
cacggacacg acgagtacgg ggtttctcat agacgtactt tattaggtca gggatgacgg 90900
ggaggtttcg ggccgacgtc aaaaataacg tcattcgtgt tgacagggct ttctgcgtcg 90960
gagctctttt catcttcttc tgtctcgtcg acgtcatcgt ctaccggcga gggtgtccgt 91020
tgcagcaacg cgtgctcggg cgtgtgggtg aaaccgatgt cgggggtggg cggcacgatc 91080
atctgtccta gggggtgact gcccaccggc agataggtaa agcggtgggt ggtaaaaacc 91140
gctttggcta cggtggtgtg tggggagatg cagacggtgg tgtgcgaagt gttgaccacc 91200
gtcacgccgg ccgcggtacc cgggagccag atggtgggtc ggatgatgag atccgattga 91260
ctaaactggc gcacgcccac tatgagggcg cagataccgg gcgcgtgcac gtaggccgcg 91320
tcaaaataga cggtttgcgt gtgacccgga ccgatcacca gcgtctgacg ggtacgtaat 91380
gaaaagaaac ggtgttcgtt gggcggcggc aagttcatga gctgccaggg ttctggcaca 91440
aaacagggga aaacgccgat atcgccttcg atggtgcccg gaaagatgga ctgaaaagtg 91500
tcgttgaggt tgacgacatc caactgcggg acttgcagcc cggattccag cagctcgggc 91560
atgcaaacga attgcgcgtc caggcatttg taaaaggtaa tgccgaaaaa accttcgggg 91620
atatagaggc tgacgcccag cgaggtgggc actttgcgct cgcgtgatag ccaaatgatg 91680
tgtttattgt aaaaggccag ctgcgtgtgg cattgtttga cgatgaaact ggaaggcatc 91740
cacttgtagg gaactttgag cggcgacggt aatggcgacg atgcttcatc ttctcccgga 91800
tgctgctctt tgtcgtattt ctcctcgatc gattggggca gcgtaaatgt ggtttgaaaa 91860
tcgctatcgc tagcgaaacg cacgcagtaa cgcatgttga cggatttctc ggctaggatg 91920
atggagcctg atgacggtgc ggactcttcc ttcattatta acgtaggggt ctcccagaat 91980
cgctgaaaac gggagcgcgg cagccgcgac agtaccagtt gagagtcgat tcggtcggtc 92040
aacatcgtaa gcatcgtggc ggtggtgcga tggagtggaa cacactagta ctaggtcttt 92100
tggttttatc ggtagcggca agttccaaca atacgtcgac tgctagcaca ccgagtcctt 92160
ctagctctac tcgcacctca acaaccgtga agtcaacggc tgttgcgaca actagtacaa 92220
ctacggcgac aagtacttca tcgacgacta gtaccaaacc cggttccacc actcacgacc 92280
ccaacgtgat gagaccacat gctcacaatg atttttacaa tgcgcattgt acatcgcata 92340
tgtatgagct ttcactgtcc agctttgcag cctggtggac tatgcttaac gctctcattc 92400
tgatgggagc cttttgtatc gtactacgac attgctgctt tcagaacttt actgcaacca 92460
ccaccaaagg ctattgaggg tggatagatt tacagcccgg cggtgttccg gcggggtaag 92520
atttccatac gcgggtaatt ggaggctaaa gttacggatt ttatctagaa acagcagcga 92580
gtctagatag tcccataggg gatctataaa cgttttctga aacctcgtcg atggtgacgt 92640
aggtgtagtt tcgttattat cggaagccgt ttcgttttcc acggacatgg tttcgttgta 92700
atataaggag ctcatgtcaa gagtgccgta aatagtgtac ggtgtttcgt tacgaatcag 92760
tacgtgcgtg tttttcataa attctgacac ggcggtacgg ttacggtctg gtttacaaaa 92820
gggttcattc cgataccgca gagtagtata cacccatgtc gctagatccc ttaactgcgt 92880
ggccataatg gacttcataa agctgctatc aggacgataa gcaatcgtag atgtgggaat 92940
ccgctttgcg ctggtggtaa ccctataagt cgcgttagta gtgacgttga gagcggtaga 93000
cgttgtatag gaaaaatatg gcgtagtagt actctgagat tttttagtct ttttttctaa 93060
ttgttctttg actggcgctt gtttacgttt tagttttcgc atagtgtttt tcaacttggt 93120
gccgttaata tacttgggga cgcggaatag attccggctc atggcgttaa ccaggtagaa 93180
actgtgtgtg cagttgcgtt gtgcgtaacg tagaagtagg gcggttaaac ccaaaaaata 93240
aatcgtttga ctatctacgt taactttagt cggacccacg tacaatttgg tattccaacg 93300
tggtacattg aaaaacatgg ggttgaacgt ggtaaaatta ccgcagcctt gttcgccagt 93360
atcattacgt ttggaaacgt ttaacatttc ggaaagacaa gtcattgaag gcactgtacc 93420
acaagatggg ggtctgaatg ttatcgtttt agccgtatga ttgtactgtg agtagacgta 93480
tttggcgggt tttctaagct gggtactata aaaatcgaac cacagatagg ttatactatc 93540
gtttcgaatg ggacccgcta gaatgtagta ttgtggaaac tgggtcatat tcatagtaag 93600
atttttaacg tgttgcctag tcatattgaa gtattttgta taaggttccc tttctaattg 93660
ttttaaaatc tctaacttga atttatctag tttttgcttg cctatcgtag aaagtactgt 93720
acctaaccag taacgtcccg gtggtctaac gaccttacag tttattatag aaaataacag 93780
gacagtcagt gatataataa agaataattt agaaatgctt ctcatgtctt cttttctccc 93840
catgacagag gaggaaaccc cgcaccgtcc gtctgccttg tggtttggct tgcctgcgtg 93900
tactcactgc tgattctggt cgttttgctg ctcatctacc gttgttgcat cggcttccaa 93960
gacgacctag tctcccgcac cttggctgtg taccgagctt gtatccaggg cccgatatgt 94020
aaccagaccc acaacagtac ctcgtaaata aagacgcaca gacctcacgc acatagtacc 94080
atcacaccgt gtggcgtgta ctttattaca acgagcaaga gtgcccctaa gtgttggggc 94140
ccgtaccgtt ttagaaggtt ttgtgtgaat gtctttaact tctctgtcct ttttctcgta 94200
aactgtcagg tcctagagtc agcatgtctt gagcatgcgg tagagcagat agatgccgat 94260
gatggccgac aacgcgtaga cggacatcat gaggagacgg ctgtcggtgg cgtccacgac 94320
gacgtcagtt acttccagga ccgtaccgtt tttcaacagc atgaggtagt gagttcgtgg 94380
agatgagacc accacttcgt tgtagggatc cagggcaaaa aggacgtcgt ccgagtcgtg 94440
catgtacatg atattaatga cgccttgcgt gtcgtcgtat tctagtaagg cgctttggca 94500
gaaggcgcag ttttctagcg aaatgttgag cgccgctgtg atgctgtgtg tggtgtgcat 94560
gttgcgcgtc agttcgcatt tactttgact gtccgtctgg gtgatgatga ggctctggcc 94620
tacgacggtg gtggagacag ggtaggagat acctttgatc aggtattggt ttgttacgac 94680
gtagctgacg tgttcggaga cggtgagcgc ggagaaggat tcgcctagtg gcagacaaaa 94740
caggtcgggg aaggtttcca gcgtgcttgg ttgcatggta gataggatgg agagggcggc 94800
gggaacggta gcggggacgg tggcatcggg gaagagacgc gtaaggcgtt cgagcgagtg 94860
atcgcgtcgc ccgctactgg aacagggtgt gtacaggtcg ctgaggtatt cgtggtgcgg 94920
atgagctagc aactgcgtaa agtgtgatag ctcggccaat gaacagaggc ccgtttctac 94980
gatgaagatt tcgcgtctct ccgtcgtatg caccagcatg gagtggacga ggctgcccat 95040
gaggtagagt tcttggcgcg cgaaggctga aagaaaagag gccaggtgcg ttttgtgtaa 95100

-continued

```
ttgtagggca aagtcggcga tctgtcgtag tgcccactgg ggaatgagat gttgctgatt  95160
ctgtttagaa agtatgtaga ccaggcgtac gaggctggtg atgtcggtga tctggtccgg  95220
cgtccagagg gctcgtttgg ccaggtccac ggccgtggga tatagcagca atgtggtgcg  95280
tggtggtgtt tgtgagaggc aggtgatcat aaattcttgt atttgtaaga gtgcggcctg  95340
gcggtctagg gcccgtggga tggagatttc ggtgccggcc tcttcttgtc gggctgccgc  95400
gaacagtgct aatgcgtagg caaaggccat ttctaccgtg cggcggtcca gcatttgaca  95460
tcgaccgctt ttgagtacgt ctacagcgta acggtgaaag ctgttacgta gcagtgcgct  95520
gaggtccagg tagttgaagt cgagtgcggc gtcgagaaag tccgagtctt tgagatagga  95580
gtgacggttc agttgagttt tcttaactag taccaggagc tcgtgttttt cagtttgtcg  95640
tagtataaag ttgtcgcgtt gatagggcgc tttgaagagt acgcgtggaa gatgaccgaa  95700
gataagcagc atgggtgtgt cgtcgtctat ggataccgta actacgaaga agtcctcggt  95760
cagtgtgatt ttaacgtaac gtagttcgtc catgaggtaa aagccctggt gcagacaggg  95820
cgtaacggtg ctgaaaagca gatcgtgtcc atcaaagagg atacaggtct ggttaaagtg  95880
tggccgatgt agtcccgagg tggtgtgcga tcccttccag tcgtgtggag tggtttgggg  95940
tggcatccag acgtgaggta ttgacagatc aatgggcggt ggcacggtgg tgggctgctg  96000
acccaggctg tcttgtgcct tcagctgctg cgaaaaagat cggtagctag ccaggtcttt  96060
ggataccaat gcgtaggtgt taagtctctg ttggtatctt tctagggttt cggtcagatc  96120
tacctggttc agaaactgct ccgccagagg acccgcaaaa agacatcgag gcatatggaa  96180
tacatagtat tgattatagc tttggaaaaa gttgaaactg atggcgtttt ccctgacgac  96240
cgtgctgtta cggaggctgc tgttgtaggt gcactgggtg gtgttttcac gcaggaaacg  96300
gatgggtctc ccataggtgt tgagtagtag gtgaaacgcg tgagggtcca gcgcttcgga  96360
tgcggcgtct gcgccatatc gttgcgaagg taggtgacta aggaggtaga cggcgaagac  96420
ggtgaggtag aaggggaggc cgggccgcat agcgcggccg cgccgctggg ttcagcggcg  96480
tgatccaggt ggtggttggc gttacacccg agagaaggag aaaaaggatc ccaggaagga  96540
gcacccgggt gcggcgctac gggttacaaa agtcgcgtct tcgtctattt aatacgatgt  96600
cattggccgc tgcgaaggga gaagagggga cacgcgaata agccatgccg tccgggcgtg  96660
gggacgacgc tgatttgacg gggaacgctc tgcggagatt gcctcacgtg cgtaagcgga  96720
tcggtaagcg caagcacctg gatatctacc gtcgcctgct gcgggtcttt ccctcgtttg  96780
tggcgcttaa ccgcctgttg ggaggtcttt tcccacccga gttgcaaaag taccgtcgcc  96840
gtctttttat cgaagtacga ttaagtcggc ggattcccga ctgcgtgttg gtgtttttac  96900
cgccggactc tgggtcgcgc ggcatcgtgt attgctacgt gattgagttc aaaaccacgt  96960
actcagacgc cgacgatcag tccgtgcggt ggcacgccac ccacagtctg cagtacgccg  97020
agggcctgcg ccagctcaag ggcgcactgg tggactttga ttttctgcgt ctgccacgcg  97080
gtggcggtca ggtttggagc gtggtgccca gtctggtttt ttttcagcaa aaggccgatc  97140
gcccatcctt ttatcgggct ttccgctcag gccgttttaa cctgtgtacc gattctgtcc  97200
tggactatct agggaggcgt caggatgagt ctgttgcaca ccttttggcg gctacccgtc  97260
gccgtcttct tcgagccgca cgaggaaaac gtgctgcgct gccccgagcg cgtgcttcgg  97320
cggttgctgg aggacgcggc ggtggcaatg cgcggcgggg gctggcgcga ggacgtgctc  97380
atggaccggg tgcgcaaacg gtatctgcgt caggagctga gggatctggg tcacagggta  97440
cagacttact gcgaggatct cgaagggcgc gtgtccgagg cggaggcgct gttgaaccag  97500
```

cagtgcgagc tcgacgaagg accgtcgccg cggacgctgc tacaaccacc gtgtcgtccg 97560
cgttcgtcgt ccccagggac cggcgtggca ggagcttccg ccgtcccaca cggtctttat 97620
agtcggcacg atgccatcac gggacccgtc gccgccgcgt cagcggccgc cggtgcttct 97680
tctacctggc tggcgcagtg cgccgagcag ccgttgcccg ggaacgtacc taactacttt 97740
ggaatcacgc agaacgatcc ctttatccgc tttcacaccg attttcgcgg cgaggtggtc 97800
aacaccatgt tcgagaacgc ctccacttgg actttctcct ttggtatctg gtactatcgg 97860
ctcaagcggg ggttgtacac gcaaccacgg tggaaacgag tgtaccatct ggcgcagatg 97920
gacaactttt ccatttcgca ggagctgctg ctcggcgtgg tcaacgcttt ggaaaacgtg 97980
acggtgtatc cgacgtacga ctgtgtactc tccgatttgg aagccgccgc ctgtctgcta 98040
gtcgcctacg gacacgcgct ttgggagggc cgcgatccgc cggactccgt gacggcggtg 98100
ttgagtgagc tgcctcagct gttaccgcgt ctggccgacg acgtgagtcg tgagattgcc 98160
gcttgggaag gccccgtcgc cgcgggtaac aactattacg cgtatcgcga ctcgcccgat 98220
ctacgctact acatgcccct aagcggtggt cgccactatc acccgggcac ttttgatcgt 98280
cacgtgctgg tgcggctttt ccacaaacgc ggcgttcttc agcatttgcc gggctacggg 98340
acgataacgg aggagctggt gcaagagcgt ctgtcgggcc aggtgcgcga cgacgtgctt 98400
tctctctgga gtcgacgtct gctggtcggc aagctgggtc gcgacgtgcc cgtctttgtg 98460
cacgaacagc aatatctgcg ttcgggcctg acctgcctgg ctggcctgct gttgttgtgg 98520
aaggtgacca acgcggatag cgtcttcgct ccgcgcacgg gcaaatttac gttggccgac 98580
ctgctgggtt cggatgccgt agccggcggc gggttgcccg gggggcgcgc gggcggcgaa 98640
gaggagggct acgggggacg gcacgggcgg gtacgtaact ttgagtttct ggtacagtac 98700
tacatcgggc cgtggtacgc gcgcgacccc gcggtcacgc tgtcgcagct ctttcccggc 98760
ctggctctgt tggccgtgac cgagagcgtg cgcagcggct gggatccctc acgtcgcgag 98820
gacagcgccg gaggtggcga cggcggcggc gccgtgctca tgcagctcag caagagcaac 98880
cccgtggccg actacatgtt cgcgcagagc tccaaacagt acggcgattt acgtcgctta 98940
gaggtacacg atgccctgct ctttcactac gaacacgggc tagggcggct gttgtcagtg 99000
accctgccgc gtcaccgtgt gtccactctg ggctcgtccc tctttaacgt caacgatatt 99060
tacgaactgt tgtacttttt agtgttgggg tttcttccga gcgtggcggt gttgtaattt 99120
ccaccacgtg tcgctcgctg cataaagggc gaacgtcctc ggagagggta tattcgttcg 99180
gcgagagcgg gcggcggtgg tgggtatgtc cccttctgtg gaggagacta cctcagtcac 99240
cgagtccatc atgttcgcta ttgtgagttt caaacacatg ggcccgttcg aaggctactc 99300
tatgtcggcc gatcgcgccg cctcggatct actcatcggc atgttcggct ccgttagcct 99360
ggtcaacctg ctgactatca tcggttgcct ctgggtgttg cgtgttacgc ggccgcccgt 99420
gtccgtgatg atttttactt ggaatctggt acttagtcag tttttttcca tcctggccac 99480
catgttgtcc aagggtatca tgctgcgtgg cgctctaaat ctcagcctct gtcgcttagt 99540
gctctttgtc gacgacgtgg gcctatattc gacggcgttg tttttcctct ttctgatact 99600
ggatcgtctg tcggccatat cttacggccg tgatctctgg catcatgaga cgcgcgaaaa 99660
cgccggcgtg gcgctctacg cggtcgcctt tgcctgggtt ctttccatcg tagccgctgt 99720
gcccaccgcc gctacgggtt cactggacta ccgttggcta ggctgtcaga tccctataca 99780
gtatgccgcg gtggacctca ccatcaagat gtggtttttg ctgggggcgc ccatgatcgc 99840

-continued

```
cgtactggct aacgtggtag agttggccta cagcgatcgg cgcgaccacg tctggtccta  99900
cgtgggtcgt gtctgcacct tctacgtgac gtgtctcatg ctgtttgtgc cctactactg  99960
cttcagagtc ctacgcggtg tactgcagcc cgctagcgcg gccggcaccg gtttcggcat 100020
tatggattac gtggaattgg ctacgcgtac ccttctcacc atgcgtcttg gcattctgcc 100080
gctctttatc attgcgttct tctcccgcga gcccaccaag gatctggatg actcctttga 100140
ttatctggtc gagagatgtc agcaaagctg ccacggtcat ttcgtacgtc ggttggtgca 100200
ggcgttgaag cgggctatgt atagcgtgga gctggccgtg tgttactttt ctacgtccgt 100260
ccgagacgtc gccgaggcgg tgaaaaagtc ctccagccgt tgttacgccg acgcgacgtc 100320
ggcggccgtt gtggtaacga caaccacgtc ggagaaagcc acgttggtgg agcacgcgga 100380
aggcatggct tccgaaatgt gtcctgggac tacgatcaat gtttcggccg aaagttcctc 100440
cgtcctctgc accgacggcg aaaacaccgt cgcgtccgac gcaacggtga cggcattatg 100500
agcggcggcg ctgtacggca gcggggagaa aagtggcaga taaatcacgt caggttcaca 100560
cgtcgttagc cagcgtcggc atatgaaggg cgcgggcggc cagtacggcc tctgggctga 100620
gacaggacga ggcagggtga gaaagaggag gatggggggg accggggtgg tggtgctgct 100680
gctgttgtgg gtgcggacgg tgcgggtgcc gggacagcgt gccggcgaac gttctgtaat 100740
cttccataat aaaagtaaaa atgcccgtct cgtgtcgact ccgctggatc tcgaaggcgt 100800
cgggggtaat gcgcatcttg ccggtgccga tgagataaaa gtaccacatt ttttgacaga 100860
tgatgcgaat caagggttcg tacgcttcgg caccccagtg gcgcgtgaag aaggccgcca 100920
gacgaaacaa gcggtgtccg tagagcgtgc ctagggagaa gaggatgttg ccgttgcgcg 100980
ccaggtcttc ggggaaaacg accggcaggc cggtgtggcg ctgcacaaag cgcgtcagca 101040
gtccgccgct caagcgcggg tgacacaggc gctggctgag acgggcggcg cgcgtttcat 101100
cgaacacggc cgcctcaaag tccagccccg ggaaggcctg gcgcagttcg cggtacagat 101160
gaggccagta gggttgcggc gtcttgcgac taagcacggc gtggtccgag acacccaggt 101220
tgttcatggt ttcgcgcagt agcagcgttt cgagaccgcg gtgaaagagg aggacgcaga 101280
tgaggcgtac gattttgagt tcttccaaac gcagcgagct cagcggctgt ccgcgcgaca 101340
tcttctcgct aatctgtaat attagatgat tggcgcaagt aaaggagaat ttgcccgtgc 101400
ggacccgcgg gacggcgggg ttctcttcgt cgcgggccat catcgttcgc tcggtgagcg 101460
ggtagcgacg gtgaggacaa tgacgatgga cgagcagcag ccgcaggctg tagcgccggt 101520
ctacgtgggc ggctttctcg cccgctacga ccagtctccg gacgaggccg aattgctgtt 101580
gccgcgggac gtagtggagc actggttgca cgcgcagggc cagggacagc cttcgttgtc 101640
ggtcgcgctc ccgctcaaca tcaaccacga cgacacggcc gttgtaggac acgttgcggc 101700
gatgcagagc gtccgcgacg gtctttttttg cctgggctgc gtcacttcgc ccaggtttct 101760
ggagattgta cgccgcgctt cggaaaagtc cgagctggtt tcgcgcgggc ccgtcagtcc 101820
gctgcagcca gacaaggtgg tggagtttct cagcggcagc tacgccggcc tctcgctctc 101880
cagccggcgc tgcgacgacg tggaggccgc gacgtcgctt tcgggctcgg aaaccacgcc 101940
gttcaaacac gtggctttgt gcagcgtggg tcggcgtcgc ggtacgttgg ccgtgtacgg 102000
gcgcgatccc gagtgggtca cacaacggtt tccagacctc acggcggccg accgtgacgg 102060
gctacgtgca cagtggcagc gctgcggcag cactgctgtc gacgcgtcgg gcgatccctt 102120
tcgctcagac agctacggcc tgttgggcaa cagcgtggac gcgctctaca tccgtgagcg 102180
actgcccaag ctgcgctacg acaagcaact agtcggcgtg acggagcgcg agtcgtacgt 102240
```

caaggcgagc gtttcgcctg aggcggcgtg cgatattaaa gcggcgtccg ccgagcgttc 102300
gggcgacagc cgcagtcagg ccgccacgcc ggcggctggg gcgcgcgttc cctcttcgtc 102360
cccgtcgcct ccagtcgaac cgccatctcc tgtccagccg cctgcgcttc cagcgtcgcc 102420
gtccgttctt cccgcggaat caccgccgtc gctttctccc tcggagccgg cagaggcggc 102480
gtccatgtcg caccctctga gtgctgcggt tcccgccgct acggctcctc caggtgctac 102540
cgtggcaggt gcgtcgccgg ctgtgccgtc tctagcgtgg cctcacgacg gagtttattt 102600
acccaaagac gctttttct cgctacttgg ggccagtcgc tcggcagcgc ccgtcatgta 102660
tcccggtgcc gtagcggctc ctccttctgc ttcgccagca ccgttgcctt tgccgtctta 102720
tcccgcgccc tacggcgccc ccgtcgtggg ttacgaccag ttggcgacac gtcactttgc 102780
ggaatacgtg gatccccatt atcccgggtg gggtcggcgt tacgagcccg cgccgccttt 102840
gcattcggct tgtcccgtgc cgccgccacc atcaccagcc tattaccgtc ggcgcgattc 102900
tccgggcggt atggatgaac caccgtccgg atgggagcgt tacgacggtg gtcaccgtgg 102960
tcagtcgcag aagcagcacc gtcacggggg cagcggtgga cacaacaaac gccgtaagga 103020
agctgcggcg gcgtcgtcgt cgtcctcgga cgaagacttg agtttccccg gcgaggccga 103080
gcacggccgg gcgcgaaagc gtctaaaaag tcacgtcaat agcgacggtg gaagtggcgg 103140
gcacgcgggt tccaatcagc agcagcaaca acgttacgat gaactgcggg atgccattca 103200
cgagctgaaa cgcgatctgt ttgccgcgcg gcagagttct acgttacttt cggcggctct 103260
ccccgctgcg gcctcttcct ccccaactac tactaccgtg tgtactccca ccggcgagct 103320
gacgagtggc ggaggagaaa cacccacggc acttctatcc ggaggtgcca aggtagctga 103380
gcgcgctcag gccggcgtgg tgaacgccag ttgccgcctc gctaccgcgt cgggttctga 103440
ggcggcaacg gccgggccct cgacggcagg ttcttcttcc tgcccggcta gtgtcgtgtt 103500
agccgccgct gctgcccaag ccgccgcagc ttcccagagc ccgcccaaag acatggtaga 103560
tctgaatcgg cggatttttg tggctgcgct caataagctc gagtaagaga gacgctatat 103620
ttagggcttc cctctctttt ttttttctac accgtgatac cctaataaag tacaccgcgg 103680
ttattatcaa cgtctctgtg tttttattat ttagaaataa atacagggaa tggggaaaac 103740
acgcggggga aaaacaaaga agtctctctc tagatgcggg gtcgactgcg tggggtgctg 103800
gaagtggaag cggtgctgat gggtgagggt cgtggcgcgg gcacggaccg caacgtgctg 103860
ctgatgtctg ccgcggtacg cacgtcgccg tccatgtcgc tgcgcagata agaggtaggt 103920
cgtaatgcgg cgtgttgcac gctcaccgtt aatggtacca agtcgtcaag gctcgcaaag 103980
acgtgccacg aggggatgac gagcgtgaga gccccgttgt taccgcttcg acgtctttgt 104040
ccggtcagga tcagtgcccg ggacagtccg gcttgggtgt ccgagtcctc gtcgccgctg 104100
gcctcctcga agccggcaaa catggcttcg gacagggggg tcggcgtcgg tgtggatgag 104160
aggtcatctt cgtcgtcctc ttcctcttct tcctcctctt cctcggtggg tggtaatccg 104220
ggggactgcg ggagaaactc ggagacggcg ccgcgcatga cgttgctccg tggaaagaga 104280
ccggcgcgca gctgcacctg gggacgcttg attttgtccg gtttaccggg tgtgagagtc 104340
caaaacccac ggcggaaaaa gtggatgcgg cctagcggct gtcggtgttc caaatgaacg 104400
gcctgatcgc cggtcagcgt gacgcggagg gtgattcgca cacgatcggg tagcgggccg 104460
gcttctatgg agacgcccgg gatgttttcc gggaaaaaga tggtgtcgtg agtctgattg 104520
gtctcgaaag cattctggat ctgcacgatg tactcgggat gtatgcgcgt cagcgtaaaa 104580
cttttgggaa tcaacagctg gaagccgttg tccggcaagc gtcgtaggtg cgggtacgga 104640
ttgtgtcgcg ccaccacctc ggcgcgatgc gtgtaaaccg aaaagtgcag aaacacgctg 104700
gtcggcgggt gcggtgagtc gtgatgcaga aacagcatga tccattggcc tcgctcgtcc 104760
gtctccgttt tgtggatgta cgtattaggg tccgaacagg ccagctgctc cagggcgtct 104820
accaacgtca gcgggatagc gccggcgcga aaggcgaact ggctgacaaa gatctggccg 104880
gcctccaagc tgctgtcggt tctgcggcgc cagttcggcg ttacagtcag tcgcacggcc 104940
cagtagtgag ccgtgcggcg gatgatggcg cgcgcctcca ctcgcggccg attttcttcg 105000
ccgccgcgcc gctggctctg aaagaggtgc agtccgctga cgggtacgcg atccagcggc 105060
agcgcaaagg ccagcaccga gaccgtgttg ttttctgagc ctggcgtcag gcgtcgtggg 105120
ccaaagttgt tgaggtccac cagtagtcgg tcctgttcgc ccaccacgca gcggcccttg 105180
atgtttagat cggtcaggtc tacggtgtcg tgcggagatt tgttctcctg aaaacagcag 105240
agaaccgagg gccggctcac ctctatgttg gtacgcaggt ccaggagtcg tagacgaccg 105300
gcttccagcg agccgccttc cacgttggtg atgagccgaa gcacctggca gtgcaggcga 105360
ccaaagctgc cgctggcggc ttcggcctcg ctgatcgcgg ccgcttccga cgagggtccc 105420
tcaccgggcg aggacgatgc ctgagacatc gcgaaggcgg gatgggggga gggtcagggg 105480
atgcgcaaag gtgaacgggt cttcgtggga ggtcgggaag ggttccggca actgtcgcaa 105540
atatagcagc ggcgacaggt gtggcgccca aaagtcgcga gtctgagtgg acgtgggttt 105600
ttatagagtc gtcttaagcg cgtgcgcggc gggtggctca acctcgatgc tttttgggcg 105660
tcgaggcgat gcatggcccg ggcagggctt cttgccggtg gcggcgacgt ttgggttgcg 105720
cagcgggctg ccatacgcct tccaattcgg cgaagatgcg gtagatgtcg ttggcgtccc 105780
agaagaactc ctggtacttc agattctgac cctgaaccgt agccaccatg ggcaccaggt 105840
tgcgggccag gatgccggcc tgccagggcg gccaggtgaa cacggccgga ttgtggattt 105900
cgttgtcgga atcctcgtcg gtgtcctctt cgggcgcgac ggtggactcg gccttaaggc 105960
ggccgcgtgt cataacgccc gacgtgcacg ccgttgccga ggatgctgat ttgcgtttgc 106020
ggcccgcgga agtggaggcg cccgccatgg cgccgccgcc ggtgacgcgg ggcgtcttgc 106080
gctcggtggt tacgagttct tcgtcggagt ccgatccgct ggtccagacg tcgtcgtcgc 106140
cctgggcggc accctcgtcg tgccggtccc aggtgtgtcg gtactcaagc ttgccctgga 106200
tgcgatactg gctggtgaag gtggggtgct cgctgtactg aggcccgcgc tgcagcagca 106260
agtcgatatc gaaaaagaag agcgcagcca cgggatcgta ctgacgcagt tccacggtct 106320
cgcgtatcgc ttgtacctcc aggaagatct gctgcccgtt catcaacagg ttacctgaga 106380
tgctcaggcc cgggatgctc ttgggacaca gcagcccaaa atgctcgtgt gaggtaaaag 106440
ccacatccag catgatgtgc gagatcttgc ccggtttgat tatcatattt ttgggacaca 106500
acaccgtaaa gccgttgcgt tcgtgggggc gcatgaaggg ttgcgggttg cgggtcatcg 106560
tcaggtcctc ttccacgtca gagcccagcg tgacgtgcat aaagagcttg ccggagggca 106620
cgtcctcgca gaaggactcc aggtacacct tgacgtactg gtcacctatc acctgcatct 106680
tggttgcgcg cgtgttctcc atggagcaaa ccagctcgtg cgcgcacacc acgtgccgca 106740
gtgccacgtc cttggtggga aacacgaacg ctgacgtgta gtagacgtcg ggctctttcc 106800
actggttctg ctgacgcgtc caggccagtc ccgagaccgt gagacgcgcc tgccacatct 106860
gcttgcccga cgcgtgaatc acagcgtcgg ctacgggcag gtgtcggtgt ttgcgctcgg 106920
ccgccgacgg gtagtggtgc acgttgatgc tggggatgtt cagcatcttg agcggcagcg 106980
cgtacacata gatcgacatg ggctcctggc tggggcagat gcttcggccc gtggggttgt 107040
gcacgttgac cgacacgttc tccacctcgc tgcccgtaaa gtacgtgtgc tgcacctgca 107100
gctgattgtc gccgcggtgg catggcgtcg agtcgggcgt gtactgcgac accaggatca 107160
gcgagggctg gctcacgcgt acgtggatac ccgtctgcag gagtcgcgtc tcgtgcggca 107220
gcaccggcgt atcgccgcga ctaaacacgg ctttcagcac gtgccccgaa atgggaccca 107280
gtacggatat catttcggga caacggcgac cgcgcgactc catgctgcct gcgcgtacgg 107340
gtgtaggcga ctgagcggcg cgccctctgc ggccgccgcc ttacataggc aggcgaccaa 107400
acgcggaacc cgaaataaaa acgttataca cagagacaac cgcggattat tgagtgtctt 107460
tttttattac aaaaaaaaag aggcaaagcc ccaccgtcac cacaccccat cacacaccac 107520
caccgatttt ttttgtttta atcccgtatt gcgcggacgc ctagtgtccg ttttccatca 107580
ccagggtcct ctgtttagag atcgccgcag accatggcta gagtgacagg actcgttttc 107640
tctgtcgtat tttccgtaag cttacagtct tgcggttccg tctccgggga cgccagtcgc 107700
atgggcagca ggtcctccag cgcgatggaa gcgcccagca ccgagagctg ctgttgcgac 107760
ggcgaatggg acgtggaccg cgagtgtagc gtggatttga cttggtgcgt cattgctgac 107820
aggcaaccgc gattcagcgt atgctttgac gagataaaat agaggcgtcc caggagcgcg 107880
tcccgtggga acgtggcgcc gttctcgtcg cttaccagta cggttaattc caaccaggag 107940
cgcggtagcc agaccgtaac gggcattttg agtccctgac ggttgtgtgg tacaaaaaca 108000
cccagataag gcccgtaaaa gcggcggtag atacgtaacg tgtgcgagtt tttcagcgtc 108060
aattcgtaag ggacgcgcac ctccagtccc tcgtccgccg cgccggagcg tggcggtaca 108120
aagtaaggca gtggcgcgtc cgaaaagaag ggtcgtcgca ccgtttcgcg tcgcagccgc 108180
aggcgaaacg ccactgggtc ggctggcgcc tcggtgcggt cgcaggtcac gttgaaacgt 108240
aacatgccgt cttggtatag cgtgagtgac gacagcgtca ggtccggcgg tgattcgttc 108300
gggtctagct ccaatcgtcc aaagacggag ggtcccaatg tcttggctgt ggtttccgag 108360
aggcgcgccg agatacggct ggtgagtcca cgcggccccg agatgccgcc ttccactcga 108420
tgccagcaca gcgcgtgtcg tacgcgcacc gtcagcgtgg gcgtcagatc cgtgtccgtt 108480
gattccgcgg aaatcgcgtt ctccgttacg ttgtttatat ccagcgtcgg ctcgaacgtg 108540
agttctggca gatgcagcgc cagacagtcg tgtaacgccg tgtgatgcgc ggctttacgt 108600
cgtagcggta gccgtttcag cagcggcgtg atgatacgga gcgcgaagag attgagtgat 108660
aagcgcacga tggccatgcg cgtcagttgt tggtcaatta ccgagcgcag gatatggcag 108720
cctgggcgtg cgggaaagag agagaaggcc gggcgcacgt cagaatcctc gttagagacc 108780
acgcatagaa tgccgcgttc acgatcgtcg ttgcggtcat cctcgtcctc ttcttctttc 108840
ttctcttctt tttccttttt tttctcgggc tcgtgggaag ccgccgtttc ttcttcttgc 108900
gacgtcgcgg gggcggtttg agactcgccg ttcgcttccc ccaattgcag cggcgtagag 108960
agcagaatct ggaagggatc ccgcaattct tcgggtcgga ggtcgaggtg caactggatc 109020
agatggtagg tgccgcggtg cacccgaggc tgacggatgt cgtgtttatc cgtcagtgtg 109080
aggatggtct gcggtgagcc gctgtgcttg tccagctcgt ccggcgtttt caggagaaga 109140
ctgtcgtcgt cggtactggc gacgcccatc atggtcgtgg tggtagtggt ggagaggaaa 109200
gtgagcggcg gcgtcgacag agctcggcgt tggcggcggc atttgccgct gtgtcggctg 109260
ctattgctgc caacgccacc gccgccgcct cgtctggctc gtggccggcg ggcccgattc 109320

-continued cgaaggttgg ggtcgacgcg tggcatgctt ggtgtctgcg ggcgcgagag ggccggctca 109380
gcctttaaat atgcaggtcg cggatttgtt atcgggtgaa acgtcacaca ccgtgaagac 109440
gacctgttcg cggatgaggt catccagctg tcgcagcatg acgaaaagcg ccgacagccg 109500
cgcgatctcg tcgtcgggcg acacgtgctg tggccgcgcg ggcgtgcgcg gctcgccgac 109560
gctgcgctcg cggtccagcc gcatcagcag ctcctggcac ttgacgagca gcatggagct 109620
gtcctctagc gccaacttgc gcacgtaggt catggtcagc tccgaggcta ggttagccac 109680
catggacatg gagaggcagg cggtcttcat gtcgatcagc aggtgctggt cgatgaccgg 109740
atcggggatg gtgaaggtgg cgtcgcgaaa agtaatggtc tgcagctgct gcacggcagc 109800
ctttacctcc tcgtacgaac ggtcgagcga gaagaggccc atgatgagta gtcgctggtt 109860
gatttccagc gccagtggca tgggtacgat ccagggcagc accagctccc actggcccag 109920
cgtcagcagg ttctcgcgcg ccagcggtcc gtggaagagc ggcggcagca cgcatagcgc 109980
gtcgcccttc tcccaagtca cgggtcccgt gttgaggacg gtgtagagca gtccgtgcgt 110040
cggtacgtgt aggaggatct ggttgccttc tacgcgccgc atcaacgtca gcgtcatatt 110100
gcgcagcagg ccgcgcagtc gtacgtagcc gcgggtgtga tctacgaact ggtgtaggcc 110160
cagctggtag tgcttgatga gatgtagacg ctgcggaatg ggcacaacgg ccgctactag 110220
tttggtcagt ttgcctacgt cggcgatgct gagcttgtgg tcgaaagtgc agaagatgtt 110280
ggcctccatg gccgccatag cggcggtgaa atcctggccg cgacggagga gaagcggaga 110340
cgaacaacgt ctgcaccggg cgcggcgtca gagcgagcgt ggcgcgtccg ggcccgcgtt 110400
tgcgtctagg tgacccgccg ctaacctgcg gtcgtcgccg tcctcctcac cggacggcct 110460
cacgagttaa ataacatgga ttgctgcagc gggatgattt cgcctacgac gtagttacca 110520
aagtgcgttt cggacgtagc aaaagccccg gcgccaccct tgagtttggt ctccatcagc 110580
gccagcgtgg tggtgctgag gatcggtagc gcttcctgcg tcagacggca cgggttttcg 110640
atgagttgtt ccgtgccttc gacgcagacg tactgcgtgt ccgtgtcgcc gcggatgcag 110700
tccttggcgc gtagcaggta ctcgtcgatg gttttgaaga gcgttttgtt ggccgcgata 110760
atctcttctg tgttaaagta ctgcgcgcag gggctgtaga atttggagtt gtagcctaga 110820
cgttcgcgat gtcgggtgtt gtagagtacg tcgctcagac agccggcttg cgaggcccag 110880
gggttgtgtg tggccgcgaa agtctgtgcg tccgcttcgc gatggtcgta gatggccttg 110940
gtggcggcct ccgtgtcgta cggatcgacg gccagcatgc aggaggcacg cccgcgcggg 111000
ttgttgggga tcttaaagta attaacgtcc atcgtcaccg gcgtaaggat tagttcgcac 111060
gcggcctttt gtccgtgcac cgtggcggcg gcattgcgct cggacatgct gccgaacgtc 111120
agcatggaga tggtctccgt atctaacagt tgcggtcgtt ctacgccggc cgcgtgccgg 111180
atccagcggt ccacctcgtc gtgccggtac acgttcatag ggaagacgcg aaagaggtcc 111240
tgcacgcgga cgcccatgtc ggttcgcacg cggtttacgt aggctacaca ggtatttgac 111300
gtgtaaccca gacccatgtc tacggtgtta atgttctgcg tgacgtggta cgtggtgctg 111360
atgtcgcgtt cctccttggt cacgataggg ttgttgatga taactgacgt gcacgacttg 111420
ccgctgtaga gcagcatgtc cacctcgaag gtgtcggtgc gtacggccgt gagtgcgaat 111480
cccgggtgga tgtgcgcctt ggtctgcagc accagtgaaa ctggtgagat tttgtataac 111540
atggcggcca gcgtcatgac tgagtgcaac acgttgggac aggtggccga gtaacgcgaa 111600
aagggcgagc gcagccagtt gtggtactcg tgtgcgaagg ctgtgggtag cgggaaacca 111660
ccgtcgtgac ggtgatagtg cgggaactcg gtcacgtagc gtttaatgtc gtcgctcaac 111720

-continued gctgcgcaga tggtggggtt tgagtagaaa cggtggaaag gtacgggtag gctgtactcg 111780
atcaacgtct taggcgccgt cacgacgcag cagccgttgt aaagcacgtg ctgacgtgag 111840
ataaagtccg gcaggccctg acgctgcgcg tggtccagag gcgcgcgtac ttcgagcacc 111900
ttgacgtgct cgcccacgaa ttgcacggcc aaaaacagtt cacgacaggc ctgcagcagc 111960
ggcgtatgcg cgtcggtggc gacgtcctcc accagctcgg tcagcatctc gcctacggct 112020
tgacgttgcg ccgctatcga gtcttcgggg gtgacgccgc ttgtgctctc tttcgacgtc 112080
gtacctgacg tggagaccgc ggtggcggcc ggcatcagga gaaacgccgg tcggtaaaag 112140
aggtctacta gcagcgtctt gaggttgagt cccaggccgc aggcccggtt gttggtcatg 112200
gcgggcatga ggcagagata aaagaccttt tgtaacgtcc attcgtcgtc ggtggcacgg 112260
taatcgtcca caaacagcgg ctcgtcggca tccatggcgc ccaaacgcgg tacgtccgaa 112320
acgccgtggt gtcgcgcctc gatgttggcc gggttcaacg gttgccggtc ggctactacc 112380
tgtacgcctt ccatgttacg cggcaggtgc gtaacgaagg ggggccacag ccggtggtcg 112440
tgcagcgcgt tcacgtaagc cgatagcggt tcctcagcca gttgaccgtt gttaagtccc 112500
ggcagcgctg agatgcgcgt caccagacgc agcacggcga tcagattgcg gtagtgaaag 112560
agcaactgcg gtggtagagc gccatcagcc aggtgttcgg cgatcaacgt caccagcgca 112620
tagctgtgcg caaaaaccag cagctgacgt gtgtgaaaca tgttgacgat acaacgtgct 112680
acgaaagtgc ggattagcaa aaaagcgtcg acgttgccgt gtaccagcac gtcaaccagg 112740
tagcagagct cagggtaatt ggggcttgtc acggtggttt taaaaagtcg caacgtgtct 112800
tcgtagtcgg gtggtggccg cagtcgcatg tgttccatga tctcccaggt gcgcagttcg 112860
tggaaggggc ccggtgccag tccatctggc aaattaccga tgacgatacg cggtgtacac 112920
agcgccaccg tttcgctgtt ttcctggcag tgcgtaaagt cgaagaaggg gtgcagctcg 112980
gtgtagagcg tgatgttgcc caccttgtag aagtcggtga ccacaaagtc ctgcttcatt 113040
tcgttcaccg tgcgcgggac ctcgcgtcgt acgcggtaaa aatgcggtat gcggcgcgcc 113100
gcaccgccca tgggttcctg ctgaaaacga cactcgagca gtcgttgcat ggcgggttcc 113160
gagggcggtc cgcgttccgt gaaggtctgt agacagggcg cgggctcgtg cagcaccggg 113220
tggcacagcg tcttgagcgc gtccacaaag tctatctttt gtacggcacg gtcccggttt 113280
agcaggtagg ccgtggtggg caacgcgttg cgaacggtgt cgttaagctt aactttgctt 113340
tctaccgtgg tgtaaccgcg atcctcgggc agatacagcc ctacggggaa gaaaaacgtc 113400
aggtccacgt tacgttctag cggatctttg gtatcggtgt ttttgtagac gcgccgcaag 113460
ttttccataa tcaccgtttt ttcgcccagt cggatcacgt ccatgctcag cggcgttaag 113520
ctgtgcgccc cggcctgcga aagcgagtcg ttgggcaaat gcggttggcc cgaagtcaga 113580
tgagccttgt acgagttgaa atcggccagg atcgagtgat aggatatggc agtgacggca 113640
ttttcgggac tgagtacaaa attgccgtag gtggccggcg ccgagaccgt ttctttggtg 113700
atgtggcttg agagcagcga catgatgatc tgcataacgt tggctgtgct taccatcacg 113760
ccgctgatct tggcccccga gctcgtggtg tacgtggtgg ggttgtctag gatgctatcg 113820
gtggccgctt cggccagacg cgtgaggaac ttgagcacat agtcgcgatc gcgcgtgcga 113880
ttcagcaaaa agagcgtggc cagcattttg gccttgaagc tctgcaagat gttgcttcgc 113940
tggatgcggt tcagcgcctg tcgcgccagc gtggcgttct ctaccagcgt ctgcaccaca 114000
aagtacggcg gcgccttgcg tagcagtgtc tgtaaaaagc tgtgaatcaa gccgcgttcc 114060

-continued

```
atggcgtcgg ccgtgttttt cagcgcgcgc agcaccgtgt gcatagcttc cacgttgagg 114120
atcttgtcca ggatggtgcc ttcgaacgtc tcgcgcagat acgtgaggca ggctgcgctg 114180
agctcaaagg ggatggtgat gggggatttt tcactgtatt tggtgaccat aatggtggtc 114240
tgacgactgg tgggcaaacc ggcgccgctg gccacacgcg gcacctgcac gtggaacagc 114300
atttttcccg tagtcagttt attgaggtcg tggaacttga tggcgtgcgc cgccgcggcc 114360
aagccgctgg tcaaaaaata aacccattcc aggcgattgc agaaggtgcc gaagatggct 114420
tcgaagtgaa tattgtaacg ctcggggtcg tcgccgtagt agatgcgtaa ggcctcgaac 114480
atctcctcgc cggcgctggt cttgacgtgc gtcagaaagt cagtgggaat gcctacttta 114540
ggcaggagct cgagcgccga ccagttctcc atcgcggcgg cggcgtgagc gcgaggcgtc 114600
ggagctcggg gaaagcagcg cgacccggat aatggccggc gctgcgccgc gccgcctcgg 114660
ctgtgacgct ctaatagtcg tcggcggctc cgctacgccg cgccgggttt tacacgtccc 114720
cgtgcacgtt cgcgcctgca acctcaccca agagctatca acgggcgagg acgcccgctt 114780
ctgtcgtccg cgacccgtta acgtcgaacg ggtgcgcgct gtttttgcgg ctctctaccg 114840
tgcctgtccg atacacgtga ggaccgagcc cgagcgtgtc aagctggtac tgggtcgtct 114900
gttactggga cccgtggccg taccctgttt ttgcgacggt gaagtggagg gccacggtga 114960
acatctggta cctacgacgc agttttgtcg cgggccgctg ctctacgtgc accgacgttg 115020
ttgttgcgga tccgtgaccg ccgggcgcgc gctgtcctac cacgttctcg aaaaccacgt 115080
ggccacgcat gtgctacgcg gattgctctc gctgacggaa tggaatcgag aattgccgag 115140
cctcttttgc gactgtcctg gcggcggtgg cgcctcggga accgaggaac gctacgctat 115200
ggcctgcctg ccgcgcgacc tcagcctgca cctggacgac tatccttacc tgatggtgga 115260
aatcggacgc gtactcagtg tcagcgaggt agacgactac gtaaccgccg tctccggcta 115320
cctgggcgag gccgcggcgc cgcgcatcca ggttcactac aagctgctct ttggactcaa 115380
cgtgcgtccg caagcgccgt gcgcgttgga cgctacacgc gactttttc tactggagct 115440
gcaaaagctt tggctgggcg ttgaatatca ccacgaagtg acgtcggagt ttttcggtcg 115500
cgtgctggct cagctgcatc gcgaccgcgc ccgcgtcatg atggcgcttc gcttgcccga 115560
gcagacggtg tgccacctga gcaccttcgt tctcagtcgc ttcaagcgac aggtactgta 115620
cttcaagtta caggtgagct acggcaagtg ccggactggc cacgctgaca gaagtggggg 115680
agggggaaac ggtggaaatc agggacacca caacctactg tgttatcgac gccttagcgt 115740
cacgtttgcc gacacggaca cggtgtggag aaaccttttc tacgtttatt atgaactagc 115800
tcgggatctg gggtcccatg ggacggggaa ccgacccgta aaccgcggtt acggtgtttc 115860
ttgcgctccg aggacgtcgc ggctatcacc gtcagaatcg acggtggttt cggcgaacgg 115920
acacgcgctg tcttccaccg cgctcccgac gacgagcgcg ggtcacaagc tgtcactgcc 115980
gcgcgacccg gccgccgatc gcgttcgacg ttacgtgtgc atcatctcgc gtctcatgta 116040
cgctcggtac ggggagagat ggcgtaaaca ccgtcaacgg cggtcggaga cgggagaaga 116100
ggaggaggaa gagacgctgg aatcggggga gactgacgcc acgccgccat ttgactttac 116160
ggggcagcag ctgcgccggg cctatcagga acaccgacgt cgtaaacatc tagccgtgca 116220
gcgttacgcg ccgtgccgtc gtaagctcat cggcgggatg gagtttgccg aggtgacggg 116280
cgtgagtctg gaccgcatcg ccgtcaacgc tttcaacacc aaccgcgtta tcaatatgaa 116340
ggccgcgctc tcgtccatcg ccgcgtcggg tctcggcgtg cgcgcgccgc ggcttcccaa 116400
gaacatgacc cacagttttg tgatgtacaa gcacaccttt aaggagcccg cttgcaccgt 116460
```

cagcaccttt gtttccaacg acgccgtcta cattaactcg ctcaacgtca atattcgcgg 116520
ttcctacccc gagtttctgt actcgctggg cgtgtaccgg ctgcacgtta atatcgatca 116580
ctttttctg ccggccgtgg tgtgcaacag caactcctcg ctggacgtgc atgggctgga 116640
ggaccaggcg gtgatccgct cggagcgcag caaggtgtac tggaccacca actttccgtg 116700
catgatctcg catactaaca acgtcaacgt gggctggttc aaagcggcta cggccattgt 116760
gccgcgcgtc tcgggcgctg acctggaagc cattctgctc aaagaactct cgtgtatcaa 116820
gaacatgcgc gacgtgtgca tcgattacgg tctgcaccgc gttttcacgc aactagagct 116880
gcgcaattcg taccagatcc ccttcctggc caagcagtta gtgctgtttc tgcgtgcttg 116940
cctgctcaag ctgcacggtc gagagaagcg gctgcagttg gaccgcctag tatttgaggc 117000
ggcacagcgg ggtctctttg actacagcaa gaacctcacg gcgcacacca agatcaagca 117060
cacttgtgcg ctcatcggca gtcgtctagc caacaacgtg cccaagatcc tggcccggaa 117120
caaaaaagtc aaattggatc acctgggccg gaacgccaac gtgctgacgg tgtgtcggca 117180
cgtggaagcc cacaagatcc ctcgcacgcg cctcaaagtg ttagtcgagg tgctgggcgt 117240
gttgcagagt atcagcggta cgccgcacac gcgcgaagtg atccaccaga cgttgtttcg 117300
attgtgctcg gcggccgcag ccacatcggg cctgtgttca tcccctcccc cattgtgtgt 117360
gtcctcatct tcctccgtcc cttctgtccc aacctccgtc agcgttgacg gcagttctga 117420
acccacgtcg ccgcgagcgc ggtttgcatc acgatgatgg aagccgcggc cgctgccgcc 117480
gcggcgtttc gtccggagga gcgtccgacg ccgggttggc acgacgcggc gttgttaatg 117540
gacgacggta cggtgcgcga gcacgcgttt cgcaacggac cgctgtcgca actgattcgc 117600
cgtgtgttac cgccgccgcc cgacgccgaa gacgacgtgg tttttgcttc cgagctgtgt 117660
ttttattgca gcggtcgttt taaccgcagg tcgtccgtct tctccatcta ttggcagaag 117720
catagcgatc tggtgtacgc gcttacgggc attacccatt gcgccaagtt ggtggtggaa 117780
tgcggtcagt tggggagtag taggctacgg tggcgcgacg gtgatgcgag tggtgaggag 117840
cgccggggag acgacgacag cagggacgag ctgtacgacg tgccgggcat ttatatgatt 117900
cgcgtcaacg acggcggcag caccggcccc agacacgtta tttggccggg taccagcgtg 117960
ctttgggcgc cggacgttgt gatcactacg gtgcagcgac gaatctcggc ggcgcgcgcc 118020
ctggtgaaca cgttccgcca atattttttt ttgctggaac ggcgctcgca cgaggagctg 118080
gttctttgtc cgcccgagat ggaggagcgt ctagcgccat tgttgcagag tgccacgcgc 118140
ggtgattcgg acatgtttga cggtgtggtg gccagcgctt atcaccgttt gcgaatgagt 118200
aatattccgc gttcatccgc ccgtctgctg gagcactgcg tggggctggc gggtgctaag 118260
aagctgctct tgctcgacgt gccgcgtctg gagaactatt ttctttgtca agtctgtctt 118320
tacgagctgg acgaggacga gatgggcgag gagatgctgg gcatgttggc cggaaagccc 118380
gaggatgccg ccgtctcggg cgcaagcggc ggttttctgc tacatcgcaa gacgatgaag 118440
ctggccgcct gtctgtgttt gttgctcaat tcgctgcatt tgcaccagga ggcgctggag 118500
gccttggatc ctccgccgcc gcgcgtcgag gagaacgacc ttgtcaacgt ggtgctgcgc 118560
cgttattatc gcagtcacgg cggcgtgcag gcgcggacgc tggcggcggc ccgggctttg 118620
ttagccgact acgctgaaac gttttcgcct ttggggagtt ttacgcgcct gggttacgat 118680
cgtctcgttt ctgccgatgc cggcgtcagt cgtcggcacc tggtggctct gctgcgtgcc 118740
tagctgaccc tgaaacggat ggcgtgtata tcgtcacaca ggtaggtggc catgatgacg 118800
gcgatgataa gatcgtccga gatacgattc tggcgcttgg ccgagtagcg tgccgtcgtg 118860
ccttcggcca gcgtgacgcg gtgcaggttc tgaatctgct ccagaagata ctcgatgggg 118920
tcgtggctca gcttgatggt gtaggagacg agctcttgcg aggctttgat gtagcccgag 118980
ttgaaacgcg agatgaactg ttctacggcc agcgccttgt cgcggcccat gaggtagaag 119040
ggctgttcga tgtggttctg gtcgggcgtg tggtagaaga gcacgcggat gagcgtgctg 119100
ctctgcacgc tctgtcggat gaggcaggcg atgcgcacgg ccgccgcctg gttggtgttg 119160
ccctccacgg cgatacgcag ttcgtccagg taagggtgca ggctcagcac cgagatgatc 119220
atatgcgccg cgcactcggc gatggctacc tcagaactct cggagaggtc gcgcaaaaag 119280
aaatgctcta ggccgtaaat gagaaactgg tgtcggtagg cgcctacggc cgccacgccc 119340
gtgcccgagg ccttgcggtt ggtggtgaag gccgggtcca gatacacgta aagcgtcttg 119400
ccgaaataat cgtaggcgtt ggtgttgagc gtgctgtaac gcaaaatgtc gaactcttcg 119460
cggctctgat ccgtgatgag cacggtgttc tgcgagattt tattggtacc gccgatgatc 119520
tcgtccatga aagcgcccgg cataaacatg ttggccgtct tgcgcacctg cgagttgagg 119580
ctgatgaagg tgggcttgtg cagtcggtag caaggacacg ccgtggcgtc gcccttctcc 119640
gtgaagctgt gcaggtgctc ttcgcacacg taagagacca cattgagcat gtcaaagggc 119700
gcattgttga ggcgcgtcaa gaaacacgtg gcgtcactgg tagtgttggt ggacgatatg 119760
aagatgatct tggtggtatt ctgggccagg aaccccagaa tggtgttgaa ggcctctttc 119820
ttgatgaagt gcgcctcgtc caccagcagc aagtggaagt tttgtcctcg gatgctctgt 119880
gtagagagga gacagaaaag ggactcttat gattacgcac gctcggctgg aagcctacag 119940
agtcggggtg gggccggaca ggtgagccag gtgagccgcc aggtgaggcg ggatcgccgt 120000
gtgccaaccg ggctgcgacc tgaaaaccgg aaccaatccg ccgacaccgg cgccgcgtga 120060
cgcgcgccca taaaaacgaa agtgtcgtcg tcgcgacccg ccacagccgc catgaactcg 120120
ttgctggcgg aactcaaccg actgggggtc gcgcacgcca ctacggagga tgtttttatc 120180
tttgtcgacc gcctctttca acacttttcc ttcctttttcc aggccgagga gtcaggcccg 120240
cgccgcttgg aactggtcgc gtccgtgttc gagcacctga cggtggagtg cgtcaacgac 120300
atcctggacg cctgcagcca cccggacgtg aacgtcgtgg agacaagcaa cacctgtcgt 120360
ccctgccctt ctcctgttcc ctccgccccc aaaactgtca gcgacgctca gacgtcatgt 120420
gcgacgcctc gggcgcctgt gacatgaggc acgtccagaa cgcgtttacc gaggagatcc 120480
agttacactc gctctacgcg tgcacgcgct gctttcgcac gcacctgtgt gatctgggca 120540
gcggctgcgc gctcgtctcc acgctcgagg gctccgtctg cgtcaagacg ggcctggtat 120600
acgaagctct ctatccggtg gcgcgtagcc acctgttgga acccatcgag gaggccgcac 120660
tggacgacgt caacatcatc agcgccgtgc tcagcggcgt gtacagctac ctcatgacgc 120720
acgccggccg ttacgccgac gtgatccaag aggtggtcga gcgcgaccgc ctcaaaaagc 120780
aggtggagga cagtatttac ttcaccttta ataaggtttt ccgttctatg cataacgtca 120840
atcgtatttc ggtgcccgtc atcagccaac tttttattca gcttatcatc ggtatctact 120900
caaagcagac caagtacgac gcgtgtgtca tcaaggttag tcgtaagaag cgtgaggacg 120960
cgcttctgaa acagatgcgt tccgaatatg gaaacgcacc tgtattcgga tctggcgttt 121020
gaggcgcggt tcgctgacga tgagcaattg cctctacacc tggtgctcga ccaggaggtg 121080
ctgagtaacg aggaggccga gacgctgcgc tacgtctact atcgtaatgt agacagcgct 121140
ggccgatccg cgggccgcgt tccgggcgga gatgaggacg acgcaccggc ctccgacgac 121200

-continued gccgaggacg ccgtgggcgg cgatcgcgct tttgaccgcg agcggcggac ttggcagcgg 121260
gcctgttttc gtgtactacc gcgcccactg gagttgctcg attacctacg tcaaagcggt 121320
ctcactgtga cgttagagaa agagcagcgc gtgcgcatgt tctatgccgt cttcactacg 121380
ttgggtctgc gctgccccga taatcggctc tcaggcgcgc agacgctaca cctgagactg 121440
gtctggcccg acggcagcta tcgtgactgg gagtttttag cgcgtgacct gttacgagaa 121500
gaaatggaag cgaataagcg cgaccggcag caccagttgg ctacgatcac gaatcaccgt 121560
cggcggggcg gactgcgtaa taacttagac aatgggtcgg atcgccgttt gcccgaagcg 121620
gctgtggctt ctctggagac ggccgtcagt actccatttt ttgaaattcc gaacggagca 121680
ggaacctcct ccgcgaacgg cggcggcaga ttcagtaacc tggagcagcg ggtagcgcgt 121740
ttgttgcgcg gcgacgagga attcatctat cacgcgggtc cattggagcc gccttccaag 121800
atacgcggtc atgagttggt gcagctgcgc ctggacgtaa atccagacct catgtacgcc 121860
accgatccgc acgaccgcga cgaggtcgcg cgtacggacg agtggaaggg tgccggtgtc 121920
tcgcgtcttc gcgaggtctg ggatgtgcag catcgcgtgc gcctccgtgt gctgtggtac 121980
gtcaattcct tttggcgcag tcgcgagctg agctacgatg accacgaagt cgaactatac 122040
cgggcgttgg acgcttatcg ggcgcgcatc gccgtcgagt acgtgctgat tcgcgccgtg 122100
cgcgacgaga tctacgctgt actacgacgg gacagcggcg cgttgccaca gcgtttcgcc 122160
tgccacgtgc cacggaacat gtcctggcgc gttgtttggg aactttgccg tcatgccttg 122220
gcgctctgga tggatcgggc ggacgtgcgt agctgtatta ttaaggcgct aacgcctcgt 122280
ctgagccggg gtgccgccgc tgccgctcag cgagctcgtc gccagcgcga gcgctcggcg 122340
cccaaaccgc aggagctgct tttcggaccg cggaacgaga gcggtccgcc cgccgaacgg 122400
acttggtacg ctgacgtggt gcgctgcgtt cgcgcgcaag tggatttggg cgtggaagtg 122460
cgcgcggcgc gttgtcctcg caccgggctt tggatcgtcc gtgatcgccg cggacgcctg 122520
cgacgttggc tctcgcagcc cgaggtgtgc gtgctctacg tcacgccaga cttggacttt 122580
tactgggtgc tgccgggcgg ctttgccgtc tcttcgcgcg tcactcttca tggcttggcg 122640
cagcgggctt tgcgagaccg attccagaac tttgaagcag ttcttgcaag aggaatgcat 122700
gtggaagctg gtcggcaaga gccggaaaca ccgcgagtat cgggccgtcg cttgccgttc 122760
gacgatcttt agtccggagg acgacggctc gtgtatcttg tgccaattgc tgttgctcta 122820
ccgcgacggc gaatggatcc tctgtctttg ctgcaacggc cgttatcaag gccactatgg 122880
cgtgggccac gtacatcggc gtcgtcgacg catctgtcat ttacctacct tgtaccaact 122940
gagcttcgga ggtcctttgg gtccagccag cattgatttc ttgccaagct ttagccaggt 123000
gaccagcagt atgacgtgcg atggtattac gcccgacgtg atttacgagg tctgcatgtt 123060
ggtgccccag gatgaagcca agcgcatcct ggtcaagggt cacggtgcca tggacctgac 123120
ctgtcagaag gcagtgacgc taggcggcgc cggcgcctgg ttgctgccgc gtcccgaagg 123180
ctacacgctt ttcttttaca ttctgtgcta cgacctgttt acctcatgcg gcaatcggtg 123240
cgatatccct tccatgacgc ggctcatggc ggcggccacg gcctgcgggc aggcgggttg 123300
cagcttttgc acggatcacg agggacatgt agatcccact ggcaattacg tgggttgcac 123360
ccccgatatg ggccgctgtc tttgttacgt gccctgtggg cccatgacgc agtcgctcat 123420
ccacaacgat gaacccgcga ctttttctg tgagagcgat gacgccaaat acctatgcgc 123480
cgtaggttct aagaccgcgg cgcaggtcac actgggagac ggcctggatt atcacatcgg 123540
tgtcaaggat tctgagggcc gatggttgcc cgtcaagacc gatgtgtggg acctggtcaa 123600
ggtagaggaa cctgtgtcac gtatgatagt gtgttcctgt ccggtgctta agaacctagt 123660
gcactaacgg ggtctgacag ttcacgggga gaagaaacaa gaaacaacaa aaaaaaaaga 123720
ggacatggac tcgccacggt ttgtggcaag gcgtatatta tcatcatgga gctactcacg 123780
ttggtgttgt agcaactggc aaaaagcgcc gtgctcttgg cgccgcggtg gtcgatgctg 123840
atcacgttgt ccttgttctc gaccacgtag tcgcgcgcga aggtgtggcg gcagcggaac 123900
tcgacctctt tgagcacaaa ctgcgacacg tgcttttggt gcgccacgta gccgatgctg 123960
atgccgatca tgtgcttaag cagaaacgag ataatgggga tgatgaacca agtcttgccg 124020
tgacgtcgcg gcaccaggaa cacggtggct ttctgcttaa agatgtcgat ggaggtctgc 124080
gagaggaagt cgatctggaa ggcgtggatg aggtactgca gcacgcgatt ggccagcacg 124140
gggatcttgg tcacggctat aaaaaagatg acgtgtatca ataaattctt ttgaaacggt 124200
tcgagtcgga tggcttttgc gtcgccctcg acggcggtac tgaagccgcc gtcgagccac 124260
tttttaaagt cggtcatgaa gttgttgatc tgctgaaact gcggatcgcg gtagagctcg 124320
gtcaacgcgt ccagcttctg gtaggaggcg cgctgctcct cggagcacgg gcgaaacgtc 124380
agttcatcga gcgcactctt gaggcgctcg tgaaacagca gctcgcgctg gctttcctcg 124440
ggcgagttgt agtcgcggtg gcggccgcag aaggccatga gcggcaggaa ggcctcgttg 124500
cacgagtggg ccagcccgag ttcggggtgc atcatctggt agcgcttgcg gcacagcgcc 124560
gccacattgg tgaaggccgt ggagatgcag gaggtggggt ggctcttgcg cttctgcagc 124620
tccgcgtagc gctcctggat cttggcggcc gaatctccgc gcaacatgat ggcggcggcg 124680
gtggtgcgag cggaggttag gcggcagcgg cgagaggaga ggaaaaagat ggcgtccgcg 124740
aggacgacgg aggatccacc cgaaaaccac gttgtcgcgg acgtggcttg tgggacgggc 124800
gccgtcactc gttcgtcttc gtcgtcccta gtggtgtcgt cttcctcggc gtcaggctca 124860
gacgaatctt cctccgcctc tcctctcagt ttccccgtct cctctccctc aactgccgtc 124920
aggtctccgg ggtccgccgg ggtttcgacg tccctgtgct cggtggaacg gatggtcgag 124980
ctgtcggcgc agtctccggc cgccgatttc tcggtctccg aggcttggcg tttcgaggag 125040
gccgtaaata tggcgctggt ggcctgcgag gccgtgtcac cttacgatcg ctttcgccta 125100
attgaaacgc ccgacgagaa tttcttgttg gtcaccaacg taattccgcg cgagtcggcc 125160
gaggtgccgg tgttggatag cagtagcagc ggtggcgata gcgggccgga ggacaaaaag 125220
aaaaacgtcg ggaataaaac cgcgggggaa aagaacggcg gtgggtctcg ggccaaacgc 125280
cgtcgtagac gacgcgctcc gaaaaacgac gccgccacgc cgtcttttct acgtcgacac 125340
gacgtgctgg agcgtttcgc ggccgcggct gagcctttgc cgtcgctttg tgtgcatgat 125400
tatgcgttac gcaatgctga ccgtgttacc tacgacggcg aattaatcta cggcagttac 125460
ctgttgtatc gcaaggctca cgtggagctg tcactctcca gcaacaaggt gcaacacgtg 125520
gaagctgtgc tgcgacaggt gtacacgccg ggcttgttag atcatcacaa cgtgtgcgac 125580
gtggaggccc tgctgtggct gctgtactgt ggaccgcgca gcttttgcgc gcgtgacacc 125640
tgtttcggtc gcgaaaagaa cggttgtcct ttccccgcgt tgttgcccaa actcttttac 125700
gaacccgtgc gggactatat gacctacatg aatctggctg agctgtacgt ctttgtttgg 125760
tatcgcggct acgaattcct tgcgccaacg ccgcaggcga cgacggcggg tggtggtggt 125820
ggtagtggtg gcggcggcgg ggccggcgct tgtacggtcg agacgagcgc gtcagcaggc 125880
cgggtcgatg acgccggcga cgaggtgcat ttgcctttaa agcccgtctc gctggaccgt 125940
ctcagagagg tgttacaggc ggtgcgcggc cgcttctcgg ggcgcgaggt gcccgcctgg 126000
ccggcctcgt cgcgcacctg tttgttgtgc gcgctctaca gtcagaaccg tctctgttta 126060
gatctcgcgc gtgacgaggc gcggaccgtg agttatagcc ccatcgttat ccaagactgc 126120
gccgcggctg ttaccgacgt cactttgagc cacatcttgc ccggccagag caccgtctcg 126180
cttttccccg tctaccacgt cggcaagttg ctggacgctc tctcgctgaa cgacgcgggt 126240
ctcatcacgt tgaatctatg acgtcggtca acaaacagct cttaaaggac gtgatgcgcg 126300
tcgaccttga gcgacagcag catcagtttc tgcggcgtac ctacggaccg cagcaccggc 126360
tcaccacgca gcaggctttg acggtgatgc gtgtggccgc tcgggaacag acccgataca 126420
gtcagcgaac gacgcagtgc gtggccgcac acctgttgga gcaacgggcg gccgtgcagc 126480
aagagttgca acgcgcccga cagctgcaat ccggtaacgt ggacgacgcg ctggactctt 126540
taaccgagct gaaggacacg gtagacgacg tgagagccac cttggtggac tcggtttcgg 126600
cgacgtgcga tttggacctg gaggttgacg acgccgtcta acaggtatag caatccccgt 126660
cacgcctctg ttcagatttt attaaaaaaa aaacacacca taacgacagt gtcggtgtgg 126720
tagctagtgc agccctagga acagggaaga ctgtcgccac tatgtcctcc gcacttcggt 126780
ctcgggctcg ctcggcctcg ctcggaacga cgactcaggg ctgggatccg ccgccattgc 126840
gtcgtcccag cagggcgcgc cggcgccagt ggatgcgcga agctgcgcag gccgccgctc 126900
aagccgcggt acaggccgcg caggccgccg ccgctcaagt tgcccaggct cacgtcgatg 126960
aagacgaggt cgtggatctg atggccgacg aggccggcgg cggcgtcacc actttgacca 127020
ccctgagttc cgtcagcaca accaccgtgc ttggacacgc gactttttcc gcatgcgttc 127080
gaagtgacgt gatgcgtgac ggagaaaaag aggacgcggc ttcggacaag gagaaccagc 127140
gtcggcccgt ggtgccgtcc acgtcgtctc gcggcagcgc cgccagcggc gacggttacc 127200
acggcttgcg ctgccgcgaa acctcggcca tgtggtcgtt cgagtacgat cgcgacggcg 127260
acgtgaccag cgtacgccgc gctctcttca ccggcggcag cgacccctcg gacagcgtga 127320
gcggcgtccg cggtggacgc aaacgcccgt tgcgtccgcc gttagtgtcg ctggcccgca 127380
ccccgctgtg ccgacgtcgt gtgggcggcg tggacgcggt gctcgaagaa aacgacgtgg 127440
agctgcgcgc ggaaagtcag gacagcgccg tggcatcggg cccgggccgc gttccgcagc 127500
cgctcagcgg tagttccggg gaggaatccg ccacggcggt ggaggccgac tccacgtcac 127560
acgacgatgt gcattgcacc tgttccaacg accagatcat caccacgtcc atccgcggcc 127620
ttacgtgcga cccgcgtatg ttcttgcgcc ttacgcatcc cgagctctgc gagctctcta 127680
tctcctacct gctggtctac gtgcccaaag aggacgattt ttgccacaag atctgttatg 127740
ccgtggacat gagcgacgag agctaccgcc tgggccaggg ctccttcggc gaggtctggc 127800
cgctcgatcg ctatcgcgtg gtcaaggtgg cgcgtaagca cagcgagacg gtgctcacgg 127860
tctggatgtc gggcctgatc cgcacgcgcg ccgctggcga gcaacagcag ccgccgtcgc 127920
tggtgggcac gggcgtgcac cgcggtctgc tcacggccac gggctgctgt ctgctgcaca 127980
acgtcacggt acatcgacgt ttccacacag acatgtttca tcacgaccag tggaagctgg 128040
cgtgcatcga cagctaccga cgtgcctttt gcacgttggc cgacgctatc aaatttctca 128100
atcaccagtg tcgtgtatgc cactttgata ttacacccat gaacgtgctc atcgacgtga 128160
acccgcacaa ccccagcgag atcgtgcgcg ccgcgctgtg cgattacagc ctcagcgagc 128220
cctatccgga ttacaacgag cgctgtgtgg ccgtctttca ggagacgggc acggcgcgcc 128280

-continued gcatccccaa ctgctcgcac cgtctgcgcg aatgttacca ccctgctttc cgacccatgc 128340
cgctgcagaa gctgctcatc tgcgacccgc acgcgcgttt ccccgtagcc ggcctacggc 128400
gttattgcat gtcggagttg tcggcgctgg gtaacgtgct gggcttttgc ctcatgcggc 128460
tgttggaccg gcgcggtctg gacgaggtgc gcatgggtac ggaggcgttg ctctttaagc 128520
acgccggcgc ggcctgccgc gcgttggaga acggcaagct cacgcactgc tccgacgcct 128580
gtctgctcat tctggcggcg caaatgagct acggcgcctg tctcctgggc gagcatggcg 128640
ccgcgctggt gtcgcacacg ctacgctttg tggaggccaa gatgtcctcg tgtcgcgtac 128700
gcgcctttcg ccgcttctac cacgaatgct cgcagaccat gctgcacgaa tacgtcagaa 128760
agaacgtgga gcgtctgttg gccacgagcg acgggctgta tttatataac gcctttcggc 128820
gcaccaccag cataatctgc gaggaggacc ttgacggtga ctgccgtcaa ctgttccccg 128880
agtaaccggg acgcggaacg tgacggttgc cgaggggaaa ggcgacagag aaggtacaaa 128940
cccaccggcg ggaaaaatac tgaggcgccg ccatcatcat gtggggcgtc tcgagtttgg 129000
actacgacga cgatgaggag ctcacccggc tgctggcggt ttgggacgat gagcccctca 129060
gtctctttct catgaacacc tttttgctgc accaggaggg cttccgtaat ctgcccttta 129120
cggtgctgcg tctgtcttac gcctaccgca tcttcgccaa gatgctgcgg gcccacggta 129180
cgccagtagc cgaggacttt atgacgcgcg tggccgcgct ggctcgcgac gagggtctgc 129240
gcgacatttt gggtcagcgg cacgccgccg aagcctcgcg cgccgagatc gccgaggccc 129300
tggagcgcgt ggccgagcgg tgcgacgacc ggcacggcgg ctcggacgac tacgtgtggc 129360
tcagccggtt gctggatttg gcgcccaact atcggcaggt cgaactcttc cagttgctgg 129420
aaaaggaatc gcgcggacag tcgcgcaact cggtgtggca tctgttgcgt atggacacgg 129480
tctcggccac caagttctac gaggccttcg tcagcggctg tctgcccggc gccgcggcgg 129540
cggacggttc gggtggcggc ggctcgcact acacgggctc gcgcgccggc gtctcgccgg 129600
gcatccagtt cggtatcaaa cacgagggct tagtcaaaac gctggtggaa tgttacgtga 129660
tgcacggacg cgagccggtg cgcgacggcc tcggtctgct catcgacccc acgtcggggc 129720
tgctgggcgc ttccatggac ctgtgcttcg gcgtgctcaa gcagggcagc ggtcgcacct 129780
tgctggtgga accgtgcgcg cgcgtctacg agatcaagtg ccgctacaaa tatttgcgca 129840
aaaaggagga ccccttttgtg cagaacgtgc tgcggaggca cgacgcggcg gccgtggcct 129900
cgctgttgca gtcacacccg gtgccgggcg tggagtttcg cggtgaacgc gaaaccccgt 129960
cggcacgcga gtttctgctt tcgcacgacg cggcgctctt cagggccacg ctcaagcgcg 130020
cgcgcccgct caagccgccc gaaccgctgc gcgagtacct ggccgatctg ctgtatctca 130080
ataaggccga gtgttcggaa gtgatcgtgt ttgacgccaa gcacctgaat gacgacaaca 130140
gcgacgggga cgccacgatc actattaacg cgagtctcgg cctagccgcg ggcgacgccg 130200
ctggcggcgg cgctgatcac cacctgcggg gcagcccggg cgattcgccg ccgccgatac 130260
ctttcgagga cgaaaacacg cccgagctgc tgggccggct caacgtgtac gaggtagcgc 130320
gcttttcact gccggctttt gtcaatccgc gtcaccagta ttactttcag atgctcattc 130380
agcagtacgt gctcagccaa tactatataa agaagcatcc ggacccggag cggatcgatt 130440
tccgcgacct gcctaccgtc tacctggtct cggccatctt ccgcgagcgc gaggaaagcg 130500
aactgggctg cgagttgctg gccggcggtc gcgttttcca ctgcgaccac atcccgctcc 130560
tgctcatcgt cacgcccgtg gtctttgacc ctcagtttac gcgccatgcc gtctctaccg 130620
tgttagaccg ttggagtcgc gacctgtccc gcaagacgaa cctaccgata tgggtggcga 130680
actctgcaaa cgaatatgtt gtgagttcgg taccacgtcc ggtgagcccc tgaaagatgc 130740
tctgggtcgc caggtgtctc tacgctccta cgacaacatc cctccgactt cctcctcgga 130800
cgaaggggag gacgatgacg acggggagga tgacgataac gaggagcggc aacagaagct 130860
gcggctctgc ggtagtggct gcgggggaaa cgacagtagt agcggcagcc accgcgaggc 130920
cacccacgac ggccccaaga aaaacgcggt gcgctcgacg tttcgcgagg acaaggctcc 130980
gaaaccgagc aagcagtcaa aaaagaaaaa gaaaccctca aaacatcacc accatcagca 131040
aagctccatt atgcaggaga cggacgactt agacgaagaa gacacctcaa tttacctgtc 131100
cccgcccccg gtcccccccg tccaggtggt ggctaagcga ctgccgcggc ccgacacacc 131160
caggactccg cgccaaaaga agatttcaca acgtccaccc acccccggga caaaaaagcc 131220
cgccgccccc ttgtcctttt aactcataaa ctttcaggtc tcgcgtacga ttcgcgagtc 131280
gggaatggga cacccgtggg tgtttctccg tgtgtatatt attttttttt gtgtgtgttt 131340
gcgcccccgt gtgtctaatg tgctgtttga aacacgtaaa gtagctggtg gaagaacaga 131400
taaaccttta ataaaaaaaa agtatgtgct cccgacccac ggtctgcgtg tctctttttt 131460
atgtccatgt ctccaagtct ggtgcgggtg gcggcggggt caagcgtcct cgaagtcttc 131520
atcatcgtcg tcgtcctctt cttcgcggag gcgacggctt tccaagctgt cgtggtgact 131580
gagcgcagcg acttcttcgc cggaggctgt ggccagcgcc tggtacttga cactgccgct 131640
accgcgtccg cgaaagtagc ggacggcgcg acacgtcgta aacatggccc atatgaaaaa 131700
gagcatgccg aacgaccagc tgatgccggt acggtaatcg tcgccgatgg taaaggcgcc 131760
gtactgcacg atggggtaga tgaggccgca gagtccgaag aaggcgccca ggtggtagcc 131820
gaattgcact ttgacgtatt gaaaaaagac ggcttcgatc agtaaaaagt agattatgga 131880
gatgatagcg tagaccacga agacggccaa caccatgtgg cctgtacgca cgaaaaagtt 131940
gtttccgaag ccgtagcaca gggccatggc taccacggtg gtgttgaaac caagtgccat 132000
ctccaccagg ttgacgatga gcgtgcgaaa ctgcaccgta cctttgagct tggggtgaag 132060
acgcgagaaa aaaaagagcg agcgtttgaa gctgcggtac tgcgtgacca tgctcacgtt 132120
gaaaatggtc aagcagaaaa agtgcacggc ggccatgaag gcgatcatgc tgggcagccg 132180
aaatgacatg gtcagtgtga atagttggaa cgtgtccatg ctgaggatga agaggaaggc 132240
tgtgaggctg tcgcccatgt acgaaatgtc acgtgtcgac tggtttaggc tcatgccttt 132300
gtccttgcgc atgctgatct tgatccagca taccaggtag tagatggtca cggctaaaaa 132360
gacgagctgc atgaacacgg cgtagcacac cagctgcacc gagtctaaga aaagcatagg 132420
cgtgtgcagg tgcattacgt tgtaggccga catgttgagc ctttcaaagt ccacgacgtg 132480
atagtagacg caggggtagc ccaggtgcgg aaaattgctc agcaccagat gcacgctgac 132540
gttgacaaaa gtcagcacca tgaaaatgat agaagcgctc catgtccgtg tattcacctt 132600
atccacgtgc gagggggcca tggcgatagc ggcggcccgc tcgctcggga ggcgatgggg 132660
gcgcgccgat gacgacaggc tcgcgggtcg ttaaatacta cgatgggagc cgccgcggct 132720
cacgacgcgg tttgagcacg tccgggcggt cggcgaaaaa agaccccgcg ggccttcgcg 132780
actctcttct gtccgaggat gaccgctcag ccgccgttgc accaccgcca ccacccgtac 132840
accctgttcg ggaccagctg tcatctcagc tggtacggcc ttctggaggc ctcggtgcct 132900
atcgtacaat gtctgttttt ggatctgggt ggcggccgtg ccgagccgcg gcttcacacg 132960
ttcgtggtgc gcggtgaccg tctgccgccg gctgaggtgc gtgctgtgca tcgcgccagc 133020
tacgccgcgc tggcctcggc cgtgactacg gacgccgacg agcgccggcg cggcctagag 133080
cagcgtagcg ccgtgttggc gcgcgtgttg ctagaaggca gcgcgttaat ccgcgtgttg 133140
gcgcgcacct tcacgccggt gcagattcag acggacgcta gcggcgtgga gattttggag 133200
gccgcaccgg cactgggcgt ggaaaccgca gcgctgtcga acgcgcttag tcttttccac 133260
gtagccaagc tagtggtcat cggctcgtat cccgaagtgc acgagccgcg tgtggttacg 133320
catgccgcgg aacgcgtctc cgaagagtat ggcacccacg cgcacaaaaa attgcgtcgc 133380
ggttactacg cctacgattt ggccatgtcg tttcgcgtcg gcactcacaa gtacgtgctg 133440
gagcgcgacg acgaggccgt cctggcacgc ctctttgagg tgcgcgaggt gtgtttttg 133500
cgcacctgtc tgcgtctggt cacgcccgtc ggtttcgtgg ccgtggcagt gaccgacgag 133560
cagtgttgtt tattgctgca gtcggcctgg actcaccttt acgacgtgct tttccgtggt 133620
ttcgctgggc agccgccgct acgcgactac ctggggccgg acctttttga gacgggcgcc 133680
gcccgttctt tctttttcc cggtttcccg cccgtgcccg tctacgcggt ccacggtctg 133740
cacacgttaa tgcgcgagac ggcgttggac gcggcggctg aggtgctctc gtggtgcggc 133800
ctgcctgaca tcgtgggctc ggccggcaag ctggaggtgg aaccctgcgc gctctcgctc 133860
ggcgtgcccg aggatgagtg gcaggtcttc ggcaccgagg ccggcggcgg cgccgtgcgt 133920
ctcaatgcca cggcttttcg cgagcgaccg gccggcggcg atcgtcgctg gctgttgccg 133980
ccgctgccgc gtgacgacgg cgacggtgaa aacaacgtcg tggaagtcag cagcagcacc 134040
ggcggtgcgc acccgccgag cgacgacgct actttcaccg tgcacgttcg cgacgccacg 134100
ctacatcgag tgctcatcgt ggatttggtt gagcgcgtgc tggccaagtg tgtacgcgcg 134160
cgcgacttca atccctacgt gcgttatagt catcgactcc acacttatgc ggtttgtgaa 134220
aagtttattg aaaatctgcg ttttcgctcg cgacgcgcct tctggcagat ccagagtcta 134280
ctgggctaca tctccgagca cgttacgtca gcctgcgctt cggccggcct tttgtgggtt 134340
ctgtcgcgtg gccaccgcga gttttatgtc tacgacggct attcgggtca cggacccgtc 134400
tcggccgaag tgtgcgtgcg gactgtggtc gactgttatt ggcgcaaact tttggcggc 134460
gacgatccgg gtcccacctg tcgtgttcaa gagagcgcgc ccggcgtgct gttggtctgg 134520
ggcgacgagc ggttggtggg tcccttcaac ttcttctacg gcaacggcgg cgccggtggt 134580
agtccgctcc acggggtggt gggtggtttc gcggcgggac attgcggtgg cgcttgttgc 134640
gcgggctgcg tcgtcactca ccgccattct agcggcggcg gcggtggtag tggcgtgggc 134700
gacgcggacc acgcgagtgg cggcggtcta gatgccgctg ccgggagtgg tcataacggc 134760
ggtagtgatc gggtttctcc ctccacgccg cccgcggcgt taggtggttg ttgctgcgcg 134820
gccggtggcg actggctctc ggccgtgggt catgtcctgg gccggctgcc ggcgctgtta 134880
cgggagcgcg tgagcgtgtc cgagctggaa gccgtgtacc gcgagatcct ctttcgcttc 134940
gtggctcgcc gcaacgacgt ggacttttgg ttactgcgct tccagcccgg tgaaaacgaa 135000
gtaaggccgc acgctggggt gattgactgc gcgcccttcc acggcgtgtg ggccgagcag 135060
ggccagatca tcgtacagtc acgcgatacg gcgttggcgg ccgatatcgg ctacggcgtc 135120
tatgtggaca aggcctttgc catgctcacg gcttgcgtgg aggtctgggc gcgagagtta 135180
ttgtcgtcct ccaccgcttc caccaccgct tgttcttctt cttccgttct ctcctccgcc 135240
ttgccgtccg tcacttcgtc ctcttcgggc acggcgacgg tgtctcctcc gtcttgttct 135300
tcttcgtcgg cgacttggct cgaggagcgc gacgagtggg tgcgctcgct ggcggttgac 135360
gcgcaacacg ctgctaagcg ggtggcttcc gagggcctgc ggtttttccg gctcaacgct 135420
taacgagtca cgtaggggaa ctacgtgggt aagtgacgtg gatactagta aaaaaaagtg 135480
cgtcaaagtt ctcagcgtgt gacgtggata ctagtaaaag ggacgtcaaa gctcactacg 135540
tgttgcgtgt ttttttttct atgatatgcg tgtctagttc gcttctcact cttcctctcc 135600
ccgttcccag cgcggtggca gcttgggggg tgagggcaaa ttggggtagt tggcgttgag 135660
cacgtctagc aggcccaggc ccacgggcca accgtccacg gtcttacgct cggtcagctt 135720
gaggctaaac gagtgtgcct cgtcttgacc ggtaaggcgg aaaaagaagc gtgctaccag 135780
ctgcaggcag gtatgccgcg tctgctggaa gagcacgaag gtagcgggca cgtactgcac 135840
aatgtgcggt tctttttcct caaagagtag gtagagcgcg ctgcagatca gccgccgggc 135900
gctgtggtgc agcagccggc cgaagctttc gcgcacgttc accgcgtcca ggtactggag 135960
caggtcgtgc aggcacttgc gcgttaagtt gcaattttcc acgcatgaaa taacggtaca 136020
gagcgcgaag tgcagcaggt tgtcggcctt gacgatgccg cagcggtgtt tgagccgcag 136080
atccgagagc ctcacctgcg tgacggcgtc ttcggtctcg agcaaaaaca cggcggagta 136140
gcccagaaag gccgaggtgc acagcaactc gctgcggtac tcggccatgg aaaccagcag 136200
cccgtgctcc gtatgcagcc acagcttgtc gccgcgcacc gtaaagtcga gcacttgcgg 136260
ctccatgatc atcacattct gtctagtgaa atccgtatgg acctccagca cgccgcggat 136320
catcagggcc tccatttcga aatcggccga cacgctctgg gccgcgccgc tcctcgtctg 136380
ccgtgatcaa gcggcgcggc gcggaccttt caagcgttcc tgggccgccg ctcgaggcag 136440
ttccccttc tggcactccg cccgccgctt cgcggctcat ttggcgccgg cgcgccttct 136500
cgcggctgca aatcagctcc acgtatcggc aaaacttgct gtcgtcgtag gcggcggcta 136560
cgatctcgcc gaaggagagc tgcaggtagg cctcgggtac ggggtccagc gtgcccagcg 136620
ccaggatgtg acacagatag ggcagggtca cgcgctctac cgtgtaattg gagtagacga 136680
tggcctcttc ggcccccctga tgcgtgacca gacgccgcag gcgaaaggtg cggaaatact 136740
cgttttccca cagctgcgtg aggaagcgtt ccagcgactc ggtgccgggc acgaactgcg 136800
agaagaagct gttggccacc aggcggttgt cctccaccgc cagcggacgg aagggcgccg 136860
cgtcgcgcgc cttgcgcacg gcctccaaca cgggcaggtg gtacagttcg gcgtcgcgcg 136920
cgcccaggct catggagtcc tcgcgccgcg aggcgtagcg cgtgagcagg tcgcgcagct 136980
cgcgcacgcg attctcccag gtctggttga gcgtgcgcag gtcctggatc tcgtccacct 137040
gcgactggat ctgctcctcc aggcacttga tgacctgctt cttaaacagg tcgcggatgt 137100
cccgctcggg cgccgccggg ccgggtggcg gcggcagcag cccgacgtgg cccgcgggtc 137160
ctcccaccac ggcgccgccg ggtcccacca cgccgggtcc acctggacca cgcgcgggta 137220
gtagacggtt ttggtccacc agcgaggggg tcaggtcctg tagaaaggac tcgacgctgt 137280
cctcgatgcc gatgcgcgat ttgctgtccg agacgttaag caaaaacttc ataatggact 137340
ttttggcgtc gctgccccgg tcgtgctgct ccatcatctc caccagcttc ttgcagttga 137400
gctcgtggcg gctggcggtc accactttca caggaaaggt attgagcaac tggcagatct 137460
tttggtggcg gcagagcccg tcgtagcgca gaatctcctc gtgcaggtgt gccaccggcg 137520
tggtgaacag cagcttgtcg cgctcataag ccagcggttc ggccgccacg tacaagcgga 137580
tgtgcttgcc gcgcagctgc gcctccagcc gctccgagcg caccttcttg aagacgcgta 137640
cctcgggcgc gttggctacg cgcacggcgc ccaggcgctc ggccacctgc agcagcagcg 137700
ccaggttagc ctgcagcagg tcctgcgcca gcgggtgtgt ctcggtggcc cgctgcacgg 137760
ccgcgcgtac aaattgcgcc cgctcggccg cctcgctcgg cttggtcttc acgtccagca 137820
gcggtaccag tcccaccgtt acgcaccaat ccacgtagag accatagtcg tcgttatcgg 137880
cgtactgata taaaatgtcg cggagcgcgc ccagcacgcc cgtttgcacg ctctggcgca 137940
acgaagcgct ccacaccaac agatactgct ccaggtcctc ttcgtccagc gcgcggtagg 138000
gaaacagcgc cgcgtgcaac ttccactcct cggccacgcg ccgcaccgtg atggtgtcaa 138060
agagcgtctt gcacactccg tagagcagct gcttgcgcag cacgcacggg tcgcgcagca 138120
cctggtgcat gctctggccg cgacacgtcc ccagaaagcc gtgcagcaac cgcaggaagc 138180
tcatcgtctg gcccgtgggg aaaatgtcga tgacggcctc gtcatccacg ccgcggccca 138240
cgcccaagta cgacgacgcc ttgatcctca acctctcgtc ggccgccaag atcgaacgga 138300
tcgtcgacaa ggtcaagtcc ctctcgcgcc agcgctttgc gcccgaggat ttttcgttcc 138360
agtggtttcg ctccatcagt cgcgttgaac gaacgacaga taacaacccc tctgccgcaa 138420
ctaccgccgc ggcaacgacg accgttcact cctccgcctc ctcttctgcc gccgctgccg 138480
cttcgtccga ggccggcggc acgcgcgtgc cctgcgtcga ccgttggccc ttctttccct 138540
tccgcgcgct gctcgtcacc ggcacggcgg gcgccggcaa gacttccagc atccaggtgc 138600
tggcggccaa tctagattgc gtgatcaccg gtaccacggt gatcgccgcg cagaacctca 138660
gcgcgatcct caaccgcact cgttcggcgc aggtcaagac catctaccgc gtcttcggct 138720
tcgtcagcaa gcacgtgccg ctggctgaca gcgccgttag ccacgagacg ctggaacgct 138780
accgcgtgtg cgagccgcac gaggagacca ccatccagcg cctgcagatc aacgatctgc 138840
tcgcctactg gccggtcatc gccgacatcg tggacaaatg cttaaatatg tgggagcgca 138900
aggccgcttc ggcctccgcc gcggctgcag ccgccgcctg cgaggacctc tcggagctgt 138960
gcgagagcaa tatcatcgtc atcgacgagt gcggccttat gctgcgctac atgctgcagg 139020
tggtggtgtt tttttactac ttttacaacg ccctgggcga cacgcgactt taccgcgaac 139080
gccgcgtgcc ctgcatcatc tgcgtcggtt cgcccacgca gaccgaggcg ctggagagcc 139140
gctacgacca ctacacgcaa aacaagagcg tgcgcaaggg cgttgacgtg ctctcggcgc 139200
tgattcagaa cgaggtgctc atcaactact gcgacatcgc cgacaactgg gtcatgttta 139260
ttcacaacaa gcgttgcacc gacctggact ttggcgacct gctcaagtac atggagttcg 139320
gtatcccgct caaggaggag cacgtggcct acgtggaccg cttcgtgcgg ccgcccagct 139380
ccatccgcaa cccctcgtac gccgccgaga tgacgcggct tttctctcg cacgtcgagg 139440 tgcaggctta cttcaagcgg ctgcacgagc agatccgcct gagcgagcgc caccgtctct 139500
ttgatctgcc cgtctactgc gtggtcaaca accgcgcgta ccaggagctc tgcgagctgg 139560
ccgacccgct gggcgactcg ccgcagcccg tcgagttctg gttccgccag aacttggcgc 139620
gcatcattaa ctactcgcag tttgtcgacc acaacctctc cagcgagatc accaaggagg 139680
cgctgcgccc cgcggccgac gtcgttgcca ccaacaactc ctccgtccag gctcacggag 139740
ggggaggatc tgtaatcggg agcaccggcg gcaacgacga gacggcgttt ttccaggacg 139800
atgataccac caccgcgccc gatagccgtg agacgctgct caccttgcgc attacctaca 139860
tcaagggcag ttcggtggga gtcaactcta aggtgcgggc ctgtgttatc ggataccagg 139920
gcacggttga acgtttcgtg gacatcttgc aaaaggacac gtttattgaa cgcacgccct 139980
gcgagcaggc ggcctacgcc tactcgttag tttcgggcct gctcttctcg gccatgtact 140040
acttctacgt gtcgccctac acgaccgagg agatgttgcg tgagctggcg cgcgttgagc 140100
tgcccgacgt gagttcgctc tgcgccgctg ccgccgccac ggccgccgct cccgcttgga 140160
gcgggggaga gaatccgata aataatcacg tcgacgcgga ttcttctcag ggcggccaga 140220
gcgtgccggt atctcaacgg atggaacatg gccaagagga gacccacgac atcccctgcc 140280
tgtccaacca ccatgacgac tcggacgcca tcacggacgc cgaactcatg gatcacacca 140340
gtctgtacgc ggatcccttt tttctcaaat acgtcaagcc acctagcctg gcgctgcttt 140400
ctttcgagga aacggtgcac atgtacacta ccttccgcga catttttctc aagcgctacc 140460
agctcatgca gcgtctcacg ggcggtcgct tcgccacgtt gccgctcgtt acctacaatc 140520
gccgtaacgt ggtgttcaag gccaactgtc agatcagctc gcagaccggc tccttcgtgg 140580
gcatgctttc gcatgtgtcg ccggcgcaga cgtacacgct cgagggctac accagcgaca 140640
acgtgctcag tctgcccagt gaccgccacc gcatccaccc cgaggtggtg cagcgcggcc 140700
tttcgcggct ggtgctacgc gatgcgctcg ggttcctctt tgtgctcgac gttaacgttt 140760
cgcgcttcgt cgagtcggcg cagggcaaga gtctgcacgt gtgcaccacc gtggactacg 140820
gccttacttc gcgcacggcc atgaccatcg ccaagagtca gggcctgtcg ctcgagaagg 140880
tggccgtgga ctttggggac catcccaaga acctcaagat gagccacatc tacgtggcca 140940
tgtcgcgagt cacggacccc gagcacctca tgatgaacgt taacccgttg cgactgccct 141000
atgagaagaa caccgctatc accccctata tctgtcgcgc gctcaaagac aaacgcacca 141060
cgcttatttt ttgacacaac accgtgtaag gaaaacgtga ctttattgag cagggtaaaa 141120
accacgtaca agaaccacgt tgtctatccc caaaaaaaca cacaccgtca gggaacacat 141180
cgcctataga tagcggcact ttacataaaa ccaccgtacc tgcatcacgg tggctcgata 141240
cactggaaat tcaataaaaa ccaccgtgtc tccgtgacgg tacttatcgg gtcagcgtct 141300
ttctcttgag atttctgttc gtaaacttat ccgtttcccc ggtccgcggt gtctcctcgc 141360
gaggctgaca gtctacgagt ggtatctaca agagaaagaa acccgggtgg gagcgacgcc 141420
gtcgctgggt atcaaccccg cggctgaccg tcgtccggta aaggaacaac ccgtcgtcgc 141480
aagccgggtt cgaccaagag aaaaaacccg ggtgcggggg gagacgggtc gtcctttggt 141540
tgttcgcgga cggcgtacat gccgcgtggg tcagtcgacg gcgtcgctcc gtgcggtcgg 141600
tcatcattct gcttcacata tatgggttgt ttgtgttttt tttataatga atacgcactg 141660
atcctatccg tgactgcgcg tgtggcagag aggatgcctt ataacatgta ttttgaaaaa 141720
ttgccaacag ctataatttc tctcatgtag cagaatagag accttttgtc gtctttttgt 141780
ttgtcattac ttgttttcca gggaattaga gagagggaac cgcgcctccg gcggcggtgc 141840
ccgcggaccc cggccccttc tcgcgtgcgc ggtgtgactg gttgagcgaa tgagcagcta 141900
ggcttggtgg tgctccgcgt gcgggggaga agacgattaa caacaaaaaa taagtggaag 141960
tggccggtgg gtctttgtcc gcgtgcgcgc ccatccgtcg ccgggaccga gcagaaagtg 142020
atgtggtggt acattgattt tttccttgac aggaaagaaa aaaaagagtt ttgttttcct 142080
atgtgagagg agaaaggtat gtgaggagat gttcgatgat cgtatgttac agttatgctg 142140
taaggaagct tttatcgtgc gtcctgtttt tcatttgatg tatatgacac aattgaaacc 142200
tatcgatagg cgtatatcga ggattcatca attcttagaa tcgtcgtctt tttggctaat 142260
tggactttgc ccatgttggt tgtcattcgt ggcctgaggt catcgtcgtc cacgacgacg 142320
tgtctatagc gtgcggtgtg atcattgtgt cgagccagag aaagcgcgcc tcgcacgacg 142380
tttgcggatc ggctcgcggg tgtgtggaat tcctaagaac ataatcagct ggtcgtcttt 142440
ctttgatgtg ttgttgtcgt cgaggtcttg cttcgttttc ttttttcttt ttagtcgatg 142500
gaacttttct tcggtacggg ttcttgttat ggaagcttgt gttttcgaac atgaattcga 142560
aaaaataaaa aggcctatct tcgtttcaaa aaaaggacag atatcaatct tcttaactta 142620
tatcatggta aattcagaat cctatggtgt cttattatct ctaaagtagt caacattatg 142680
gtctaacttg tatttccctg acgagatata tatgatcctt ataacctggc tactatcatg 142740
aacaacaata tccttactta cagtcatctt cgtgagttaa tgaagtataa tatcggtcat 142800
ctatcaactt atctgctatg taacgtaccc ttttaggtat tttgcgtttc ttaacgagtg 142860
tacccgcctg tgtgaggcga aactctgaga agtctaccga gtcgagttac aagtcactaa 142920
aacacttaca cgagttatct atactaaaat cactatctat gttgtttgct tacctaatta 142980
ttatcctaca tgacgaagct acctcccaac gtaaggtagg gggagaggag acagaacaat 143040
aaaaagtaac taatgtttct tagaacttac ccgctaagga cttaccaaac tatattcacc 143100
aaaaaacaac agctacgtgt ttcatttgtt ttaatctacc gaagtaaaaa aaaaagatga 143160
ttagctatcc agaacctact tacttcttaa tgttttaact aaggatgcct atgggattgg 143220
aaaaaaaatc acagcaactt gctactaatc agttgacagc gaagagactc ataacaaaga 143280
tttctgggta atacggttat aataatgctt atggactaaa ggatacttgg aaaaaaagaa 143340
cgggctatga ctatagagat tcatcgagat atcaaacttc aaataggcgg ctatcattca 143400
tggttgtggt gactatatcg tggagaaaaa atgtgatcgt tagttagcta ggtgagactt 143460
acagctatcc atccgtctag tttttcgttg taatgatgat agtacgtcta tggtggtgat 143520
cgattttggt tagcaatttg ttcgtttaaa ggcttaatgt acttatgcta catgatgtat 143580
tattctttga ttcatcgttc ctcctaaggg ggtgtatgta tgtatgtact agtcgtatag 143640
tgttcctaac atcatgacta ttcagactat ggcttcatct atcgtgtcta aagttcactt 143700
attctactat tactatatat atgcactact atgtaactag gatatggtcc tataaggtgt 143760
cttctatcac ggtggcttgt ttatcgcttg gcggttacga gcaagagttc atcacggacc 143820
agccgtgagg cagggcacac gcgggtcggc ggcgatgatg tcccccgcga aggggacaac 143880
aaaaacaaga caagaggccg ccggccgcgg ccacggacgc gtagcggtta cacaatgttt 143940
ggttgagcgt tttgtttcat cgtcgtggtg gtggttttgt tgttctctgt atatatcgtg 144000
tggtggcttt atcgtcatca ttattatcat cattcttgtt tccatcatca cgatgagttt 144060
tctccgtttt cctctcctcc agtggtagtc gtgtatcatc atcaatcatc gtagtgacgt 144120
cgttgctgct gctgctcttg ccttcatggc ggtatttctc ttcctccccc ctaaccccat 144180
attaactcgt gagtgtgatg gttagagtgg ctgcttgttt tttttctttt tctctttgga 144240
acaacaaaag aggataaaga tggtcggtga atgtattatt attatcatca tcattatgat 144300
acggtcgcgg tcttcttctc cgatgacgaa acctgcgcac atcgaagaaa agacgagcgc 144360
gcgaaccgat agccgtccgt ctgggacgaa ggagaagatg atggggagag gaggagagcc 144420
ccagaagcca gagcgagaag ggagacgaca gacatacgtc gtcaccgtcc tctggaggag 144480
gcacggcggc gctgtttgtt gtttggatgc ttgattatat cctgttctat ggggtagatt 144540
attatcaata ggcttggttt tcaaaggtca gcctgtgtat tgtcgtgtct tttttttcgt 144600
tctcatgatc gcggagacca cacagacgtg cgcgtctccc aatggctagg cgttcttttt 144660
aggtagtaat tttttgatct ttttttttc ttaacaagtc tggcttgatt tcttttatct 144720
atgatcgatt cttctttttc tcgggggttg catcttccgt gaaagtaaag tgacactact 144780
ctaaatggta accatattat ctgttgatta ggagaaaaaa taattttttc gcacgaaatc 144840
gatcctaagt gaggtgattt acttgctatc acacgaaatg attcttttgc tgctaacgta 144900
ctgaattttt taacagaatt gcttctccgt aactatttcc gcagattcag acagattgtc 144960
aaaaaaaaaa tacggcacag aaatagtggg tctgtggctt ttggttcgtg tacattcgcg 145020
tttgcgtgtc gagatttcta cggtatgttt attcttcctg cgatgatgta gggtccttgg 145080
tgtaagtagg atttcgagta tctctcttag agcgaacaaa ataatcaaaa aacaacagct 145140
aggaaatcga gggttactct acgataaagt gtctctacaa agtgaagaat gttacgttgt 145200
ggtggaataa taagactcgc gtgatcgatg agtgatcgag agcggctcga accttcttta 145260
agagctttgt ttagtgcaac tttaaattac aaggagtaga aagctgaaat gaatctatga 145320
aggtgctatt ctttgaatat cttactttgt acgcttcaca ttcgttattt ggatagagag 145380
ttgtctagag aaaatctgtg attctctatg agtgttattt ttattatcct tttggggact 145440
acgatttttc ttcttctaca taccactact actcgtaatc acatacatgg acgaaaaaaa 145500
aattcgtcag gcagtagata ccagattctc cgacgttacg gcgtcttttt ttcttttgag 145560
agagtatctg ctgagattgt ccgtggtgta tctagtcgct atttttgttg ttactagtag 145620
ttttgcacac agtttattca gtatagtttt tcttcttgcc atgatcaatt gagcccacca 145680
cctttttttt aagagaggag gaatttcgtc ttgatctcca gccggagata acggcggtgg 145740
tggtggtggc gggagagact tcaaggcaat gaaaaaaaaa atttcgtttt gccatcaagt 145800
ggtgacgata acccgtcaga ttgataattg gttcctacag aaactattct aaccgcggaa 145860
gaaagaaatt gaaaaaaaaa attgacaaaa acatcataac ataaaggacc acctacctgg 145920
gacgcgcagt tgggtggcgg actggggcgg catgctgcgg cgatgctgtc ggtgatggtc 145980
tcttcctctc tggtcctgat cgtctttttt ctaggcgctt ccgaggaggc gaagccggcg 146040
acgacgacga cgataaagaa tacaaagccg cagtgtcgtc cagaggatta cgcgaccaga 146100
ttgcaagatc tccgcgtcac ctttcatcga gtaaaaccta cgttggtagg tcacgtaggt 146160
acggtttatt gcgacggtct ttcttttccg cgtgtcgggt gacgtagttt tcctcttgta 146220
gcaacgtgag gacgactact ccgtgtggct cgacggtacg atggtcaaag gctgttgggg 146280
atgcagcgtt atggactggt tgttgaggcg gtatctggag atcgtgttcc ccgcaggcga 146340
ccacgtctat cccggactta agacggaatt gcatagtatg cgctcgacgc tagaatccat 146400
ctacaaagac atgcggcaat gcgtaagtgt ctctgtggcg gcgctgtccg cgcagaggta 146460
acaacgtgtt catagcacgc tgttttactt ttgtcgggct cccagcctct gttaggttgc 146520
ggagataagt ccgtgattag tcggctgtct caggaggcgg aaaggaaatc ggataacggc 146580
acgcggaaag gtctcagcga gttggacacg ttgtttagcc gtctcgaaga gtatctgcac 146640
tcgagaaagt agcgttgcga tttgcagtcc gctccggtgt cgttcaccca gttactttaa 146700
taaacgtact gtttaaccac gttgcgtcgt gacgttgttt gtgggtgttg ctaggcgggc 146760
tggaaagatg atgtataaat agagtctgcg acggggttcg gcgctctgcc ggctgcggcg 146820
gcactcgctc cacggcctcc gacgagcgtt gcgctcgcgc tttgcgccgc cgcgtcatgg 146880
atctccctac taccgtcgtg cgaaaatatt ggacttttgc gaatcctaac cgcatcctgc 146940
atcagagcgt caatcagact ttcgacgtgc gccagttcgt ctttgatacc gcgcgtctgg 147000
tcaactgcgt ggacggcgat ggcaaggtgt tgcacctcaa caagggctgg ctctgcgcta 147060
ccattatgca gcacggcgag gcttcggccg gtgctaagac gcagcagggc ttcatgtcca 147120
ttgacattac gggcgacggg gagctgcagg agcacctgtt tgtacgcggc ggtatcgtct 147180
tcaacaaatc cgtctcctcg gtggtgggct ccagcggacc caatgagagc gcgctgctca 147240

-continued ccatgatttc cgagaacggt aatttgcaag tgacttacgt gcgccattac ctgaaaaacc 147300
acggcgaatc ctccggtgga ggcggtggtt gcggcgccgc gtctaccgcc tccgccgttt 147360
gcgtgtcctc gttgggcggc agcggcggga ctcgcgacgg tccttctgcg gaggaacagc 147420
aacggcgaag gcaggaacag cgtcacgaag aacggcgcaa aaagtcgtcc tcgtcggccg 147480
gtggtggtgg aggcggcggc gctggtggtg gcggtggcgg cggcgggagc ggcggtcagc 147540
actcctcgga ctccgccaac ggactgctgc gggatccccg gttgatgaac cggcagaagg 147600
agcggcggcc gcctccctcc tccgagaacg acggtgagtc ccggccctcc tcgcgtcacg 147660
gtgctttccg agtggactcg tgagcccccc gtagcgcacg agcgagcagg cgagcggtgt 147720
tggtgcgctg gtggttgtgt ggatgataac catgtgcttt ttcgtgcgct atgtgtcgtc 147780
ccgtctgtag gctctcctcc cctccgggag gcgaagagac aaaagaccac cgcacagcac 147840
gaaggccatg gcggcggcgg caagaacgag acggagcagc agtccggtgg tgctggcggt 147900
ggtggtggcg gcggcagcgg ccgcatgtcg ctgccgctgg acacgtctga agcggtggcc 147960
tttctcaatt actcgtcctc atcctccgcg gtctcttctt cctccaataa ccaccaccac 148020
catcatcacc accataacgc cgtgacggac gtggccgccg gcaccgacgg tgcgttactt 148080
ctacccattg agcgcggagc ggtggtttcg tcgccgtcgt cgacgtcgcc gtcgtcactt 148140
ctttcgctcc ctcgacccag cagcgcccac agcgcgggcg agacggtgca ggagtccgag 148200
gcggcggcga cggcggcggc tgcggggtta atgatgatga ggaggatgag gagggctccg 148260
gctgaggcgg cggaggcacc accgcagtcg gaggaggaga atgattccac cactccagtc 148320
tctaactgcc gtgttcctcc gaattcgcag gaatccgcgg cgcctcagcc tcctcgcagt 148380
ccgcgttttg atgacattat acagtcattg accaaaatgc tcaatgattg taaggagaaa 148440
agattgtgcg atctccccct ggtttccagc agactcttgc cagagacgtc gggcgggact 148500
gtcgtcgtca accacagcag cgtcgcgagg accgccgcag ctgtctccac agccggcgtt 148560 ggcccccag cagccgcatg tccgccactc gtcaccaccg gtgttgtacc ctcaggttcc 148620
gtcgccggtg tcgcgcccgt tgccgccgca gtcgaaacac cagctgctcc tccccggccc 148680
gtgtgtgaaa tcaagcccta cgtggtaaac cccgttgtcg ccaccgccgc ggctgccagt 148740
aactcttcct cgtcttcttc ggctccactg ccgccgccac caccaccgcc gggcggacgt 148800
cggggtcggg cccggaacaa tacccgagga ggcggcggtg gtggcggtgg tagaaacagc 148860
cggcggcagg ccgcatcgtc gtcgtcctcc tcctctcgga gatcgcgacg gagaaacaac 148920
cgccatgagg acgaggacaa cgatcctctg ctccggttgt cgcaagtcgc cggcagcggc 148980
cgccggcgag ggccctcgtt cctcgaggac ggactcgaaa ttatcgatcc cagcgaggag 149040
gctgcgatcg ccgccgcctc gatcgcggcg tttttcgacg attaaaaaac agagccgaga 149100
ccggaaaaat tatgaaacag gacgcgcttg gacatttggg tttccacccc tttcggtgtg 149160
tgtctatata tattgtggtc actgattttt ttttacaata aagagataga catcacagtt 149220
caccaccttg tctccccggt gtgtctatta tcatcaatca cccacagagt cgccagtcca 149280
tggtctctcg gtaatgcgtg tccagatacg cgttggccag tataaagtgg tcgttgccca 149340
cgaaggcgcg ggtggtgttg cgcggcgacg ggtggcagga cttgagtacc aagtgccgcc 149400
gtcggtcgat caggtactcg caggtgtgcg cgtcggcgcc ccacagcatg aacaccagat 149460
gctcccggcg ctctgacagc ctccggatca catggttact cagcgtctgc cagcctaagt 149520
gacggtgaga tccaggctgt ccgtgcacca cggtgaacac ggtgttgagc agcagcacgc 149580
cgcgtcgcgc ccaggcgtcc aggcaacccg aggccggacg ctgaaacccg tccaccgtac 149640
gcgccagttc gcgaaacacg ttgttgaggg agggcggcgg tggtcggcct gccagcgtgc 149700
cgaaggccag gccgctggcg ctgccgtcgc agtacgggtc ctggcccacg atcaccacgc 149760
gcacctgctc gggcggacac agatagctcc agcggtgtac gtgctcgggt gccgggtaca 149820
ccatctcgag ttgccgcgcg ccctccaccg ccgccaccgt gtcgcgcagc agcaccgtgt 149880
cgtggtcggg caagctgagg aagcggatcc agtcggcgct cagacaaaac acgcgagcct 149940
gctcgtcggg ggttaacaga gagcctttat tatcagcaat gttagcgagc atccactgct 150000
tgagggccat agcgcgagtg agccggcagg ttgacgcgcg tctgcttcag ctcgggcggc 150060
agtccggcgt agtatttatc taggtggcgt agcagcggcg ggtccagctg gtgacgcagg 150120
caaaattcct tcactgcgtt gtacaggccg taaaagagcg tgatgccctc gggcgcggca 150180
gcggtgctca cgggcagacg cacggcgcgg ttggtacgcg tggcttcgtt gcgtatggcc 150240
accaccacgt taaagagaga cggtggcacc agctcgaagc ctaacacgtg ttccgtgaag 150300
atgctgcgcc cgtatgacag tcgcgtgagg tcgtagccgc ggcacaggtc gtccacgcac 150360
gtgtacacgg ccggcgagcc atcgccgcac tcgctgtagc cgcgcatcac cgtcatccag 150420
cgcggcgctg tgtccgagct caacagtgtc agcagggccc gcaattgatc cggattgttg 150480
tacagcaggg ccagagtgtc caggaaagca tcgtccaaca gcacggagtt ggcggcctcc 150540
ggcgtaacgg gacggtaacg gataagttgc gatagcgggc cattgcgccc ggtaacattc 150600
accaacggac gcagccaact ttcatacttg tcaccctgaa acacctcacc caacaggcat 150660
cggcgcgtta gttcgggaca ctccgcgggg actttctcgg cggcggtagg agcgacgctg 150720
acggcgactg aggaaacaat gggcagcaga aggcaacacc acagcagtac caccggtcca 150780
ggtgagaaag agaagccgca atccgggcgg cggcacatca agtctgcggc acgatgagag 150840
tgtgacggta aggagccagt tggcgccgaa agttggcgct caggtcttcg atccctaaaa 150900
cgttatatat tgcatccagc aggtgagcca ggctaaacgg attcacgtac caggtttggt 150960
tacccgcgac gatgacggcc agaccgtggg cgctacagtt ggagaggttc ctgggtacga 151020
aggtaactga gtcgatgtcg cgccacgggg ggaatgagac agacgactgg cgcacgctgt 151080
aatcacaact gtgattgacg tattgtagcg tgtaatttag gttgcactca gcctcgaagt 151140
agagggggaa ccacagttcg tcgtactcgt cgtcgtcctc cagttctggc tcttcttcat 151200
ccaccgcaat gtctacgctg ctctgagatt cctcttcgta caggatgatt gacaggttat 151260
ggctacaaag gtcctgggcg ggaggacgcg tgggagcgcg ggtggtggta atgttttcca 151320
ggtcaaaagt tggagtgtag tcggatgtta catccccgtt gttggaggtg gtagaagtcg 151380
cggccggtgt cacggtggta agtatggata cagaagggga gggggaagta acgttcgtac 151440
cgatggttgt ggtattatta ttccttgtgt ttcttgttcc agaaaccgtt gacgttgaga 151500
tgggaatcga cgtggcgctg gatgtcagat tgctgaccga ggaaaccgtg gtgggagtga 151560
tgacggtgtt actcgtggtt gaagtgacgt taggggaggt agtagtggta ccggtggtgg 151620
cgacggtagt gtttgtcgtg gcggcggcag cggtggtact ggtaacggtg gtcgcgttgg 151680
tttccaccgc ttcacacagt aagcaaaagc acagggccag gaaaagcaac cagccccgcc 151740
atcgccgccg ccgcttcatg aggtgggcag gcgaaagctg gtgaattcgt tgtacagcgg 151800
caagtggggc gccgcgatcg aagggtacgt caacaagctg acgttgatat taaatacgtc 151860
tggctgcttt tctacgatgg aagcgcacag ggttacggcg tcgaacaggt ctttcttggt 151920
ggcgcccgag acccacatct ggtatacacc cgtctcgtgg tacgaagtag agcgcggcac 151980
caccggacgg atgcagtcca gaacgcggtt gggatcctgg tgaaagaatt tgaacgtggc 152040
tacggcctgt ggcgtgtgcg gcatcgtctg cgtgatgagc tgctggcccg ctaacacggt 152100
gacgttgtgc aacttgagca gggcactctt gagggcctgg aaagcgttgc cgcacgaggc 152160
gctgatttgc agctgcacgg ccgtggagtc gtgcagccgc atgagacgtg acacctcttc 152220
gaagacgtac ttatacttac tggcaaagag tggcgcgtac cgacagtcgg ccggcaaaat 152280
gtaggtggcg ttgccgccgt tggtggccac ggcgggcgca gcggccgcgg aggccggcgt 152340
aaacagcgtc agcggccggt ggtggctggt aaggtcgatc atgggcggcg tggtgaccgt 152400
ggcggtggcg ggcatgacgg ggtttgcggc gacgggcact ccggccacag cggcggcagc 152460
ggcggccacg gcggcgctgg ccgagcccac acctgccggc agtcctccgc cacccatgac 152520
gccgccgggc agagcgtcgc ccagacagac ttccacagtg gcgggcgcgc tctcggcggt 152580
cagtacggtt tgccgatcga cctcgcgacg aaagctggtg aggaactcac tatgatccat 152640
ggccgcaggg cccgagatcc cgggattctg cgggtgctga ccgagtgcgg gccgagttat 152700
atggaagacg attagcttgg agcggagttt tgcgtcccta gctgacctgc ggatcagcga 152760
cgtgccatag ggatagactg tgagcggcgg ccgcaacggc ggggtcggcc gccgttcgtc 152820
gtcacggggc ggcgcgaggg aggaggaggt ggtggtgggt acgatcttga cgtggttaac 152880
gtcctgcccg tccgggggaa tacgcaaaaa accccgccgc ggcgctacca cgatggtgcg 152940
atgggtcttt ctcttgttgg ccggggccag ggacttgcag atgcgtgtgg agccgtagac 153000
gatctggacg tggtcctggg agaacatgac catcgccgcc aacgctcagc ggggggacgg 153060
gttgggaaca cagaggctga ggggaaaccc cgtagaagtc agcgaaataa agacaacaca 153120
gcagccgctc ctctcgtttc gggccctacc actgcttgaa gtagggcacc gggtgtttct 153180
tttcttcaac gggctcctcc agtctcttat aggaccagtc ccgccggcgc gccagcatgt 153240
aggtcacgta caaaagaata attaccatga acaccaggaa agccagcacg ccgtaggcca 153300
gcagccggtc ctcgaacagc gggtcgctct tgataaacac gtaggtggtg gtaaaacttc 153360
ggcccgcgat ctggacgtgg agacgcacga cagtatacgt gccgttgagg tagaagacaa 153420
actcgcgtaa ccgttgtccg ttatacgtca cgttactaat attccacggc ggaatgagct 153480
ggtcgccctg atgcagatgc acggtgctgt tggggtgata gaggctgcta ccgttgagca 153540
agcagtgttc gtgttcctga agcagcacgc ggacccgcat cgtggtagcg ttcaagcgag 153600
tcccgtacac ggcgtaaatg ggataggtga aaaggtccca agtggcgttg tgatggcggc 153660
cccaactgaa gaaagagcac gtgtactcag tggtctcctg cggcctgagt cccgagataa 153720
gcagctcttg agcagtagcg ttgtaggaga gatgtagttt tcctgtggaa aaaattaatg 153780
agttgtttat tttgttagca ggttggcgag ggaggaaggg gaacaaaaca gaaaggtacg 153840
tgttacttac ctttatcgtt ggagggaaaa gcgctaagat atcccacctg agtgaaggga 153900
cccttgcagt ctgtccgtgc ataacaagta actgataaaa tgtctggatt tttggtatta 153960
ttcaacagga taactttgca ggtggcgttt agagacactt ggtcgtagct gtagctggct 154020
tcgcaattca cagtatacag gtgcccctct ttctgcgtcg tggctatcac ggaggtggag 154080
gcggacgagg tagaggtttg taccgtggtg gtgacagcag aactgacgtt gttagaggta 154140
cttattgacg tagtagacgt gacggtggta ttactagggg aagtgacggc gcttgtggtg 154200
ctacttttca ctcccgggtg catgtcgccc aagagcgcaa ctacgagcgc gatcgccagc 154260
acggaacaca tgttgccgtg tgacgagacg gcgtgtggac gagctatatg tggcaggagg 154320
tcgcgtcacc tcttgtgacg cctaaacgtc cagctccaga taaaagaggc gttaataatg 154380
aagactacaa aaaccacttg cgtcagtatg acaatcataa aggctcggtg attgctacgc 154440
ctaaagtacg cgggattatc caccagttca tccttctgaa caaagtggat gattgacgta 154500
ttggtgttac tatccgtatt gttgatcatg gatttgacta agaaagtctt ggcaccaaaa 154560
gtcccgttag agccccagca ggtgacgctg ctatttacat aagttccagg tgccccccgct 154620 agcatgtatt tcagttggtg ggtataattt tttctgtcgt tatccatgtc attgctgtag 154680
ttgaccttgc tggtgagaaa gcgtgttttc aacggggtac ttatcatcat ccctgaggcc 154740
aaaaagggcg aattgcaagc tgtagtgtta caaaaaatag tcaagttagt gtcattgtgt 154800
tgatacatgt aagccatgct cacttcaggc tcataccacc cgatcccaat cgcggccgcc 154860
accgtcacca cgtcccatct ccccaaactt accaccgcca ccactaatag cgtcaccccc 154920
gcacggtaca tagttaccct ctcgacgtcg ccggctgtca atgacgtgcc tgcgtcagtg 154980
gctatgattt atagcttttg gacacaaccg caacggatct gtcgtaatct accttccaca 155040
gggccgccgc gacgatgctg aacgacagga tcagacagac ggcgtatagg agtcctaggt 155100
cggcgtcgac gcggcaggtg cggatgtctc gcagggtggg tagatgggcg atgcacaact 155160
ccttctcccc ccgcccgtac atctcatccc gtatcagcag ccgtagcgtg gcattgatgg 155220
tcagcggggt aaccaaagaa atcacatagg gatgtgtaca ggaagtgcag tgacgggtat 155280
ccgtgagatg taagtcatca ccctcctcac cgtcatcatg aaagaccagg actcgggtga 155340
gacgacccga tgaatactgg atctcccacc acagtctttg atccaacacc gagagggcgc 155400
aagagattct aagtctccct gggttgggtg agcagatgta agccccgtat gtgcctctcg 155460
ccatcagggc tatacacatg agggggagaa ggacaagtat ccgggaccac ccgcaccccc 155520
acatcacgag accagagaca gagatgtata aaaaaagcta cttttattaa acagcattct 155580
caccacacgt taatactgtc acggggaatc actatgtaca agagtccatg tctctttcca 155640
gtttttcact tactgagact tgttcctcag gtcctggatg gctgcctcga tggccaggct 155700
cagggtgtcc aggtcttcgg gaggggtctc ggtgggctgc tcaaactgcc ccacggcgta 155760
ggccttcgcg gccgtctcgt agataggcag catgaaccca ccctggttgg tggagaagat 155820
gcgcaccatg acctgtttgg gaaacttttg catcaggggt aggcacaggt tgagagcgcc 155880
caacaggtcc acgggggtgg cagcgtggat gatcatgttg cggtaatcgg aagaacgggg 155940
gcataattgg tgggtgtgca attctttgag gctccacgcg gctttgacgc cttcgttaca 156000
agcatcggcc gtgcgctgcg ccacttcggg tgggtgtgtc acaggcatgg tgtgctccat 156060
gaggaaggga gtggagaggg ccaggttgca catggtgccc aggcgacacc gcaccgcatc 156120
cacctcactc ttcacctcat gattgcgggt gtagatgatc tggatgccct tgttgttcac 156180
ctgcatggtt ttgcaagctt tgatggcctc atctaacacc tggtccatac tgggaatcgt 156240
gaagggcagg ttcttgtact caagagagcg attggtgttg cggaacatgc ggctcacctc 156300
gtcaatcttg acgcgacccc gccgagtctg cacgttgggt gtgcagaagg gggtgttctt 156360
atctttcatg atattgcgta ccttctcgtt gtccaactcg gagatgcgtt tgctcttctt 156420
cttgcggggt ccggtgctcg ccccgccgct gctctgatgg ccgcagctca gcagagagga 156480
ggaggccgcg ccaccaaaac cgccgcgccc atggtggctc gaggtcacgg atgctcctcc 156540
gccactgctg catttcatct cctcggactc actctccgag tccgaagccg aactgcagga 156600
ggaggaagac gaagaggaac tatcttcatc gggccggccc aagggatcgg gaagaggagg 156660
gtggttcatc tgggagagcg ggtgcgtggg agaggtcact cgcggcgtgc cgctgccggt 156720

-continued ggaaggggaa gacgcggtag caccgcgggt ttcgacttct tcaccctgtt cttcctcgct 156780
atcagagatc acgatacagc cggcggtatc gataatcttg ttgcggtact ggatggtaaa 156840
gtcgggctcg ggcttgatgt cttcctgttt gatgaggggc agcatgatag gcgcgggagg 156900
cacgggcggt ttaataatca ccttgaaagg acgcgtggtt ttgcgcggtt tcttacgcgg 156960
gctgagctcg ggagtagcgg atgccccggg gagaggagtg ttagtaaccg cgacgctggt 157020
gggggtcggc ttgttaagag gggcgctgct aacgctgcaa gagtgggttg tcagcgtggg 157080
gccggtgcta ctggaatcga taccggcatg attgacagcc tgggcgagga tgtcacctga 157140
tggtgataag aagacacggg agacttagta cggtttcaca ggcgtgacac gtttattgag 157200
taggattaca gagtataaca tagagtataa tatagagtat acaatagtga cgtgggatcc 157260
ataacagtaa ctgatatata cacacaatag tttactggtc agccttgctt ctagtcacca 157320
tagggtgggt gctcttgcct ccagaggtgg tgggttcctc agcaccatcc tcctcttcct 157380
ctgaggcaac ttcctctatc tcagacactg gctcagactt gacagacaca gtgtcctcct 157440
gctcctcctg agcaccctcc tcctgttcct catcactctg ctcactttct tcctgatcac 157500
tgttctcagc cacaatcact gaggacagag ggatagtcgc gggtacaggg gactctgggg 157560
gtgacaccag agaatcagag gagctagcac cagcggtggc caaagtgtag gctgcaatag 157620
catcttcctc atctgactcc tcagcgatgg cccgtaggtc atccacacta ggagagcaga 157680
ctctcagagg atcggccccc agaatgtact gggcaaagac cttcatgcag atctcctcaa 157740
tgcggcgctt catgacattg ataacctcag gcttggttat cagaggccgc ttggccagca 157800
tcacactagt ctcctctaag atatagcagc acagcacccg acaaaactca cttaagagag 157860
agatggaccc gtacatggtc atcatacaag cgtcactggt gaccttgtac tcattacaca 157920
tggtttccac acatgtagtg aggatatcca taaatatgtg atcaatgtgc gtgagcacct 157980
tgtctctctc ctcatccaaa atcttaaaga ttttctgggc ataagccata atctcatcag 158040
gggagcactg aggcaagttc tgcaatgccg ccatggcctg actgcagcca ttggtggtct 158100
tagggaaggc tgagttcttg gtaaagaact ctatattcct gtagcacata taaatcatct 158160
ttctcttaag ttcatccttc ttagcacggg ccttagcctt cagtgcaccc cctaacttgt 158220
tagcggcgcc cttggtcaca tcatgcagct ccttaataca agccatccac atctcccgct 158280
tatcctcggg tacaatgtag ttctcataca tgctctgcat agttagccca atacacttca 158340
tctcctcgaa aggctcatga accttatcta agatatctaa ggcattctgc aaacatcccc 158400
ccatcatatt aaaggcgcca gtgaatttct cttccgtctg ggtatatttt ttcagcatgt 158460
gctccttgat tctatgccgc accatgtcca ctcgaacctt aatctgtttg actgtggagg 158520
aggataacaa cacatataag tatccgtcct cctgactcat ttatcgctac ctcgatgccc 158580
cgctcacatg caagagttaa tcttcactct atctgacata cacaagtaaa tccacgtccc 158640
atgcaggtta gtatatatca catacatgtc aacagactta ccgagttctg ccaggacatc 158700
tttttcgggg ttctcgttgc aatcctcggt cacttgttca aaggttttga gagattcttc 158760
ggccaattct gggaacagcg ggtctcccag gctcagctga ctgttaacct ccttccttaa 158820
catagtctgc aggaacgtcg tggccttggt cacgggtgtc tcgggcctaa acacatgata 158880
aacaaagtca taagcacatg ggtcacatac agaaaatatg tatataacat taaagatata 158940
actttttatt aaaaaaaggg gaacacaagt cccgacacgt accgtggcac cttggaggaa 159000
gggccctcgt cagggttgtc agggtccatc tttctcttgg cagaggactc catcgtgtca 159060
aggacggtga ctgcagaaaa gacccatgga aaggaacagt ctgttagtct gtcagctatt 159120
atgtctggtg gcgcgcgcgg cagcaacgag tactgctcag actacactgc cctccaccgt 159180
taacagcacc gcaacgggag ttacctctga ctcttatcag aacacaacaa ctcagctgcc 159240
tgcatcttct tctgccgctg ccttaagtct tccaaatgcg tcagcggtgc aagcccgctc 159300
cccgagctca ttttcagaca cataccctac cgccacggcc ttgtgcggca cactggtggt 159360
ggtgggcatc gtgctgtgcc taagtctggc ctccactgtt aggagcaagg agctgccaag 159420
cgaccatgag ccgctggagg catgggagca gggctcggat gtagaagctc cgccgctacc 159480
ggagaagagc ccatgtccgg aacacgtacc cgagattcgc gtggagatcc cacgctatgt 159540
ttaataaaaa ctgcgggtac tggggacggt gttgttgtat atgtgaattt gtaaataata 159600
aatgggaccc catcctgtaa aaatacagag tccgtgtcag tctctgaagg acagagtatt 159660
ggcatatagc caataaagag agttgtggca aagagccatg ttatggatta gtaatggaaa 159720
gtatcgtcac caatagggga gtggtcaata atggtcaata acccacacct ataggctaag 159780
ctataccatc acctatagca taaggaagcg gggtgtata gaccccaagc caaaaacagt 159840
atagcatgca taagaagcca agggggtggg cctatagagt ctataggcgg tacttacgtc 159900
actcttggca cggggaatcc gcgttccaat gcaccgttcc cggccgcgga ggctggatcg 159960
gtcccggtgt cttctatgga ggtcaaaaca gcgtggatgg cgtctccagg cgatctgacg 160020
gttcactaaa cgagctctgc ttatatagac ctcccatagt acacgcctac cgcccatttg 160080
cgtcaatggg gcggagttat tacgacattt tggaaagtcc cgttgaattt ggtgccaaaa 160140
caaactccca ttgacgtcaa tggggtggag acttggaaat ccccgtgagt caaaccgcta 160200
tccacgccca ttgatgtact gccaaaaccg catcaccatg gtaatagcga tgactaatac 160260
gtagatgtac tgccaagtag gaaagtcccg taaggtcatg tactgggcat aatgccaggc 160320
gggccattta ccgtcattga cgtcaatagg gggcgtactt ggcatatgat acacttgatg 160380
tactgccaag tgggcagttt accgtaaata ctcctcccat tgacgtcaat ggaaagtccc 160440
tattggcgtt actatgggaa cccacgtcat tattgacgtc aatgggcggg ggtcgttggg 160500
cggtcagcca ggcgggccat ttaccgtaag ttatgtaacg cggaactcca tatatgggct 160560
atgaactaat gaccccgtaa ttgattacta ttaataacta gtcaataatc aatgtcaaca 160620
tggcggtcat attggacatg agccaatata aatgtacaca ttatgatata gatgcaacgt 160680
atgcaatggc cattagccaa tattgattta cgctatataa ccaatgacta atatggctaa 160740
tggccaatat tgatgcaatg tatatatcga tatccattgg ccatgtgcca actcgatgtc 160800
gcctctatcg gcgatatggc ctcatatcgt ctgtcaccta tatcgaaact gcgatatttg 160860
cgacacaccg aatcgcccaa gtcgccaaag tcgtctatcg ccatcccccg taaacgatat 160920
aagcgctatc gccagatatc gcgtatgccc aaaaatcact tttggaaaaa tggcgatatc 160980
agttacacag aaactcacat cggcgacatt ttcaatatgc catattttca aatattgatt 161040
tttccaatat cgccatctct atcggcgata aacaccacta tcgcgcgaca tgaatttagt 161100
cggcgacaga aatctcaaaa cgcgtatttc ggacaaacac acattttatt attcactgca 161160
gcatatagcc cattttagcg cggcacacat ccagccgttt gtgtttctta acgctctcca 161220
ggtactgatc caggcccacg atccgggtta tcttgtcgta ttccaggttg atccatcgat 161280
agggaacgct gccagcggcg cccagcaggt actgcgcctt gtcgttcact ttgccgcagc 161340
gtattcgccc gtcagcttcg aggtataacc tacaacacgg aagggggta caaaacgtga 161400 aattagactt tttttttaa tgatgttttg tccctctctg tcttactctc ccataggctg 161460

-continued taaggccctc gaggaagaga cttacggatt gtagttgcag ctcgtcagtt tgttgtgtac 161520
gacctggcgt gtcaatgaat gggtcatggt ggtgacgatc ccgcgaatct cagccgtttt 161580
ctcgggactg tagcagactt cgccgtccgg acaccgcagc ctgtgtattc atgaaaatct 161640
actctggcat tcccgaggat cgtcgatgga acatggctat cagaaacgtc gagagacaga 161700
tccagacgca ccacagaacg cagacaatca tgaaaatacg tacgcgacgg tgaagcgatt 161760
gcacattttg aaatcgtaac agcgttccgg cgggtggttg acgtttatga attcgcaaca 161820
ttcttctgcg cgtacccgcg gcacgcggct gtgatccaat aacagccaca acgccgtcaa 161880
gaacggcgtc aggtttttgg gactcatgac gcgcggtttt caaaattccc tgcgcgcgcg 161940
acgggctcaa acgatgagat tgggatgggt gcagaaggtg taagtctggt tattggcctc 162000
ggtgaacgtc aatcgcacct gaaaagacac gctgtagtcc cggaagacgt gagcccagct 162060
ctccagcttc atcacacaca tctgataacg tgtgccatcg ttgacgacga agcgtagcag 162120
cttggtctgc ttgggcacca tgtgcgctcc aaaaatcttg gcgtcttcca cgctgatctg 162180
cacgtttccg tcgctcggtt ttgaagccgt tcggggcatc cgttggagga tggtctggtt 162240
gcgaccgctc aggtaccaga tcaccttttt cacccaggtg gagcttctct ccaccaaggt 162300
ctggccttcc cggttgtaca gcagatacag ggtctcgttg cgacactcgg gacccgttaa 162360
tacccgctgg aaccccgaga attgcaaggg ggaccgtggg ggcgagggat agataaaagg 162420
acagtaaaac gtcgccgcgt catgcggttt ggaatacgtc agtttagacc atagcgggga 162480
cggattctgg ttcgccgtta gcgttgacca cggagacgcc agacagggcg ttgcccaaac 162540
cgcgcacaga agcaggcagt gaaagtggtg acgaagcaga agccgtagca tattatttcc 162600
cgtgacgcag gctagttggc aaagagccgc acgctgaact cgaggctccg ggcgtgcggc 162660
gccagcgaac cggcggcgtt gaacgtggtc cttttgttgg tgccgccgcg acggttctga 162720
cgtctaaagt cgctgatgag caacgacacc tcggtcacgt tgattctgca agcacaggtt 162780
ccgaacgtca tttcacaccc catgcggtta cctgcccgtt acccgttcgc ccttaccttc 162840
ccgttgtcat acacctttag cgcgtatcct cacctcttga gcacgtcaaa gttgtccaag 162900
ccgtggctcg catcgtagtg gtagttcaac gtgaggtcca cgagctgttc cacatacttg 162960
taacgggttt ggtcgggcag cgcgcgagag cacgcgtccc agtaatgcgg tactcggtaa 163020
taatcgtttt tttctgcggt ctcccgctgg cactgaccca gcaccacggc gcacagacaa 163080
acagacagcc acacccgaca cagccgcatg ttgcagactg agaaagaaag ctttattatg 163140
agacatcata cacatagtat aggcgaggtg atggggcggg gaaagagttg gaaccgaaag 163200
ataaaaaaaa aaaagcctag tcgtactcgg gatctctgag cgagacgggt tgcatggcaa 163260
ctttcattag tttgggaatc tgccagctgg tgctgttcga aggttcttcc atttccgagg 163320
cggtcagttc atcgtacacc gagacgtagt acctgatggg gtcttcctca ttgtccgaga 163380
ggtgagattc gatggtcaaa ggcgagcctc tcccataatt gggattcacg aacgacgtgt 163440
ccaagttgcc atcctttctg aaatagatga cgttctcagg atcatgtttc atgcgctcgc 163500
gggccgcgga cgcctcctcc tcctcgtccc agtcccgagt ttccaaccgc tgataagggc 163560
tcgaggaaca aaatccggcg gggatctgag aacctcgtcg ggaaccgctg ccaaacgggc 163620
tgccaccgcc actgtcgtcc gtgtcgtcca acaggttgac ggcttcttcg tcggcgaaac 163680
gaaagcggcc cgggtgcttg caacacgagg agtaaactac cgcgatcagt accgctatga 163740
agctgaaaat ggaggtgcct gtcacgatgt agaagaggat agccagcact ttcatgattt 163800
cgtcattgcg cacgctgtga acggaagact cgtgggtggt ggtcatgttg atcccggtcg 163860

-continued tgggtccgct actcgtggca ttgtcgacgc tatttctgct gctggtgcta gtagggactt 163920
ttgtgctgct ggtcacattc gtagcgtcgc tgaggtctat ctgaagcagc aacccgaacg 163980
cgaccagggc caggaatgtt gcgcgaaggg gaccccgcgg ggccggcatt ctcgagacgt 164040
ggcgacgtgg atttcttgct atgtccgcga acgacgtgtg acgaggacgt ggtttccgca 164100
agcctctacc gacgccgcga caccaggtag gttatcaaaa cgcgagccca tatcgccgcc 164160
atcattgtaa tcagcaatgt gttgaggtac tgcacgatga atctgtctag tgacaccagc 164220
caaccctctg cttttgcggg caagcgcgct ttcggtgaca gggtgtatcg tacgtagccg 164280
cgggtcaggc gcgcgttgta gcggtacacg cagaaatcta tccacaggcc aacgcccggc 164340
tgtagcttcg gatggtggat aatagcgcgg tgacgtacgc cgcggggctt tagaatctcc 164400
acctgtaagg ccatctcctc caggtagtgg gtctgactgc gacgcagcgt ccagttcatg 164460
taaaagtcgg tctcgccgtg tccggccacg aagaggctgc ttactaaatc gggcgccaga 164520
gctaggtcag gcgtatcaaa ttccactgcc aggcgacctg attctaacgg ttccacgatc 164580
cgggagagcg tctctagata tagagcaaag cgtaccacgt ctacctgcgg tgtaaaaaac 164640
tgctgtgggc gttcaccgtc gttgaccacg taggccacgt agaggccaac attttccacc 164700
acgggttcta gctgcaggcg gcacgtaaag cttagaaacg acggctgtac ggtttggttc 164760
ccgtgaagct gaagcgtcac ttccttgccg gggctcactg tgctgtaacg ccgcaccgag 164820
tcggtcatct gctccggatc ggtagaccag aagggcgtgc aatgcatact gtcccagtcg 164880
cgacacgcag cccagcctag ctcggtgaag ggtcgacgca cacccgaaaa agtgtgcttg 164940
aagaccaggg ggtcgcctcg gtagctcaat agccgaacat gcacatagtc gcggctagca 165000
ttgacagacg gcccgtggag ggccagcagg acgagcgtga acagcaagcg caacatgctg 165060
cgcgggttag gaaatgcggc gtgccggcca ccgcccgact cataaacact accagcatga 165120
cgtctcagat cacacaagtg acgaggagcg taccgcaaat cactagggaa aaggccagca 165180
gagcccgata gtcttgctct tcgcgaacga tctcgtccgg ttcctcacac tcttcgtggt 165240
ccacagaaga tgaggagcag gaattttcgt taatctctgc gaggatacta gtgctgtacc 165300
acaccagagc gcttagtgtg cccagagcta ccgcacggta aaatagggac atgatcacca 165360
gcgcagtctg aagtggtggt agttcaattt cttggcgtat ttccagagaa aggctttgta 165420
ggccgtaggg gctggccagg caccaaactc aatattggta gacactacgt cgtaaatgcg 165480
ttgttcttcg tctaagatta accgaaaaaa tagccggttg atgtgacgac gcacagcttg 165540
cgcgttagga ttgagacact tggtgccctt gtcctttaaa atagccagca cttcctgacg 165600
attgcagctt tcgctcgctg cgattggctt aagcagttga gttccgactg gcagggtatt 165660
caacagaatt tggttgttgc aacgacagcg cttgtcgtaa tcttccaatt ctaagagata 165720
gacgaatagg ggacacgtgg aaaataacac atatgcggtc aaatacaggt atcgtaccga 165780
taagactttg atgtgcgaat ttggaatcgg atggtgtaac catgtcaaaa ccatgtcgaa 165840
aacacattgt attacctttt tcgctatata cgtgatattg ccaactcgtt ttacaattta 165900
taaaaaatta tagtcgccaa ggcgggtgtc tattggtgtc acttttgtct tctatatgtg 165960
gtccattatc agagtttttc tttataaaca ctttatgcca ccagttactt cgtttgccat 166020
caacccattt cgatagataa tgatcaggag acaaacatac aggtgtttgt cggggaggta 166080
ataaaaagtg ttgcgttttg tcgcatgtag gatctggagg tttatagccg acccaaaaaa 166140
cgccgaatac gggatgattt gaaccattgc tacaccgaca acgtagttcc acactttcca 166200
ccttatagca caacgcgatc aaaagaccaa acagactaaa aataaatcgc attataattt 166260
tattatctac gtcactatca gtaattcgta atatccggta ttcccggaaa atcactcaaa 166320
actacgtcca tgacacatca actcccgata actacctccc tttgaaatcg gatcccccca 166380
cgtaccaatc aatcacacaa cacacaggtt taaaaatcga tcactcgtca attaggtttc 166440
aaaatcgata ccgtttatta tcaggaatct agactaattc tacaatgaca gctctgaatt 166500
tctctctcgt cttccttgtc aggttctcat catcagttat cacttccacc catcgaggag 166560
tcatcgtcgc tccaaaatcc tttggggtcg ctagttggaa aagtctctga cacgatccag 166620
gcaccccgca cccagtccga ctgatctagc ttgcggagca tctcaacagg catgagctgc 166680
agggccatgg ctgtcacggc actgtatcga tgtaacacta gggactttct ttgcgatgta 166740
gccatcaaca cggcgtatgc cccatagttc gcgtgatacg acgcatgatg ggttaaacgt 166800
tcccatccgg cagtgccgtc tcgggtccgt gcacacaaca gctgcacggc attatgatgc 166860
ttaaaattaa ccataacgct ggggctactg atgaaggagt agtaatgagc caggacgccg 166920
tacatcgaag gcagcaagaa agagtgacag cacaatagca ccgggctctt atgtaggcga 166980
cagcttattt ttcctgacgt cggcaaaaag tacctaaatt ccccacagat attcagacac 167040
ggttccgcaa agtgcttctt tttttagtgc aggaattgga aaaaataata aaaaatatga 167100
acagctcatc tgtaattatc tgtgtgactt catcgtaccg tgatgtaaaa acaacaacag 167160
gaagcttaca gggtgcggta gaaaattttg ccgattgagc aacactgttg gcatctctca 167220
ctccgatagg cggctataag atagaaaatt aaaagtatga tacccacgag aaagatgaag 167280
agggacaacc aggctagagt atgacgacca cttttccctt gtttgacggt tacatgtgcg 167340
gtatgatttt gtcgttgctt gtgatgttgg acgcctggaa cggacaacga cgtataattc 167400
ttagatgcgc atacggtgtt attagtggaa gtgcagttac gaattgtaac ctcagtgtca 167460
ctacactcag tgcaattggt acaattgtaa agccctgata catacgtacc gttagggcaa 167520
agtgtacatg ttgtactcgt atattgcgta cattgtcctg taacacgata tccttgttta 167580
catgggggac aacactgact tcctaattgc acttcttcgg gtttgcatat ttcagttttc 167640
cctatgcatg ccaatagcat actcagcaaa ataagcatca ccagaggctt catgcctcct 167700
accggaagaa taaaaataac tcatggggcc gaacggtatc atcctctccg cggtttgtaa 167760
tacgagatcg taaacgtaaa taaatgacat aacttcacta acccgcatac tgcaaagtcc 167820
acctacgacg ctgaaagctt ttccaggaca caacaggata gtcagccatc ttcacaggta 167880
accagtttct agtcacagta tagcgagcct aagagaccgc acacggtccc tgctggaaac 167940
acataccact acatcgattt gtcgtgtcgt acaaccgtca agttttccga acttttatac 168000
acgccaatgg cgttaggact atgtgtgctg ctgtgattgg aggcttcgag agttatgtga 168060
cagctgtgat tacacctgtc gccaaggctg acagcgatta cccaggtaga gcacaatcac 168120
atagctgatg gacgttggtt gatccgttga ttcccatgga cattttaacg gcgacagtac 168180
agctccccgtt aaacattaga ttaatagacg ctagtggatg acagcatgtt attcgcccaa 168240
ttgtgatggt ggttatactt tcttgttttt tgctcatatg ctgtaaggtg ttcgaggatc 168300
gtggggagta tatgtgttaa atcggaatca tatttactga ccgcgccata cttcgtatac 168360
gaacctaacc ggcgtaaagt gttttccgat atataaactg gcgcctattg tggctgtagc 168420
gcccataggt atggcatata cccacggtga tgttgtgtta ttcgtttttt gtgataaaac 168480
gtagtttatg tttaacgtgt gttccgtcac gttatgtgtg tcgttaaaag acggcgtctg 168540
tacagtatgg ctttgagttg tatcttgaat tgttattgca tttggaggtg tgtacagagt 168600

-continued ggttgttgtg tgctgaggtg ttgttacgtt ttgaggcaca gttgtggtgt atacggactt 168660
caaggtgtag ttacggagtc tttctatgca ggtagtgttg agatatttgt gaatgctggt 168720
tatgttcgat tctgtgaggt taaagtgtgt actatttatg gcggtataat ttagacggtc 168780
ttgccatccc gaggatgtta gtgttaggta attcgtgttg tttacgtttg cttgatatgt 168840
ataggtaggt gtactgtttg tgaggtcgca agtgtgattt tcttgcagag attttatcca 168900
tcttgtgtga aaatattgag atacgcgatg aatgttttcg ctatctatat tgtaaagcgt 168960
ttcggtggta cttaggggtt gtttgctgta actcttattt tggacccagg atgtgaacca 169020
tgactccaat gtttgtatag taaggtgtcc tattaataaa gacgaactga ttcctaccgt 169080
aatgttatat cgcacaccta gggtgccgtt tacaaacacg gaaatgtttc cgttacaaac 169140
cacgttggca gatgaattag attccaggtg gtaacgatag gataatgacc gttcgctccc 169200
aacggatgac acaaagtatc cgaataacca acacgcccat tcaatccgca tattttaatc 169260
acactattca catttcacac actgcatttt ttaacatgtt attttttat tttatgcgtg 169320
ttctcacctc ttcatctttt taacaccggg gtaactatcg taagtcggta ggcgtcgata 169380
gccctcacca cctcgtcgtc cccttcccgg cgtggggcac cagcgtccac agcactgcag 169440
gtaacacagg tagcatagga aacatacggt gaaaatactc caaaatccca aaaatgccgc 169500
gattccccga gtggcccagg gagacatccc ggtgtctatg tcggccggcg gtgctggcgt 169560
caccggtaaa aatttcggcg ggtgtggctg cgaacggtag cagtcgccgg ggagccggta 169620
acgctgtatc actgtccaac agcggtcggg ttcctcgtcc ggacatgcgg gtttccagca 169680
atcctcggcg tcggcgcggc cgatatagaa gtagttgcgt tgaaaaccgc ggtacatccc 169740
gcagtcgtga ttccgtagac gccagggcgt cggcgaccag atctggtctc ccagcgagta 169800
acgacctaac gccggcgtgc agcaaggttc gtcgggccgg ctgagcgtct ccagttgcgt 169860
gagaattacg aagcgttgca tgatgaggcc gtggctgtag ttgcgcagca cgcattcgta 169920
catgccggcc gtgtccgtcg atacgttgaa agtcagcgag aatatttggc cgagatgcaa 169980
ttgcgagaaa ttccaagtgg cgtacggcag gcggtactgg agtccgttca tcagccgatg 170040
gcctttgacg gcgtccagga tgagctcgtc gctgccgtcg tgggaacgac agaaacgtgc 170100
gcgaatggag accatgggcc aggagtgtgt catgaccgtg caggggatgg tataacttgc 170160
tctccctcgg cgaccaacac cggcgccggc gacgtggtct cataattctc ggcccacatc 170220
ttttcggcaa tgtcagcggt ggcgaagggg aacgaagagg aagaatattc gaggagtcgc 170280
gggcagctca acagcaccca gaacagccac ggcagagttc ggagcgactc tcggcggcac 170340
atgatgattc tttctttccc tttttcgcag agacgctgcg cgcctgctcc tgctccgtgt 170400
gtcggccgct caaacgtcgg gccggcgtgg tggtgaccac cgtgcgacgc agcttctcgc 170460
ccgggatgcc cgcgactgag cgtccggttt ttttgcaggt ctttttttgct gcctcctcct 170520
cgccgtcgcc gtcgcggccg acgtggtgga ccagcaccgc gcaggaactc tcgcgtcgcc 170580
ggcggtacgc gacctgtctc attgctacct cggatgttta agaaggaacg ttcatctgcg 170640
tcacagggtc tgatgaagct gccaagagtc gtggctgtgg cgcagcgcgt tctgtacggc 170700
gcgtttcacc gctttctgca tggccgctac cacgtcgggt gggagcggct ccggcggaag 170760
ctcgatgagc agttgctgcg agtctcggcg ctcggtgtcc gccgtttcgt cggacgtggc 170820
gtaaaaaacc gaggtggttg cccagtcgtc cacgctgtcg acggcctctg tcagtgccgg 170880
gttgtcaaaa ccgccatcgg acgcgggtga taaaagaacg tacgatgaca cgctgttagt 170940

-continued acgactctcg tcgtcgctct gggaacgacg tgatggacga cggtagatga cctcgtcttg 171000
ccacgcgtcg aagcggtcgc agcagcgctg gatccaagcg cagcgaagca gcttacggaa 171060
cacgtcgttg ttccaaaagt agagcataaa gagaaagaaa agtagcgtaa taatgaagcc 171120
gaaaacgacg agggtcggca gggcactacc gccgctgccg ttttttgtgt cgtgcgggtg 171180
cacggtggta gtggcgttag tctgagctgg ggtcatgaca agtctgaaga gatgagagcg 171240
tgggtgctca tcaggaacag ttgaggtctc tccctaccga agccttagcc tccacggtgt 171300
tttatgatca acgtgtctac gaacgtcatt gtgaaagtga cgtctcaggc tttccgaaac 171360
cgcgtcagat tcaacgtggg tttcggttta gcctgcgtca ccgaggcgga ggtggaaatg 171420
agccgtcctg tgggggagtg tacgaccctg tagtgcccat gggtaacgtc gcgtcggaag 171480
aagtgaatgc ggcattggtg tacgcgtggg ttgttttgct ctctgactcg gaggaattgc 171540
cgcagcagct gcagatttta cgtactaacc aaaagcagca aaagcagcag gtaaataaga 171600
gaaggagtcc agataatgtc cagccgctag cggcaagcag cgcgagctgt ggtactgtcc 171660
agctactgcc gttagaggca ttaatacatg tcgatacggt cgtgttggcg gtagcactag 171720
tagattgact ggaattagag ctggtacctg tagtggtttc actcgccgat gcggcgagtg 171780
caaataaaat taatatccac agcatgttta ttactatata attgatatac gaacccgtct 171840
gtcgtaacaa tcagcgttat acacgctgta tcggcatcgt tttaccggaa agtttatcgt 171900
aatgtaaccc gcgttgtgta cattcgtact gacagggaac ccccggtgat gtgcacatta 171960
tactctttca ttctggggtt tcccaatgac gtaaaaattt ccactacaca ataaaattac 172020
tgactcatgt gaaaagtgtg ctttttatta acagagcaga gggtttacag tagatatatg 172080
tttgccaggg ccaccgtttt ctaacaccga tcaccgccac cattaccacc cgttgaactc 172140
cacacccggg agccgcctga tcgccaggga ctcctcaccg tccatcgtcc gaacaagctc 172200
ccgccaccga tgctgccacc atcaccgaga gaaagaaccg cttgctgcag atacgcttgg 172260
gctcgcctcc gtgcggacgc cgtttcgtgc agacgctgag tagatcgagc agagaatgtc 172320
aaaacgacat taccgcgatc cgctcccctc ttttttcttt ttctcattca cgtgtattct 172380
tgatgataat gtaccatggc tacggtggtg aactgcgtcg cggatcccgt cacgggtttc 172440
aacagatcga cgtcggtcag cggcgccgtc accgccatgt ccggcggagg cacgctgttt 172500
ctctggttag cgacgtggac cgacgacgaa gacgatgaac ccgcgcggcg gtctgttatc 172560
cgcgacgacg cgtagctgca ctgggaagac acttcctccc aacggaccaa gatctcatcg 172620
ggccgttcgg agaaacggta tcgtctgtcc gactcccgcc gtacggcgcc gaggcccagc 172680
gacgacaggt ccgcgaaccg gcgctcgtat tccccgtaca gctcgcaaca gcggatcagc 172740
cagcggtagc tcaaaaacat gcgcaccagt ttgaaggtgt cgtgccaatg gtaagctaga 172800
tagcagagaa tggccacgat cagcacgagc atcacgccga tgatgggtaa cccgacgttc 172860
agcggcagat cgtccatggt gaccgtcctc tgtccggatc tacgtcccag tctctctctt 172920
ttgtacagca ctcgcgcggg aacggccccc tcaaccctct tacgtagcgg gagatacggc 172980
gttctcccgc gggccactta cttgcacggt cgcttgaacg gcggcttgga ccgccacatg 173040
taccgcatcc atccattctg gcagcagcgc gttcgacgac gtcgtacgag tcgcggatga 173100
tgttaccccg ccagcacctc cgccggcaac cgcgtcgtcg ttgctatcgt cgccggtttc 173160
gggcgatgac agcgccggcg gcgcgggtct cgtctcgtcc accatttcca ccgtgtcgaa 173220
gcgacagccg ctgccgtagt acatggcccc gttcaacggc cggcgggccg ggtcgccgag 173280
ttccgggtcg ggcacatcca tggctcgccg tctgcttctc tgccgctcgt ggtgccgacg 173340
gcacttctca ggataatgac agccgcaaaa tagatcgtgg agcatgtctc gccaactgtc 173400
ctggtggtaa tatcttaagt acgcgatgag cgcgccgatg gccataatca taagcgtaag 173460
caaaacggca cagataacgt gaaacaccgc ggtcatccaa gtcgggcggc gtcggggacg 173520
cggtgggtcg gtttctctta cgccggcgtc actcagccac cacacccgta gtcgacattc 173580
ccagaaccgg tgaatgcgac tcagggcctt tcgacgccgc catttatttc caacgtccaa 173640
gtcccacgtc atttctggca tctccacgcc cttgactgac atactctctt tctctctctt 173700
agctgcggtg aaaaagaggg aaggcgtgtg ctgctataca actgtacaac ggacgcgctc 173760
gctgtttcgg tctcaggtca tctgcattga ctcggcgtcc ttcatgacgc tctgcaccgc 173820
cttttccaag agttcctcga tgtccgacca tcgaggaggc ggggctaact cggaaaccga 173880
cacgataggc agcgtggtcg gctccgtcgg cgtgcggggt cggggacagg gacacgagag 173940
tcccaccttc gagagattct ccagcccgac ggtgcgcggc agtctcggat tccgcggtgg 174000
cttttgtggc gtcggcgttt tcgggaaggg cctgggcgtc accggcggtg tccagccgac 174060
cggcttgggt ttcgtgggcg gcggtgtttt cttggtgggc ggcgtgctca ggttcttacg 174120
cggcgcgggt atcggcgtcg ggggcctgtg cgacgacagc cgcgtggtgg gggcccggac 174180
cggcggcgta ggcggccgct tcttgcgccc gggcggcgga ggtggcttcc aggatggcgg 174240
cggctgatgc agtaccgtgt cgacgctggc cgaggacgac aaagagctcg acgaggagca 174300
atgcgacgga gatcggccga tgctggtcgg cgttcccggc gtggatacgt cggggatctc 174360
gaatcgcgcc ggaggaaact cgggtttatc tatcggcaga ccatcctctc ctatgtagag 174420
cgacgtacac cgcggcacct gcggcgtcgg cgggtgggtg gccacccgca tgagccccag 174480
ttccagatcc agcggctcga cgacgtcttc tttcggaatt cgatagcagc acgcgcaggc 174540
accacgctta tcagaagcag cacccgggag ccggcctcgc gacgaagtct cgtcggatcg 174600
cttgcggcct cggcgctggg taaataagga aatggccagg accagggaag ccagtccggt 174660
accgccgagg agcccgacgc cgagccacag ccacaccatg atcttctctc ctgcttggaa 174720
tctcaaactc cgtgtcggga agggccggtg tacggacatt tatgccttgg atttctggaa 174780
acgtcatttt ttggcaagga atgtgtttat tgtccaaaca ctgaggaagg agatgtgagc 174840
caagtcggaa aattccttat cacaccgggg gcgggttacg ttccggtctg atgctgctgc 174900
tgttgttgta gagccgcggc catggccgcc tgcacggcag cttgtaccgc ctcggccacg 174960
ccgggtggca tctgcggcat ggcgggggga gacgcgtcgg gcggaccgcc gggcatcgcc 175020
gtcggctgcg acggtggttg tgaactcacc gtcggctcgc acggaggttt gtccttcggt 175080
ttgctcttcg gtttatcttt cgccctacct ttcttcggtt tgggttccga tgtcggtgtt 175140
ggcggctgcg gtgggatgac gggctggtgg gactcctccg acggcggggg gacgaatact 175200
gtcggcgccg aaaccggggg actctcgact atctcgcaga tcaccctgtc gggatcgtcg 175260
ccgtgtccgg gacgccgtcg atgaccatat tgaaccatgt cgtaaatcat cgtctccttg 175320
taacacgctg aacagcagcg gctacaagga cccgaaatgc atttgcagct gcacttacag 175380
ctgcagctgc agtagcgcac ccatcggcag gtgaagacgt cgattacgga gtccttgaag 175440
aattcccggt aacggatgag atacgcgcag aggaaaatca tgaaaacaga acagccgact 175500
acggctgcga tgccgggtcc cgaaaacgta ttcggtgatc ctaccaaaca ccaaattccc 175560
agggccgcgc atgttatcca ggccacaata atcgtgggaa cgccccattg gcattgccac 175620
gaaggatcgt gcacgtcgca acccatcgct actgcgttct cccacaaacg ccatcgcact 175680

-continued atttatccct acagcggctg ccgagtcacg tccgccggcg cccatcggcc gcggcgatct 175740
cctagtaaca ctcgtccgac acttccacca tctccagctc cgccggcggt tcggcatcct 175800
ccactagcgg cgtcgtctca tcttttccgc agcagcgaac gcacaccttc tccaggcaga 175860
acgccaccag ctgccgccga acgtaccaca agtacacgtg cagacctgcg aacaggacta 175920
cggaggtcat gaccaccacg acgcacacgg gaatccaagg atcgagattg tcgctggaac 175980
tcatggctat cgccaccggc gtgcccgcgt ctgtctcacc gccgctcgcc cgatgtcgcg 176040
cggcttgtta tacgctagcc cgtcgccgcc ttggggcacg gtgccctcct acccacgtaa 176100
cttcctccgt gacttaaagt cgcgtgtggt agatctcctg ttccgtggac gaaccgtccg 176160
gcaggatagc ggttaaggat tcggtgctaa ggccgtgtcg ccaacgtcga atgctacgtt 176220
gcaacagctt cgacggacgg ccatcctccc tctcatcgca ataataaaac accagcagcg 176280
cgcacgacgc gatcacggtg acacccatga ccagacccac gcagatagcc agccccgcta 176340
gcgtatccag cgccatcccg ttcgctcccg tcgtcgtctc ctgaacaaag caactccgca 176400
gtccccgttt tcaaccgttt ttgtttcctt cttcgcgact agatgttaac gcccgcggtc 176460
tttccggccg tgctctacct cctggcgctt gtcgtctggg ttgagatgtt ctgcctcgtc 176520
gccgtagccg tcgtcgagcg cgagatcgcc tgggcgctgc tgctgcggat gctggtcgtt 176580
ggcttgatgg tggaagtcgg cgccgccgcc gcttggacct tcgtgcgttg tctcgcctat 176640
cagcgctcct tccccgtgct tacagccttc ccctgaaacc cacgttaacc gaccgtcccg 176700
aaaacaccgg tgttaacaca ggaaaaaaag gaaccgcgca ggaaccacgc ggaacatggg 176760
acactatctg gaaatcctgt tcaacgtcat cgtcttcact ctgctgctcg gcgtcatggt 176820
cagtatcgtc gcttggtact tcacgtgaac caccgtcgtc ccggtttaaa aaccatcatc 176880
gacggccgtt ataaagccac ccggacacgc gccgcggcac ttgcctacgg cgctgctcca 176940
gggaaactcc tcttccttct gctcttcctc cttcaccgca gggatcgttt ccctcgacca 177000
gggacccacc gaagcaacta ccggaacaac ctggaggagt cgcggcatga cggcgcccaa 177060
gtgtgtcacc accactacct atctggtgaa gaccaaggag cggccctggt ggcccgacaa 177120
cgccatcagg agatggtgga tcagcgttgc catcgtcatc ttcatcggag tatgtctggt 177180
ggccctgatg tactttacgc agcggcaagc gcagagcagc aacggcggca gcagcggcta 177240
gacgagtctc tggcggctac agctccaggc gccgtagccg gcccgcctgc cgatcgcgac 177300
gtcgtggacc atcgaacaga gactcacgcg tacgagaccc cgaggtacgc cacgcggtgc 177360
ctaacgcggt ataccacatc cgtacggtct gcagtgcggc gtacaacgtg tggaaaacgc 177420
gtcgcgtcgc agagtccgcc acgtccctgt cttgtcgctc cccaatcgtc tcccgcacac 177480
cccccgcggc acccaggggg cgggtgagcc aagcattgtt aaggccgttc tctgttccat 177540
agcccataaa ttgttgattc cggagctcgt tggcgcggaa atagccggat aaggggagca 177600
acaaccgtcg gcgaaagccg tcccgctcat tcagtccggg tttcgcgtcc agtcggacgt 177660
gtgaccgttg ggcaacggaa cggcgtttca ctaccaaaat cgtatcgggt agtgtacgag 177720
acgtcggcgg tgcagaatgc gactcgcggc gtagctcgcc gtcgctatgc ggctcgtcgc 177780
cgtgtggcgc ggcctggccg gctgtctgcg cccagatctg ttggcctttt ggttcctctg 177840
gctgctgctg cgtgtgtgct ttggcagacg cggtggcagt ttgcggtctg cggtaagtga 177900
ggatgttgcc gagcaagcgc acttgcggcg cgtgatcggc acgcgtgtta ttgtaggttc 177960
gttgccagat ggcaagtgct gtcaacagca gacgttgtgg gcggtcggtg tatttttgtg 178020
ggttgcggtg agagtcggca ctcggtgttt tgtgagtgat ctcaaccgtt tgtgttgctt 178080
ttagcagcgt ccaaaacagc gacgcgactt tggggatggc ctcgtgctca ccgccgcgga 178140
gagtgtcgcc ggacctgctc gtcagcagcg agctacgcag acggaatatc tggaggagag 178200
ttacgtgtgt cacaggagag cgcgggtctc cggcggtaac gacggcggtg tcgtcgacac 178260
gtgtgcggcc tgctgtgctc tgcggaaaag cgccggtctc ggagaccgtg gacgaaaaag 178320
agaacggagc agctaccgct ggcggcggcg gcgttaatgc tgccgttgat gttagacgtt 178380
gtgagtactc ggaaacagcg gtgaggcaga agctcgatcc ttcagggaac gacagtcgat 178440
gtgtggtagc cgcagcaggt gaggttgggg cggataacgt gttgcggatc gtggcgagaa 178500
cgtcgtcctc cccttcttca ccgccccacc caccctcggt tggtgtttct tttttcttgt 178560
gtcctgcaga tagttccacg gacagcgacg gcaagtccat aatcaccggt gtgcaagtgg 178620
tggaccacga cgaagatatc atcgcgccgc agagtttgtg gtgcacggcg ttcaaggaag 178680
ccctttggga tgtggctctg ttggaagtgc cgcgttgggc gtggcagggc tggaagaggt 178740
ggcgcaacag cgagtctggg cgtcgatgga gtgctgggtc tgcgtcggct tccagcttgt 178800
ctgacttggc gggcgaggcc gttggagaat tggtgggatc ggtcgtcgcg tacgtgatcc 178860
ttgaacgtct gtggttggca gccagaggct gggtgtgcga aaccggtgtg gaagccgagg 178920
aggctatggc gcggcggcga cagcgcatgc tgtggcgtat gttctctcgt ggaggcgacg 178980
gcgaatgcag cagacggtgt tcgatggaga tggcgtgcga ggaagaaagc gccgtgttgt 179040
gagcagacga cgttggatgc gggacgtcgg agcacatggg ccatgtgtgg tggcagatgg 179100
cggtgtccac ttgtgcttgt cgcggcagtg cacagacgaa gcaacatgtc gctgtgaaga 179160
gatagagtgt gagcatagct gtatgcagcg ttgcgtgtag aagcgggggg attaagacgt 179220
taataaagag tagcggcggt tgtgataggg cgaccgctga ggcgagctgc gtgtgcgtgc 179280
cgtctgtgtt ccccgtcccc gccgcaagag tcccccgtcc ccgccacgca acagcccgcc 179340
atcccgcaac tccccgtccc cgccgcgaaa ggcccccgtc cccgtcctca ccaccgtccc 179400
cactcccgtc cccgtctccg caacgccccg tccccgccgc aaaaggcccc cggccccgca 179460
acgcatcgtc cccgccgcaa aaggcccccg tggccgtacc cgcacacccc ccgtccccgc 179520
cgcaaccccc gtccccgtcc ccagcgtaac tcccgttact agcgccggcg cccagcacgc 179580
ccgaaaacac cgccgtcgcc gccccgaaaa gcgaagcgcc gcgcaaaagc tgcctagaaa 179640
cgccgcgcaa acaccgtaga aacacccgcc gccaaccccc gagcgcgcgc aacaccccgt 179700
ccccggcgcc ggtccgcgaa acaaaaaaca ccgcgggacg acacgcaccg gcagtgcgca 179760
caaagcgccg gacacagcac gccgcaaacg cgctgaggac accgctgcgc ttacttatgt 179820
ccagagacac acgcaccgcc agcgcgcaga aagctccgtg gacaaaactc ccgcagccct 179880
gtccagccct cagtcctatt ccgcgaatcg gcgcgctgac ggtggcaaaa cctccctcag 179940
ccccgtcccc agcgtaactc ccgttactag cgccggcgcc cagcacgccc gaaaacaccg 180000
ccgtcgccgc cccgaaaagc gaagcgccgc gcaaaagctg cctagaaacg ccgcgcaaac 180060
accgtagaaa cacccgccgc caacccccga gcgcgcgcaa caccccgtcc ccggcgccgg 180120
tccgcgaaac aaaaaacacc gcgggacgac acgcaccggc agtgcgcaca aagcgccgga 180180
cacagcacgc cgcaaacgcg ctgaggacac cgctgcgctt acttatgtcc agagacacac 180240
gcaccgccag cgcgcagaaa gctccgtgga caaaactccc gcagccctgt ccagccctca 180300
gtcctattcc gcgaatcggc gcgctgacgg tggcaaaacc tccctcagcc ccgtccccag 180360
cgtaactccc gttactagcg ccggcgccca gcacgcccga aaacaccgcc gtcgccgccc 180420
cgaaaagcga agcgccgcgc aaaagctgcc tagaaacgcc gcgcaaacac cgtagaaaca 180480
cccgccgcca acccccgagc gcgcgcaaca ccccgtcccc ggcgccggtc cgcgaaacaa 180540
aaaacaccgc gggacgacac gcaccggcag tgcgcacaaa gcgccggaca cagcacgccg 180600
caaacgcgct gaggacaccg ctgcgcttac ttatgtccag agacacacgc accgccagcg 180660
cgcagaaagc tccgtggaca aaactcccgc agccctgtcc agccctcagt cctattccgc 180720
gaatcggcgc gcttacggtg gcaaaacctc cctcagcccc gtcccgcacc ggcggcggtc 180780
ggggtgtgtc gggggcgcgg ctgggtggat gcgtgcgtgg ggtgggtgtc gggtgtgtca 180840
gggcgtgtgg cgggtgtgtc tgggtgtgtc gcgggcgtgt ggcgggtgtg ttggcggggt 180900
gtgtcagggg tgtgtcgggg tgtgttggcg ggccgtgtct gcgtgtgtgc cccggggtcc 180960
gcgacccccc ccctcccctg ggcgatcgct tctgcgtgtg tcctcgacgc gggttgtgcc 181020
gtacttcgtc tgtcgtttcc cccgcggtcc cctagggact tcctcttttc cgcgtcttgc 181080 ccccccctccc ttgcgccccc gagcttcctc tggccgttgt tttgcgtgtg tctgttcttt 181140
cctcttttcc gcgtcttgtc tctggccgtt gttttgcgtg tgtccccagg gacccgcgct 181200
gccgtcccct gggaacttcc tcttttcccc ggggaatcaa acagacacag acgcgcgtct 181260
gcttttcgcc gtgcgcggcg cacgtcgctt ttattcgccg tcgccggcct ccgcgaccgc 181320
cgtccccacc gcaccacacc gcaccacacg caactcttcg ccgtcgccgt ccacacacgc 181380
aacctcaaat ttcacccccc cgctaaaaac accccccgc ccctcgggga cccagcacac 181440
ggcccggaat ggagggtaat gtttatggag taaaacacta ttgtccaggc cacatgcgtg 181500
tatgacttcc gcaccatccc gtactgcatg ttccacatgt acgcgctaga cgtgtaatcc 181560
actcgcagtt cggggacgca acgcagccag atcacatccc cttgcagtac cagacgcagg 181620
gctagttcta gagcggccgc cacggcgata tcggatccag acatgataag atacattgat 181680
gagtttggac aaaccacaac tagaatgcag tgaaaaaaat gctttatttg tgaaatttgt 181740
gatgctattg ctttatttgt aaccattata agctgcaata aacaagttaa agcggggttt 181800
gaacagggtt tcgctcaggt ttgcctgtgt catggatgca gcctccagaa tacttactgg 181860
aaactattgt aacccgcctg aagttaaaaa gaacaacgcc cggcagtgcc aggcgttgaa 181920
aagattagcg accggagatt ggcgggacga atacgacgcc catatcccac ggctgttcaa 181980
tccaggtatc ttgcgggata tcaacaacat agtcatcaac cagcggacga ccagccggtt 182040
ttgcgaagat ggtgacaaag tgcgcttttg gatacatttc acgaatcgca accgcagtac 182100
caccggtatc caccaggtca tcaataacga tgaagccttc gccatcgcct tctgcgcgtt 182160
tcagcacttt aagctcgcgc tggttgtcgt gatcgtagct ggaaatacaa acggtatcga 182220
catgacgaat acccagttca cgcgccagta acgcacccgg taccagaccg ccacggctta 182280
cggcaataat gcctttccat tgttcagaag gcatcagtcg gcttgcgagt ttacgtgcat 182340
ggatctgcaa catgtcccag gtgacgatgt atttttcgct catgtgaagt gtcccagcct 182400
gtttatctac ggcttaaaaa gtgttcgagg ggaaaatagg ttgcgcgaga ttatagagat 182460
ccgcgtcacc ttaatatgcg aagtggacct gggaccgcgc cgccccgact gcatctgcgt 182520
gttcgaattc gccaatgaca agacgctggg cggggtttgt gtcatcatag aactaaagac 182580
atgcaaatat atttcttccg gggacaccgc cagcaaacgc gagcaacggg ccacggggat 182640
gaagcagctg cgccactccc tgaagctcct gcagaagctt cgaattcgag ctcccgggta 182700
ccatggcatg catcgataga tcgcagcctt aattaaggat gcatgtttaa actcgacagc 182760
gacacacttg catcggatgc agcccggtta acgtgccggc acggcctggg taaccaggta 182820
ttttgtccac ataaccgtgc gcaaaatgtt gtggataagc aggacacagc agcaatccac 182880
agcaggcata caaccgcaca ccgaggttac tccgttctac aggttacgac gacatgtcaa 182940
tacttgccct tgacaggcat tgatggaatc gtagtctcac gctgatagtc tgatcgacaa 183000
tacaagtggg accgtggtcc cagaccgata atcagaccga caacacgagt gggatcgtgg 183060
tcccagacta ataatcagac cgacgatacg agtgggaccg tggtcccaga ctaataatca 183120
gaccgacgat acgagtggga ccgtggttcc agactaataa tcagaccgac gatacgagtg 183180
ggaccgtggt cccagactaa taatcagacc gacgatacga gtgggaccat ggtcccagac 183240
taataatcag accgacgata cgagtgggac cgtggtccca gtctgattat cagaccgacg 183300
atacgagtgg gaccgtggtc ccagactaat aatcagaccg acgatacgag tgggaccgtg 183360
gtcccagact aataatcaga ccgacgatac gagtgggacc gtggtcccag tctgattatc 183420
agaccgacga tacaagtgga acagtgggcc cagagagaat attcaggcca gttatgcttt 183480
ctggcctgta acaaaggaca ttaagtaaag acagataaac gtagactaaa acgtggtcgc 183540
atcagggtgc tggcttttca agttccttaa gaatggcctc aattttctct atacactcag 183600
ttggaacacg agacctgtcc aggttaagca ccattttatc gcccttatac aatactgtcg 183660
ctccaggagc aaactgatgt cgtgagctta aactagttct tgatgcagat gacgttttaa 183720
gcacagaagt taaaagagtg ataacttctt cagcttcaaa tatcacccca gctttttttct 183780 gctcatgaag gttagatgcc tgctgcttaa gtaattcctc tttatctgta aaggcttttt 183840
gaagtgcatc acctgaccgg gcagatagtt caccggggtg agaaaaaaga gcaacaactg 183900
atttaggcaa tttggcggtg ttgatacagc gggtaataat cttacgtgaa atattttccg 183960
catcagccag cgcagaaata tttccagcaa attcattctg caatcggctt gcataacgct 184020
gaccacgttc ataagcactt gttgggcgat aatcgttacc caatctggat aatgcagcca 184080
tctgctcatc atccagctcg ccaaccagaa cacgataatc actttcggta agtgcagcag 184140
ctttacgacg gcgactccca tcggcaattt ctatgacacc agatactctt cgaccgaacg 184200
ccggtgtctg ttgaccagtc agtagaaaag aagggatgag atcatccagt gcgtcctcag 184260
taagcagctc ctggtcacgt tcattacctg accatacccg agaggtcttc tcaacactat 184320
caccccggag cacttcaaga gtaaacttca catcccgacc acatacaggc aaagtaatgg 184380
cattaccgcg agccattact cctacgcgcg caattaacga atccaccatc ggggcagctg 184440
gtgtcgataa cgaagtatct tcaaccggtt gagtattgag cgtatgtttt ggaataacag 184500
gcgcacgctt cattatctaa tctcccagcg tggtttaatc agacgatcga aaatttcatt 184560
gcagacaggt tcccaaatag aaagagcatt tctccaggca ccagttgaag agcgttgatc 184620
aatggcctgt tcaaaaacag ttctcatccg gatctgacct ttaccaactt catccgtttc 184680
acgtacaaca ttttttagaa ccatgcttcc ccaggcatcc cgaatttgct cctccatcca 184740
cggggactga gagccattac tattgctgta tttggtaagc aaaatacgta catcaggctc 184800
gaacccttta agatcaacgt tcttgagcag atcacgaagc atatcgaaaa actgcagtgc 184860
ggaggtgtag tcaaacaact cagcaggcgt gggaacaatc agcacatcag cagcacatac 184920
gacattaatc gtgccgatac ccaggttagg cgcgctgtca ataactatga catcatagtc 184980
atgagcaaca gtttcaatgg ccagtcggag catcaggtgt ggatcggtgg gcagtttacc 185040
ttcatcaaat ttgcccatta actcagtttc aatacggtgc agagccagac aggaaggaat 185100
aatgtcaagc cccggccagc aagtgggctt tattgcataa gtgacatcgt ccttttcccc 185160
aagatagaaa ggcaggagag tgtcttctgc atgaatatga agatctggta cccatccgtg 185220
atacattgag gctgttccct gggggtcgtt accttccacg agcaaaacac gtagcccctt 185280
cagagccaga tcctgagcaa gatgaacaga aactgaggtt ttgtaaacgc cacctttatg 185340
ggcagcaacc ccgatcaccg gtggaaatac gtcttcagca cgtcgcaatc gcgtaccaaa 185400
cacatcacgc atatgattaa tttgttcaat tgtataacca acacgttgct caaccccgtcc 185460 tcgaatttcc atatccgggt gcggtagtcg ccctgctttc tcggcatctc tgatagcctg 185520
agaagaaacc ccaactaaat ccgctgcttc acctattctc cagcgccggg ttattttcct 185580
cgcttccggg ctgtcatcat taaactgtgc aatggcgata gccttcgtca tttcatgacc 185640
agcgtttatg cactggttaa gtgtttccat gagtttcatt ctgaacatcc tttaatcatt 185700
gctttgcgtt tttttattaa atcttgcaat ttactgcaaa gcaacaacaa aatcgcaaag 185760
tcatcaaaaa accgcaaagt tgtttaaaat aagagcaaca ctacaaaagg agataagaag 185820
agcacatacc tcagtcactt attatcacta gcgctcgccg cagccgtgta accgagcata 185880
gcgagcgaac tggcgaggaa gcaaagaaga actgttctgt cagatagctc ttacgctcag 185940
cgcaagaaga aatatccacc gtgggaaaaa ctccaggtag aggtacacac gcggatagcc 186000
aattcagagt aataaactgt gataatcaac cctcatcaat gatgacgaac taaccccccga 186060 tatcaggtca catgacgaag ggaaagagaa ggaaatcaac tgtgacaaac tgccctcaaa 186120
tttggcttcc ttaaaaatta cagttcaaaa agtatgagaa aatccatgca ggctgaagga 186180
aacagcaaaa ctgtgacaaa ttaccctcag taggtcagaa caaatgtgac gaaccaccct 186240
caaatctgtg acagataacc ctcagactat cctgtcgtca tggaagtgat atcgcggaag 186300
gaaaatacga tatgagtcgt ctggcggcct ttctttttct caatgtatga gaggcgcatt 186360
ggagttctgc tgttgatctc attaacacag acctgcagga agcggcggcg gaagtcaggc 186420
atacgctggt aactttgagg cagctggtaa cgctctatga tccagtcgat tttcagagag 186480
acgatgcctg agccatccgg cttacgatac tgacacaggg attcgtataa acgcatggca 186540
tacggattgg tgatttcttt tgtttcacta agccgaaact gcgtaaaccg gttctgtaac 186600
ccgataaaga agggaatgag atatgggttg atatgtacac tgtaaagccc tctggatgga 186660
ctgtgcgcac gtttgataaa ccaaggaaaa gattcatagc ctttttcatc gccggcatcc 186720
tcttcagggc gataaaaaac cacttccttc cccgcgaaac tcttcaatgc ctgccgtata 186780
tccttactgg cttccgcaga ggtcaatccg aatatttcag catatttagc aacatggatc 186840
tcgcagatac cgtcatgttc ctgtagggtg ccatcagatt ttctgatctg gtcaacgaac 186900
agatacagca tacgtttttg atcccgggag agactatatg ccgcctcagt gaggtcgttt 186960
gactggacga ttcgcgggct atttttacgt ttcttgtgat tgataaccgc tgtttccgcc 187020
atgacagatc catgtgaagt gtgacaagtt tttagattgt cacactaaat aaaaaagagt 187080
caataagcag ggataacttt gtgaaaaaac agcttcttct gagggcaatt tgtcacaggg 187140
ttaagggcaa tttgtcacag acaggactgt catttgaggg tgatttgtca cactgaaagg 187200
gcaatttgtc acaacacctt ctctagaacc agcatggata aaggcctaca aggcgctcta 187260
aaaaagaaga tctaaaaact ataaaaaaaa taattataaa aatatccccg tggataagtg 187320
gataacccca agggaagttt tttcaggcat cgtgtgtaag cagaatatat aagtgctgtt 187380
ccctggtgct tcctcgctca ctcgagggct tcgccgtcgc tcgactgcgg cgagcctact 187440
ggctgtaaaa ggacagacca catcatggtt ctgtgttcat taggttgttc tgtccattgc 187500
tgacataatc cgctccactt caacgtaaca ccgcacgaag atttctattg ttcctgaagg 187560

-continued catattcaaa tcgttttcgt taccgcttgc aggcatcatg acagaacact acttcctata 187620
aacgctacac aggctcctga gattaataat gcggatctct acgataatgg gagattttcc 187680
cgactgtttc gttcgcttct cagtggataa cagccagctt ctctgtttaa cagacaaaaa 187740
cagcatatcc actcagttcc acatttccat ataaaggcca aggcatttat tctcaggata 187800
attgtttcag catcgcaacc gcatcagact ccggcatcgc aaactgcacc cggtgccggg 187860
cagccacatc cagcgcaaaa accttcgtgt agacttccgt tgaactgatg gacttatgtc 187920
ccatcaggct ttgcagaact ttcagcggta taccggcata cagcatgtgc atcgcatagg 187980
aatggcggaa cgtatgtggt gtgaccggaa cagagaacgt cacaccgtca gcagcagcgg 188040
cggcaaccgc ctccccaatc caggtcctga ccgttctgtc cgtcacttcc cagatccgcg 188100
ctttctctgt ccttcctgtg cgacggttac gccgctccat gagcttatcg cgaataaata 188160
cctgtgacgg aagatcactt cgcagaataa ataaatcctg gtgtccctgt tgataccggg 188220
aagccctggg ccaactttg gcgaaaatga gacgttgatc ggcacgtaag aggttccaac 188280
tttcaccata atgaaataag atcactaccg ggcgtatttt ttgagttatc gagattttca 188340
ggagctaagg aagctaaaat ggagaaaaaa atcactggat ataccaccgt tgatatatcc 188400
caatggcatc gtaaagaaca ttttgaggca tttcagtcag ttgctcaatg tacctataac 188460
cagaccgttc agctggatat tacggccttt ttaaagaccg taaagaaaaa taagcacaag 188520
ttttatccgg cctttattca cattcttgcc cgcctgatga atgctcatcc ggaattccgt 188580
atggcaatga aagacggtga gctggtgata tgggatagtg ttcacccttg ttacaccgtt 188640
ttccatgagc aaactgaaac gttttcatcg ctctggagtg aataccacga cgatttccgg 188700
cagtttctac acatatattc gcaagatgtg gcgtgttacg gtgaaaacct ggcctatttc 188760
cctaaagggt ttattgagaa tatgtttttc gtctcagcca atccctgggt gagtttcacc 188820
agttttgatt taaacgtggc caatatggac aacttcttcg cccccgtttt caccatgggc 188880
aaatattata cgcaaggcga caaggtgctg atgccgctgg cgattcaggt tcatcatgcc 188940
gtctgtgatg gcttccatgt cggcagaatg cttaatgaat tacaacagta ctgcgatgag 189000
tggcagggcg gggcgtaatt tttttaaggc agttattggt gcccttaaac gcctggttgc 189060
tacgcctgaa taagtgataa taagcggatg aatggcagaa attctgatga taagctgtca 189120
aacatgagaa ttggtcgaga agctaggcgc gcctgtttaa acatggatcc ggccgccctt 189180
aattaacgtg ggagtctgat ccaacactga acgctttcgt cgtgtttttc atgcagcttt 189240
tacagaccat gacaagcctg acgagagcgt tcatcggggc atgaagtacg cattacacaa 189300
actccatata tttgttacga tagaatacgg aacggaggag gctttcgcca cacctatcct 189360
gaaagcgttg cattctttat gataggtgtg acgatgtctt taccattccc acggctgctt 189420
tgcgtgatga tgacattcat catgtatttc cattcacaca taccttttgt gcatacggtt 189480
tatatatgac catccacgct tataacgaac ctaacagttt attagccctt gacaggatag 189540
gtcaaaagat tatatgtagg ttttccggta aaccgaattg tgatatttct ctgcaggaaa 189600
tagaacagcc tggtacctat aaaacggaca atgcagtact gtagcagcgt aaccaagtag 189660
gtccacatga acacgtacaa aattatggta agccatcgtt tttcatacca cagcctgtag 189720
ctgtcgtaca tgaatgagga cggtcgagga acccagggta gttgtaattg ggggcgacat 189780
tcgtactgtc cagaagacaa ttgcacgggt ttcagtgaga tgagtacttt agcgatgtcg 189840
gcgggggcgc tacgtttcac cgtgacggtg agaacttgac cgtcgttttg tatttcatga 189900

-continued

```
ggcacgttat acaagccact ggtatcatga aggatgacct ctgatgcgat gtgaggatta 189960
aattgtccct caaaccgcca aacgctggtc atgtttccac cgtcaattac gcagctgacg 190020
gtgtgagata ccacgatgtt ggacttaggt ttgggggcta attgcctttt tacaaattcc 190080
cttctgtatt gcaggtcctg ctgccactgc ttttccgtgc ggaaagtcgc catgtcttcc 190140
acacgtgtgg cgacgataga cgccaccaag gtagctacca gaagcagctg gatccgcatg 190200
gcattaccgt atgtcaatta gaaagttgag cggacacggt tatcgttcct ggcggatata 190260
agtatataaa cgcgagttag cctttcccgt ccgttttgta cacccgttcc ccacacaaat 190320
gacgaatacg accttttttt ttataaaaat aaaccacgtg tattatataa aaacatttac 190380
atagaaaaga gacacacgga tcaacataag gacttttcac acttttgggg tacacaggcg 190440
tgccaccgca gatagtaagc gctggataca cggtacacag tcctggccag cacgtatccc 190500
aacagcagca ccatcgccat ctgtatggcg atcacgaccc cgagctctaa gtgtctgtat 190560
tcatagtgta gtcgtcgcag gttatccact gaattcccgt aactgaaata acgtatatgg 190620
taccgaggct ggcaccacat gggtttgcat ttggtgcacg gcaccaaatg cagagtgaga 190680
tggtccaagt ccgtgggcac ccactggcgc aaacggaata cggcttcggt ggtctccacg 190740
aggcactccg gggcgtgcag acggccccac tttcgtccgt gacggcccga ccagccgacc 190800
cgagccacta tccctttctc gggatagaac gtaccctgta cacgccacac agcgtccaac 190860
acgccgtcct tgacgacgca gctggcctga tagctggaca cgttgttaag cggcggaaag 190920
cgaaactgac gtgccggcgg agccacatag ttcggttcac cgtgttgtcg cggttcgtcc 190980
tccctatagt aatagtagtc gtcctcatag gggttgccgg cgtgagccag cgttacccaa 191040
cagcagccca ggccgacgag gaggcgcagc caccgcctca tggcggcttc gccagtcaat 191100
cgtctttagc ctcttcttcc cgtgaggtcc ttccggtggc gcggtgccga cctcggaccc 191160
agggacgtat ccacctcagg tacacacagc aggctacctg gacaccgaag ctgaacaagg 191220
ctacgtgttt cacaaactgc accagtacca catagaggaa tgtcaggtag cgtctctccg 191280
caaacagccg ttccaagtct gagggcgtta cccgcagcgg caaccagggc agcctggacg 191340
ccggccggca atggagcacg ctccggttac aggcactgca ggggtaaacg gttaacatca 191400
cgtaagagag tcgtgcgtcc acctgtggga gctcagtttc gtaacgtaga gccccgtcat 191460
tttccagctg gggtgcgccg accttgaaat gggtcgcgct ccgctcgtta ccccaggtgc 191520
cgtaggctct cggggccgta tcggagaagt tgccacgcac aagccaggcg gccacgagta 191580
ccccgtgctg gacgtaacat tcggacacgg aactggagac acggtagccg gacacgtccc 191640
caaacccgcg agggtactgg ggcagacgga cggacttgct atttgacaac ggacagatac 191700
gagacgacga ggacgcagac gactcgtcgc tggaccacga caaccggagc gactccttgg 191760
agcggctcga gagtacactt actgcgatca gacaccagtg ccagaagaag gaacaggtgg 191820
acggggacca caggatcata gccgccggca ccgcggccgg ccgcaggaag ccgcccggcg 191880
cgtcgtctgt gtgcgggagc cgaaacaccg tgcctcttta tatcgtcccg acgtgacgcg 191940
agtattacgt gtcaggggaa accccgtca cgacgaacgt gatttgtaag tgacgcgggg 192000
tgctgacggg gttcggcccg agaggtgacg gagcgcctca cgtcagtatg atgtccgatc 192060
cgcgtcagcc ccgacgtggt tgtggtcacc gaaacccacg tttatatgga cgttgagagc 192120
agcgcctgac cacatgattc atcataccat ttctcggaat cgggcccatg ccgggaaagc 192180
acattccttt tcagtaaaca acaatgacat cataacaaat cattttattc gcgaggtgga 192240
taataaccgc atatcaggag gagggatcgg gtgatgacgc aggccccgca gaacagtccg 192300
```

aaataaattt ttagtattgc cccatagtcg cctagatacc agaggtacgt caagttcatc 192360
aaaacgccca tcggcgtccc ggaatcgtat accgggcaca cgaagcgttc ataacaatcc 192420
cgggaggcga gtgttagggt agcagagtag tttcggggtc ggtttccttc cggcgacgac 192480
agttccgtgg gcagcagaat gtacagcgcc tcggtagctg tcgcggtgcc ttccacgagg 192540
atgggctgcc ggtgcctttc gtgattttcc ccgtcgtgta gccaagccga ggcccgcaaa 192600
gtcttaggcg aggggaattg tccatagagt ttcaccgcac ccttcagtac atggttctga 192660
ataacacagc cgcacgtgaa gtaggtaggt tctctcgtct cctccgtggc tgccgccacc 192720
actcccagcc accacaacag gcagatcgcc agagggttcc ggaggcttcc ccggcgtagc 192780
atggttttgg gttaaagcaa aaagtctggt gagtcgtttc cgagcgactc gagatgcact 192840
ccgcttcagt ctatatatca ccactggtcc gaaaacatcc agggaaaatg tcggtgcagc 192900
caacctttca catacagccc ccaaaacact tgaatcactg ccaccatcat cagcgtatac 192960
tgcgccgact taatcgtgag cgcgtagtac gccattagac ggcgatcttc gaacaatagt 193020
cgttcgatgt cctctaacga gctccacagg ggaacccaag gcacgaggca ccggggttcg 193080
cactctacat aataagtttg gcattggtgg caggggggaaa agtagaacaa cacgagtttt 193140
gtgcgttggg gaacacgata gtcccggagc cagtaacgtt ttgcgacgag gctttcggag 193200
acgtcctcca ccggcgtcgg cactcgatcc gcgtagccct ccagcgtctg gtagtacacc 193260
cggggtgtcg gcgtgggcac ggacaggttc ccgcgcaggg tccacagagc ctccaatcga 193320
ccgcccgatc ggagcacgca gcgcgcctcg gaatactcta ctcggtactc cgaaacatcg 193380
ggcagaggcg gtaacggctc cgtctccacc aagggcggag gttcatcgaa aagagtcaag 193440
gataattcag gcatactacc cgcgaccggg gcccagaggg ctagaataag cattacaaga 193500
ttcattctgt cttacaaggg aaggctgttc ccctgtctag actcaaaagc tgtaaggctg 193560
tcttatagca tgtagtcttg cacgtcatgg ggaacagggt ggtgatctag tgacgtcggg 193620
agaacacggt gttttagggt gcgggggaca aaggacagta cgacagatta ggtgatagaa 193680
acgttttttt tttatttatg aaaaagccag tgtgccgtgc ggcctagggc cccggcgtag 193740
tttggatacc agatgggggc cgtcaggggt actaccacga gcagaaacat aatgacttgg 193800
tccatgtata gcagcatagc ggtgcgcagc aggtcgccgt ccgtgtagca atttgacggt 193860
gagcgataaa gcaccgttaa tgtgtcgcgg ataagcacga tcttgaggcc gtagatgaag 193920
ctcacagtca gtgctaaaat gatgcgctgg tatggttccc aggactgcac ggcgatgaag 193980
agccagagta tgggaagcat gaagcttagc aaacagagga tggctaaccg tcgttgcatg 194040
ttccaggcca taagccaggc taggcccgta caccagacgc agagcatgga tgacaggaca 194100
taggcctgga ttaccacggt gcgatcgaaa cacagcccga tggtggacac ggatatcgta 194160
gtgagggtgg tatataccat gaccagcatc agggtcccgg gtcggcgccg acgttccagc 194220
cagtacgcgt ggcaacgcag agcgcagggt agcagtgtgc tccagaaggg cagtgtatcg 194280
cgcaggtagg gggttgtcac gcgccacggt atgagcatga aaaggatggt agtggctatg 194340
gtggcgctgg tctggaacac gacggtgccg tagagacgta ccatccagag aaagtgttga 194400
acgctccgca gggtgtcttc atctttggtg attacggtga ctcgacggat cggcggtggt 194460
gacggcggcg acacgggtgg gggtttctct ttcttatggc cgagtggctc gccttggtga 194520
aactggatct gtaccatgac gggtgctcga cgaacagtcg tcggggcttc aggtacccgg 194580
caagttttat agagaaaggg ggacgatggg tggtggctac gagccaccgc caccttcgca 194640
atacgaggat ctgaaggcgg caaagacggt cgtccagggc aggcgccaga ggttgggact 194700
gagcacgatc agcgtgattt taaacatggt caccagtcct acgtagatta gcagcgagcc 194760
gcgtaacgtc tgagcagccg gcagttcgtc gcggatgtaa cgcgtgccgt agaaagtcac 194820
ggtcatcata aggaagacga tggcgccgta gccgtagagt agaatacgct gatgatggaa 194880
cacggtctgg tcgccgataa cccaaagcgt gatgaaaaaa acgctggtga gcacccgtga 194940
gcatatgagc tcccaacgct taacgcgaaa gctgtcccca accatgacag cgccggtgca 195000
agctatccac agcgtgagga ccagtgtgta gtcgatgagg atggcgggca ggtcggagca 195060
ccaggtgtag aaaatcgtgg taacggagag gaggcctacg tagcccatgg tcaataccac 195120
gtcgtcgggg tgcctttcgc cctgtatcaa gaccaaacac cagagaaggg agggggcaaa 195180
aaccagcagc agaggggaag attcatgttg acatatgttg tgggaatcgg ggatacccag 195240
ccaaatcatt ccgcagaaag ccgtactgat ggcgatgtga aagaccacta gggcgtagac 195300
ccggacgagg acagcaaaac ggcgcagcca cataaggccg tggtgcagct gcaggaggga 195360
agcccattgc ggcgaatgta gcgacggcag cggcgggtcc atgaggcggg tgatgcgccc 195420
gagtgaacgg gtgagcgtct cggtggagtc ttcttataaa ccagcgggtc tcaagcaacc 195480
ctgctctgga acgtcgcggt ggtgctgttg aggatgacgc tgagcgtgcc gttgtcgatc 195540
agataatgat gataggtgcc gagcttggcc aggtagctga acatttggtc ccagcgtgcc 195600
gaccacacca cgggcgtgag catcaggagt gtggtgtgat agattagtgt ttcggtggcg 195660
taaagtatca gcgagctgcg gatgacgtgg ttcacgggca ttttggtggc gatgtagcgc 195720
acgtcttgga aaaggacggc caggatgcag cccacgaaca cggtgtagag acacagcaaa 195780
gtcttatgta accaggtgta agtagaagcc aggacgctga ccatcaccgt caaaagtgtg 195840
gaggtaaaaa gcgcgtcacg ccacacggag ctgagacggt gctcccaagc cacgccgttg 195900
caggccacga acaacgtcca cgttaggatg aggctagaaa tgccgatggg cgctgtggcg 195960
cacaggttga gcccggcggt ggtgaacgag agaagcgcca catacagcgc aaacaccagg 196020
ccgttgctgg ggtgtctgtg atcggtgagc tccagcgcgc ccagaaccaa tactggtgtg 196080
cagctaagca atagcggcga gggatcgtcg ctgcactcgt agcccagcga ggggtaaccc 196140
agccaaacca gcgcgctaat gagtacgctg aaagcggttt ccagcgtcag caatccgtag 196200
acacgcatga cgatcgcggt ccgccgtagc caacacacgg cattttcgga aactgtggac 196260
gctgtttccg aataccggga ggagatcgtg cttccctctt ccaaggatcg gaaagtagcg 196320
tccgtcgttt ccgcggacgc ggcttccctg gtacgctccg tttccgacga cgcggtttcc 196380
cgctgcgtgg aaactgtctt catgtcggga ccgcagcgcc cggcggcgta tccgcaaggt 196440
ctcgaagcta cagcttgtca gaggaaaagt aggtttgcaa aaaggtgcgc agggtcatga 196500
ttctcagcac catcagcaga gtgaaaacca gactgagaaa caccttgacg gccgccaaaa 196560
gcgcgcgttc cagcggcgtc tcgtagcgta cagccagggc cgcttcgtgg aaatgcgaga 196620
cggctagaca ggtaatgagc acgctgaagg acaagacgat cttaaagcac caggaccaac 196680
cacgcctcaa gatgaccacc acgattgccg tgaaggtcaa cgtgatcaaa gcatggacga 196740
ccacgatctg acggcggacg gtacgttcgg gagccaacaa cgctacgccg gtgcagctga 196800
gaaaggccag taaggtgaac aacgcggccg agatgaccaa cgtaccgtcc aggcagagac 196860
atatcacgat caacggcggc acgtgaagca gcgtgtaaaa gagcagaacg ccgatattgc 196920
tgggatgcga tgtttcgtaa cagtgaatga agatcactga cgtgacgggt atgacaaaga 196980
cgaggctggg cgaggactcc gtgagacaca gacgagaatg gtgaaaccac gtcgcgggcg 197040
ccgcgtagca gaaggcgctc aacaacgcgg tcaagccggc cagctgccaa cccacggcgc 197100
cataggtgtg cagcgccacg cggcaacagt cgacccaagc cagactgcgg gtcgccagcc 197160
gggtctcttg gatcccgggg ggcacgtaga tgaccgtgcc atcggtgggt acttgaaacc 197220
ctttttctct tctcatggtg cgctgcgttc tctggaaacg gctgctctgt ccgaaaacca 197280
gttccgaacg aaaatctagg gcgagagggt ggacaacggc gtcgacgacg aagcatggga 197340
caggtcgttc ggcgttaacg tcatcgcgtc ggacgacggt agttctaaga gacgtagatc 197400
gctcagcagg tcctgacagt tgcggattcg caagatcaga aaaaaaaggg aaatgaacgt 197460
aataaagagc tgtagcgacg tatgcgccac atcgcgtggc ataagaacgt gacggacgaa 197520
aaggacctgc tgcgaaaagt gaccggcgaa gataaggccc accgtgctgt agaagcccaa 197580
aagcagccgc aggggccaag tccagggccg cgtgaagacg atgagaacgt tgaccagaaa 197640
gaccacgacc cagacgccgt tgatgagggt aaattgatcg gacagggtgc agttgtcgcg 197700
acagatgaag actacttccg cgcagagcaa ggtgatgacc aacgtgagca caaacgacgt 197760
caacacctcg cggggctcct ggcaggcaca cgtgacacct agcgccggga tgtgcgccag 197820
gaggccggcg agtaatagca ccagctgtcg gaacggacga cggcagcgcg ggtgccggtt 197880
tcgctgagcg agaaccggtc gctcatagcg gaaatacacg aagagcgcgg aggccacagg 197940
caccaggagg agcacctcgg gcgcccagac aacgtgacaa ggaaagcccg gacgcgactt 198000
gagagtcgct gtagggaaga ccagagagaa gctacccaag acggccaccg ccgcggagat 198060
ttggaagagg agcaagccgg cgattcggac gacaacctcg aagcgatgca cccagcccag 198120
cacggccacc acggccgctt catcatagtc gtcgttgttg ccgctgtcga acagccgccg 198180
aaacacgatc tgtcgctggg tcgcggtggg aaagcgcaga cccatgacag ccggaggcta 198240
tatgaccgcg cgtctaagac gcgagatccg tggggggact tttagatgtt tgggcggccc 198300
gcagttctaa caggcttgat tggtggagac ggccggcgcg gcgggtgggg gaaacgacga 198360
gtttttccgt tacgccatgg ttcgcgtgag gtttctctgt acctcccgca aaaggtcaca 198420
gcccgaaatg gaggccgcgt tggtggcccc ggtggcgcgt gacgataacc aggtcatcca 198480
agcgatgagt ttgtctaatg agtcctcggt ggtgaagagg atgagaatga gcaggtacag 198540
gtacaccagg ttctcataga gacacaaggt gagcaggtcg gcctcggacc acgcgatctc 198600
aaacaggcgc gtggtgtcaa agaccgtgac gaccagcatg aagctgagcg ccatggcgta 198660
atagcccaaa aaaagtttgt gccccaacgg tacgggctgc aggtaaagtg cgatcaagaa 198720
cgcgataacg ccgatcacaa acagcgtgac gatgacctgc catcgacggt gattatggcc 198780
ggctagaccc gtgacgcagc tgcagaggct aaaaagcacg caagccaaga ggcccgagaa 198840
ggtcaccagc gtagaggagg agcaggcgct ggccacgatc accgaaagcg tcgtgagcac 198900
gctataaatg gtgagcaggc ccgggctcgg cggcgacgtg aacgatcctt catcgcgttt 198960
gccgtgcagc agggccaaac agatggtggg caccatcaaa ctcaagggcg gcataaagcc 199020
ggtgcaacag agaaagacgg tgcctttaag atgcggaaaa gccagcacca ggcccagaca 199080
gagcaagaag gtgcaggtgc cctgcacggc cacggtgctg tagacccgca tacaaagtaa 199140
aaagcgacgt acgtcgttcg tcgagacgga ggaaatcata atgactccgc gcgagggtcg 199200
cgggggtggg ggcgcccagg ccgtcccggt ggcctctgag ttcggagaca tgacggcggt 199260
ggctatcaaa aggcgcgtat gagaaaccgt ttatagagtg taatagaatc accgtcattc 199320
ccacacggcg ttcccccata aagtcacgtc acactcgagt aagcgtgaaa aagctttatt 199380
gttgaataaa aaacacgagt acaacaccga gttgcggtgt cctgtctgtc tactgggtgg 199440
ggggggttca tcgtctgtct ctagagggaa ggtggggaac gtctaagcga gcgggagcgt 199500
gtcatctccc ccatcttttt acaacaagct gaggagactc acgccgtcga tgcgtccgcc 199560
gtgtttctcg gcgtactgct gcacccagac gtggccgcta aagatggcga cgctcatgtt 199620
taggagactc atgacgatgg tgtacaacac gacgctgaca catacgctgt ttttagacaa 199680
cgttccacgc tggtagatga gatccagggt ctcgtaaata agcacggccg aagcggcggt 199740
caccaccagg acgtagagtc cgctgtagat cttgctgacc cacagcacgg gcgaaaagta 199800
aagcaatagg taaaagacga tgacggacca gccgtagcca atcccgatga ctttccagcg 199860
cgtgggattg ttgccggcca ggtaggtgag accgctgcag agaacgaaaa agaccatcac 199920
cagggcaaac gacagaccga tgacgcgcct ttctccgcaa aagcccgtgc acacggtgat 199980
gccggtgttg atcagcaagc acgccaccgt gagatgagca aaattggtgg tgtgtgggcg 200040
aaactcggcg aaaccgcgta gcatagccag cgtggacacg ggtacgatgg aggatagggc 200100
tggcactatg ccgttggcgc actgtccctg cacatcgggg aaggcgagcc aagccagcaa 200160
gcagaccgtg agggtacaag ccagctgcca cacgagcccg tgatagacct ccatgagcag 200220
cttaaagcgt ttcaaccatt ggaagagctg ctgttcggcc accagcgcgt ggctgcgatg 200280
gagcggcacg atggtgaccg tcggcgactc atggtgttcg gaaaccgagg cggtgtcgcc 200340
catgctgccg cttacgaccg ctgtcggtct aaggtaggcg tcgatgaaac agtccgtctt 200400
atcagcaccc ggttaccgcg gatttgattg acgtcacgag tgtggtcaaa ccgtggcggc 200460
accctgtatc cgacccgtcg tcatgggctc cacaaccaga gcctcagaag atggtacatg 200520
ccgatgaata aagccacatt ttcgacatag aggcgtagcg agggctgaaa actctccggg 200580
aaagaactct gacaggtgat cagggacaga tcgtgaatta gcatcagcgt caccgtcaac 200640
agcgtcgtcg cgtgtaaacc gagaaagaac ggggccgcgg cccgcagcag ccaaagtccc 200700
agcgccgtag cgcagagcag agacaggacc gacggtagcc acagccgccg gagagacgcg 200760
ccaggatcgc aacccaaaag cgaggccccc aggcagctga gatctaccgc cagggcgaga 200820
agagccgcgc cgacaaaggc ctgcggcgac ggctggcaca tcagcaaggt cagaaaggct 200880
agcgcgtgcg gcaggcagta agccaacagg agtgggagtt tgcggggaca acggtcgatc 200940
gacggaccgc gtagcagcag gaacaggcag ccgacgggca cgacgaggct gagatgagaa 201000
agcggcggtg ggtcgtcgtc ccgtccccgc tcgcatagct cggccaccgg tggcggcatg 201060
agccaccagc tgagcacgct gagggcgacg gtggcggtaa gctggaaggc gacgaggacg 201120
gaggcgcgca gccataccgc cagcctctct aggtagggga ctacctcctc gacggtccat 201180
tctagcggga cgacatgaag catggcgaca agcgcggctg ctgtgaaaac gggcgcggtt 201240
ttataggcat taggacttcc ccgtcgtact ggcggctgtc aaagtcccgt tgtccaaagg 201300
cgcgccgtcc gaaagactaa tccaacgggg acccgagagc atgagcaaca acgtgagaaa 201360
gatggccatg ctgtccaggt agagacagac ggcgtgacgg atgcattggt taggtgggca 201420
gaaaaagatg accatgagac tgtcgtaggc cagaataccc aaaaagaagc tgatagagaa 201480
ggcgcacaac gtcaccacta tcttctgcag ccaatcggcg tcgcttagca gagcgagcgt 201540
gaggaacgaa agcagcatca ccacgtagac gcagctgatg catttccagc gacgtcggtc 201600
acggccacct agaaacgcca gccccgtaaa ggagataaac aacgccaggg tcatcacgta 201660
ggaacctact agtacgcggc tttcagagca catttggaag atggccgccg tcaggctgtt 201720
ggccaacaga tagatgaaaa gcaccgtggc gttactaggg tgttcgttgc ccaacgtgta 201780
cgtgatgaac atgcagacga tgggcacgag cacggtgaga aagaagctgt agttctcgac 201840
gcaaaagttg cggttttgtg ggaaccccaa ccaaaaaacg cttcccaagc cgaagctgaa 201900
agccagctga aagatgaaga tggcgtacac gcgcagccat acggtgaact ttttgaacca 201960
ctcgagagcc tccatgcggg agagcagcag cgcgttagcc tcctgcgcct gcatggtggc 202020
gacggtctcg gcacaaagcc gctgcggcgc acctaccctt ctcttataca caagcgagcg 202080
agtggggcac ggtgacgtgg tcacgccgcg gacacgtcga ttaggagacg aactggggcg 202140
acgccgctgc tgtggcagcg accgtcgtct gagcagtgtg ggcgctgccg ggctcggagg 202200
gcatgaagta gagcacggag acaaagaggt acatgaggtc catgtacaag cagagcgcgc 202260
ccgggatata actctcatac tcgatgtcgt gcaggatgtc ctgcgtatcg cacaccaccg 202320
aggtcacgat gacggccaaa ccggctatca tcaccaggat ctcacttacc gcctcgggaa 202380
aaagagaaaa tacggcgaac agtaagagaa tcagcgtgga tgcgcccgtc aatagggaac 202440
gctgtaattc cacgtcgcgg gcaaacagat acgtagcgag cgtgaggaaa caaaatagcg 202500
tcactgtggc caccatggca taaatgactg aacgatgact aaagtggaag cctgacgccg 202560
tgacagccac gctggtaagc aacgtgtacg tcagtaagat ccatacgttt ttgggaaagt 202620
tgggctcggc ccaacgcaac agacctaggc acacgatgga gatcattaag caagacagcg 202680
tcagacgcac gctggaaaag agctgctcca gccggtgcgg caacaccagc cagcaaaagg 202740
cgcagacgct cataaggatg aggcattgca cccagataag gatgtagatg cgcagcagga 202800
agaccgaccg ggctatctgg acctgaccgc ggagcgacat ggcggcaacg ccggcggtta 202860
tcgccgagat tcgtctaaat acacgaagcg aactagaaaa cgcacacacg tgatttgcaa 202920
aaagaaagca gctgccggct tattatttta ttaaaaattt atctgtgcag aatcataagt 202980
ttatgatgaa taaaaacggg gaaagggaat ctgcttttag ggacccgggt ctggtccgtc 203040
gtctcccatc tggtcgggtt cggggatggg gacctgtttc agcgtgtgtc cgcgggcgtg 203100
catggctttt gctcgccggc cgcgctgtaa ccaggcctct ttctctgtgg tcggcgagtc 203160
ttccgacggg tagggaacct gggagtccat cgcttcaggc ccaccgctcg ttccctcgac 203220
cgtcgtgtcg tcctcgtttt cgctattaca cggggtttct ggagtatcgc ctatacggtt 203280
ggcgattctc cgggggcggc cgctctcgtc ctcgtcgctg ctatcgccgc ccggtaattc 203340
gacgccgcat tcgttgtacg gagcgcggca catgggcggc ggaaagagct tgggcatgcg 203400
aaagcagcgt tgtccatcca cggtctgcgt ggtttcatcg ttatcctccc ataatccccc 203460
ctgtagcgcc ggcagcgttt cgacgctgtg agaggggaag gcccagttct ggttgtcttg 203520
cagcgcgccc gtgggcagta ggtccgtgcg gccccatgcg ctgctgttgt tgggtacctt 203580
gtcagtgccg cgagtaggtc gcagaaacca gtccagagcg ctctctagct gcgagcgtgt 203640
gatggtgccc agtgcgccgt gccagcgcag cacgtctctt ttcagcgtgt ggtgacagac 203700
gggcagctcc tccaaccgac actcgccgcg caatccgcgg tcgaagcggc agagaccacg 203760
cagtttaagc agaccgcact tgagaaacat gtgaaaatta tcggcaatgc gatacaggtc 203820
tgagtcctcg atcttgtgta ggtagaccac gccaaacttg tcgagcagca ccaggccgct 203880
gggcacaaaa ggcccgtagg ccaggtaata gcccacgagg ccgacgacgt accactcgca 203940
gcacaagcgt tgacgaataa agttcagaag atcgcgaaag tccgcggccg gcatgtggtc 204000
aaaaggtctg caggcgcgca ggccctcgat ggagccaagc atgagcaacg gctccacctc 204060
ggtgcgaccc ggcgtgcgga tgaccaggtt gagaccgctc atttcgcggg ccgtcttggc 204120

-continued cacggccgca gcgtcagtgg ggtcggtgca gaggaatttt tgcacatgat agcgcggttc 204180
ggtggtggcg aacggcgttt gtgggtgccg atacacatat tcgcaccaga gtaagccgtt 204240
cttggaaaag gctttgatat cactggccac ctcgtagagc ccgtcggtct cccagtcgta 204300
gacgtagacg gtgccgtaat gacttagcat gagcacacag ggcagttcct gcgcctgctt 204360
ggtgtttcgt gttagatcgc tgtcgggtgg acgtacggct aatacaccga cggcttccag 204420
ggtgtcatcg cagcagagat agtcggcggc cagagaacgt gcgtaaatct gcgggatagc 204480
ggcctgttcg cgcatcacta ggaaccagtt ggcggggttg cgcagtgcta cggtggttcc 204540
ctggtgacgc tgcacgtagg ttctcagcgc cggaggatcg tactggcgca gatagaggcc 204600
ttgcagcatc gataacgtct tttgaaagac ggtgtttcta aattggaaaa cgccgtagtc 204660
gcagcggata gcatcttcgc agcgctcgtc gcgctgtcgg agataggtgc cccaggcttc 204720
ggcggcggct ttggtgagta gggacatgcc ggcaaagccg tctcgacagc gaatcggata 204780
aagcgcgctg cgcgaaagct taatatagga gcagcgtcag acgaatcgcg gctggtggcc 204840
cggggggtgg gacgcgccgc ctacacaaag tgctcccgaa aatcgaaact cttgacccac 204900
tccggagaca aatccgtatt cagattgatg cgtcgcgctt ccacttcggc ttccgaaacc 204960
tcggcctccg tccggtaggc gttaacgata cgctgaccca ggtgccaacg ctctttctct 205020
gccaaacgcc gttgctcaaa ccattcgtct acgtccttga ggtcaaagac agtgtcctcc 205080
tcaaggtcaa agcctaggtc ttcccactcg tcgtcatcgc tctcgtggcc ggcggccata 205140
cgcgcggcaa ccgcgtcttc ccctcctctt ctttcaacgt ttggtaccac gttgttttct 205200
tcgggttcca taggttctgc gccactgtcg tcatcgtcct ctccctgctc ctcatcgtcc 205260
gccaaggcgt cgtggattac ctccaggttc tgattgtcgg gtacgacgtg gttatcttcg 205320
tcgtcgtcgc gtggcatggg tggcggccga cggcggacga ccggcatggc gcggccgtcg 205380
tttccttcgt cttcctcttc accgtctccc agggaacgcg gtcgacggcg ttccgcgaag 205440
tcgccgcgga ccacgcgcgc ctgccagatg gtaaatgcgt cccaaccgtc ccagttattg 205500
agcatttcgg cgcggaaacg gtcgcctcga cagagccagc gaaactgccg cgcgtagtcg 205560
cggtctacgc cgctgtcgaa catggtaaag tgcagacgcg ccgcttcgcc catgtgtacg 205620
cagcctccgt tgcgttccag cctggccgcg cgccgcagac cgtgttcgta gcggcgacgc 205680
acgtacacct tcatgaggcc ggcgcgaaaa agttcctcta ggctgtcagc cagacggtag 205740
atttcaccgg caagacgctg caggggcggc gagcggtcca ggtgcgactt gacgatcacc 205800
acgtaaaaac gacagaaacg gtcgaagatg atgaggaagg acgtgtcaaa aaaaccacca 205860
gcgcggtagg agcccacggc gcccagcagg taccagcggc aacgcagttg cagcgtgacg 205920
tacatttcgc actcggccaa gcgggcggct ggcgctacct cgaagggcca gcagtccgtc 205980
aagcagccga aactggtcag gagtttcaac gttttggcat gacgcccagg tgtgtgaaag 206040
ttcacgtcgc gtccgtggtg ttcaccaacg caggcggcca acgcgtcggc gtcacgagcg 206100
tgacgcagca gcatcgctac cacgtcgtgc ggtacccgcg tagcaaacgg cgtctgtggc 206160
tgacggtaca cggcttcggt gtacatcata ccgtaacgcg ccagctcgtc cagatgacgc 206220
gcgcacaaca gcagaatctc ttgcgagggt tcgtagatgt agaggcgcgt accgccaccc 206280
atgcagagca ccagctccgt ttcttcgtag tgatcttcca ccatgatcac gcacttgcct 206340
agcacgataa ggcgttcggg gcaacaaatc acgtcgtcca gcaactggtc gcgtagctcc 206400
ggcatggtgc tgccgggccg cacctgcagg aaccagttgt gcggaatgcc gagcgacagc 206460
acctggtcga cgtggttacg gacccagtcg cgaagcacgt cggcgctgta ctggcactca 206520
aagatgccct gaaagtcgcc catgacccgc agaaaagttt cgtagcgcgt gtggcaatag 206580
aggaattcat cgtttcgcgt aaacgtggga gctccgtctt cccaacgtgt acgccacatg 206640
tcaaaagagg ccgccagcta gacaccccag aaaagaagca gagaaggaga cttctttgtg 206700
cgacacgttt tattccgcgt cctccgctcg acgttcaaat ctggatgtac tcgcgcacac 206760
ccgtcaggct ctttaaggga aaagggtccg agtacgtcac taaccgcgac tgatgcacca 206820
gggcggtaat cacccgctcc gcgccctcgc gcgtcgacga acgcgtcgtc accaggcagt 206880
gcagccgcgg gcccgtatcg tcctgatgac cagcggcctc gcgctcggct gcttccacac 206940
cgacaatgtc gggatccaac acgtagctct gcgagttggt gtcgtagcgg tgtagcacca 207000
acgtgttggg gtccagacgc tcccacgcgc cctcgtgcgg gtcaaaacgc tccgttaaac 207060
agagccagtc atactgctgc tgcagaatac gccgctcgcg ctcgcgtcgc tcatcgggca 207120
acgcggcgtc ttcgttgaag agaatgtccc gcttgtggtc tacggcacgc tcgtggtggt 207180
gcgggcacag atgacggtgt tccatacgcg tctgacgttg acgctcgcgc tcaaaacgcc 207240
ggtgtcgaaa gaccattttc agcaacccca tgcggaaaaa ctccgtgatg gtgttggcaa 207300
cgcgccgcac atagtggttg gggtcgtcca tctggatggc gtacacggca ccgaaccagt 207360
ccagcagtac cagcacttcg gccacaaagc tgcgtcccgg tcgcggacgt cccgtcacgc 207420
ctagcacata ccacggcgtg gccagattag cacggacagc ccaccaccaa cgacggctct 207480
ccacctcggt gagcgcacaa aagggccaaa tgcggtgtaa ttgctgcacc gttttcatca 207540
gccgcataat caccgtgccg taacccggtg tatgcaactt cacgtcgcaa cccaggattc 207600
gttcggccgt ggcgtacgag ccctcaggcg tggtgtcatt gagaaacaaa acatgcatgg 207660
tacgcgcgcc cttagggtat cgtcgcggaa caggtaccgt cattctccgc aaagtggtgt 207720
gaatcacgtc gcgatacgca atctccgaac gtgacacacc gtaacgtgcc agttcgtcca 207780
ggttgtgcga taccaacacc atgtactttt cacgagtgtc gtaggcgtag acgcgagaaa 207840
agcgacccat aaaaaccacg tacggggtag ccaccatgcc atcatggtga tcgcgacgtg 207900
gctcgggcaa caaaataaca gcgtatccca acggcgtcag cggctcgcgg caacagatga 207960
gctttgacgc cgcctgtttg gcggcggtaa tgatcccgtc ctccgtacgt aacatcacat 208020
gccagccctt ggggggaccc aaggacagac agcgtccctc gttacgatga acgtaacgcg 208080
tgatttccat tggctccagg caaaagaaca gttccttaaa atcccgcaac acttgtcggt 208140
ataacgccat gggatcctcg gccgccacag gcagcgcggg gagctccggc ggcataactg 208200
cagcgccgtc agggccagaa cccgcagccg gatccatcat tgcgcgacac tctcagccgg 208260
acaaccggcg tcactgacag aagccgagcc aaatacagag aaagcaacgc tacaccgtca 208320
ccccgctccc aagcgccgcg aaaagtgctc cgatttttca ccgtcgttcg cgacgttgat 208380
ttgcctcggt ctgagaaccg acctagcgtt cggaccggtg cgcagaaaca gccggcggtc 208440
cgagccactg agcggttcac agccccggcc gccgatagtt accggagaga cgttcgagct 208500
gcaggtacat cggcgctccc cgcttcgcca ccccgcgccc gccccagttt atactctccg 208560
acgccccgtc caacgcgcct gtggagggcc aatcggaccg cgggagctct ccaagtggat 208620
gacaggcaca gccgggtgcc cgaccgtaaa gagccctcat ccacctgaac agaccgctaa 208680
ccgaaggacc ccgagtcgcg tccgtcggtc ccgacgtccg tcgtcatctg gctccctgct 208740
gttggctacc tctcggattt caaaaaagag cacgtgccga tgacggtgca caggaaagag 208800
ccaaagtgtc acagcgtcct tttttatttg tattcctttc ctgttttgta ctcgtaaact 208860
gttgatgttg tttttacatc caaaagggca agtaagaaac aggatgaggc atggtaggtt 208920
tgggcgcggg gcggccctcc agcacggcgg cccgggccgc ccggcgggtg agcacccggc 208980
gttgcgccgt atctatcttg tgtttcttct gtgtcttttt cctatcttgt tccgcgacgg 209040
cctctttcat cacgttcagc atgcgttcct cgacgccctc caggggtcct ggggaggagg 209100
gagtcctagt gaggcttcca atgttgtttt gtggattttc ggtttcctct tcttggtcgt 209160
catcgtcgga cgtgtcgtct tcctcttgat cctcttcttc gtccgaatag tagacgcata 209220
gtccttggtt catcaggctg ggattcatca ggttctgacg gggaatccgc tgttgtagac 209280
gtttaaccgc ccgttccagg cgagagctca tgccgcacca gacgctgtaa cgccgcacgg 209340
gcccgtagcg ggctgtttgt tcgcgtacat gatcgttgag ctcttgccaa tattgtttgg 209400
cacactccag atcggaggtt tgtggatagt cgggtcggat ccgcggatcc caactgacat 209460
cggcggtgcc agagacttcg tccagactgt tacgcataga gcaccagtcg ggtcggacga 209520
taaacctgtc cttgcggatt aaccatttat aacgtagttc gtgatggcgt gtagaggccc 209580
gtacacgctc cacggtccca aagcggtccc agaagggaaa gttttcgtga gggcagcgac 209640
ccggcacttc cagacgttcg gcgtcgtcca cggcgtagtg aaaacgccgg ccggcctggt 209700
aaattttgag cagacccacg gttaacaaca tgtccacgct gtcagccaac cgccagatct 209760
cgcgccgaga cacgtcaaaa tagaaaaatt cgcaggctcg gtcgaccagg atcacgaaat 209820
cggcgtgaaa gacgccggag ggtagcgact cgcccaccac acccattatc atggtttcac 209880
agcataagcg gtccacaaag aacttcaaca ggtcgttgaa ttgctcagtc tccatacaga 209940
tgaagggcca gacgcctttg aggttctcgg cctggccgca gagcagcaac ggacgcgtca 210000
tctcgcctgg agtgcgcaga ggcacgcatt cgccgcgata acgacaggtc acacgctgca 210060
gttcgctgat gctgttgtcg tgcaggcgaa ggtcgcagat aatatgatcc ggttgcgtgg 210120
ttagcagcgg cgtgcgcatt tgctcgccgt agatggcctc gcagtgcaac agcccgtgtc 210180
gtgcaaaatc gtccagactg tgcgccaggt agtaaagcac cccgcgatcg cggtctagac 210240
accacacagt ttcgtaacgt cctagcagga gcaccagacg ggcctggcta ggcggctcta 210300
tctcctctac gtagacaaaa aagtcgtcgt cgtctgagtc ctcgtcctcg gaagaggatc 210360
tcggcccatg tactctgggc aacacggtgg tcgaaaactg caggacgccc agggactcga 210420
gcgactcttc gcagcagatg agctgacccc agggcgtttc gggcccatcg gtgacggccg 210480
cgctgccaaa gatgtcctca aactctacaa aatctagacg ccatccgggt ggcgctgaga 210540
cgggaaggct aatgttcatg tcagcgtagc tacggactaa gtggcggatg tcctgacgcg 210600
agtcttgaca gagaatgagt tttcgtagac ccttgagggt tcgccgaaca acggccccag 210660
acgcgtagcg ataggactgg cgcatggtgc cgcggcgtgg agaggcactt ggcagcctat 210720
tttatggagt ttcttcaatg acgtggcttg ttcacgtcgt tcgtgggctg cggtcggcag 210780
ctccggtctg taaaccaccc gaaaagactg acatcgacgt caaagactca cgtaatttgg 210840
aacatgtgca actgcaaagt gcgtcagaat agcacgtgac tttgggacat aaaaagtacc 210900
gtgagttata gacgtggttt ttgtgattga cacttacagc aggtaagaca agggacgata 210960
aaactgtatg tgaggaacct gggtgcttag acaactaacg tgttatgctt tttacaggac 211020
cgttcagcag gtaacactac ctgtaaggtg atgaccacct ctacaaacca aaccttaaca 211080
caggtgagca acatgacaaa tcacaccttg aacaacaccg aaatctatca gctgttcgag 211140
tacactcggt tgggggtatg gttgatgtgc atcgtgggca cgtttctgaa cgtgctggtg 211200
atcaccacca tcatgtacta ccgtcgtaag aagaaatctc cgagcgatac ttacatctgc 211260
aacctggcta tagccgatct gctgattgtc gtcggcctgc cgttttttct agaatatgcc 211320
aagcatcacc ctaaactcag ccgagaggtg gtttgttcgg gactcaacgc ttgtttctac 211380
atctgtcttt ttgccggcgt ttgttttctc atcaacctgt cgatggatcg ctactgcgtc 211440
attgtttggg gtgtagaatt gaaccgcgtg cgaaataaca agcgggccac ctgttgggtg 211500
gtgatttttt ggatactagc cgtgcttatg gggatgccac attacctgat gtacagccat 211560
accaacaacg agtgtgttgg tgaattcgct aacgagactt cgggttggtt ccccgtgttt 211620
ttgaacacca aagttaacat ttgcggctac ctggcgccca ttgcgctgat ggcgtacacg 211680
tacaaccgta tggtgcggtt tatcattaac tacgttggta aatggcacat gcagacgctc 211740
cacgttcttt tggttgtggt tgtgtctttt gccagctttt ggtttccttt caacctggcg 211800
ctatttttag aatccatccg tcttctggcg ggagtgtaca atgacacact tcaaaacgtt 211860
attatcttct gtctatacgt cggtcagttt ttggcctacg ttcgcgcttg tctgaatcct 211920
gggatctaca tcctagtagg cactcaaatg aggaaggaca tgtggacaac cctaagggta 211980
ttcgcctgtt gctgcgtgaa gcaggagata ccttaccagg acattgatat tgagctacaa 212040
aaggacatac aaagaagggc caaacacacc aaacgtaccc attatgacag aaaaaatgca 212100
cctatggagt ccggggagga ggaatttcta ttgtaattcg atcctctttc acgcgtccgc 212160
cgcacatcta tttttgctca ttgcacgttt cttcgtggtc acgtcggctc gaagaggttg 212220
gtgtgaaaac gtcatctcgc cgacgtggtg aaccgctcat atagaccaaa ccggacgctg 212280
cctcagtctc tcggtgcgtg gaccaggcgg tgtccatgca ccgagggcag aactggtgct 212340
accatgacgc cgacgacgac gaccacggaa ctcacgacgg agtttgaata cgaccttgga 212400
gcaacccctt gtaccttcac cgacgtgctt aatcagtcaa agccggtcac gttgtttctg 212460
tacggcgttg tctttctctt cggttccgtc ggcaacttct tggtgatttt caccatcacc 212520
tggcgacgtc ggattcaatg ctccggcgat gtttacttta tcaatctcgc ggccgccgat 212580
ttgcttttcg tttgtacact acctctgtgg atgcaatacc tcctagatca caactcccta 212640
gccagcgtgc cgtgtacgtt actcactgcc tgtttctacg tggctatgtt tgccagtttg 212700
tgttttatca cggagattgc actcgatcgc tactacgcta ttgtttacat gagatatcgg 212760
cctgtaaaac aggcctgcct tttcagtatt ttttggtgga tctttgccgt gatcatcgcc 212820
attccacatt ttatggtggt gaccaaaaaa gacaatcaat gtatgaccga ctacgactac 212880
ttagaggtca gctacccgat catcctcaac gtagaactca tgctcggtgc tttcgtgatc 212940
ccgctcagtg tcatcagcta ctgctactac cgcatttcca gaatcgttgc ggtgtctcag 213000
tcgcgccaca aaggtcgcat tgtacgggta cttatagcgg tcgtgcttgt ctttatcatc 213060
ttttggctgc cgtaccacct gacgctgttt gtggacacgt taaaactcct caaatggatc 213120
tccagcagct gcgagttcga aagatcgctc aaacgtgcgc tcatcttgac cgagtcgctc 213180
gccttttgtc actgttgtct caatccgctg ctgtacgtct tcgtgggcac caagtttcgg 213240
caagaactgc actgtctgct ggccgagttt cgccagcgac tcttttcccg cgatgtatcc 213300
tggtaccaca gcatgagctt ttcgcgtcgg agctcgccga gccgaagaga gacatcttcc 213360
gacacgctgt ccgacgaggt gtgtcgcgtc tcacaaatta taccgtaata aaaaagcgct 213420
acctcggcct tttcatacaa accccgtgtc cgcccctctt ttccccgtgc ccgatataca 213480
cgatattaaa cccacgacca tttccgtgcg attagcgaac cggaaaagtt tatggggaaa 213540
aagacgtagg aaaggatcat gtagaaaaac atgcggtgtt tccgatggtg gctctacagt 213600
gggtggtggt ggctcacgtt tggatgtgct cggaccgtga cggtgggttt cgtcgcgccc 213660
acggtccggg cacaatcaac cgtggtccgc tctgagccgg ctccgccgtc ggaaacccga 213720
cgagacaaca atgacacgtc ttacttcagc agcacctctt tccattcttc cgtgtcccct 213780
gccacctcag tggaccgtca atttcgacgg accacgtacg accgttggga cggtcgacgt 213840
tggctgcgca cccgctacgg gaacgccagc gcctgcgtga cgggcaccca atggagcacc 213900
aacttttttt tctctcagtg tgagcactac cctagtttcg tgaaactcaa cggggtgcag 213960
cgctggacac ctgttcggag acctatgggc gaggttgcct actacggggg ttgttgtatg 214020
gtgggcgggg gtaatcgtgc gtacgtgata ctcgtgagcg gttacgggac cgccagctac 214080
ggcaacgctt tacgcgtgga ttttgggcgc ggcaactgca cggcgccgaa acgcacctac 214140
cctcggcgct tggaactgca cgatggccgc acagacccta gccgttgcga tccctaccaa 214200
gtatatttct acggtctgca gtgtcctgag caactggtta tcaccgccca cggcggcgtg 214260
ggtatgcgcc gctgtcctac cggctctcgt cccaccccgt cccggcccca ccggcatgac 214320
ttggagaacg agctacatgg tctgtgtgtg gatcttctgg tgtgcgtcct tttattagct 214380
ctgctgctgt tggagctcgt tcccatggaa gccgtgcgtc acccgctgct tttctggcga 214440
cgcgtggcgt tatcgccgtc cacttccaag gtggatcgcg ccgtcaagct gtgtcttcgg 214500
cgcatgctgg gtctgccgcc gccaccgtca gtcgcaccac ctggggaaaa gaaggagcta 214560
ccggctcagg cggccttgtc gccgccactg accacctggt cactaccgcc gtttctgtcc 214620
acgcggatac ctgacagtcc gccgccaccg taccagcttc gtcacgccac gtcactagtg 214680
acggtaccca cgctgctgtt atatacgtca tccgacatcg gtgacacagc ttcagaaaca 214740
acgtgtgtgg cgcacgctac ttatggggaa cccccggagc ccgctcgatc gacggctacg 214800
gttcaggaat gtacggttct taccgccccg aattgcggca tcgtcaacaa cgacggcgcg 214860
gtctctgaag gccaagacca tggagatgcg gttcaccata gcctggatgt ggtttcccag 214920
tgtgctgctg atactggggt tgttgacacc tccgagtaac gggtgcaccg tcgatgttgg 214980
acgaaacgta tccattcgag aacagtgccg ccttcgaaac ggtgcgacgt tctccaaggg 215040
agacatcgaa ggtaacttca gtgggcccgt cgtcgtggag ttggactacg aagacatcga 215100
tattactggc gaacggcagc gacttcggtt ccatctcagc ggactcgggt gtcctacaaa 215160
ggaaaatata agaaaagaca atgaaagcga cgtcaacggt ggaattcgct gggctctata 215220
tatacaaacc ggcgacgcca agtacggtat tcgtaaccag catttgagta tacggttaat 215280
gtatcctggg gaaaaaaata cacaacagct gttgggttct gatttcagtt gcgaacgtca 215340
ccggagaccg tccacgccgt tgggaaagaa cgccgaagtg cctcccgcga cccgcacgtc 215400
ttctacatac ggcgtcctca gcgcttttgt agtgtggatt ggatccggcc tcaatatcat 215460
ctggtggacc ggcatcgtgc ttctggcggc ggacgctctc ggacttggcg agcgttggct 215520
gaggttggca ctgtcccacc gggataaaca tcacgcatcg agaaccgcgg cgctccagtg 215580
tcaacgcgac atgttacttc ggcaacgtcg acgggctcgg cggctgcacg ccgtttctga 215640
aggcaaactg caggaagaga agaaacgaca gtctgctctg gtctggaacg ttgaggcgcg 215700
accctttccg tccacacatc agctgattgt gctgccccct cctgtagcgt cagctcctcc 215760
tgcggttccc tcgcagcccc ccgagtattc gtctgtgttt ccgcctgtat aaaaataaag 215820
agacgggagg ctgatcgcgg ccttcagcgt ctcatttgtc tttactctcg agtgcggtcg 215880
gtgtctcatc ggtgagacga ggccgccgcc cgacaagttc gatctcatgt cgctcttgga 215940
gcgcgaagag agttggcgtc gcgtagtcga ctactcgcac aacctgtggt gtacgtgcgg 216000

-continued taactggcaa agccacgttg agattcagga ccaggagccc aactgcgagc agccggagcc 216060
cgcacactgg ctagaatacg tggcggtcca gtggcaggcc cgggttcgcg attctcacga 216120
tcgctggtgt ctctgcaacg cctggcgtga tcacgccttg cgcggccgtt ggggtacggc 216180
gtattcctcg ggttcctcgg cctcttcctc cggtttcgtc gcggagagca agttcacctg 216240
gtggaaacga ctgcgccaca gtacccggcg ctggttgttt cgccgccggc gagctcgata 216300
cactccgtct aactgtgggg aaagtagcac tagcagcggc cagagtagcg gtgacgagag 216360
taactgcagt ctacgcaccc acggcgtgta cacacggggt gaacaacact aatcgataag 216420
tcgcgtgtag gcgactggct acatcaaccg gatatctgcg gggatttaaa aagacgaccc 216480
gttgtcatcc ggcttagagc aaaccgtcct tttatcatct tccgtcgcca tggctatgta 216540
cacatccgaa tccgaacgcg actggcgtcg tgtaatccac gactcgcacg gcctgtggtg 216600
cgattgcggc gactggcgag agcacctcta ttgtgtgtac gacagccatt ttcagcgacg 216660
acccacgacc cgagccgaac ggagggccgc caattggcgg cgacagatgc ggcggttaca 216720
ccgtctgtgg tgtttttgtc aggactggaa gtgtcacgcg ttatacgccg agtgggacgg 216780
caaagaatcc gacgacgagt cgtcggcgtc ttcctcgggc gaagcgccag agcaacaggt 216840
ccccgcttgg aagaccgtgc gagccttctc gcgggcctac caccaccgca ttaaccgggg 216900
tctgcggggc acgcccccac cgcgcaactt gccgggatac gagcacgcct ccgagggctg 216960
gcggttttgc aatcgacggg aacggcgaga ggacgatctt cgcacgcggg ctgagccgga 217020
ccgcgtggtg ttccagttag gggagtaccc tcctcgccgt caccgggaaa cttacgtgta 217080
agaacacggc gtgacaataa acaacatagc gtaaatcccc gtgtgatgtg tgtgattgac 217140
gttcgggaaa catgtcccca tcatcagcgt cacaactgac gtgggttggt cactgacgtg 217200
caggatgtta cgcgagtcag agaatcgcat aagaacgggg tggtgagcgg gttcccacag 217260
gagtctctgg cgcaaaagca ccatgagcct caggttcccc gagagggcgg gttacgagaa 217320
actgggatac cgcccgcatg ccaaacgcgt gtgggtgcat gacccgttgg gattgacgcg 217380
gtttatcatg aggcaactca tgatgtaccc gctggtgttg ccgttcactt ttccgtttta 217440
cgtgccgcgg tcctagcacg tcagtggtga cgctgataat tgcaacatgg cccatgacga 217500
acccgcttgg gacgaacgtc aataccacgt caaaccaccg tgacttggct gaacgttgaa 217560
acataaagcc aaagcgccgt cggcacttgg cttcagagca gcgcctcggg gcgatgcgac 217620
ggcgatgaac ttagagcaac tcatcaacgt ccttggtctg ctcgtctgga ttgccgctcg 217680
tgctgtcagc cgcgttggtc cgcatggctc cggactcgtt tatcgtgagc ttcatgattt 217740
ctacgggtat ctgcagctgg accttctggg accagtggtg gcggggaatc gctcagtccg 217800
gacctggaga gagcaggcgg accgagccag agggaccttc gttcggcgtt caggccttaa 217860
tactagccac atcttacctg tcggcggcct gtctgggggc tccggtacct tacccgccgg 217920
cctgtatcgt cccgaagaag aggtgttcct cctcttgaac cgctgccatg ggccactgtc 217980
aacgccgaaa agcgcttttc tggctgaggt tggtgtcgct aatgccagtt ttttatctcg 218040
cttcaatgtc ggtgattttc acggagcgtc atgggaaaac ggtaccgctc ccgatggaga 218100
gcccggggta tgctgaaatt cttcttaaaa ttacgtaaac gacgtcgtcc agtcgttgtg 218160
ccgcgattcg tacggttcat cgtctacgtc gttttgttca ccgtcgctgt gcaacgcgtg 218220
aaacaagagc gtgatgcgca ccttcggcgg tatgaagaac gattgcagaa aaaccgtgca 218280
cggcgtcggc agagttttcc gtgacttggg gcggtgggtc cgagctgcgg tatgggtcac 218340
ggcggcgtgc gtcttattga caaagatgcc gatgtgtgac taaaaaacgt cccagcccca 218400
gagcgatgtg tttcaataaa aattatgtag tatcatatta tgcgtgtcct ggtttttcat 218460
tttttggatg tatttgtcgc ataaaaggcg gtgggatgtg gggatgaaat atatccagat 218520
acgcagtttt gttatcctaa caaaacccgt gtcatgctaa aaacggtaat gcaggatgaa 218580
agtcccgtgg gggggggggg gaggcagaca gtagtcgttt ttgccgctgg gcgtacgcta 218640
tgcttgtatt tatgactata atatgtgcac tcgtgtgtcg atgttcctat tgggaagggt 218700
gtgaatgtag gaggtataaa gaatggtggg atgcggagag gcatcgctag acacaggttg 218760
atcgttgtgc tagccccacc tgagcagcgt catgaataaa gcggtgatta agcgtgaaaa 218820
caccgtgagg ggggggggc aggacgcttg gtggcagtgg ccgttggata ccttacgtgt 218880
ctgtattggt acatttgcaa atcgtcgggt gcgacggtat agtttaacga taattatatt 218940
atgtatgcgc agtatacaat gccgtaaacc attgtaacac gaaacgttac aatgatggga 219000
aagatgccga taaaaaacac ataaaacaca taaaaggcat atacacgaat tactagttac 219060
acgtttgtct atgtgcgagt tcaaggacac ttgtataatg catatcccta taatcggatg 219120
tgtgttactc attcgtggcg ttgttatagt attgtgaaaa agaattctcg taagcatgtt 219180
gacaactgca aaataaaagc attttattga gcattgtaat ggtagtgtgt ggctacatta 219240
gaaaacgtga cgcgtcgcat gtcgcggcac aatctggcag cggggtcggg gtagggtacg 219300
gtgggaggca tgtacacaga tggaacaaaa gcagaagtaa cgtgagacgg agcatatagt 219360
ccagtatccg gcggttcctg agtagcacca cccatcaact gaatgccctc atgagtaaaa 219420
gtctgcgggc gacagccctt ggggaccgtt ggcatgggac gatcaatctc caaaccacag 219480
cgtaacacgg ttttcttcca acgtcgttga tagacgtcgt ttttacggtt actccccaga 219540
acccagaaag tctcgtccaa gtcgtaccag gagtcttccc cagggagacg tggcggtttc 219600
caatcctcat cgtcccgtcg caaagcacgt cccaaactgg cttggggagt caacggtggt 219660
tctgtgggtc gggtgtagcg cgagtgtttt cccttcatga gcgattcgtc ctccttgcct 219720
ttaggctttt tggtcttttt gtgtatcatc tggccgccgg cctccataac caccgtggcc 219780
aagtccagtc ccagagcttg agcgtcggcg cggcgtcggg cgtcttgcag atagtcttcc 219840
acatttgcac agatggccgg gtgtttggtg gctagggtga gcacctcagc ctcgccgcgg 219900
cccggacgta gcaaaaaagc taactgcccg tgcggctcgc gcgcccacag cgcggcgcgc 219960
gggtgcaggt gcagcgcgtc ccagcgcggc cgctcccact gctcgcggtc cagctcgggc 220020
agcagccgcc gcgcggcctc ggcggcgggc gccgactcgc gccccagcgc cagcgcgccc 220080
agcacgcccg cgcgcagaaa gtgcgacagc tccgccgcca gtgggtacac gtgcccgtcc 220140
agcgggcagt acccgaacac ggcgcccagc tcgtccagca ccaccaccag catggcgcgc 220200
ggtacggtcc ccgacgccgc cggacccacc atcgccgccg gacccaccat caccgtcggc 220260
gccgccgctg ctgccgctgc cgccgcgtcc gccccgacca ccgcgtgcgc gtccgcgctt 220320
ggcacgcaaa tcgcgctccc gccggcggcg ccgtacggct gcggaggtaa agtcacagca 220380
gaccccacgg ctcccgctat cgcgcacggc gcgtccccgc cggcggcctc cgtctccgtg 220440
ccgctcgccc ccggcggcga cgtcgtcccc gccgccgtcc ctgtcgccgg ccccgccgcg 220500
cagcccagcc accgcgacgg cagcaccgcg cccagcgcca gccagccgca gcacagacgc 220560
tggttcaggt gccgacgcac ggccgtcagc agcgacgcgg ggtgcggcgc cgacgcgaac 220620
ggctcgtact gcgccagctc ctgccacgcg cccagcagca ccatcggctg cagtcgcctg 220680
cccggcgtct gcagtgccac cgtcgtgccg gcccaccggc ggcgcagctc ccgtccgagc 220740
gccgtcgcct cctcggcgcg cagcaacgtc tggcgaagcg ccggctgagg cagcagcgtc 220800
gcgcgcgggg tgcccacgcc cagccggttg cagcggtaca gccgcaccac ctcgcccgcg 220860
ccgtgccgaa accactcgtc cgcgtcgcgc gccgccagga tcagcgtgtt gttcgccagg 220920
tcgtacacga acacgcggaa cccggcgccc agcgccaggt acagtccgtc ctgcgcgcac 220980
agaccctcgg gatggccggc cttgtcgccc accgtcgggt cggccgcggg gtccacctcg 221040
tgcaccacgg tcgccaccag cacgatccac gcgtcccgcg gcgacagctg acgcaggtcc 221100
gtcgcgccca cgccgttcat ctggctgcgc ggcgtcaccc gcgcgtagaa tccgtacggc 221160
cgtccgagcg gcagcagcgt gcccgcgtcg cgctgcgacc acttgcgcat ggcgcggccc 221220
gtgctgttgg ccaaaaacgc cgcgcgccac acggcgccca tggcctggta ttccagctcc 221280
gtcagcgcct ggcgctccac cggaatctga gacagcagca agcgctccgg gccgtgccaa 221340
aagttgctgt tgttgccgct acccggaggg gcgcccggcg gcccgcgggg ttctacccgg 221400
tggacggcgt gggccggtgt cgccgtaccc gcagcactcg tactagtccc cgctgttgac 221460
gtcgcttcca aagaagaaga acgagaggaa ccaacccccg aaggccctcc ggcttcgcgg 221520
ccgcgaccga ggggcggggg gcgcggcgac atgccgttgc gctgggccat ggccgccgga 221580
cacctccgac gtccactata taccaagcaa acccgcgtca gcgaccacgc cgtttacaca 221640
tgcggacgcc gcagtcgccc gtgtgccccg gccgacacgc atctggcttt tataggcagc 221700
gacgtgcacg gcgcttgctg gcgccgcctc gccgcgcagt cgggaagccc gtggaaatgc 221760
acccggcagc cgacggcgca ctggactggc aaaggcagcc cgagcgagaa cccatctagg 221820
tggacgcccg acatccattc cggccgtgt gctgggtccc cgaggggcgg gggggtgttt 221880
ttagcggggg ggtgaaattt gaggttgcgt gtgtggacgg cgacggcgaa gagttgcgtg 221940
tggtgcggtg tggtgcggtg gggacggcgg tcgcggaggc cggcgacggc gaataaaagc 222000
gacgtgcgcc gcgcacggcg aaaagcagac gcgcgtctgt gtctgtttga ttccccgggg 222060
aaaagaggaa gttcccaggg gacggcagcg cgggtccctg gggacacacg caaaacaacg 222120
gccagagaca agacgcggaa aagaggaaag aacagacaca cgcaaaacaa cggccagagg 222180
aagctcgggg gcgcaaggga gggggggcaa gacgcggaaa agaggaagtc cctaggggac 222240
cgcgggggaa acgacagacg aagtacggca caacccgcgt cgaggacaca cgcagaagcg 222300
atcgcccagg ggaggggggg ggtcgcggac cccggggcac acacgcagac acggcccgcc 222360
aacacacccc gacacacccc tgacacaccc cgccaacaca cccgccacac gcccgcgaca 222420
cacccagaca cacccgccac acgccctgac acacccgaca cccaccccac gcgcgcaccc 222480
acccagccgc gcccccgaca caccccgacc gccgccggtg cgggacgggg ctgagggagg 222540
ttttgccacc gtaagcgcgc cgattcgcgg aataggactg agggctggac agggctgcgg 222600
gagttttgtc cacggagctt tctgcgcgct ggcggtgcgt gtgtctctgg acataagtaa 222660
gcgcagcggt gtcctcagcg cgtttgcggc gtgctgtgtc cggcgctttg tgcgcactgc 222720
cggtgcgtgt cgtcccgcgg tgttttttgt ttcgcggacc ggcgccgggg acggggtgtt 222780
gcgcgcgctc gggggttggc ggcgggtgtt tctacggtgt ttgcgcggcg tttctaggca 222840
gcttttgcgc ggcgcttcgc ttttcggggc ggcgacggcg gtgttttcgg gcgtgctggg 222900
cgccggcgct agtaacggga gttacgctgg ggacggggac ggggtttgcg gcggggacgg 222960
gggggtgtgc ggggacgggg ggtgtgcggg gacgggggt gtgcggggac ggccacgggg 223020
gccttttgcg gcggggacga tgcgttgcgg ggccgggggc cttttgcggc ggggacgggg 223080

-continued cgttgcggag acggggacgg gagtggggac ggtggtgagg acggggacgg gggcctttcg 223140
cggcggggac ggggagttgc gggatggcgg gctgttgcgt ggcggggacg ggggactctt 223200
gcggcgggga cggggaacac agacggcacg cacacgcagc tcgcctattt aacctccacc 223260
cactacaaca cacacatgcc gcacaatcat gccagccaca gacacaaaca gcacccacac 223320
cacgccgctt cacccagagc accaacacgc gttaccctta caccacagca ccacacaacc 223380
gcatgtccaa acttcggaca aacacgccga caaacaacac cgcacgcaga tggagctcga 223440
cgccgcggac tacgctgctt gcgcacaggc ccgccaacac ctctacggtc aaacacaacc 223500
ccaactacac gcataccccca acgccaaccc acaggaaagc gctcattttt gcacagagaa 223560
tcaacatcaa ctcacgaatc tacttcacaa cataggcgag ggcgcagcgc tcggctaccc 223620
cgtcccccgc gcggaaatcc gccgcggcgg tggcgactgg gccgacagcg caagcgactt 223680
cgacgccgac tgctggtgca tgtggggacg cttcggaacc atgggccgcc aacctgtcgt 223740
aaccttactg ttggcgcgcc aacgcgacgg cctcgctgac tggaacgtcg tacgctgccg 223800
cggaacaggc tttcgcgcac acgattccga ggacggcgtc tctgtctggc gtcagcacct 223860
ggttttttta ctcggaggcc acggccgccg tgtacagtta gaacgaccat ccgcgggaga 223920
agcccaagct cgaggcctat tgccacgcat ccggatcacc cccatctcca catctccacg 223980
cccaaaacca ccccagccca ccacatccac cgcatcgcac ccacatgcta cggctcggcc 224040
agatcacacg ctctctcctg tcccttctac accctcagcc acggttcaca atccccgaaa 224100
ctacgccgtc caacttcacg cagaaacgac ccgcacatgg cgctgggcac gacgcggtga 224160
acgtggcgcg tggatgccgg ccgagacatt tacgtgtccc aaggataaac gtccctggta 224220
gacggggtag ggggatctac cagcccagga atcgcgtctt tcgccgccac gctgcttcac 224280
cgatatccaa taaacccatc ccctcgccac gacgtctccg cgtatctttg tagcctcagg 224340
aatacgtccc cacgtccacc catcccaagc actccacacg ctatcacaga ccacggacac 224400
ggcaaaaaat gcatgcaaac ttctcattta ttgtgtctac tactctgtgt tgctacaggg 224460
agtgaagggg gtgaaggcaa agaaaaaaaa aagaacaaaa taatagatta gcagaaggaa 224520
taatccgtgc gaccgagctt gtgcttcttt tcttataagg aggcaaatat actagggaaa 224580
acataacaat aggaagaaac cgaggtttgg gagaaaagct gagataaaat agcgcatttt 224640
ccatacagag gttgttgttt ttgtggatcc taagaggttt caagtgcgaa tctcaaagtt 224700
ctcacgagaa tattgtcttc aagaatcgac aactgtggtc caagattttt ttttggtctt 224760
tttaggttct gcgagggaca tcacgatgga tcgttgcgat gaagtcacgc gtacgcctct 224820
ggtgtggcgc ggtgtcgtga caggagagtg tgttttcagt gcagagctgt cttgattcct 224880
atatccgagt atctgttttc tcgtaaggac ggtaatcttc tttggtgtaa gtacatctaa 224940
aagctgcaaa ctatatttta agggctgtct ctaggtgtac tttgatgctg gagtttttcg 225000
ctgtgttgat gtgaataaat ctactactac tattatatgc agaaagagtg attatgccga 225060
gacaagattg cattggctga actgtttcaa aaacgcctac actctactta tccgtaaacc 225120
taaggtaata ctatgtgtaa gttgtttttt tttctttttg tagtaaaatg gtgatacgtg 225180
caattaaaac tgtattccat gtttccatcc tttcatttca actttaaagg cggctttgag 225240
agcgaagaag tgcgaggata aaaatggatg actccttcgt gtccagggag tcgactactg 225300
caacgctgat tgattaaaag atggtctccg atgatgttgt tattgatcga atcatggtgc 225360
agaacggcga cggagaggag cgtgtccgcc gccgggaagg tggtctcttt ctcttttctt 225420
ttttcaagaa atcttccatg tgtttatcgt agtgatcgaa atcgactgat ctcgggttct 225480
ttttgttggt ttcttttcgg ttaatcatgt attgttttct ttttttacag aaagatactt 225540
ttttcatgag caattcctcg cccggcgccg gcatgccgag gtggggccac tgcgatcagc 225600
ggcatgccga cgccgacccg gggatcttgg attcaccgtt ttctctcttc tctctctaca 225660
tacagaccgg gtggcaggag cggtaaggaa tcatcgtcgt ctttcattct tcgatgatta 225720
tggtaatact aaatcttatc taggagcata tacatctaag attggagtac tagtagtcgt 225780
ttgtggtttc tatttttttt tatatttatc tatgacagtt tttctgtttt tcgttttgat 225840
aataatataa taaaaactca tggacgtgaa atctggcttg gttgtggtga tttcattctc 225900
attattgttg ttttctttcc gtcttgcgga tgaagatgtt gcgatgcggt tgttgttggt 225960
gttgctatac accgagagag atgatctttt tgttcttctg gttcatttcc tatgattgtt 226020
tggctgctga ccgacgcgtc aggatgtgca gggcatgcgg ggaatcagga ccggacacgg 226080
gataatttca tctacctata cggagatcgc ggtcctcgcc atgaggatcg cgacaggcgc 226140
gtcgaggggg gcaggaacac ccttgcggat tgacattctt ggtggtgttt cgttgttgtc 226200
ggtagttgtt gttgacgatg aggataaata aaaatgacct tgtttttgtt ctgttttctc 226260
ttgttgggaa tcgtcgactt tgaattcttc gagttatcgg aaagctgagg tacccaaatg 226320
tctgtagctt ttttcttttt accctcttgt ttatcatctg cgattcgtgg taggtaggag 226380
agggaaatga taatccgaga ttaaggaaag gagaagataa aaaaaaaaaa aataataaaa 226440
cagaagccga ccggccgccg acccgttccc caggaccagc ctacgaggaa cggataacgc 226500
ggtggcgacg gcagcggtgg tggcgctggg ggtggcggta gtggtgctgc tgatggtagt 226560
cgggacggag gagagacgat gcatacatac acacgtgcat gctgcatggg tggatggacc 226620
gaccgggaga cgcggaagag aaactcacat aaaaaggtga caaaaagagc ggttgaaaag 226680
agaaaacgag attcgaccag acagaagaga aggaccgggg cttggcgacc cttccacgac 226740
tgctgttgtc atctcggctc ctccgtcttc tcccggccac gggcggctaa gtcaccgccg 226800
ttctccccat ccgtccgagc gccgaccgac cagccggccg attcgcccgc cggggcttct 226860
ggagaacgcc ggagcagcag cgatctgggg aagccgctaa acccctgcgt ttttatatgg 226920
tagctctgcc gagcgcgggc tgacgcgttg agtaagcgga aagacgtgtg tgacgaaaag 226980
gggtcccatg gtatttcacg tgacgatgag gagatgcggt ttggagcaca tacggtttaa 227040
aaaaagggag ttgtcgtgac aagggctgag ggacctctgt ctccatgtgt gtataaaaag 227100
caaggcacgt tcataatgta aaaaagaaca cgttgtaaac aagctattgc tgtatcattc 227160
ggctgactat gcttcattcg gactgatttt cttttcctaa cggcgtaact taaagtgatt 227220
aacgtatgat atttgttccc cagagttata ctatagtcat catcctaaaa ttcagatata 227280
aggtgctaaa acaaatctat acgttgatcc tacacgttct acgattaacc aacagagacc 227340
aaccatgtct ctttaacctc gcttgggccg ctaccgtctt tccaaaccag atcgtaacct 227400
ccttcattta cagacgtaac gttacacagc gttaaatgca catggctgca attacatatg 227460
ccaccgaccg atcccaacgt aaaattgttt acgcctgtca cggtacaaac cgtggtctca 227520
ttatgtttag ttccatccgt aagcttccaa gttgacgtaa gatcgtgttt tagatttgta 227580
ttttcaccaa cctttatact agaactttta aaactttcaa cttcaaggca taatgccaaa 227640
attaagcacg ttattagtcc cccccccccc accgaggaat gtgactggac cggttcttag 227700
cagctttggg agccatcttc aaggtggacc gcagctacag cgaaaccgag tccagtgacc 227760
gataaccacg tgcaaccctg cgtatgtacc agtccaagta cgtccggtca ttgttccaca 227820

```
caggaaatct aactaggtca acggacaaaa ccaaattgtc aatccaccat atgcacaaca 227880
caaaagcact gacgtttatt tgttgaatta tcaacgttac ttagttacaa taaggaacca 227940
tgtatccact tgaatgttgc ccaactgggt cttccccgtt atagtcatag cgttcccagg 228000
caaaagctaa cgccgaacct aatgcagtaa accgcgcttg cacccagaac cagcttatgt 228060
atcagccaca ataacatccg gttattgttt ccacaggaaa tcctaccagg caaagccccg 228120
cttgttttgt ttctaaccat cttgtttagc aactcgtaaa ctgtcagccc agcgacgtcc 228180
gtttggatca aaagccacgt atactgagac gctgtttcta cccgtttccc catcccgcca 228240
ttcccgggca acccacccaa gtcccgacaa ccaaccacca acagaaaaca tacacagacc 228300
accgggagtt cagttaaaga tttcatcagg tttattttgg ctgctgctag tcttttgctt 228360
cttagaaaaa aaatacccat atagagaaat aatgatagtt tgacaacaca tatggcaggg 228420
atttcttctt catcaataag atatgcaatt cccccaggga gagactttca acaattgaat 228480
ttacaaaaac aaaattacat caggagaaag agaggataca ttaataaata tattatatct 228540
ggtgtatata ctgaatgctg ctggttcata aggtaacgat gctacttttt ttaattccaa 228600
gatgattttt ctttgttagt cttttgttga cttgctggtt cctaaaagtt cgcaaaaacg 228660
attgtgtgaa gattttatga cgttggttga ctagttcatg agattctgct gtacgtgtga 228720
tggttattcg ctggttcgtt ctaagatgag tatcgtactg tgtctgcgat ggtcgtctct 228780
tactggcatt ctctcggctg cctcttgctt tcatgattga aaaggaaaaa aggactccga 228840
gggcgcggtc atcttttact tttcggtttt ctcgttggcg ggtcagaggt agtcagatca 228900
tgagactgtc gtggtcgatg aaactgtgtc tgctcaagtg acgtccattt cttgtacgga 228960
gaaaaaagtc atcgggataa ataaggctat acaaggcgtt gtcaagcgtg cggctctaaa 229020
caaattaagc gatacaaaat tacagtaata cgaataataa attacccccc tccccctgtg 229080
gtcccccgag gcgagagcca cccatcgtgt actctcgcac cacccacgac cacagaggga 229140
gacgggacga agagacgacg cagagcgcca tctcctcctg gaggccggcg gcgttaactg 229200
ctacagctgc ggcggcgacg acagctgcga tttgtcggcc gacatgccga tggtatgggc 229260
ggcggcggca gtggccgcgg cagcggggag gagaggagag agaagaggag cggggcgtcc 229320
gaaggcgagg atggcatgat ctcgccggag cgcccggctt ttatgggata ctcgcgtccg 229380
gtcgggcagc gcccacagga agatgagtca aaactttttaa accatcctga gacccgagta 229440
gcggtttaca ggccgcacgc cagtcttagc taaaaacagc ggacagtccc acgctgtttc 229500
tgttgtggct ctctccagtt tcctcatcgc cgtcccgatc tccgtcgtca tcggaagaat 229560
accatccgct ctcatgcggc agtcgatcga cctcgacgaa cgagacgcgg cgacgcctct 229620
ctacggccga ctggttgtgg tggtgaaaga agagcaccag caatcccagg aggagcaaca 229680
agccctcaca tgtccaggag gtcggggaga gggcctgtcg gagatggccg tgaggcatca 229740
cgtacggcag ctgaggagaa acggagaata aaggaaaatt accgtcaggg gccggggttc 229800
ttattagaga aacagcacgt aggtcaggat ccagatacta atggcgatca tgatgacgat 229860
gatcatgcag gccaagacgc ggcgcaccaa tgccgaatcc aagagccgcc gtgccgccgg 229920
ttggtggctg gcggcatcta gagacatggt ttggggggac cggcggcgcg aaaagacagg 229980
gagatggaca gtgtcacggt gttttgttat gattaggaca tggggaccgg aagccgagac 230040
agagtactac agagtgttga agggtaacgt gagggagatc atgtcatggg cgggctgaag 230100
accgtgcggg gaggatcgac gtgtgcggtg cttgtggaac acggtgtttt aatatgtatc 230160
cgcgtgtaat gcacgcggtg tgctttttag cattcggctt ggtaagctac gtggccttct 230220
```

gcgccgaaac cacggtcgcc accaactgtc ttgtgaaaac agaaaatacc cacctgacat 230280
gtaagtgcag tccgaataac acatctaata ccggcaatgg cagcaagtgc cacgcggtgt 230340
gcaaatgccg ggtcacagaa cccattacca tgctaggcgc atactcggcc tggggcgcgg 230400
gctcgttcgt ggccacgctg atagtcctgc tggtggtctt cttcgtaatt tacgcgcgcg 230460
aggaggagaa aaacaacacg ggcaccgagg tagatcaatg tctggcctat cggagcctga 230520
cacgcaaaaa gttggaacaa cacgcggcta aaaagcagaa catctacgaa cggattccat 230580
accgaccctc cagacagaaa gataactccc cgttgatcga accgacgggc acagacgacg 230640
aagaggacga ggacgacgac gtctgacaaa gaaggcgaga acgtgttttg caccatgcag 230700
acctacagca ccccccctcac gcttgccata gtcacgtcgc tgtttttgtt cacaactcaa 230760
ggaggttcat cgaacgccgt cgaaccaacc aaaaaaaccc taaagctcgc caactaccgc 230820
gccacctgcg aggaccgtac acgtactctg gttaccaggc ttaacactag ccatcacagc 230880
gtagtctggc aacgttatga tatctacagc agatacatgc gtcgtatgcc gccactttgc 230940
atcattacag acgcctataa agaaaccacg catcagggtg gcgcaacttt cacgtgcacg 231000
cgccaaaatc tcacgctgta caatcttacg gttaaagata cgggagtcta cctcctgcag 231060
gatcagtata ccggcgatgt cgaggctttc tacctcatca tccacccacg cagcttctgc 231120
cgagctttgg aaacgcgtcg atgcttttat ccgggaccag ggagagttgt ggttacggat 231180
tcccaagagg cagaccgagc aattatctcg gatttaaaac gccagtggtc cggcctctca 231240
cttcattgcg cctgggtttc gggactgatg atctttgttg gcgcactggt catctgcttt 231300
ctgcggtcgc aacgaatcgg ggaacaggac gctgaacagc tgcggacgga cctggatacg 231360
gaacctctat tgttgacggt ggacggggat ttggagtaaa agatgcgtac acaacatcga 231420
cggcgaaaca agtcatcgta cacgcaaata acatgcatgt ttatcatttt ttggattctg 231480
cagaaaagca agtgtaacaa caccactatc gctaatactt ccacgtcaat tacactcaca 231540
agcttgatat ctactgcaca actaacatct actttacaaa ccaccggaat gtctaccact 231600
acattcacat cctccgatgt caacgccaac acatccacag gattcactgc aagctctgca 231660
aaaagcacag acgtgatctc aactatttcc accataccca ctcaaacatc tacaattaac 231720
gcgactgtaa tgacaacctc accaaacgga ggcatgaatt tatcgacaca acatataatc 231780
agcagtaccg cgacttcgca agcaactaca tcattaccaa tcaatactag tacaatggta 231840
acaaatacaa ctcaaaacat cagtacacca ctcccaactt gctcatcatc taatagcaca 231900
ttcaatgata catcaaacaa ccgtacttgt catgaaaaca gtacaatatc acaagaatct 231960
gaaacattgt tgaaggcaat acaaggagac aatatcacta taatacacaa cctaaccacc 232020
acatcgtgct acaagacagc ttggcttaga cattttaata tatccacaca cagaaaatac 232080
acccatccca acataaagag tggaaaattt agtaaccatt cattaaagat cctccattcg 232140
cgtgtactgt gtgagtggca gacacattac ctaaaacatc actacgattt atgttttaca 232200
tgcgatcaga atttatcttt gtctctgtac ggtcttaatt ttactcactc tggtaaatat 232260
agctttcgat gttacaaaag tggccatccc tctgaacaaa atcaaaattt taatctacaa 232320
gtacatccta gaaacaacac gaacgagaca catgtgaacc cctggatatg cgaagaacca 232380
aagcacgaat gggatacttt ggctgctaca tctgataaac cgaccagtca taaagacgat 232440
acaaccacat catctacaga tcatctatac cgctataata atcattccaa cacatcacac 232500
ggcagacaca ctacgtggac tttagtgtta atttgtatag cctgcattct cctatttttc 232560
gtccgacgag ctctaaacaa aaaataccat ccattaaggg acgatatcag tgaatcagaa 232620
ttcatagttc gatacaatcc tgagcatgag gattaagcaa cgtttccgga taaacatctt 232680
atgagaccac accacaaagt aaatgactat gaaagatcaa caacatccga agaaacatca 232740
atgcccatta accgaaatcc aacaacgtta tggactggca gtttacggtt aagtggaggt 232800
tactgatcat cacgttatct gaaggttgta atgatacatg cccttgttcg tgcaactgcc 232860
tcacctccac cgcctcaacc atcaaaaatt cgtctgattt tgtcactaac gctaccaaca 232920
tttcaactac tgcaaataaa accacgcaca aaccctctac cgcctcgtca gatacatcaa 232980
caattactcc aacgctgttg gaatcaccgt caagcgttac gcgaatatta acaacgttct 233040
ctaccgttca tagtaccatt ccctggttga ataccagcaa cgtaacttgc aacggtagtt 233100
tgtacaccat ctataaacaa tctaatttaa attacgaggt aattaacgta acagcgtatg 233160
tcggtggata cgtcactctg caaaattgca ctagaacgga tacatggtat gatgtagaat 233220
ggataaaata tggaactcgt acacaccaac tgtgcagaat tggaagttat cattcaacgt 233280
ctccactaaa cggcatgtgt ctagactgta acagaacctc tctcaccatc tacaacgtaa 233340
ccgtcgaaca cgctggaaaa tacgttttac atcgctacat tgacggtaaa aaggaaaact 233400
actatctaac tgtattatgg ggaaccacaa catcgtctcc tatacctgac aaatgcaaaa 233460
caaaagagga gtcagatcag cacaggcgcg gagcgtggga cgacgtaata acaactgtaa 233520
aaaacactaa cattcccctg ggaattcatg ctgtatgggc gggtgtagtc gtatctgtgg 233580
cacttgtagc cttatacatg ggtagccgtc gcgcttccag gaaaccgcgt tataaaaaac 233640
ttcccaaata tgatccagat gagttttgga ctaaaacctg a 233681

<210> SEQ ID NO 21
<211> LENGTH: 4159
<212> TYPE: DNA
<213> ORGANISM: artificial
<220> FEATURE:
<223> OTHER INFORMATION: synthetic

<400> SEQUENCE: 21
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccgg 660
gccccccctc gaggtcgacg gtatcgataa gcttgatccc aagcttgata tcgaattcgg 720
atgggctccg gaatcggcgc agcaagcatg gaattttgtt ttgatgtatt caaggagctc 780
aaagtccacc atgccaatga gaacatcttc tactgcccca ttgccatcat gtcagctcta 840
gccatggtat acctgggtgc aaaagacagc accaggacac agataaataa ggttgttcgc 900
tttgataaac ttccaggatt cggagacagt attgaagctc agtgtggcac atctgtaaac 960
gttcactctt cacttagaga catcctcaac caaatcacca aaccaaatga tgtttattcg 1020
ttcagccttg ccagtagact ttatgctgaa gagagatacc caatcctgcc agaatacttg 1080
cagtgtgtga aggaactgta tagaggaggc ttggaaccta tcaactttca aacagctgca 1140
gatcaagcca gagagctcat caattcctgg gtagaaagtc agacaaatgg aattatcaga 1200
aatgtccttc agccaagctc cgtggattct caaactgcaa tggttctggt taatgccatt 1260
gtcttcaaag gactgtggga gaaaacattt aaggatgaag acacacaagc aatgcctttc 1320
agagtgactg agcaagaaag caaacctgtg cagatgatgt accagattgg tttatttaga 1380
gtggcatcaa tggcttctga gaaaatgaag atcctggagc ttccatttgc cagtgggaca 1440
atgagcatgt tggtgctgtt gcctgatgaa gtctcaggcc ttgagcagct tgagagtata 1500
atcaactttg aaaaactgac tgaatggacc agttctaatg ttatggaaga gaggaagatc 1560
aaagtgtact tacctcgcat gaagatggag gaaaaataca acctcacatc tgtcttaatg 1620
gctatgggca ttactgacgt gtttagctct tcagccaatc tgtctggcat ctcctcagca 1680
gagagcctga agatatctca agctgtccat gcagcacatg cagaaatcaa tgaagcaggc 1740
agagaggtgg tagggtcagc agaggctgga gtggatgctg caagcgtctc tgaagaattt 1800
agggctgacc atccattcct cttctgtatc aagcacatcg caaccaacgc cgttctcttc 1860
tttggcagat gtgtttcccc ttaagcggcc gccgcatcga attcctgcag cccgggggat 1920
ccactagttc tagagcggcc gccaccgcgg tggagctcca gcttttgttc cctttagtga 1980
gggttaattg cgcgcttggc gtaatcatgg tcatagctgt ttcctgtgtg aaattgttat 2040
ccgctcacaa ttccacacaa catacgagcc ggaagcataa agtgtaaagc ctggggtgcc 2100
taatgagtga gctaactcac attaattgcg ttgcgctcac tgcccgcttt ccagtcggga 2160
aacctgtcgt gccagctgca ttaatgaatc ggccaacgcg cggggagagg cggtttgcgt 2220
attgggcgct cttccgcttc ctcgctcact gactcgctgc gctcggtcgt tcggctgcgg 2280
cgagcggtat cagctcactc aaaggcggta atacggttat ccacagaatc aggggataac 2340
gcaggaaaga acatgtgagc aaaaggccag caaaaggcca ggaaccgtaa aaaggccgcg 2400
ttgctggcgt ttttccatag gctccgcccc cctgacgagc atcacaaaaa tcgacgctca 2460
agtcagaggt ggcgaaaccc gacaggacta taaagatacc aggcgtttcc ccctggaagc 2520
tccctcgtgc gctctcctgt tccgaccctg ccgcttaccg gatacctgtc cgcctttctc 2580
ccttcgggaa gcgtggcgct ttctcatagc tcacgctgta ggtatctcag ttcggtgtag 2640
gtcgttcgct ccaagctggg ctgtgtgcac gaaccccccg ttcagcccga ccgctgcgcc 2700
ttatccggta actatcgtct tgagtccaac ccggtaagac acgacttatc gccactggca 2760
gcagccactg gtaacaggat tagcagagcg aggtatgtag gcggtgctac agagttcttg 2820
aagtggtggc ctaactacgg ctacactaga aggacagtat ttggtatctg cgctctgctg 2880
aagccagtta ccttcggaaa aagagttggt agctcttgat ccggcaaaca aaccaccgct 2940
ggtagcggtg gtttttttgt ttgcaagcag cagattacgc gcagaaaaaa aggatctcaa 3000
gaagatcctt tgatcttttc tacggggtct gacgctcagt ggaacgaaaa ctcacgttaa 3060
gggattttgg tcatgagatt atcaaaaagg atcttcacct agatcctttt aaattaaaaa 3120
tgaagtttta aatcaatcta aagtatatat gagtaaactt ggtctgacag ttaccaatgc 3180
ttaatcagtg aggcacctat ctcagcgatc tgtctatttc gttcatccat agttgcctga 3240
ctccccgtcg tgtagataac tacgatacgg gagggcttac catctggccc cagtgctgca 3300

-continued atgataccgc gagacccacg ctcaccggct ccagatttat cagcaataaa ccagccagcc 3360
ggaagggccg agcgcagaag tggtcctgca actttatccg cctccatcca gtctattaat 3420
tgttgccggg aagctagagt aagtagttcg ccagttaata gtttgcgcaa cgttgttgcc 3480
attgctacag gcatcgtggt gtcacgctcg tcgtttggta tggcttcatt cagctccggt 3540
tcccaacgat caaggcgagt tacatgatcc cccatgttgt gcaaaaaagc ggttagctcc 3600
ttcggtcctc cgatcgttgt cagaagtaag ttggccgcag tgttatcact catggttatg 3660
gcagcactgc ataattctct tactgtcatg ccatccgtaa gatgcttttc tgtgactggt 3720
gagtactcaa ccaagtcatt ctgagaatag tgtatgcggc gaccgagttg ctcttgcccg 3780
gcgtcaatac gggataatac cgcgccacat agcagaactt taaaagtgct catcattgga 3840
aaacgttctt cggggcgaaa actctcaagg atcttaccgc tgttgagatc cagttcgatg 3900
taacccactc gtgcacccaa ctgatcttca gcatctttta ctttcaccag cgtttctggg 3960
tgagcaaaaa caggaaggca aaatgccgca aaaaagggaa taagggcgac acggaaatgt 4020
tgaatactca tactcttcct ttttcaatat tattgaagca tttatcaggg ttattgtctc 4080
atgagcggat acatatttga atgtatttag aaaaataaac aaataggggt tccgcgcaca 4140
tttccccgaa aagtgccac 4159

<210> SEQ ID NO 22
<211> LENGTH: 6379
<212> TYPE: DNA
<213> ORGANISM: artificial
<220> FEATURE:
<223> OTHER INFORMATION: synthetic

<400> SEQUENCE: 22
ctcgagttta ccactcccta tcagtgatag agaaaagtga aagtcgagtt taccactccc 60
tatcagtgat agagaaaagt gaaagtcgag tttaccactc cctatcagtg atagagaaaa 120
gtgaaagtcg agtttaccac tccctatcag tgatagagaa aagtgaaagt cgagtttacc 180
actccctatc agtgatagag aaaagtgaaa gtcgagttta ccactcccta tcagtgatag 240
agaaaagtga aagtcgagtt taccactccc tatcagtgat agagaaaagt gaaagtcgag 300
ctcggtaccc gggtcgaggt aggcgtgtac ggtgggaggc ctatataagc agagctcgtt 360
tagtgaaccg tcagatcgcc tggagacgcc atccacgctg ttttgacctc catagaagac 420
accgggaccg atccagcctc cgcggccccg aattcgagct cggtacccgg ggatccacca 480
tgtaccccta cgacgtgccc gactacgcca cgtccagact atccgtgaaa agtttgagaa 540
gcatcagtag gttcgtccag tgggagtgtt gttggatgct cgtcaacaag agcgcgcgct 600
accgagagtt ccgcgccgtc accagccagt cgccggggct ggggaaggtc tcctccaccg 660
acgacgggag atgtctcgcc gcctccatga tgcttttcag acgtgacggt aattttgtcc 720
tctgtctggt cgtcaataag gagccggtgg gtcagttcgg ctgcagtggc atgcggcgcg 780
agaagatggt catcgatgga ctccaggagc ccgtctacgt gatgcgtctc ctggcccccc 840
tcatccccgt caagctagga ttctcgccct acatgttgcc gcctaagagc atcggcggct 900
ccggcggtct ggaccccagc gtcatctacc agaacgcgag tgtggtcacg cccgaagagg 960
ccgccaccgt cactatgcag ggttccggca tcgtgaccgt ggggctcagt ggcgttggct 1020
cctgggtgca gatcaaggat ggtgggaaca tgaagctctt cgtcttcgcc ctctgcttcg 1080
acgtctttac cgcctgctgc gatcggctcg ccttcccgtc cctggccaag atctacagcg 1140
aaactgtgtc ctgcgaggcc gacaagtgcg gattctgtcg agattccggt cggcacgtcg 1200
atcccaccgg ccgcttcgtc ggctgcgtcc ccgacagtgg cgtgtgtctc tgttactcgc 1260
cgtgtcgcgg gacggatgcc gcggtcagcg tcagaagctg gttaccttac ctggaactgg 1320
aagacggtgc gaacacgcac agcctcttcg tgcggcgcta cgacggcagg aaaggactgc 1380
cggccacgat atctgactac ctcggcgcca ggaacagcga gggcgacgag atcccgctga 1440
ggaccgagcc ctggcagctc ttgaagatag aaccgacgct gtccgccatg atcatcatgg 1500
cctgtccctt actcaaaaag atcgttctcg agcacatgtg aagtcgactc tagcgcggcc 1560
gcatcgataa gcttgtcgac gatatctcta gagctgagaa cttcagggtg agtttgggga 1620
cccttgattg ttctttcttt ttcgctattg taaaattcat gttatatgga gggggcaaag 1680
ttttcagggt gttgtttaga atgggaagat gtcccttgta tcaccatgga ccctcatgat 1740
aattttgttt ctttcacttt ctactctgtt gacaaccatt gtctcctctt attttctttt 1800
cattttctgt aactttttc gttaaacttt agcttgcatt tgtaacgaat tttaaattc 1860
actttcgttt atttgtcaga ttgtaagtac tttctctaat cacttttttt tcaaggcaat 1920
cagggtaatt atattgtact tcagcacagt tttagagaac aattgttata attaaatgat 1980
aaggtagaat atttctgcat ataaattctg gctggcgtgg aaatattctt attggtagaa 2040
acaactacat cctggtaatc atcctgcctt tctctttatg gttacaatga tatacactgt 2100
ttgagatgag gataaaatac tctgagtcca aaccgggccc ctctgctaac catgttcatg 2160
ccttcttctt tttcctacag ctcctgggca acgtgctggt tgttgtgctg tctcatcatt 2220
ttggcaaaga attcactcct caggtgcagg ctgcctatca gaaggtggtg gctggtgtgg 2280
ccaatgccct ggctcacaaa taccactgag atctttttcc ctctgccaaa aattatgggg 2340
acatcatgaa gccccttgag catctgactt ctgggtaata aaggaaattt attttcattg 2400
caatagtgtg tgggaatttt ttgtgtctct cactcggaag gacatatggg agggcaaatc 2460
atttaaaaca tcagaatgag tatttggttt agagtttggc aacatatgcc atatgctggc 2520
tgccatgaac aaaggtggct ataaagaggt catcagtata tgaaacagcc ccctgctgtc 2580
cattccttat tccatagaaa agccttgact tgaggttaga tttttttat attttgtttt 2640
gtgttatttt tttctttaac atccctaaaa ttttccttac atgttttact agccagattt 2700
ttcctcctct cctgactact cccagtcata gctgtccctc ttctcttatg aactcgactg 2760
cattaatgaa tcggccaacg cgcggggaga ggcggtttgc gtattgggcg ctcttccgct 2820
tcctcgctca ctgactcgct gcgctcggtc gttcggctgc ggcgagcggt atcagctcac 2880
tcaaaggcgg taatacggtt atccacagaa tcaggggata acgcaggaaa gaacatgtga 2940
gcaaaaggcc agcaaaaggc caggaaccgt aaaaaggccg cgttgctggc gtttttccat 3000
aggctccgcc cccctgacga gcatcacaaa aatcgacgct caagtcagag gtggcgaaac 3060
ccgacaggac tataaagata ccaggcgttt ccccctggaa gctccctcgt gcgctctcct 3120
gttccgaccc tgccgcttac cggatacctg tccgcctttc tcccttcggg aagcgtggcg 3180
ctttctcaat gctcacgctg taggtatctc agttcggtgt aggtcgttcg ctccaagctg 3240
ggctgtgtgc acgaaccccc cgttcagccc gaccgctgcg ccttatccgg taactatcgt 3300
cttgagtcca acccggtaag acacgactta tcgccactgg cagcagccac tggtaacagg 3360
attagcagag cgaggtatgt aggcggtgct acagagttct tgaagtggtg gcctaactac 3420
ggctacacta gaaggacagt atttggtatc tgcgctctgc tgaagccagt taccttcgga 3480
aaaagagttg gtagctcttg atccggcaaa caaaccaccg ctggtagcgg tggttttttt 3540

```
gtttgcaagc agcagattac gcgcagaaaa aaaggatctc aagaagatcc tttgatcttt   3600
tctacggggt ctgacgctca gtggaacgaa aactcacgtt aagggatttt ggtcatgaga   3660
ttatcaaaaa ggatcttcac ctagatcctt ttaaattaaa aatgaagttt taaatcaatc   3720
taaagtatat atgagtaaac ttggtctgac agttaccaat gcttaatcag tgaggcacct   3780
atctcagcga tctgtctatt tcgttcatcc atagttgcct gactccccgt cgtgtagata   3840
actacgatac gggagggctt accatctggc cccagtgctg caatgatacc gcgagaccca   3900
cgctcaccgg ctccagattt atcagcaata aaccagccag ccggaagggc cgagcgcaga   3960
agtggtcctg caactttatc cgcctccatc cagtctatta attgttgccg ggaagctaga   4020
gtaagtagtt cgccagttaa tagtttgcgc aacgttgttg ccattgctac aggcatcgtg   4080
gtgtcacgct cgtcgtttgg tatggcttca ttcagctccg gttcccaacg atcaaggcga   4140
gttacatgat cccccatgtt gtgcaaaaaa gcggttagct ccttcggtcc tccgatcgtt   4200
gtcagaagta agttggccgc agtgttatca ctcatggtta tggcagcact gcataattct   4260
cttactgtca tgccatccgt aagatgcttt tctgtgactg gtgagtactc aaccaagtca   4320
ttctgagaat agtgtatgcg gcgaccgagt tgctcttgcc cggcgtcaat acgggataat   4380
accgcgccac atagcagaac tttaaaagtg ctcatcattg gaaaacgttc ttcggggcga   4440
aaactctcaa ggatcttacc gctgttgaga tccagttcga tgtaacccac tcgtgcaccc   4500
aactgatctt cagcatcttt tactttcacc agcgtttctg ggtgagcaaa aacaggaagg   4560
caaaatgccg caaaaaaggg aataagggcg acacggaaat gttgaatact catactcttc   4620
ctttttcaat attattgaag catttatcag ggttattgtc tcatgagcgg atacatattt   4680
gaatgtattt agaaaaataa acaaataggg gttccgcgca catttccccg aaaagtgcca   4740
cctgacgtct aagaaaccat tattatcatg acattaacct ataaaaatag gcgtatcacg   4800
aggccctttc gtctcgaggc agtgaaaaaa atgctttatt tgtgaaattt gtgatgctat   4860
tgctttattt gtaaccatta taagctgcaa taaacaagtt aacaacaaca attgcattca   4920
ttttatgttt caggttcagg gggaggtgtg ggaggttttt taaagcaagt aaaacctcta   4980
caaatgtggt atggctgatt atgatcctct agaactctat tcctttgccc tcggacgagt   5040
gctggggcgt cggtttccac tatcggcgag tacttctaca cagccatcgg tccagacggc   5100
cgcgcttctg cgggcgattt gtgtacgccc gacagtcccg gctccggatc ggacgattgc   5160
gtcgcatcga ccctgcgccc aagctgcatc atcgaaattg ccgtcaacca agctctgata   5220
gagttggtca agaccaatgc ggagcatata cgcccggagc cgcggcgatc ctgcaagctc   5280
cggatgcctc cgctcgaagt agcgcgtctg ctgctccata caagccaacc acggcctcca   5340
gaagaagatg ttggcgacct cgtattggga atccccgaac atcgcctcgc tccagtcaat   5400
gaccgctgtt atgcggccat tgtccgtcag gacattgttg gagccgaaat ccgcgtgcac   5460
gaggtgccgg acttcggggc agtcctcggc ccaaagcatc agctcatcga gagcctgcgc   5520
gacggacgca ctgacggtgt cgtccatcac agtttgccag tgatacacat ggggatcagc   5580
aatcgcgcat atgaaatcac gccatgtagt gtattgaccg attccttgcg gtccgaatgg   5640
gccgaacccg ctcgtctggc taagatcggc cgcagcgatc gcatccatgg cctccgcgac   5700
cggctgcaga acagcgggca gttcggtttc aggcaggtct tgcaacgtga caccctgtgc   5760
acggcgggag atgcaatagg tcaggctctc gctgaattcc ccaatgtcaa gcacttccgg   5820
aatcgggagc gcggccgatg caaagtgccg ataaacataa cgatctttgt agaaaccatc   5880
ggcgcagcta tttacccgca ggacatatcc acgccctcct acatcgaagc tgaaagcacg   5940
```

agattcttcg ccctccgaga gctgcatcag gtcggagacg ctgtcgaact tttcgatcag 6000
aaacttctcg acagacgtcg cggtgagttc aggctttttc atggaagctt tttgcaaaag 6060
cctaggcctc caaaaaagcc tcctcactac ttctggaata gctcagaggc cgaggcggcc 6120
tcggcctctg cataaataaa aaaaattagt cagccatggg gcggagaatg ggcggaactg 6180
ggcggagtta ggggcgggat gggcggagtt aggggcggga ctatggttgc tgactaattg 6240
agatgcatgc tttgcatact tctgcctgct ggggagcctg gggactttcc acacctggtt 6300
gctgactaat tgagatgcat gctttgcata cttctgcctg ctggggagcc tggggacttt 6360
ccacacccta actgacaca 6379

<210> SEQ ID NO 23
<211> LENGTH: 9400
<212> TYPE: DNA
<213> ORGANISM: artificial
<220> FEATURE:
<223> OTHER INFORMATION: synthetic

<400> SEQUENCE: 23
ttcccggaaa atcactcaaa actacgtcca tgacacatca actcccgata actacctccc 60
tttgaaatcg gatcccccca cgtaccaatc aatcacacaa cacacaggtt taaaaatcga 120
tcactcgtca attaggtttc aaaatcgata ccgtttatta tcaggaatct agactaattc 180
tacaatgaca gctctgaatt tctctctcgt cttccttgtc aggttctcat catcagttat 240
cacttccacc catcgaggag tcatcgtcgc tccaaaatcc tttggggtcg ctagttggaa 300
aagtctctga cacgatccag gcaccccgca cccagtccga ctgatctagc ttgcggagca 360
tctcaacagg catgagctgc agggccatgg ctgtcacggc actgtatcga tgtaacacta 420
gggactttct ttgcgatgta gccatcaaca cggcgtatgc cccatagttc gcgtgatacg 480
acgcatgatg ggttaaacgt tcccatccgg cagtgccgtc tcgggtccgt gcacacaaca 540
gctgcacggc attatgatgc ttaaaattaa ccataacgct ggggctactg atgaaggagt 600
agtaatgagc caggacgccg tacatcgaag gcagcaagaa agagtgacag cacaatagca 660
ccgggctctt atgtaggcga cagcttattt ttcctgacgt cggcaaaaag tacctaaatt 720
ccccacagat attcagacac ggttccgcaa agtgcttctt tttttagtgc aggaattgga 780
aaaaataata aaaaatatga acagctcatc tgtaattatc tgtgtgactt catcgtaccg 840
tgatgtaaaa acaacaacag gaagcttaca gggtgcggta gaaaattttg ccgattgagc 900
aacactgttg gcatctctca ctccgatagg cggctataag atagaaaatt aaaagtatga 960
tacccacgag aaagatgaag agggacaacc aggctagagt atgacgacca cttttccctt 1020
gtttgacggt tacatgtgcg gtatgatttt gtcgttgctt gtgatgttgg acgcctggaa 1080
cggacaacga cgtataattc ttagatgcgc atacggtgtt attagtggaa gtgcagttac 1140
gaattgtaac ctcagtgtca ctacactcag tgcaattggt acaattgtaa agccctgata 1200
catacgtacc gttagggcaa agtgtacatg ttgtactcgt atattgcgta cattgtcctg 1260
taacacgata tccttgttta catgggggac aacactgact tcctaattgc acttcttcgg 1320
gtttgcatat ttcagttttc cctatgcatg ccaatagcat actcagcaaa ataagcatca 1380
ccagaggctt catgcctcct accggaagaa taaaaataac tcatggggcc gaacggtatc 1440
atcctctccg cggtttgtaa tacgagatcg taaacgtaaa taaatgacat aacttcacta 1500
acccgcatac tgcaaagtcc acctacgacg ctgaaagctt ttccaggaca caacaggata 1560

-continued

```
gtcagccatc ttcacaggta accagtttct agtcacagta tagcgagcct aagagaccgc   1620
acacggtccc tgctggaaac acataccact acatcgattt gtcgtgtcgt acaaccgtca   1680
agttttccga acttttatac acgccaatgg cgttaggact atgtgtgctg ctgtgattgg   1740
aggcttcgag agttatgtga cagctgtgat tacacctgtc gccaaggctg acagcgatta   1800
cccaggtaga gcacaatcac atagctgatg gacgttggtt gatccgttga ttcccatgga   1860
cattttaacg gcgacagtac agctcccgtt aaacattaga ttaatagacg ctagtggatg   1920
acagcatgtt attcgcccaa ttgtgatggt ggttatactt tcttgttttt tgctcatatg   1980
ctgtaaggtg ttcgaggatc gtggggagta tatgtgttaa atcggaatca tatttactga   2040
ccgcgccata cttcgtatac gaacctaacc ggcgtaaagt gttttccgat atataaactg   2100
gcgcctattg tggctgtagc gcccataggt atggcatata cccacggtga tgttgtgtta   2160
ttcgtttttt gtgataaaac gtagtttatg tttaacgtgt gttccgtcac gttatgtgtg   2220
tcgttaaaag acggcgtctg tacagtatgg ctttgagttg tatcttgaat tgttattgca   2280
tttggaggtg tgtacagagt ggttgttgtg tgctgaggtg ttgttacgtt ttgaggcaca   2340
gttgtggtgt atacggactt caaggtgtag ttacggagtc tttctatgca ggtagtgttg   2400
agatatttgt gaatgctggt tatgttcgat tctgtgaggt taaagtgtgt actatttatg   2460
gcggtataat ttagacggtc ttgccatccc gaggatgtta gtgttaggta attcgtgttg   2520
tttacgtttg cttgatatgt ataggtaggt gtactgtttg tgaggtcgca agtgtgattt   2580
tcttgcagag attttatcca tcttgtgtga aaatattgag atacgcgatg aatgttttcg   2640
ctatctatat tgtaaagcgt ttcggtggta cttaggggtt gtttgctgta actcttattt   2700
tggacccagg atgtgaacca tgactccaat gtttgtatag taaggtgtcc tattaataaa   2760
gacgaactga ttcctaccgt aatgttatat cgcacaccta gggtgccgtt tacaaacacg   2820
gaaatgtttc cgttacaaac cacgttggca gatgaattag attccaggtg gtaacgatag   2880
gataatgacc gttcgctccc aacggatgac acaaagtatc cgaataacca acacgcccat   2940
tcaatccgca tattttaatc acactattca catttcacac actgcatttt ttaacatgtt   3000
atttttttat tttatgcgtg ttctcacctc ttcatctttt taacaccggg gtaactatcg   3060
taagtcggta ggcgtcgata gccctcacca cctcgtcgtc cccttcccgg cgtggggcac   3120
cagcgtccac agcactgcag gtaacacagg tagcatagga aacatacggt gaaaatactc   3180
caaaatccca aaaatgccgc gattccccga gtggcccagg gagacatccc ggtgtctatg   3240
tcggccggcg gtgctggcgt caccggtaaa aatttcggcg ggtgtggctg cgaacggtag   3300
cagtcgccgg ggagccggta acgctgtatc actgtccaac agcggtcggg ttcctcgtcc   3360
ggacatgcgg gtttccagca atcctcggcg tcggcgcggc cgatatagaa gtagttgcgt   3420
tgaaaaccgc ggtacatccc gcagtcgtga ttccgtagac gccagggcgt cggcgaccag   3480
atctggtctc ccagcgagta acgacctaac gccggcgtgc agcaaggttc gtcgggccgg   3540
ctgagcgtct ccagttgcgt gagaattacg aagcgttgca tgatgaggcc gtggctgtag   3600
ttgcgcagca cgcattcgta catgccggcc gtgtccgtcg atacgttgaa agtcagcgag   3660
aatatttggc cgagatgcaa ttgcgagaaa ttccaagtgg cgtacggcag gcggtactgg   3720
agtccgttca tcagccgatg gcctttgacg gcgtccagga tgagctcgtc gctgccgtcg   3780
tgggaacgac agaaacgtgc gcgaatggag accatgggcc aggagtgtgt catgaccgtg   3840
caggggatgg tataacttgc tctccctcgg cgaccaacac cggcgccggc gacgtggtct   3900
cataattctc ggcccacatc ttttcggcaa tgtcagcggt ggcgaagggg aacgaagagg   3960
```

aagaatattc gaggagtcgc gggcagctca acagcaccca gaacagccac ggcagagttc 4020
ggagcgactc tcggcggcac atgatgattc tttctttccc tttttcgcag agacgctgcg 4080
cgcctgctcc tgctccgtgt gtcggccgct caaacgtcgg gccggcgtgg tggtgaccac 4140
cgtgcgacgc agcttctcgc ccgggatgcc cgcgactgag cgtccggttt ttttgcaggt 4200
ctttttttgct gcctcctcct cgccgtcgcc gtcgcggccg acgtggtgga ccagcaccgc 4260
gcaggaactc tcgcgtcgcc ggcggtacgc gacctgtctc attgctacct cggatgttta 4320
agaaggaacg ttcatctgcg tcacagggtc tgatgaagct gccaagagtc gtggctgtgg 4380
cgcagcgcgt tctgtacggc gcgtttcacc gctttctgca tggccgctac cacgtcgggt 4440
gggagcggct ccggcggaag ctcgatgagc agttgctgcg agtctcggcg ctcggtgtcc 4500
gccgtttcgt cggacgtggc gtaaaaaacc gaggtggttg cccagtcgtc cacgctgtcg 4560
acggcctctg tcagtgccgg gttgtcaaaa ccgccatcgg acgcgggtga taaaagaacg 4620
tacgatgaca cgctgttagt acgactctcg tcgtcgctct gggaacgacg tgatggacga 4680
cggtagatga cctcgtcttg ccacgcgtcg aagcggtcgc agcagcgctg gatccaagcg 4740
cagcgaagca gcttacggaa cacgtcgttg ttccaaaagt agagcataaa gagaaagaaa 4800
agtagcgtaa taatgaagcc gaaaacgacg agggtcggca gggcactacc gccgctgccg 4860
tttttgtgt cgtgcgggtg cacggtggta gtggcgttag tctgagctgg ggtcatgaca 4920
agtctgaaga gatgagagcg tgggtgctca tcaggaacag ttgaggtctc tccctaccga 4980
agccttagcc tccacggtgt tttatgatca acgtgtctac gaacgtcatt gtgaaagtga 5040
cgtctcaggc tttccgaaac cgcgtcagat tcaacgtggg tttcggttta gcctgcgtca 5100
ccgaggcgga ggtggaaatg agccgtcctg tgggggagtg tacgaccctg tagtgcccat 5160
gggtaacgtc gcgtcggaag aagtgaatgc ggcattggtg tacgcgtggg ttgttttgct 5220
ctctgactcg gaggaattgc cgcagcagct gcagatttta cgtactaacc aaaagcagca 5280
aaagcagcag gtaaataaga gaaggagtcc agataatgtc cagccgctag cggcaagcag 5340
cgcgagctgt ggtactgtcc agctactgcc gttagaggca ttaatacatg tcgatacggt 5400
cgtgttggcg gtagcactag tagattgact ggaattagag ctggtacctg tagtggtttc 5460
actcgccgat gcggcgagtg caaataaaat taatatccac agcatgttta ttactatata 5520
attgatatac gaacccgtct gtcgtaacaa tcagcgttat acacgctgta tcggcatcgt 5580
tttaccggaa agtttatcgt aatgtaaccc gcgttgtgta cattcgtact gacagggaac 5640
ccccggtgat gtgcacatta tactctttca ttctggggtt tcccaatgac gtaaaaattt 5700
ccactacaca ataaaattac tgactcatgt gaaaagtgtg ctttttatta acagagcaga 5760
gggtttacag tagatatatg tttgccaggg ccaccgtttt ctaacaccga tcaccgccac 5820
cattaccacc cgttgaactc cacacccggg agccgcctga tcgccaggga ctcctcaccg 5880
tccatcgtcc gaacaagctc ccgccaccga tgctgccacc atcaccgaga gaaagaaccg 5940
cttgctgcag atacgcttgg gctcgcctcc gtgcggacgc cgtttcgtgc agacgctgag 6000
tagatcgagc agagaatgtc aaaacgacat taccgcgatc cgctcccctc ttttttcttt 6060
ttctcattca cgtgtattct tgatgataat gtaccatggc tacggtggtg aactgcgtcg 6120
cggatcccgt cacgggtttc aacagatcga cgtcggtcag cggcgccgtc accgccatgt 6180
ccggcggagg cacgctgttt ctctggttag cgacgtggac cgacgacgaa gacgatgaac 6240
ccgcgcggcg gtctgttatc cgcgacgacg cgtagctgca ctgggaagac acttcctccc 6300

```
aacggaccaa gatctcatcg ggccgttcgg agaaacggta tcgtctgtcc gactcccgcc   6360
gtacggcgcc gaggcccagc gacgacaggt ccgcgaaccg gcgctcgtat tccccgtaca   6420
gctcgcaaca gcggatcagc cagcggtagc tcaaaaacat gcgcaccagt ttgaaggtgt   6480
cgtgccaatg gtaagctaga tagcagagaa tggccacgat cagcacgagc atcacgccga   6540
tgatgggtaa cccgacgttc agcggcagat cgtccatggt gaccgtcctc tgtccggatc   6600
tacgtcccag tctctctctt ttgtacagca ctcgcgcggg aacggccccc tcaaccctct   6660
tacgtagcgg gagatacggc gttctcccgc gggccactta cttgcacggt cgcttgaacg   6720
gcggcttgga ccgccacatg taccgcatcc atccattctg gcagcagcgc gttcgacgac   6780
gtcgtacgag tcgcggatga tgttaccccg ccagcacctc cgccggcaac cgcgtcgtcg   6840
ttgctatcgt cgccggtttc gggcgatgac agcgccggcg gcgcgggtct cgtctcgtcc   6900
accatttcca ccgtgtcgaa gcgacagccg ctgccgtagt acatggcccc gttcaacggc   6960
cggcgggccg ggtcgccgag ttccgggtcg ggcacatcca tggctcgccg tctgcttctc   7020
tgccgctcgt ggtgccgacg gcacttctca ggataatgac agccgcaaaa tagatcgtgg   7080
agcatgtctc gccaactgtc ctggtggtaa tatcttaagt acgcgatgag cgcgccgatg   7140
gccataatca taagcgtaag caaaacggca cagataacgt gaaacaccgc ggtcatccaa   7200
gtcgggcggc gtcggggacg cggtgggtcg gtttctctta cgccggcgtc actcagccac   7260
cacacccgta gtcgacattc ccagaaccgg tgaatgcgac tcagggcctt tcgacgccgc   7320
catttatttc caacgtccaa gtcccacgtc atttctggca tctccacgcc cttgactgac   7380
atactctctt tctctctctt agctgcggtg aaaaagaggg aaggcgtgtg ctgctataca   7440
actgtacaac ggacgcgctc gctgtttcgg tctcaggtca tctgcattga ctcggcgtcc   7500
ttcatgacgc tctgcaccgc cttttccaag agttcctcga tgtccgacca tcgaggaggc   7560
ggggctaact cggaaaccga cacgataggc agcgtggtcg gctccgtcgg cgtgcggggt   7620
cggggacagg gacacgagag tcccaccttc gagagattct ccagcccgac ggtgcgcggc   7680
agtctcggat tccgcggtgg cttttgtggc gtcggcgttt tcgggaaggg cctgggcgtc   7740
accggcggtg tccagccgac cggcttgggt ttcgtgggcg gcggtgtttt cttggtgggc   7800
ggcgtgctca ggttcttacg cggcgcgggt atcggcgtcg gggcctgtg cgacgacagc   7860
cgcgtggtgg gggcccggac cggcggcgta ggcggccgct tcttgcgccc gggcggcgga   7920
ggtggcttcc aggatggcgg cggctgatgc agtaccgtgt cgacgctggc cgaggacgac   7980
aaagagctcg acgaggagca atgcgacgga gatcggccga tgctggtcgg cgttcccggc   8040
gtggatacgt cggggatctc gaatcgcgcc ggaggaaact cgggtttatc tatcggcaga   8100
ccatcctctc ctatgtagag cgacgtacac cgcggcacct gcggcgtcgg cgggtgggtg   8160
gccacccgca tgagccccag ttccagatcc agcggctcga cgacgtcttc tttcggaatt   8220
cgatagcagc acgcgcaggc accacgctta tcagaagcag cacccgggag ccggcctcgc   8280
gacgaagtct cgtcggatcg cttgcggcct cggcgctggg taaataagga aatggccagg   8340
accagggaag ccagtccggt accgccgagg agcccgacgc cgagccacag ccacaccatg   8400
atcttctctc ctgcttggaa tctcaaactc cgtgtcggga agggccggtg tacggacatt   8460
tatgccttgg atttctggaa acgtcatttt ttggcaagga atgtgtttat tgtccaaaca   8520
ctgaggaagg agatgtgagc caagtcggaa aattccttat cacaccgggg gcgggttacg   8580
ttccggtctg atgctgctgc tgttgttgta gagccgcggc catggccgcc tgcacggcag   8640
cttgtaccgc ctcggccacg ccgggtggca tctgcggcat ggcgggggga gacgcgtcgg   8700
```

-continued

```
gcggaccgcc gggcatcgcc gtcggctgcg acggtggttg tgaactcacc gtcggctcgc   8760

acggaggttt gtccttcggt ttgctcttcg gtttatcttt cgccctacct ttcttcggtt   8820

tgggttccga tgtcggtgtt ggcggctgcg gtgggatgac gggctggtgg gactcctccg   8880

acggcggggg gacgaatact gtcggcgccg aaaccggggg actctcgact atctcgcaga   8940

tcaccctgtc gggatcgtcg ccgtgtccgg gacgccgtcg atgaccatat tgaaccatgt   9000

cgtaaatcat cgtctccttg taacacgctg aacagcagcg gctacaagga cccgaaatgc   9060

atttgcagct gcacttacag ctgcagctgc agtagcgcac ccatcggcag gtgaagacgt   9120

cgattacgga gtccttgaag aattcccggt aacggatgag atacgcgcag aggaaaatca   9180

tgaaaacaga acagccgact acggctgcga tgccgggtcc cgaaaacgta ttcggtgatc   9240

ctaccaaaca ccaaattccc agggccgcgc atgttatcca ggccacaata atcgtgggaa   9300

cgccccattg gcattgccac gaaggatcgt gcacgtcgca acccatcgct actgcgttct   9360

cccacaaacg ccatcgcact atttatccct acagcggctg                         9400
```

<210> SEQ ID NO 24
<211> LENGTH: 387
<212> TYPE: PRT
<213> ORGANISM: artificial
<220> FEATURE:
<223> OTHER INFORMATION: synthetic

<400> SEQUENCE: 24

```
Met Gly Ser Gly Ile Gly Ala Ala Ser Met Glu Phe Cys Phe Asp Val
1               5                   10                  15

Phe Lys Glu Leu Lys Val His His Ala Asn Glu Asn Ile Phe Tyr Cys
            20                  25                  30

Pro Ile Ala Ile Met Ser Ala Leu Ala Met Val Tyr Leu Gly Ala Lys
        35                  40                  45

Asp Ser Thr Arg Thr Gln Ile Asn Lys Val Val Arg Phe Asp Lys Leu
    50                  55                  60

Pro Gly Phe Gly Asp Ser Ile Glu Ala Gln Cys Gly Thr Ser Val Asn
65                  70                  75                  80

Val His Ser Ser Leu Arg Asp Ile Leu Asn Gln Ile Thr Lys Pro Asn
                85                  90                  95

Asp Val Tyr Ser Phe Ser Leu Ala Ser Arg Leu Tyr Ala Glu Glu Arg
            100                 105                 110

Tyr Pro Ile Leu Pro Glu Tyr Leu Gln Cys Val Lys Glu Leu Tyr Arg
        115                 120                 125

Gly Gly Leu Glu Pro Ile Asn Phe Gln Thr Ala Ala Asp Gln Ala Arg
    130                 135                 140

Glu Leu Ile Asn Ser Trp Val Glu Ser Gln Thr Asn Gly Ile Ile Arg
145                 150                 155                 160

Asn Val Leu Gln Pro Ser Ser Val Asp Ser Gln Thr Ala Met Val Leu
                165                 170                 175

Val Asn Ala Ile Val Phe Lys Gly Leu Trp Glu Lys Thr Phe Lys Asp
            180                 185                 190

Glu Asp Thr Gln Ala Met Pro Phe Arg Val Thr Glu Gln Glu Ser Lys
        195                 200                 205

Pro Val Gln Met Met Tyr Gln Ile Gly Leu Phe Arg Val Ala Ser Met
    210                 215                 220

Ala Ser Glu Lys Met Lys Ile Leu Glu Leu Pro Phe Ala Ser Gly Thr
225                 230                 235                 240
```

Met Ser Met Leu Val Leu Leu Pro Asp Glu Val Ser Gly Leu Glu Gln
245 250 255

Leu Glu Ser Ile Ile Asn Phe Glu Lys Leu Thr Glu Trp Thr Ser Ser
260 265 270

Asn Val Met Glu Glu Arg Lys Ile Lys Val Tyr Leu Pro Arg Met Lys
275 280 285

Met Glu Glu Lys Tyr Asn Leu Thr Ser Val Leu Met Ala Met Gly Ile
290 295 300

Thr Asp Val Phe Ser Ser Ser Ala Asn Leu Ser Gly Ile Ser Ser Ala
305 310 315 320

Glu Ser Leu Lys Ile Ser Gln Ala Val His Ala Ala His Ala Glu Ile
325 330 335

Asn Glu Ala Gly Arg Glu Val Val Gly Ser Ala Glu Ala Gly Val Asp
340 345 350

Ala Ala Ser Val Ser Glu Glu Phe Arg Ala Asp His Pro Phe Leu Phe
355 360 365

Cys Ile Lys His Ile Ala Thr Asn Ala Val Leu Phe Phe Gly Arg Cys
370 375 380

Val Ser Pro
385

<210> SEQ ID NO 25
<211> LENGTH: 498
<212> TYPE: PRT
<213> ORGANISM: artificial
<220> FEATURE:
<223> OTHER INFORMATION: synthetic

<400> SEQUENCE: 25

Met Ser Gly Gln Gly Thr Lys Arg Ser Tyr Glu Gln Met Glu Thr Asp
1 5 10 15

Gly Glu Arg Gln Asn Ala Thr Glu Ile Arg Ala Ser Val Gly Lys Met
20 25 30

Ile Gly Gly Ile Gly Arg Phe Tyr Ile Gln Met Cys Thr Glu Leu Lys
35 40 45

Leu Ser Asp Tyr Glu Gly Arg Leu Ile Gln Asn Ser Leu Thr Ile Glu
50 55 60

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asn Gly Lys Trp Met Arg Glu Leu Ile Leu Tyr Asp
100 105 110

Lys Glu Glu Ile Arg Arg Ile Trp Arg Gln Thr Asn Asn Gly Asp Asp
115 120 125

Ala Thr Ala Gly Leu Thr His Met Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Met Val Met Glu
180 185 190

Leu Val Arg Met Ile Lys Arg Gly Ile Asn Asp Arg Asn Phe Trp Arg
195 200 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Asp Ala Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 26
<211> LENGTH: 99
<212> TYPE: PRT
<213> ORGANISM: artificial
<220> FEATURE:
<223> OTHER INFORMATION: synthetic

<400> SEQUENCE: 26

Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
    50                  55                  60

```
Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln


<210> SEQ ID NO 27
<211> LENGTH: 345
<212> TYPE: PRT
<213> ORGANISM: artificial
<220> FEATURE:
<223> OTHER INFORMATION: synthetic

<400> SEQUENCE: 27

Met Ala Trp Arg Ser Gly Leu Cys Glu Thr Asp Ser Arg Thr Leu Lys
1               5                   10                  15

Gln Phe Leu Gln Glu Glu Cys Met Trp Lys Leu Val Gly Lys Ser Arg
            20                  25                  30

Lys His Arg Glu Tyr Arg Ala Val Ala Cys Arg Ser Thr Ile Phe Ser
        35                  40                  45

Pro Glu Asp Asp Gly Ser Cys Ile Leu Cys Gln Leu Leu Leu Leu Tyr
    50                  55                  60

Arg Asp Gly Glu Trp Ile Leu Cys Leu Cys Cys Asn Gly Arg Tyr Gln
65                  70                  75                  80

Gly His Tyr Gly Val Gly His Val His Arg Arg Arg Arg Arg Ile Cys
                85                  90                  95

His Leu Pro Thr Leu Tyr Gln Leu Ser Phe Gly Gly Pro Leu Gly Pro
            100                 105                 110

Ala Ser Ile Asp Phe Leu Pro Ser Phe Ser Gln Val Thr Ser Ser Met
        115                 120                 125

Thr Cys Asp Gly Ile Thr Pro Asp Val Ile Tyr Glu Val Cys Met Leu
    130                 135                 140

Val Pro Gln Asp Glu Ala Lys Arg Ile Leu Val Lys Gly His Gly Ala
145                 150                 155                 160

Met Asp Leu Thr Cys Gln Lys Ala Val Thr Leu Gly Gly Ala Gly Ala
                165                 170                 175

Trp Leu Leu Pro Arg Pro Glu Gly Tyr Thr Leu Phe Phe Tyr Ile Leu
            180                 185                 190

Cys Tyr Asp Leu Phe Thr Ser Cys Gly Asn Arg Cys Asp Ile Pro Ser
        195                 200                 205

Met Thr Arg Leu Met Ala Ala Ala Thr Ala Cys Gly Gln Ala Gly Cys
    210                 215                 220

Ser Phe Cys Thr Asp His Glu Gly His Val Asp Pro Thr Gly Asn Tyr
225                 230                 235                 240

Val Gly Cys Thr Pro Asp Met Gly Arg Cys Leu Cys Tyr Val Pro Cys
                245                 250                 255

Gly Pro Met Thr Gln Ser Leu Ile His Asn Asp Glu Pro Ala Thr Phe
            260                 265                 270

Phe Cys Glu Ser Asp Asp Ala Lys Tyr Leu Cys Ala Val Gly Ser Lys
        275                 280                 285

Thr Ala Ala Gln Val Thr Leu Gly Asp Gly Leu Asp Tyr His Ile Gly
    290                 295                 300

Val Lys Asp Ser Glu Gly Arg Trp Leu Pro Val Lys Thr Asp Val Trp
305                 310                 315                 320

Asp Leu Val Lys Val Glu Glu Pro Val Ser Arg Met Ile Val Cys Ser
```

```
                325                 330                 335

Cys Pro Val Leu Lys Asn Leu Val His
            340                 345


<210> SEQ ID NO 28
<211> LENGTH: 12
<212> TYPE: PRT
<213> ORGANISM: artificial
<220> FEATURE:
<223> OTHER INFORMATION: synthetic

<400> SEQUENCE: 28

Val Thr Leu Gly Gly Ala Gly Ala Trp Leu Leu Pro
1               5                   10


<210> SEQ ID NO 29
<211> LENGTH: 190
<212> TYPE: PRT
<213> ORGANISM: artificial
<220> FEATURE:
<223> OTHER INFORMATION: synthetic

<400> SEQUENCE: 29

Met Gly Gly Glu Leu Cys Lys Arg Ile Cys Cys Glu Phe Gly Thr Thr
1               5                   10                  15

Ser Gly Glu Pro Leu Lys Asp Ala Leu Gly Arg Gln Val Ser Leu Arg
            20                  25                  30

Ser Tyr Asp Asn Ile Pro Pro Thr Ser Ser Ser Asp Glu Gly Glu Asp
        35                  40                  45

Asp Asp Asp Gly Glu Asp Asp Asp Asn Glu Glu Arg Gln Gln Lys Leu
    50                  55                  60

Arg Leu Cys Gly Ser Gly Cys Gly Gly Asn Asp Ser Ser Ser Gly Ser
65                  70                  75                  80

His Arg Glu Ala Thr His Asp Gly Pro Lys Lys Asn Ala Val Arg Ser
                85                  90                  95

Thr Phe Arg Glu Asp Lys Ala Pro Lys Pro Ser Lys Gln Ser Lys Lys
            100                 105                 110

Lys Lys Lys Pro Ser Lys His His His His Gln Gln Ser Ser Ile Met
        115                 120                 125

Gln Glu Thr Asp Asp Leu Asp Glu Glu Asp Thr Ser Ile Tyr Leu Ser
    130                 135                 140

Pro Pro Pro Val Pro Pro Val Gln Val Val Ala Lys Arg Leu Pro Arg
145                 150                 155                 160

Pro Asp Thr Pro Arg Thr Pro Arg Gln Lys Lys Ile Ser Gln Arg Pro
                165                 170                 175

Pro Thr Pro Gly Thr Lys Lys Pro Ala Ala Pro Leu Ser Phe
            180                 185                 190


<210> SEQ ID NO 30
<211> LENGTH: 345
<212> TYPE: PRT
<213> ORGANISM: artificial
<220> FEATURE:
<223> OTHER INFORMATION: syntehtic

<400> SEQUENCE: 30

Met Ala Thr Ser Arg Leu Ser Val Lys Ser Leu Arg Ser Ile Ser Arg
1               5                   10                  15

Phe Val Gln Trp Glu Cys Cys Trp Met Leu Val Asn Lys Ser Ala Arg
            20                  25                  30
```

-continued

Tyr Arg Glu Phe Arg Ala Val Thr Ser Gln Ser Pro Gly Leu Gly Lys
35 40 45

Val Ser Ser Thr Asp Asp Gly Arg Cys Leu Ala Ala Ser Met Met Leu
50 55 60

Phe Arg Arg Asp Gly Asn Phe Val Leu Cys Leu Val Val Asn Lys Glu
65 70 75 80

Pro Val Gly Gln Phe Gly Cys Ser Gly Met Arg Arg Glu Lys Met Val
85 90 95

Ile Asp Gly Leu Gln Glu Pro Val Tyr Val Met Arg Leu Leu Ala Pro
100 105 110

Leu Ile Pro Val Lys Leu Gly Phe Ser Pro Tyr Met Leu Pro Pro Lys
115 120 125

Ser Ile Gly Gly Ser Gly Gly Leu Asp Pro Ser Val Ile Tyr Gln Asn
130 135 140

Ala Ser Val Val Thr Pro Glu Glu Ala Ala Thr Val Thr Met Gln Gly
145 150 155 160

Ser Gly Ile Val Thr Val Gly Leu Ser Gly Val Gly Ser Trp Val Gln
165 170 175

Ile Lys Asp Gly Gly Asn Met Lys Leu Phe Val Phe Ala Leu Cys Phe
180 185 190

Asp Val Phe Thr Ala Cys Cys Asp Arg Leu Ala Phe Pro Ser Leu Ala
195 200 205

Lys Ile Tyr Ser Glu Thr Val Ser Cys Glu Ala Asp Lys Cys Gly Phe
210 215 220

Cys Arg Asp Ser Gly Arg His Val Asp Pro Thr Gly Arg Phe Val Gly
225 230 235 240

Cys Val Pro Asp Ser Gly Val Cys Leu Cys Tyr Ser Pro Cys Arg Gly
245 250 255

Thr Asp Ala Ala Val Ser Val Arg Ser Trp Leu Pro Tyr Leu Glu Leu
260 265 270

Glu Asp Gly Ala Asn Thr His Ser Leu Phe Val Arg Arg Tyr Asp Gly
275 280 285

Arg Lys Gly Leu Pro Ala Thr Ile Ser Asp Tyr Leu Gly Ala Arg Asn
290 295 300

Ser Glu Gly Asp Glu Ile Pro Leu Arg Thr Glu Pro Trp Gln Leu Leu
305 310 315 320

Lys Ile Glu Pro Thr Leu Ser Ala Met Ile Ile Met Ala Cys Pro Leu
325 330 335

Leu Lys Lys Ile Val Leu Glu His Met
340 345

<210> SEQ ID NO 31
<211> LENGTH: 353
<212> TYPE: PRT
<213> ORGANISM: artificial
<220> FEATURE:
<223> OTHER INFORMATION: synthetic

<400> SEQUENCE: 31

Met Tyr Pro Tyr Asp Val Pro Asp Tyr Ala Thr Ser Arg Leu Ser Val
1 5 10 15

Lys Ser Leu Arg Ser Ile Ser Arg Phe Val Gln Trp Glu Cys Cys Trp
20 25 30

Met Leu Val Asn Lys Ser Ala Arg Tyr Arg Glu Phe Arg Ala Val Thr
35 40 45

```
Ser Gln Ser Pro Gly Leu Gly Lys Val Ser Ser Thr Asp Asp Gly Arg
    50                  55                  60

Cys Leu Ala Ala Ser Met Met Leu Phe Arg Arg Asp Gly Asn Phe Val
65                  70                  75                  80

Leu Cys Leu Val Val Asn Lys Glu Pro Val Gly Gln Phe Gly Cys Ser
                85                  90                  95

Gly Met Arg Arg Glu Lys Met Val Ile Asp Gly Leu Gln Glu Pro Val
            100                 105                 110

Tyr Val Met Arg Leu Leu Ala Pro Leu Ile Pro Val Lys Leu Gly Phe
        115                 120                 125

Ser Pro Tyr Met Leu Pro Pro Lys Ser Ile Gly Gly Ser Gly Gly Leu
    130                 135                 140

Asp Pro Ser Val Ile Tyr Gln Asn Ala Ser Val Val Thr Pro Glu Glu
145                 150                 155                 160

Ala Ala Thr Val Thr Met Gln Gly Ser Gly Ile Val Thr Val Gly Leu
                165                 170                 175

Ser Gly Val Gly Ser Trp Val Gln Ile Lys Asp Gly Gly Asn Met Lys
            180                 185                 190

Leu Phe Val Phe Ala Leu Cys Phe Asp Val Phe Thr Ala Cys Cys Asp
        195                 200                 205

Arg Leu Ala Phe Pro Ser Leu Ala Lys Ile Tyr Ser Glu Thr Val Ser
    210                 215                 220

Cys Glu Ala Asp Lys Cys Gly Phe Cys Arg Asp Ser Gly Arg His Val
225                 230                 235                 240

Asp Pro Thr Gly Arg Phe Val Gly Cys Val Pro Asp Ser Gly Val Cys
                245                 250                 255

Leu Cys Tyr Ser Pro Cys Arg Gly Thr Asp Ala Ala Val Ser Val Arg
            260                 265                 270

Ser Trp Leu Pro Tyr Leu Glu Leu Glu Asp Gly Ala Asn Thr His Ser
        275                 280                 285

Leu Phe Val Arg Arg Tyr Asp Gly Arg Lys Gly Leu Pro Ala Thr Ile
    290                 295                 300

Ser Asp Tyr Leu Gly Ala Arg Asn Ser Glu Gly Asp Glu Ile Pro Leu
305                 310                 315                 320

Arg Thr Glu Pro Trp Gln Leu Leu Lys Ile Glu Pro Thr Leu Ser Ala
                325                 330                 335

Met Ile Ile Met Ala Cys Pro Leu Leu Lys Lys Ile Val Leu Glu His
            340                 345                 350

Met
```

<210> SEQ ID NO 32
<211> LENGTH: 179
<212> TYPE: DNA
<213> ORGANISM: artificial
<220> FEATURE:
<223> OTHER INFORMATION: synthetic

<400> SEQUENCE: 32

```
gaccgcgcca cagcagagcc agcaccagca gaagagccag caccagcggg cccagagtcg      60

caaagcgcgc gggcagccac ggcccagact gcggtcgcga tggcccggag cgcgctcgcc     120

accacgatga cggtgcccaa cgataaccag tccgctcccg caccgacgcc accgccgat      179
```

<210> SEQ ID NO 33
<211> LENGTH: 38

<212> TYPE: DNA
<213> ORGANISM: artificial
<220> FEATURE:
<223> OTHER INFORMATION: synthetic

<400> SEQUENCE: 33
atgtctagcg ttttctcaac agcattcgtg cgccttga 38

<210> SEQ ID NO 34
<211> LENGTH: 252
<212> TYPE: DNA
<213> ORGANISM: artificial
<220> FEATURE:
<223> OTHER INFORMATION: synthetic

<400> SEQUENCE: 34
cacggcctgg cccagcgagc cctgcgggac cggttccaaa acttcgaggc cgtgctggcc 60
cggggcatgc acgtggaggc cggccggcag gagcccgaga ccccccgggt gagcggccgg 120
cggctgccct tcgacgacct gtgatccgga ggacgacggc tcgtgtatct tgtgccaatt 180
gctgttgctc taccgcgacg gcgaatggat cctctgtctt tgctgcaacg gccgttatca 240
aggccactat gg 252

<210> SEQ ID NO 35
<211> LENGTH: 67
<212> TYPE: DNA
<213> ORGANISM: artificial
<220> FEATURE:
<223> OTHER INFORMATION: synthetic

<400> SEQUENCE: 35
ctgggtcgcc aacagcgcca acgagtacgt cgtcagctcc gtgccccgcc ccgtcagtcc 60
gtagaag 67